United States Patent
Su et al.

(10) Patent No.: US 12,239,777 B2
(45) Date of Patent: Mar. 4, 2025

(54) THROMBECTOMY SYSTEMS AND METHODS FOR CONTROLLED CLOT ASPIRATION

(71) Applicant: Penumbra, Inc., Alameda, CA (US)

(72) Inventors: Bo-Yu Su, Alameda, CA (US); Vinita Verma, Pleasanton, CA (US); Scott Teigen, West Fargo, ND (US); Steven Loisel, Castro Valley, CA (US); Stephen Pons, Alameda, CA (US); Ben Tompkins, Danville, CA (US)

(73) Assignee: Penumbra, Inc., Alameda, CA (US)

(*) Notice: Subject to any disclaimer, the term of this patent is extended or adjusted under 35 U.S.C. 154(b) by 0 days.

(21) Appl. No.: 18/658,292

(22) Filed: May 8, 2024

(65) Prior Publication Data

US 2024/0285846 A1 Aug. 29, 2024

Related U.S. Application Data

(63) Continuation-in-part of application No. 18/492,674, filed on Oct. 23, 2023, and a continuation-in-part of application No. 18/469,445, filed on Sep. 18, 2023, said application No. 18/492,674 is a continuation of application No. 17/463,939, filed on Sep. 1, 2021, now Pat. No. 11,793,542, said application No. 18/469,445 is a continuation of application No. 16/977,431, filed as application No. PCT/US2019/043095 on Jul. 23, 2019, now Pat. No. 11,759,219.

(Continued)

(51) Int. Cl.
*A61B 17/3207* (2006.01)
*A61M 1/00* (2006.01)
(Continued)

(52) U.S. Cl.
CPC ............ *A61M 1/75* (2021.05); *A61M 1/76* (2021.05); *A61M 1/77* (2021.05); *A61M 1/774* (2021.05);
(Continued)

(58) Field of Classification Search
CPC ........ A61B 17/3498; A61B 17/320758; A61B 17/320725; A61B 17/32075;
(Continued)

(56) References Cited

U.S. PATENT DOCUMENTS

| | | |
|---|---|---|
| 3,042,042 A | 7/1962 | Blanck |
| 3,086,528 A | 4/1963 | Eichelman |

(Continued)

FOREIGN PATENT DOCUMENTS

| | | |
|---|---|---|
| EP | 3806757 A4 | 5/2022 |
| JP | 2009506817 A | 2/2009 |

(Continued)

OTHER PUBLICATIONS

U.S. Appl. No. 18/532,982, filed Dec. 7, 2023, Teigen.
(Continued)

*Primary Examiner* — Tuan V Nguyen
(74) *Attorney, Agent, or Firm* — Baker Botts L.L.P.

(57) ABSTRACT

A thrombectomy system includes a catheter having a proximal end and a distal end, a valve in fluid communication with the catheter, and a cutting instrument associated with the distal end of the catheter. The cutting instrument may be configured for axial and/or rotational motion. A controller of the system may be configured to detect operational parameters of the cutting instrument. The controller may determine whether the cutting instrument is engaging with occlusive material based on the detected operational parameters. The controller may operate the valve in one or more operating modes to alter a level of pressure in the catheter based on whether the cutting instrument is engaging with the occlusive material.

20 Claims, 101 Drawing Sheets

Related U.S. Application Data

(60) Provisional application No. 62/778,708, filed on Dec. 12, 2018, provisional application No. 62/702,804, filed on Jul. 24, 2018.

(51) Int. Cl.
*A61B 17/00* (2006.01)
*A61B 17/3203* (2006.01)
*A61B 90/00* (2016.01)
*A61M 39/10* (2006.01)

(52) U.S. Cl.
CPC ..... *A61B 17/00* (2013.01); *A61B 2017/00022* (2013.01); *A61B 2017/00075* (2013.01); *A61B 2017/00123* (2013.01); *A61B 2017/00561* (2013.01); *A61B 17/32037* (2013.01); *A61B 2017/320775* (2013.01); *A61B 90/06* (2016.02); *A61B 2090/064* (2016.02); *A61B 2217/005* (2013.01); *A61M 39/105* (2013.01); *A61M 2205/3334* (2013.01); *A61M 2205/3344* (2013.01)

(58) Field of Classification Search
CPC ........... A61B 17/320783; A61B 2017/320733; A61B 2017/320775; A61B 2017/320791; A61B 2017/00561; A61B 2017/00022; A61B 90/06; A61B 2090/064
See application file for complete search history.

(56) References Cited

U.S. PATENT DOCUMENTS

| | | | |
|---|---|---|---|
| 3,659,605 A | 5/1972 | Sielaff | |
| 3,955,574 A | 5/1976 | Rubenstein | |
| 4,315,506 A | 2/1982 | Kayser | |
| 4,634,435 A | 1/1987 | Ingraham | |
| 4,935,005 A | 6/1990 | Haines | |
| 5,094,961 A | 3/1992 | Del Valle | |
| 5,300,043 A | 4/1994 | Devlin | |
| 5,536,242 A | 7/1996 | Willard | |
| 5,827,229 A | 10/1998 | Auth | |
| 6,206,014 B1 | 3/2001 | Cameron, III | |
| 7,618,382 B2 | 11/2009 | Vogel | |
| 8,657,821 B2 * | 2/2014 | Palermo | A61B 17/320758 408/1 R |
| 9,254,144 B2 | 2/2016 | Nguyen | |
| 9,510,854 B2 | 12/2016 | Mallaby | |
| 10,258,240 B1 | 4/2019 | Eberle | |
| 10,531,883 B1 | 1/2020 | Deville | |
| 10,722,253 B2 | 7/2020 | Deville | |
| 11,076,808 B2 | 8/2021 | Levine | |
| 11,096,712 B2 | 8/2021 | Teigen | |
| 11,197,683 B1 | 12/2021 | Teigen | |
| 11,232,868 B1 | 1/2022 | Sutherland | |
| 11,337,712 B2 | 5/2022 | Teigen | |
| 11,759,219 B2 | 9/2023 | Teigen | |
| 12,150,660 B1 | 11/2024 | Teigen | |
| 12,156,666 B2 | 12/2024 | Trosper | |
| 12,156,667 B2 | 12/2024 | Trosper | |
| 2001/0051811 A1 | 12/2001 | Bonnette | |
| 2006/0229488 A1 | 10/2006 | Ayre | |
| 2007/0129679 A1 | 6/2007 | Bonnette | |
| 2008/0108960 A1 | 5/2008 | Shapland | |
| 2008/0125695 A1 | 5/2008 | Hopkins | |
| 2008/0243153 A1 | 10/2008 | Nguyen | |
| 2009/0156895 A1 | 6/2009 | Higgins | |
| 2010/0125276 A1 * | 5/2010 | Palermo | A61B 17/320758 408/1 R |
| 2010/0204672 A1 | 8/2010 | Lockhart | |
| 2011/0172687 A1 | 7/2011 | Woodruff | |
| 2012/0041360 A1 | 2/2012 | Gerg | |
| 2012/0138833 A1 | 6/2012 | Matteo | |
| 2014/0114236 A1 | 4/2014 | Gordon | |
| 2014/0276390 A1 | 9/2014 | Eubanks | |
| 2014/0276920 A1 * | 9/2014 | Hendrick | A61B 18/245 606/127 |
| 2014/0323906 A1 * | 10/2014 | Peatfield | A61B 5/7475 600/561 |
| 2015/0283309 A1 | 10/2015 | Look | |
| 2015/0327875 A1 | 11/2015 | Look | |
| 2016/0220741 A1 | 8/2016 | Garrison | |
| 2016/0367272 A1 | 12/2016 | Garrison | |
| 2017/0049470 A1 | 2/2017 | Mallaby | |
| 2017/0056032 A1 | 3/2017 | Look | |
| 2017/0150993 A1 | 6/2017 | Ganz | |
| 2017/0181760 A1 * | 6/2017 | Look | A61B 17/320758 |
| 2017/0188796 A1 | 7/2017 | Olden | |
| 2017/0215854 A1 * | 8/2017 | Todd | A61M 13/003 |
| 2017/0238953 A1 | 8/2017 | Yang | |
| 2017/0239447 A1 | 8/2017 | Yang | |
| 2017/0252051 A1 | 9/2017 | Wan | |
| 2017/0259042 A1 | 9/2017 | Nguyen | |
| 2017/0290598 A1 | 10/2017 | Culbert | |
| 2017/0354777 A1 | 12/2017 | Ofek | |
| 2018/0015244 A1 | 1/2018 | Isaza | |
| 2018/0021098 A1 | 1/2018 | Hemphill | |
| 2018/0024022 A1 | 1/2018 | Beden | |
| 2018/0064453 A1 | 3/2018 | Garrison | |
| 2018/0126130 A1 | 5/2018 | Nitzan | |
| 2018/0207330 A1 * | 7/2018 | Ovchinnikov | A61M 1/743 |
| 2018/0207397 A1 | 7/2018 | Look | |
| 2018/0318501 A1 | 11/2018 | Hochman | |
| 2019/0059703 A1 | 2/2019 | Ting | |
| 2019/0126006 A1 | 5/2019 | Rehm | |
| 2019/0239910 A1 | 8/2019 | Brady | |
| 2019/0247050 A1 | 8/2019 | Goldsmith | |
| 2020/0009301 A1 | 1/2020 | Yee | |
| 2020/0022711 A1 | 1/2020 | Look | |
| 2020/0093503 A1 | 3/2020 | Deville | |
| 2020/0237977 A1 | 7/2020 | Panotopoulos | |
| 2020/0297362 A1 | 9/2020 | Deville | |
| 2020/0397957 A1 | 12/2020 | Teigen | |
| 2021/0393336 A1 | 12/2021 | Sganga | |
| 2022/0280171 A1 | 9/2022 | Teigen | |
| 2022/0409857 A1 * | 12/2022 | Saadat | A61B 17/320783 |
| 2023/0026412 A1 | 1/2023 | Teigen | |
| 2024/0000469 A1 | 1/2024 | Teigen | |
| 2024/0138859 A1 | 5/2024 | Teigen | |
| 2024/0341784 A1 | 10/2024 | Trosper | |
| 2024/0341785 A1 | 10/2024 | Trosper | |
| 2024/0341786 A1 | 10/2024 | Trosper | |

FOREIGN PATENT DOCUMENTS

| | | |
|---|---|---|
| JP | 2016030119 A | 3/2016 |
| JP | 2017510346 A | 4/2017 |
| JP | 2017532074 A | 11/2017 |
| JP | 2018508270 A | 3/2018 |
| JP | 2018510729 A | 4/2018 |
| JP | 7423594 B2 | 1/2024 |
| WO | WO 2014151209 A1 | 9/2014 |
| WO | WO 2016054051 A1 | 4/2016 |
| WO | WO 2016126974 A1 | 8/2016 |
| WO | WO 2017142874 A2 | 8/2017 |
| WO | WO 2017155994 A1 | 9/2017 |
| WO | WO 2018019829 A1 | 2/2018 |
| WO | WO 2020023541 A1 | 1/2020 |

OTHER PUBLICATIONS

Thorpe et al., "Endovenous management of Iliocaval occlusion", in the Vein Book Academic Press, 2006, retrieved Mar. 2022, pp. 559-574.

Fornell, "Catheter-Based Clot Busting Therapies", Diagnostic and Interventional Cardiology, https://www.dicardiology.com/article/catheter-based-clot-busting-therapies, downloaded on Mar. 27, 2021, 4 pages.

Rioufol, et al., "Large tube section is the key to successful coronary thrombus aspiration: findings of a standardized bench test", Cath-

(56) References Cited

OTHER PUBLICATIONS eterization and cardiovascular interventions (67) 2: 254-257 (2006), retrieved Mar. 2022.
Haude, "Mechanical Thrombectomy Catheter Systems", 2 Interventional Cardiology, pp. 58-60, retrieved Mar. 2022.
Simon, et al., "Exploring the efficacy of cyclic vs static aspiration in a cerebral thrombectomy model: an initial proof of concept study", Journal of neurointerventional surgery (6)9:677-683, downloaded on May 10, 2016.
Munich, et al., "Overview of mechanical thrombectomy techniques", Neurosurgery 85, No. suppl_1: S60-S67, Jul. 2019.
Partial Supplemental ESR received from EPO for EP Patent Application No. 19842275.0-1113, mailed on Feb. 8, 2022, 19 pages.
EESR received from EPO for European Patent Application No. 19842275.0-1134, mailed on Apr. 26, 2022, 24 pages.
U.S. Appl. No. 18/922,209, filed Oct. 21, 2024, Trosper.
U.S. Appl. No. 18/922,216, filed Oct. 21, 2024, Trosper.
U.S. Appl. No. 18/750,607, filed Jun. 21, 2024, Trosper.
U.S. Appl. No. 18/741,638, filed Jun. 12, 2024, Teigen.
U.S. Appl. No. 18/750,634, filed Jun. 21, 2024, Trosper.
U.S. Appl. No. 18/750,647, filed Jun. 21, 2024, Trosper.

\* cited by examiner

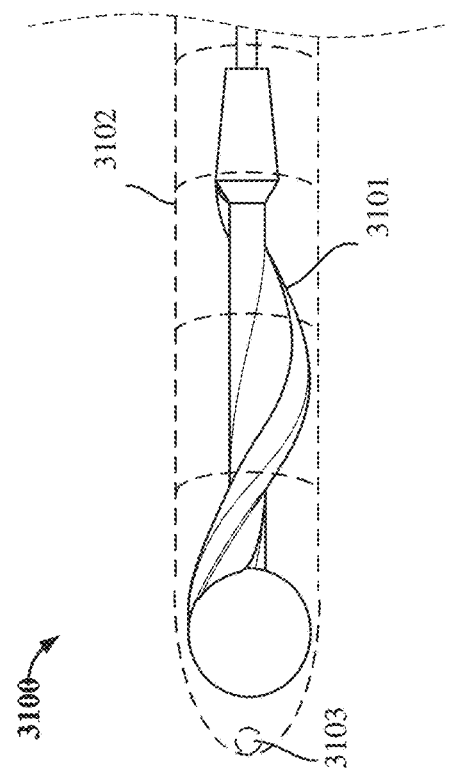
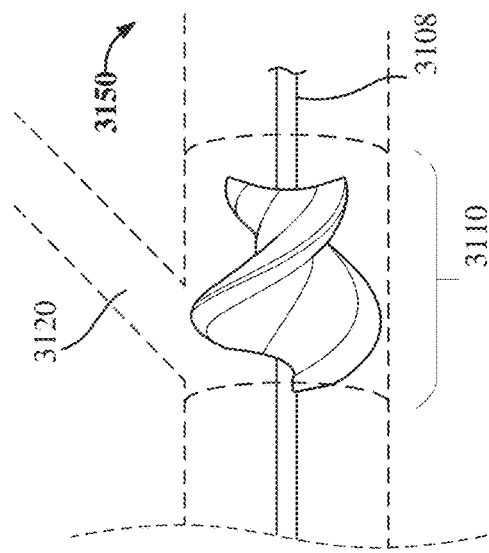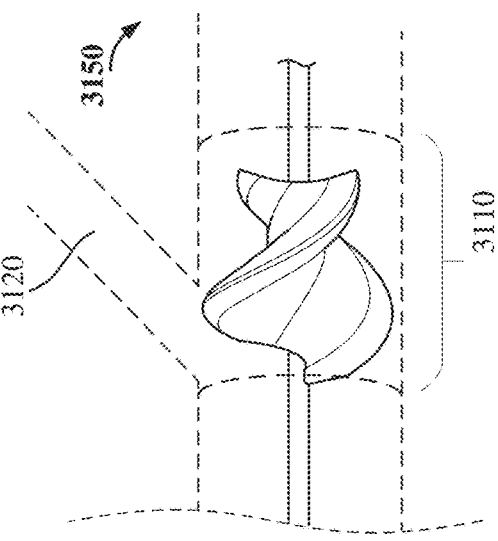
FIG. 31A  FIG. 31B

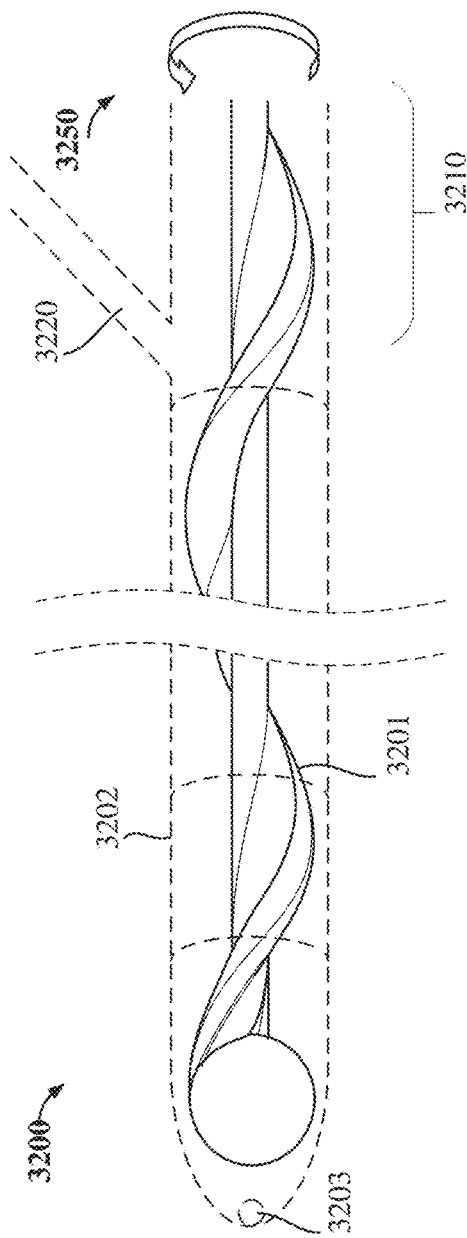
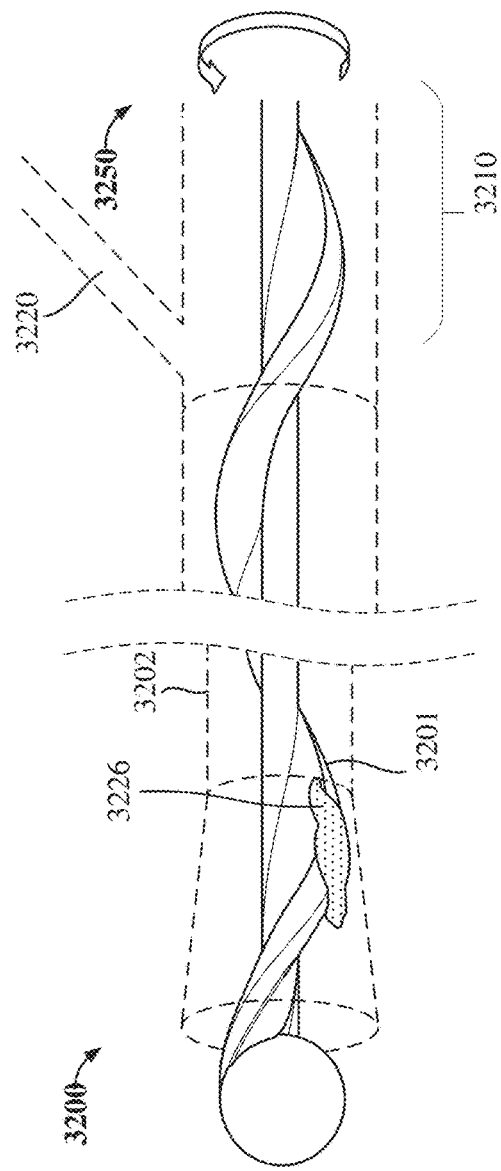
FIG. 32A
FIG. 32B

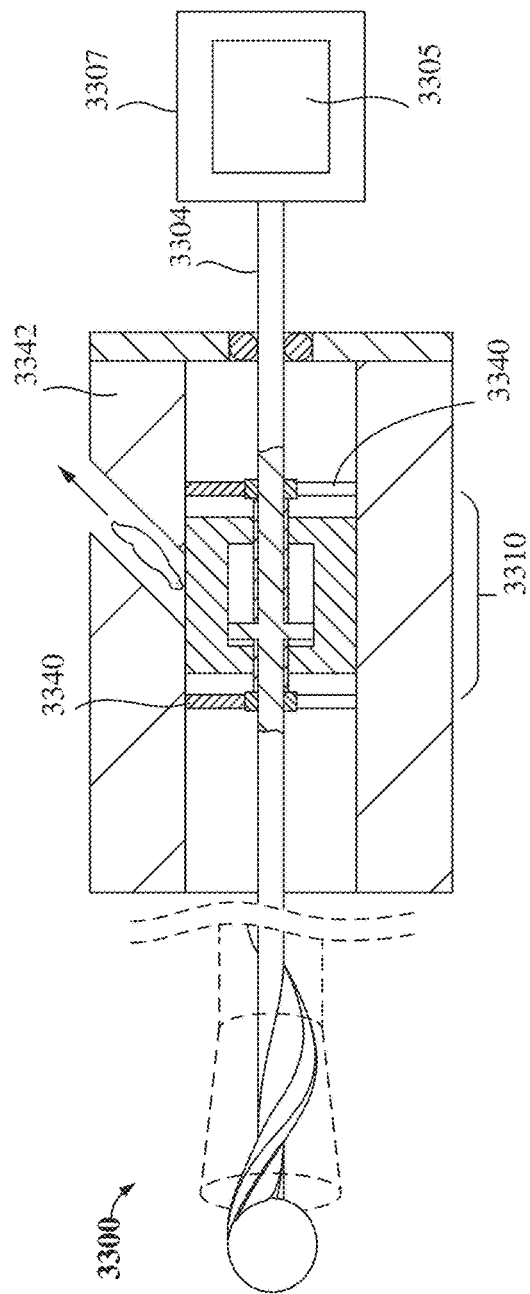
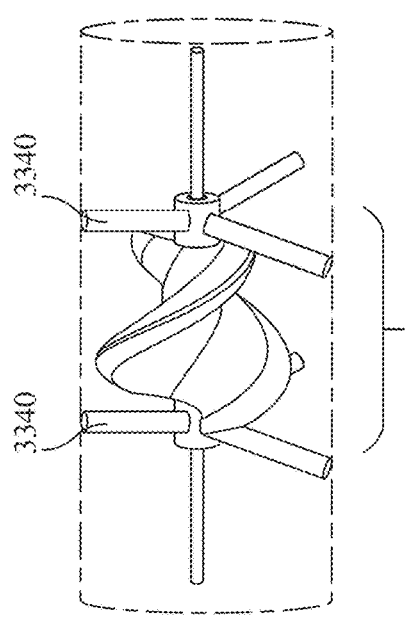
FIG. 33A
FIG. 33B

THROMBECTOMY SYSTEMS AND METHODS FOR CONTROLLED CLOT ASPIRATION

PRIORITY

This application is a continuation-in-part under 35 U.S.C. § 120 of U.S. patent application Ser. No. 18/469,445, filed 18 Sep. 2023, which is a continuation under 35 U.S.C. § 120 of U.S. patent application Ser. No. 16/977,431, filed 1 Sep. 2020 and issued as U.S. Pat. No. 11,759,219, which is a U.S. National Stage Patent Application under 35 U.S.C. § 371 of PCT International Application No. PCT/US2019/043095, filed 23 Jul. 2019, which claims the benefit under 35 U.S.C. § 119(e) of U.S. Provisional Patent Application No. 62/778,708, filed 12 Dec. 2018, and of U.S. Provisional Patent Application No. 62/702,804, filed 24 Jul. 2018, all of which are incorporated herein by reference.

This application is also a continuation-in-part under 35 U.S.C. § 120 of U.S. patent application Ser. No. 18/492,674, filed 23 Oct. 2023, which is a continuation under 35 U.S.C. § 120 of U.S. patent application Ser. No. 17/463,939, filed 1 Sep. 2021 and issued as U.S. Pat. No. 11,793,542, all of which are incorporated herein by reference.

TECHNICAL FIELD

The present disclosure relates generally to the field of medical devices and methods. More specifically, the particular embodiments described herein relate to devices and methods for clot removal from a patient's vasculature.

BACKGROUND

Stroke is a significant cause of disability and death, and a growing problem for global healthcare. Stroke may be caused by a blockage in a cerebral artery resulting from a thromboembolism (referred to as an "ischemic stroke"), or by a rupture of a cerebral artery (referred to as a "hemorrhagic stroke"). Hemorrhagic stroke can result in bleeding within the skull, limiting blood supply to brain cells, and placing harmful pressure on delicate brain tissue. Blood loss, swelling, herniation of brain tissue, and pooling of blood can result in formation of clot mass inside the skull, and can rapidly destroy brain tissue. Hemorrhagic stroke is a life-threatening medical emergency with limited treatment options.

Aside from cerebral stroke, thromboembolism throughout the vasculature, in both arterial and venous circulation, is characteristic of numerous common, life-threatening conditions. Examples of potentially fatal diseases resulting from thrombotic occlusion include pulmonary embolism, deep vein thrombosis, and acute limb ischemia. Acute pulmonary embolism is a significant cause of death in the United States. Pulmonary embolism may be a complication from deep vein thrombosis. The aforementioned are some non-limiting examples of conditions in which treatment may include aspiration or evacuation of clot and/or blood.

SUMMARY OF PARTICULAR EMBODIMENTS

Particular embodiments described herein provide systems and methods that improve catheter aspiration by enabling a more efficient procedure, by enhancing the ingestion of occlusive material, or both. In particular embodiments, the amount of fluid flowing through an aspiration catheter under vacuum aspiration is monitored to determine whether the flow is unrestricted, restricted, or clogged. Depending on the determined flow state, particular embodiments may employ different techniques and methods to improve catheter aspiration. In particular embodiments, unrestricted flow is detected, and aspiration is automatically and temporarily restricted for blood saving purposes. Minimizing blood loss and increasing the ratio of occlusive material to healthy blood removed may thereby allow more complete removal of occlusive material. In particular embodiments, restricted flow is detected, and full vacuum aspiration is automatically applied. In yet another particular embodiment, a clogged catheter is detected, and pulsed aspiration is automatically applied. This may beneficially enhance the ingestion of large, tough, or otherwise troublesome occlusions. Alternatively, pulsed aspiration, full aspiration, or restricted aspiration may be applied on demand by a user of particular embodiments.

In particular embodiments, the systems and methods described address the problem of excessive blood loss through dynamic aspiration cycling. The nature and flowability of the material being withdrawn by the aspiration catheter is monitored so that the system may either allow continuous aspiration when in clot, or sampling of extraction rate to determine whether the tip of the catheter is in contact with clot, in order to reduce the risk of excess blood loss. While determining and monitoring of blood flow rate is disclosed in the exemplary embodiments below, other measurements of the flowability and/or structural composition of the aspiration effluent, such as monitoring the collection chamber's volume, monitoring the collection chamber's fill rate, visually monitoring the aspiration tubing (clot is darker than fresh blood), or placing a strain gauge on aspiration tubing, could also be used.

The systems and methods of particular embodiments may respond to variations in flow rate, pressure, differential pressure, or other indicators of the composition of the material inside or adjacent to an aspiration catheter in a sub-second time frame to limit the unnecessary aspiration of blood during a thrombectomy procedure. Particular embodiments may be useful with any thrombectomy, embolectomy, atherectomy, or other catheter or probe system where blood and clot are withdrawn wholly or partially by application of a vacuum to the proximal end of any reperfusion, aspiration catheter or probe for the purpose of clot extraction.

Particular embodiments may provide a vacuum aspiration control system for use with a vacuum source and an aspiration catheter. In particular embodiments, the system comprises a flexible connection tubing, an on-off valve, a sensing unit, and a controller. In particular embodiments, the connection tubing may be linear in an unconstrained configuration and is configured to connect the vacuum source to an aspiration lumen in the aspiration catheter. In particular embodiments, the on-off valve may be configured to be operatively connected to the connection tubing, and the sensing unit may be configured to determine flow rate within the connection tubing and to produce a signal representative of such flow, such as either unrestricted flow, restricted flow, or clogged flow. In particular embodiments, the controller may be connected to receive the signal representative of flow through the connection tubing and to open and close one or more on-off valve(s) in response to the signal. In particular embodiments, the controller may be configured to automatically close the on-off valve to stop flow through the connection tubing when the signal indicates unrestricted flow, for e.g., that primarily healthy blood or blood free of vessel-obstructing clot is flowing through the connection tubing, and/or that the catheter is substantially free from contact with clot or other occlusive material. In particular embodiments, the controller may be configured to initiate pulsed aspiration when the signal indicates a clog, which may be caused by some occlusive material in or adjacent to the catheter or connecting tubing.

In particular embodiments, the controller may be configured to automatically open the on-off valve at a predetermined interval to sample effluent material through the connection tubing and the valve will typically only remain open if the signal indicates a return to clot. In particular embodiments, the controller algorithm may be configured to determine differences between healthy blood and clot independent of aspiration source and the inner diameter of the attached catheter.

In particular embodiments, the sensing unit may comprise any one or more of a variety of sensors, including differential pressure sensors, acoustic (including ultrasonic) flow sensors, optical flow sensors, thermal flow sensors, magnetic flow sensors, sensors which detect circumferential expansion of the connection tubing, rotational aspiration pump torque sensors, and the like. While differential pressures are described in more detail below, it will be appreciated that any sensing unit capable of detecting when flow or extraction rate through the connection tubing is excessive and/or clogged, would be suitable for use in particular embodiments, and are contemplated herein.

In particular embodiments, the sensing unit may comprise multiple pressure sensors at spaced-apart locations along the connection tubing, such as to measure differential pressure. In particular embodiments, the controller may calculate flow based on the differential pressure, and may determine whether the calculated flow rate indicates unrestricted flow, restricted flow, or a clog.

In particular embodiments, the sensing unit may use optical sensors that measure transmission, absorption, or both of light to characterize the contents flowing through the connection tubing. In particular embodiments, visible light is used determine whether flow contains clot or is primarily clot-free. By way of example and not limitation, flow with clot can be darker, which is detectable by optical sensors. Additionally or alternatively, in particular embodiments, the optical sensors may sense infrared, ultraviolet, visible light, or a combination, such as to analyze contents within the connecting tubing.

In particular embodiments, the sensing unit may use circumferential expansion sensors to determine the contents flowing through the connection tubing. In particular embodiments, the internal pressure of the connecting tubing and/or the contents flowing through the connecting tubing may affect the circumference of the connecting tubing. By way of example and not limitation, under strong vacuum, such as during a clog, the tubing may experience relatively large contraction and/or larger decrease in circumferential extent. By way of example and not limitation, during high flow rates comprising primarily clot-free blood, the tubing may experience relatively lower contraction and/or lower decrease in circumferential extent. By way of example and not limitation, during restricted flow, clots and/or blood may cause a relative expansion of the connecting tubing.

In particular embodiments, the sensing unit may be integrated into a rotationally-driven inline aspiration pump. In particular embodiments, the consistency of the effluent in the tubing may affect the torque required to pump the effluent. By way of example and not limitation, when removing occlusive material, the torque may approach relatively large values. By way of example and not limitation, during removal of primarily clot-free blood, the torque required may be relatively low.

In particular embodiments, the on-off valve may take a variety of specific forms. In particular embodiments, the on-off valve may comprise an actuator, such as a solenoid actuator, that is powered to open the valve. In particular embodiments, a valve may take a variety of forms, such as a pinch valve, an angle valve, or any of a variety of other valves, or a combination thereof, that can provide suitable actuation. Additionally or alternatively, in particular embodiments, a manual on-off valve may be provided that allows a user to initiate and/or terminate functions and features of particular embodiments.

In particular embodiments, the controller may be configured to open the valve and hold the valve open until a flow pattern which indicates unrestricted flow is detected whereupon the controller closes the valve. In particular embodiments, the controller may be further configured to automatically re-open the on-off valve. In particular embodiments, in what may be referred to as "sampling mode", the controller may be further configured to periodically sample, or test flow to re-characterize flow and determine if it is safe to recommence aspiration. By way of example and not limitation, in particular embodiments, the controller may periodically test flow by opening the on-off valve for a fixed time interval, such as 150 milliseconds, to establish a "test" flow. In particular embodiments, the test flow may be characterized and, if it so indicates, the on-off valve may be reopened into a "treatment" mode to allow continued aspiration treatment. In particular embodiments, if the system characterizes the flow as unrestricted, e.g. excessive, then the system may dwell in a closed configuration for a fixed time interval, for example between a quarter second and two seconds, before an additional pressure differential sample is taken.

In particular embodiments, the controller may not be configured to automatically reestablish flow when safe conditions have been reached. By way of example and not limitation, in particular embodiments, the controller may be configured to allow a user to reposition the aspiration catheter and, after repositioning, to manually open the on-off valve (typically by actuating a switch which causes the controller to open the on-off valve) to resume aspiration treatment. In such instances, the controller may immediately return to the "sampling mode," however, and if the reestablished flow is characterized as unrestricted flow, the controller may again close the on-off valve, and the user may again reposition the aspiration catheter in order to engage clot and manually resume aspiration. In particular embodiments, some systems may provide a manual switch to allow the user to manually open the on-off valve.

In particular embodiments, the controller may be configured to control two or more valves. In particular embodiments, the controller may control a first on-off valve between an aspiration catheter and a vacuum source and a second on-off valve between an aspiration catheter and a pressure source with a pressure at least above that of the vacuum source. In particular embodiments, the controller may alternate between opening the first on-off valve and the second on-off valve to generate pressure variations within an aspiration catheter and/or tubing adjacent to such a catheter. In particular embodiments, the controller may sample flow while the first on-off valve is opened to determine whether an attached catheter is still positioned in clot or otherwise occluded. In particular embodiments, the controller may hold the first on-off valve open if occlusions or clogs are detected. In particular embodiments, the controller may hold the second on-off valve closed if no occlusions or clogs are detected. In particular embodiments, the controller may operate one or more valves to alternate between providing a low pressure, such as a vacuum, and a high pressure, such as by introducing a fluid medium, to the aspiration catheter and/or tubing. In particular embodiments, the controller may operate one or more valves to simultaneously connect the aspiration catheter and/or tubing to a low pressure source, such as a vacuum, and to a high pressure source, such as by introducing a fluid medium. By way of example and not limitation, simultaneous connection of a high pressure source and a low pressure source may be used to facilitate flushing a fluid medium through the aspiration catheter and/or tubing.

In particular embodiments, the vacuum aspiration systems comprise a base unit which incorporates at least one on-off valve and the controller. In particular embodiments, the base unit may be configured to be mounted directly on or near a vacuum pump or console, and/or may include a connecting cable in order to receive power from the vacuum console or line and optionally exchange information with the controller and the vacuum console. In particular embodiments, the connection tubing may have a proximal end configured to connect the vacuum source and distal end configured to connect to the aspiration catheter. In such instances, the vacuum aspiration system may further comprise an external unit configured to be secured to the connection tubing at a location between the distal end and the proximal end thereof. In particular embodiments, exemplary external units may comprise at least a portion of the sensing unit. By way of example and not limitation, in particular embodiments, the sensing unit may comprise a first pressure sensor in the base unit and a second pressure sensor in the external unit. In particular embodiments, the controller may be configured to determine if a differential pressure exists based on the signals from the first and the second pressure sensor.

In particular embodiments, a vacuum aspiration method may be provided. In particular embodiments, the vacuum aspiration method may comprise engaging a distal end of an aspiration catheter against an occlusion in the blood vessel. In particular embodiments, a vacuum may be applied through an aspiration lumen of the aspiration catheter using a vacuum source coupled to a proximal end of the aspiration lumen by a connection tubing. In this way, portions of clot and other occlusive material may be drawn into the aspiration lumen, through the connection tubing, and into a collection receptacle by the vacuum source. In particular embodiments, flow through the connection tubing may be sensed, and a valve may be automatically closed to stop flow through the connection tubing when the sensed flow exceeds a determined value while the vacuum source remains on. In particular embodiments, flow through the connection tubing may be later reestablished by opening the valve, and the steps may be repeated until a desired amount of clot has been aspirated.

In particular embodiments, an assembly for generating pressure differentials may be provided that may result in pressure pulses to execute an extraction cycle. In particular embodiments, the assembly may include a fluid injection apparatus, a mechanical displacement apparatus, gravity induced pressure head, or a combination thereof. In particular embodiments, a fluid injection apparatus may provide a source of relative positive pressure for a catheter currently or previously under vacuum aspiration. By way of example and not limitation, the fluid may be at a pressure above that of the vacuum aspiration system, between full vacuum pressure and ambient pressure, at ambient pressure, between ambient pressure and systolic pressure, at systolic pressure, or above systolic pressure. In particular embodiments, the fluid injection apparatus may utilize an aperture, a valve, a pump, a pressure chamber, or a suitable combination. In particular embodiments, a mechanical displacement apparatus may physically displace the volume of a catheter system to provide relative increases and decreases of pressure depending on the direction of displacement. In particular embodiments, a mechanical displacement assembly may assist vacuum recovery after a catheter has had its pressure increased above the pressure of the vacuum source.

In particular embodiments, the controller may include an algorithm that is used to interpret pressure sensor signals to determine whether the contents flowing through a catheter should be characterized as unrestricted, restricted, or clogged. In particular embodiments, unrestricted flow can be a high flow that may be characterized as excessive, and/or may be primarily or completely comprised of healthy blood, clot-free blood, or blood free of vessel-obstructing clot, and/or blood that is not helpful to aspirate. In particular embodiments, restricted flow may be comprised of a mix of healthy blood and clot or other occlusive material. In particular embodiments, a clog may be caused by a clot or other occlusive material within an aspiration catheter, such as partially within an aspiration catheter, adjacent to an aspiration catheter, and/or in other connecting tubing attached to the aspiration catheter. By way of example and not limitation, healthy blood may be blood with a low enough proportion of cross-linked fibrin such that it is not sufficiently integrated to cause ischemia or other similar vessel occlusions. In particular embodiments, when the algorithm detects unrestricted flow, it may cause the system to initiate a sampling mode. In particular embodiments, when the algorithm detects restricted flow, it may cause the system to enable full vacuum aspiration. In particular embodiments, when the algorithm detects a clog, it may cause the system to generate a variety of pressure pulses with an extraction cycle. In particular embodiments, the algorithm may be responsive and adaptable to changing circumstances, such as changing to a catheter of a different size mid-procedure. In particular embodiments, the algorithm may adjust sampling modes and pressure pulse magnitudes if the catheter state remains static, changes too quickly, changes to slowly, or improves as expected.

In particular aspects of methods disclosed herein, particular embodiments may remove clot and other occlusive material from a blood vessel that comprises a vein or an artery. In particular embodiments, sensing of flow may comprise one or more of differential pressure measurement, acoustic flow measurement, optical flow measurement, thermal flow measurement, measurement of circumferential expansion of the connection tubing, rotational aspiration pump torque sensors, and/or other suitable sensing devices and methods.

In particular aspects of the method, sensing flow may comprise measuring the differential pressure using a first sensor located proximate the vacuum source and a second sensor located on or adjacent the connection tubing between the vacuum source and the aspiration catheter.

In particular embodiments of the method, resuming flow through the connection tubing may comprise opening the valve for an interval, such as a sub-second interval, detecting when the sensed flow is characterized as acceptable, and automatically resuming flow. In particular embodiments, automatically resuming flow may comprise automatically detecting when the sensed flow may be characterized as acceptable, and/or holding the valve open as long as the flow is so characterized. In particular embodiments, resuming flow may comprise manually opening an on-off valve.

In particular embodiments of methods disclosed herein, pressure differentials may be generated by closing a valve to a vacuum pump, and/or opening a valve to a source of pressure, wherein the pressure of the source is at least above that of the vacuum, followed by re-opening the valve to the vacuum pump. Alternatively, or in combination, in particular embodiments, pressure differentials may be generated by mechanical displacement, wherein a volume of a chamber may be reduced to increase pressure within a catheter, and/or a volume of the chamber may be increased to decreases pressure within a catheter, whereby the actuation of the mechanical displacement chamber may result in pressure differentials. In particular embodiments, the pressure differentials may be tailored to have a specific or dynamic amplitude and frequency, so as to facilitate the removal of clot or other occlusive materials.

In particular embodiments, some catheter-based devices may include rotating blades, high pressure water jets, laser ablation, and/or other means of breaking up target material. By way of example and not limitation, such methods may be used in atherectomy-specific tools where the occlusion may be formed by well-adhered plaque. In particular embodiments, such devices may suffer from particular shortcomings. By way of example and not limitation, the methods of removing targeted substances once the substances are fragmented may be either ineffective or non-existent. For example, some devices have small lumens that are prone to clogging or inefficient pressure gradients that fail to pull dislodged clot or plaque into the system. If not removed, dislodged clot or plaque may be released into downstream blood vessels, and/or may pose a risk for further complications, in particular embodiments. Secondly, devices that use blades to fragment a tough clot or plaque may lead to damage of the wall of a blood vessel, in particular embodiments.

For the reasons discussed above, there is an unmet need for methods, devices, and systems that may remove a wide range of occlusive materials, including at least clot, thrombus, and atheroma, quickly and safely without damaging the surrounding blood vessels.

In particular embodiments, a catheter, e.g., a thrombectomy catheter, for use in a subject's vasculature may include a rotatable and/or axially movable cutting instrument. In particular embodiments, the cutting instrument may be a spiral-shaped, e.g., helical-shaped, cutting instrument. In particular embodiments, the cutting instrument may include a rounded, e.g., spherical, substantially spherical or partially spherical, element at its distal end. In particular embodiments, the rounded element may be connected to a body having a twisted shape, e.g., a spiral and/or helical shape. In particular embodiments, the cutting instrument may be disposed in a lumen of the catheter, and/or may be configured for axial and/or rotational motion within the lumen. By way of example and not limitation, the cutting instrument may be configured to move between a proximal-most position and a distal-most position. In particular embodiments, the body may include at least one edge configured to promote the movement of a target substance towards a proximal end of the lumen upon contact, or close proximity to, the target substrate.

In particular embodiments, a cutting instrument may extend out (e.g., slightly) beyond the distal-most position of the lumen such that at least part of the cutting instrument may extend external to the lumen of the catheter. Additionally or alternatively, in particular embodiments, the cutting instrument may be flush or recessed into the catheter. Accordingly, in particular embodiments, the separator instrument may incorporate a positive displacement pump, or other related architecture, for displacing fluids with viscosities greater than water or other room temperature liquids.

In particular embodiments, the cutting instrument may be configured to distally advance outside of the lumen of the catheter. In particular embodiments, the cutting instrument may be configured to proximally retract inside of the lumen of the catheter. In particular embodiments, the body of the cutting element may include at least two edges positioned on opposite sides. By way of example and not limitation, two edges may be positioned on radially opposite sides of the body of the cutting element. In particular embodiments, a first edge of the two edges of the body may be blunt, e.g., substantially blunt, and a second edge of the two edges of the body may be sharp, e.g., substantially sharp. In particular embodiments, the second edge may be configured to promote cutting of the target substance. In particular embodiments, the term "blunt", when describing an edge, may be understood to mean not sharpened. In particular embodiments, the term "sharp", when describing an edge, may be understood to mean sharpened, e.g., to a knife edge or razor edge to enable it to cut or pierce something. By way of example and not limitation, a blunt edge may be a rounded edge. By way of example and not limitation, a rounded edge may have a radius of approximately $\frac{1}{32}$ of an inch. In particular embodiments, a sharp edge may be a chamfered edge. By way of example and not limitation, a sharp edge may have approximately a 30-degree Knife edge chamfer in particular embodiments. In particular embodiments, the terms "sharp" and "blunt" may be used relatively. By way of example and not limitations, the first edge of the body may be an edge that is sharper than the second edge. By way of example and not limitation, the second edge of the body may be an edge that is less sharp than the first edge. In particular embodiments, the first and second edges of two exemplary edges of the body may be configured in the same, or similar, manner. By way of example and not limitation, the first and second edges may each be blunt. Alternatively, the first and second edges may each be sharp in particular embodiments. In particular embodiments, either the first edge or second edge of the body may be configured to sever a portion of the target substance, such as by urging a portion of the target substrate against an edge of an opening in the lumen of the catheter.

In particular embodiments, the catheter may include at least one motor coupled with the cutting instrument. In particular embodiments, one or more motors may be configured to impart rotational motion and/or axial motion, for e.g., reciprocal axial motion, to the cutting instrument. In particular embodiments, the body may include a shaft. By way of example and not limitation, the shaft may be a cylindrical shaft. In particular embodiments, the body may comprise a spiral shape surrounding the shaft. In particular embodiments, the body may include a central smooth surface configured to urge a cut portion of the target substance from a distal end of the body towards a proximal end of the body.

In particular embodiments, a portion of the instrument such as the rounded element may include one or more scooped-out portions. By way of example and not limitation, one or more scooped-out portions may be disposed at, or near to, where the rounded element connects to the body. In particular embodiments, at least one scooped-out portion may include an edge configured to promote cutting of the target substance. In particular embodiments, at least one scooped-out portion may include a blunt, or substantially blunt, leading edge. In particular embodiments, at least one scooped-out portion may include a sharp, or substantially sharp, trailing edge. In particular embodiments, one or more edges of a scooped-out portion, for e.g., a sharp trailing edge, may be configured to promote cutting of the target substance. In particular embodiments, a leading edge may be configured to engage the target substance and/or pull the target substance into the at least one scooped-out portion, during use.

In particular embodiments, a rounded element may include a wire element. By way of example and not limitation, a wire element may comprise a loop of wire, a coiled loop of wire, and/or a wire hooked element. In particular embodiments, a wire element may extend from a first edge of the body to a second edge of the body.

In accordance with an implementation of the subject matter disclosed herein, there may be provided a method for removal a target substance from a body passageway using an instrument, such as any appropriate instrument described herein. In particular embodiments, the instrument may comprise a catheter comprising a lumen having a distal edge, and a rotatable body comprising one or more edges configured to promote removal of the target substance from the body passageway upon contact with the target substance. In particular embodiments, the method may comprise urging, e.g., pulling, the target substance into the lumen. By way of example and not limitation, the method may include using an edge of the body (e.g., the first edge) to cause a portion of the target substance to engage the distal end of the catheter. In particular embodiments, the method may comprise separating the portion of the target substance from the body passageway using a cutting. By way of example and not limitation, the method may include shearing action. By way of example and not limitation, shearing may implemented based on cooperation between an edge (e.g., the second edge) of the body and the distal end of the catheter. In particular embodiments, such as where the second edge comprises a curved, e.g., spiraled edge, a shearing action may be implemented as a result of the rotation of the second edge relative to the distal edge of the catheter. In particular embodiments, an action of urging the target substances into the lumen using the first edge and separating the portion of the target substance from the body passageway using a cutting action may occur in parallel.

In particular embodiments, with respect to dynamic system state detection, the controller may generate pressure level changes in the connection tubing by operating the vacuum valve, such as by selectively opening and closing the vacuum valve. In a second step, the controller may detect pressure levels using the distal pressure sensor, where changes in the detected pressure levels are correlated with the generated pressure level changes. In a third step, the controller may determine one or more system states in the aspiration catheter or the connection tubing based on the detected pressure level changes. In a fourth step, the controller may operate the vacuum valve to take action based on the one or more determined system states.

In particular embodiments, system states may comprise flow states within the aspiration catheter and/or connection tubing. In particular embodiments, flow states may comprise an open flow state, an occluded flow state, and/or a partially occluded flow state. In specific aspects, system states may comprise the presence of specific fluids in the aspiration catheter and/or connection tubing.

In particular embodiments, the controller may be configured to detect the presence of saline liquid in the system based on dynamic system state detection, such as for priming, flushing, or repriming the system, or to detect loss of saline during pulsing. In particular embodiments, the controller may be configured to detect the presence of gas in the system, such as air bubbles, based on dynamic system state detection. In particular embodiments, the controller may be configured to detect the absence of a catheter attached to the system based on dynamic system state detection. In particular embodiments, the controller may be configured to detect clot engagement with the tip of the catheter based on dynamic system state detection.

In particular embodiments, dynamic system state detection may separately or additionally use pressure sources and/or valves other than vacuum valves. In particular embodiments, systems may use a vacuum valve, a pressure valve such as a saline vent valve, and/or multiple other pressure valves.

Particular embodiments of this dynamic system state detection methodology may separately or additionally use sensors other than the distal pressure sensor. In particular embodiments, systems may use one or more pressure sensors associated with the connection tubing and/or aspiration catheter, and other pressure sensors, such as a vacuum pressure sensor, and a saline pressure sensor. Sensors used in particular embodiments may not be limited to pressure sensors. In some embodiments, a variety of sensors may be used, for instance, sensors for detecting pressures, sonic energy, ultrasonic energy, and/or flow rates.

In particular embodiments, one or more system scores may be determined for determining system states, wherein each system score, independently or in combination with other system scores, may indicate a likelihood of specific system states in the aspiration catheter or the connection tubing. In this respect, system scores may function as metrics for quantifying the corresponding likelihood of specific system states.

In particular embodiments, system scores may be directly or indirectly derived from sensor data, such as pressure profiles. In particular embodiments, system score determination may be based on automatically identifying specific features from the detected pressure profiles, extracting pressure parameters based on values and trends derived from those specific features, and calculating one or more system scores based on the pressure parameters of those features. In particular embodiments, determining system scores based on pressure parameters may further comprise appropriate weighting of the parameters, and/or use of correction factors. In particular embodiments, the pressure parameters may comprise one or more of a starting pressure level, a differential in starting pressure levels, an ending pressure level, a differential in ending pressure levels, a peak pressure level, and a variance in pressure levels.

In particular embodiments, system scores may be determined based on machine learning. In particular embodiments, training data sets may be assembled from detected pressure profile data taken over a broad range of scenarios, incorporating statistical variations, and corresponding to system states of interest. Trained machine learning models may be then used to make predictions of system state for novel situations. In particular embodiments, machine learning algorithms may employ semi-supervised and unsupervised learning. The algorithms may employ clustering, dimensionality reduction, and reinforcement learning to further improve prediction accuracy. In particular embodiments, an algorithm that uses a combination of the above algorithmic flow analysis techniques may be employed.

In particular embodiments, one or more of the system state scores may be based on one or more geometric characteristics of the aspiration catheter, and wherein the one or more geometric characteristics of the aspiration catheter may be determined based on the one or more detected pressure levels. In particular embodiments, one or more of the system state scores may be based on one or more ambient environmental parameters of the aspiration thrombectomy system. In particular embodiments, one or more of the system state scores may be based on one or more material parameters associated with the aspiration thrombectomy system, and wherein the one or more material parameters may be determined based on the one or more detected pressure levels. In particular embodiments, one or more of the system state scores may be based on one or more thrombi parameters associated with one or more thrombi in the aspiration catheter or the connection tubing, wherein the one or more thrombi parameters may be determined based on the one or more detected pressure levels. In particular embodiments, one or more of the system state scores may be based on one or more fluid parameters associated with one or more fluids in the aspiration catheter or the connection tubing, wherein the one or more fluid parameters may be determined based on the one or more detected pressure levels.

In particular embodiments, an escalation feature may be used wherein an Escalate Count of consecutive determinations of identical system state is maintained by the controller, and specific action may be taken if the count exceeds a threshold. In particular embodiments, the count may be reset in the iteration following the threshold crossing iteration. In specific aspects, the action taken if the count exceeds a threshold may be generating a notification, such as a user notification. In particular embodiments, the action taken if the count exceeds a threshold may involve the operation of one or more valves by the controller.

In particular embodiments, which may include aspects of the above embodiments, with respect to tube and system flushing, the apparatus may include connection tubing configured to act as a fluid conduit between an aspiration catheter, a fluid source, and a vacuum source; a first pressure sensor associated with a distal portion of the connection tubing; a second pressure sensor associated with a proximal portion of the connection tubing; a first controllable valve configured to control a level of vacuum in the connection tubing provided by the vacuum source; a second controllable valve configured to control an introduction of a fluid medium into the connection tubing from the fluid source; and a controller.

In particular embodiments, a third pressure sensor associated with a pressure of the fluid source may be included. In particular embodiments, a fourth pressure sensor may be used to compare pressure sensors to a reference atmospheric pressure. In particular embodiments, a fifth pressure sensor proximal to the first controllable valve and/or in the same static or contiguous fluid path as the second sensor may be included.

In particular embodiments, which may include aspects of the above embodiments, the controller may be configured to detect, via one or more of the first pressure sensor and the second pressure sensor, one or more pressure levels associated with the connection tubing; and determine, based on the one or more pressure levels detected, whether the connection tubing is occluded, wherein, based on determining that the connection tubing is occluded, the controller is further configured to determine, based on the one or more pressure levels detected, a location of an occlusion; and operate, based on determining the location of the occlusion, one or more of the first valve and the second valve to introduce the fluid medium into the connection tubing during one or more time intervals.

In particular embodiments, which may include aspects of the above embodiments, prior to the detecting of the one or more pressure levels, the controller may be configured to operate the first valve to provide fluid communication between the distal portion of the connection tubing and the vacuum source.

In particular embodiments, which may include aspects of the above embodiments, the controller may be configured to determine whether the connection tubing is occluded based on one or more differences between the one or more pressure levels detected, respectively, via the first pressure sensor and the second pressure sensor.

In particular embodiments, which may include aspects of the above embodiments, the controller may be configured to determine, based on the one or more differences between the one or more pressure levels detected, respectively, via the first pressure sensor and the second pressure sensor, that the connection tubing is occluded between the first pressure sensor and the second sensor.

In particular embodiments, which may include aspects of the above embodiments, the controller may be configured to operate, based on the determination that the connection tubing is occluded between the first pressure sensor and the vacuum source, the first valve and the second valve to introduce the fluid medium into the connection tubing during a first time interval.

In particular embodiments, which may include aspects of the above embodiments, the first time interval is a predetermined time interval. In particular embodiments, which may include aspects of the above embodiments, the predetermined time interval is between 200 ms and 800 ms. In particular embodiments, which may include aspects of the above embodiments, the predetermined time interval is between 15 ms and 900 ms.

In particular embodiments, which may include aspects of the above embodiments, the controller may be configured to determine whether the connection tubing is occluded based on one or more of the pressure levels detected via the second pressure sensor exceeding a threshold value.

In particular embodiments, which may include aspects of the above embodiments, the controller may be configured to determine, based on one or more of the pressure levels detected via the second pressure sensor exceeding a threshold value, that the connection tubing is occluded between the second pressure sensor and the vacuum source.

In particular embodiments, which may include aspects of the above embodiments, the controller may be configured to operate, based on the determination that the connection tubing is occluded between the second pressure sensor and the vacuum source, the first valve and the second valve to introduce the fluid medium into the connection tubing during a second time interval. In particular embodiments, the second time interval is a predetermined time interval. In particular embodiments, the second time interval is between 70 ms and 300 ms. In particular embodiments, the second time interval is between 150 ms and 200 ms. In particular embodiments, the second time interval is between 15 ms and 800 ms.

In particular embodiments, which may include aspects of the above embodiments, the controller may be configured, during the one or more time intervals, to selectively open or close one or more of the first valve and the second valve.

In particular embodiments, which may include aspects of the above embodiments, the controller may be configured to hold open the first valve during at least a portion of the one or more time intervals. In particular embodiments, which may include aspects of the above embodiments, the controller may be configured to repeatedly open and close the second valve during at least a portion of the one or more time intervals.

In particular embodiments, which may include aspects of the above embodiments, the aspiration thrombectomy system may further include a controllable bypass valve, wherein opening the bypass valve when the first valve is closed concurrently introduces the fluid medium into the connection tubing and disconnects fluid communication between the aspiration catheter from the vacuum source.

In particular embodiments, which may include aspects of the above embodiments, the aspiration thrombectomy system may further include a third controllable valve configured to control an introduction of the fluid medium into the aspiration catheter.

In particular embodiments, which may include aspects of the above embodiments, the aspiration thrombectomy system may comprise a fluid medium including one or more of air and saline.

In particular embodiments, which may include aspects of the above embodiments, the aspiration thrombectomy system may comprise a third pressure sensor associated with the fluid source. In particular embodiments, which may include aspects of the above embodiments, the aspiration thrombectomy system may comprise a fourth pressure sensor configured to compare one or more detected pressure levels to a reference atmospheric pressure level.

In particular embodiments, which may include aspects of the above embodiments, the aspiration thrombectomy system may comprise a fifth pressure sensor provided proximal to the first controllable valve. In particular embodiments, which may include aspects of the above embodiments, the controller is configured to determine whether the connection tubing is occluded based on one or more differences between one or more pressure levels detected, respectively, via the second pressure sensor and the fifth pressure sensor.

In particular embodiments, the techniques described herein relate to a method for aspiration thrombectomy, including: detecting, by a controller, via one or more of a first pressure sensor and a second pressure sensor, one or more pressure levels associated with a connection tubing, wherein the connection tubing acts as a fluid conduit between an aspiration catheter, a fluid source, and a vacuum source, wherein the first pressure sensor is associated with a distal portion of the connection tubing, and wherein the second pressure sensor is associated with a proximal portion of the connection tubing; determining, based on the one or more pressure levels detected, whether the connection tubing is occluded; determining, based on a determination that the connection tubing is occluded and on the one or more pressure levels detected, a location of an occlusion; and operating, based on the determination of the location of the occlusion, one or more of a first controllable valve and a second controllable valve to introduce a fluid medium into the connection tubing during one or more time intervals, wherein the first valve is configured to control a level of vacuum in the connection tubing provided by the vacuum source, and the second valve is configured to control introduction of the fluid medium into the connection tubing from the fluid source.

In particular embodiments, the techniques described herein relate to a method, further including, prior to the detecting of the one or more pressure levels, operating the first valve to enable fluid communication between the distal portion of the connection tubing and the vacuum source.

In particular embodiments, establishing the baseline of one or more operational parameters may comprise processing a selective data set that is representative of a heterogeneous population. Additionally, or alternatively, the at least one deviation from the established one or more baseline operational parameters of the separator instrument may comprise at least one of a change in one or more of a rotational rate, a torque load, or a direction of rotation. In particular embodiments, a baseline of one or more operational parameters may be established by retrieving a data structure from memory corresponding to stored predefined expected ranges of the one or more operational parameters. In particular embodiments, a current operating state of the separator system may be identified. In particular embodiments, a baseline value for the one or more operational parameters may be selected based on the identified current operating state from the expected ranges of the one or more operational parameters. In particular embodiments, at least one deviation may comprise interruptions, or pauses of operation, of the separator instrument. In particular embodiments, at least one engagement condition of the separator instrument may comprise an engagement of the separator instrument with one or more of a saline solution, a blood solution, valve tissue, at least one blood clot, unusual tissue mass, foreign material, plaque, or a blood vessel.

In particular embodiments, one or more operational parameters may comprise a torque. Additionally, or alternatively, in particular embodiments, establishing the baseline of the one or more operational parameters for the separator instrument may comprise receiving a signal comprising torque information for a motorized separator, and processing the signal to calculate a baseline torque in real-time. In particular embodiments, identifying at least one deviation from the established one or more baseline operational parameters of the separator instrument may comprise determining that one or more torque measurement values determined from the signal are anomalous relative to the baseline torque. In particular embodiments, determining at least one engagement condition of the separator instrument may include distinguishing the anomalous one or more torque measurements between being caused by an occlusion in a vasculature or being caused by something other than an occlusion.

In particular embodiments, a signal may be received from a sensor coupled to a motor of the motorized separator. In particular embodiments, the sensor coupled to the motor may be a torque sensor configured to measure torque values associated with the motor of the motorized separator. Additionally, or alternatively, in particular embodiments, the sensor coupled to the motor may be an electric current sensor configured to measure electric current values associated with the motor of the motorized separator, and the electric current measurement values may be used to calculate torque measurement values. By way of example and not limitation, if a clot is engaged by the separator instrument, the electric current measurement values may indicate that the motor is drawing a high level of electric current which correspond to particular torque measurement values, whereas if the clot either partially or fully becomes no longer engaged by the separator instrument (e.g., due to being macerated and extracted), the electric current measurement values may indicate that the motor is drawing a lower level of electric current which correspond to particular torque measurement values. Additionally, or alternatively, in particular embodiments, torque information may comprise at least one torque measurement value measured by the sensor at a sampling rate. In particular embodiments, a real-time baseline torque may be determined based on one or more of a current torque measurement value, a previously calculated baseline torque, or preclinically derived values. In particular embodiments, the system may store in memory communicatively coupled to the processing circuitry a maximum value corresponding to the one or more operational values and a minimum value corresponding to the one or more operational parameters for each respective manufactured iteration of the system. In particular embodiments, the processing circuitry may utilize these values for additional processing. For example, the baseline of the one or more operational parameters may be compared to the maximum value and the minimum value. In particular embodiments, based on the comparing, a value corresponding to the baseline of the one or more operational parameters may be determined to exceed the maximum value or the value is determined to be less than the minimum value. In particular embodiments, in response to the determining, the processing circuitry may cause one or more of modifying the one or more operational parameters or terminating operation of the system without updating the baseline. In particular embodiments, a current torque measurement value and a previously calculated baseline torque may be weighted based on a total number of torque measurement values received from the signal. In particular embodiments, a rate of change of torque values of the current torque measurement value may be determined based on the sampling rate. In particular embodiments, a maximum calculated baseline torque and/or a minimum calculated baseline torque may be computed by modifying the previously calculated baseline torque based on the rate of change of torque values. In particular embodiments, a range of updated baseline torque values may be determined based on a comparison of the maximum calculated baseline torque and the minimum calculated baseline torque to the previously calculated baseline torque.

In particular embodiments, a previously calculated baseline torque may be weighted based on a first value calculated based on a tuning parameter and a total number of torque measurements values. In particular embodiments, a first value may be calculated by subtracting the tuning parameter divided by the total number of torque measurement values from one, and/or the real-time baseline torque may not be dynamically updated based on the current torque measurement value when the current torque measurement value is above an amplitude threshold. In particular embodiments, an amplitude threshold may be calculated based on the previously calculated baseline torque multiplied by a limit tuning parameter.

In particular embodiments, a method may incorporate determining a dynamic threshold based on the calculated baseline torque and a previously calculated baseline torque, and/or determining that at least one torque measurement is anomalous relative to the baseline torque based on comparing a value of the at least one torque measurement to the dynamic threshold.

Additionally, or alternative, in particular embodiments, a dynamic threshold may comprise an upper bound and a lower bound. In particular embodiments, an upper bound of a dynamic threshold may be a multiplier of the previously calculated baseline torque. In particular embodiments, a lower bound of a dynamic threshold may be a multiplier of a previously calculated baseline torque.

In particular embodiments, a method may incorporate determining that at least one torque measurement is anomalous based on whether the value of the at least one torque measurement is larger than an upper bound of a dynamic threshold or lower than a lower bound of the dynamic threshold. In particular embodiments, for two subsequent (e.g., consecutive within a specified sampling period) consecutive measurements that exceed a bound of the dynamic threshold, a number of measurements in between may be determined. In particular embodiments, a number of measurements in between may be compared to a threshold. In particular embodiments, a threshold may be determined based on the sampling rate of the signal. In particular embodiments, distinguishing an anomalous one or more torque measurements as being caused by the occlusion in the vasculature may comprise identifying a pattern in one or more torque measurement values associated with the occlusion in the vasculature.

In particular embodiments, something other than the occlusion may comprise one or more of a change in direction of the motorized separator, a vessel wrapping, a valve, vessel wall, variance, noise, or an erroneous reading. Additionally, or alternatively, in particular embodiments, an anomalous one or more torque measurements may be determined to be caused by a vessel wrapping. In particular embodiments, in response to the determining, an operational parameter of the motorized separator may be changed.

In particular embodiments, the system may be configured for detecting different engagement conditions of a separator instrument. In particular embodiments, the system may include control circuitry communicatively coupled to a separator instrument, wherein the control circuitry may be configured to transmit operational instructions to the separator instrument. Additionally, or alternatively, in particular embodiments, processing circuitry may be communicatively coupled to control circuitry, wherein the processing circuitry may be configured to cause one or more other circuitries to execute the methods and processes described herein. By way of example and not limitation, one or more of the control circuitry or the process circuitry may be configured to receive and execute instructions, such as may be determined by processing a non-transitory computer-readable medium having non-transitory computer-readable instructions encoded thereon that, when executed by circuitry, may cause the circuitry to execute one or more of the methods or processed of this disclosure.

In particular embodiments, which may combine the features of some or all of the above embodiments, a thrombectomy system may include: a catheter having a proximal end, a distal end, and a lumen configured to accommodate fluid; a first valve in fluid communication with the catheter, wherein the first valve may be configured to operate in a plurality of operating modes, wherein one or more of the operating modes may be configured to alter a level of pressure in the catheter; a cutting instrument associated with the distal end of the catheter, wherein the cutting instrument may be configured for one or more motions including one or more of axial motion and rotational motion; a first sensor associated with the cutting instrument; and a controller. In particular embodiments, which may combine the features of some or all of the above embodiments, the controller may be configured to: detect, via the first sensor, one or more operational parameters associated with the cutting instrument; determine, based on one or more of the detected operational parameters, whether the cutting instrument is engaging with occlusive material; and operate, based on a determination that the cutting instrument is engaging with the occlusive material, the first valve in a first operating mode of the plurality of operating modes to alter the level of pressure in the catheter.

In particular embodiments, which may combine the features of some or all of the above embodiments, the first operating mode may be configured to alter the level of pressure by moving at least a portion of the occlusive material through the lumen towards a proximal region of the catheter. In particular embodiments, which may combine the features of some or all of the above embodiments, the first operating mode may be configured to remove fluid from the catheter.

In particular embodiments, which may combine the features of some or all of the above embodiments, the first valve may be configured to allow fluid communication between the distal end of the catheter and an aspiration source.

In particular embodiments, which may combine the features of some or all of the above embodiments, the controller may be further configured to: operate, based on a determination that the cutting instrument is not engaging with the occlusive material, the first valve in a second operating mode of the plurality of operating modes, and wherein the second operating mode may be configured to stop the removal of fluid from the catheter associated with the first operating mode.

In particular embodiments, which may combine the features of some or all of the above embodiments, a first set of the operational parameters associated with the cutting instrument may include one or more of (i) one or more torque levels, (ii) one or more rotational rates, (iii) one or more motor current levels, (iv) a rotational direction, or (v) a change of a rotational direction.

In particular embodiments, which may combine the features of some or all of the above embodiments, a second set of the operational parameters associated with the cutting instrument may include one or more of (i) one or more axial positions, (ii) one or more axial motion rates, (iii) one or more axial motion acceleration levels, (iv) one or more axial motion force levels, or (v) one or more motor torque levels associated with the axial motion.

In particular embodiments, which may combine the features of some or all of the above embodiments, the cutting instrument may be configured to distally advance outside of the lumen of the catheter. In particular embodiments, which may combine the features of some or all of the above embodiments, the cutting instrument may be configured to proximally retract inside of the lumen of the catheter. In particular embodiments, which may combine the features of some or all of the above embodiments, the axial motion of the cutting instrument may include a reciprocal axial motion. In particular embodiments, which may combine the features of some or all of the above embodiments, the rotational motion of the cutting instrument may include a rotationally oscillating motion.

In particular embodiments, which may combine the features of some or all of the above embodiments, a thrombectomy system may include at least one motor operatively coupled with the cutting instrument, wherein the at least one motor may be configured to operate the cutting instrument based on one or more of the rotational motion and the axial motion.

In particular embodiments, which may combine the features of some or all of the above embodiments, the cutting instrument may include a spiral body having one or more helical structures. In particular embodiments, which may combine the features of some or all of the above embodiments, the cutting instrument may be configured to fragment the occlusive material, wherein the fragmenting of the occlusive material may be confined within the lumen of the catheter based at least in part on one or more of the helical structures of the cutting instrument and the first operating mode configured to alter the level of pressure.

In particular embodiments, which may combine the features of some or all of the above embodiments, the cutting instrument may include one or more of a rounded element and a macerating portion.

In particular embodiments, which may combine the features of some or all of the above embodiments, the thrombectomy system may include a second valve in fluid communication with the catheter, wherein the second valve may be configured to control an introduction of a fluid medium into the catheter via one or more portions of a set of connection tubing.

In particular embodiments, which may combine the features of some or all of the above embodiments, the thrombectomy system may include one or more pressure sensors associated with one or more of the connection tubing and the catheter.

In particular embodiments, which may combine the features of some or all of the above embodiments, a thrombectomy method for removal of occlusive material from a body passageway may include: positioning a cutting instrument within the body passageway, wherein the cutting instrument may be associated with a distal end of a catheter of a thrombectomy system, and wherein the cutting instrument may be configured for one or more motions including one or more of axial motion and rotational motion; detecting, via a first sensor associated with the cutting instrument, one or more operational parameters associated with the cutting instrument; determining, by a controller, based on one or more of the detected operational parameters, whether the cutting instrument is engaging with the occlusive material; and operating, by the controller, based on a determination that the cutting instrument is engaging with the occlusive material, a first valve of the thrombectomy system in a first operating mode of the plurality of operating modes to alter a level of pressure in the catheter.

In particular embodiments, which may combine the features of some or all of the above embodiments, the first operating mode of a method for removal of occlusive material from a body passageway may be configured to alter the level of pressure to remove fluid from the catheter.

In particular embodiments, which may combine the features of some or all of the above embodiments, a method for removal of occlusive material from a body passageway may further include: operating, by the controller, based on a determination that the cutting instrument is not engaging with the occlusive material, the first valve in a second operating mode of the plurality of operating modes, and wherein the second operating mode may be configured to stop the removal of fluid from the catheter associated with the first operating mode.

The embodiments disclosed herein are only examples, and the scope of this disclosure is not limited to them. Particular embodiments may include all, some, or none of the components, elements, features, functions, operations, or steps of the embodiments disclosed herein. Embodiments according to the invention are in particular disclosed in the attached claims directed to a method and a system, wherein any feature mentioned in one claim category, e.g. method, can be claimed in another claim category, e.g. system, as well. The dependencies or references back in the attached claims are chosen for formal reasons only. However any subject matter resulting from a deliberate reference back to any previous claims (in particular multiple dependencies) can be claimed as well, so that any combination of claims and the features thereof are disclosed and can be claimed regardless of the dependencies chosen in the attached claims. The subject-matter which can be claimed comprises not only the combinations of features as set out in the attached claims but also any other combination of features in the claims, wherein each feature mentioned in the claims can be combined with any other feature or combination of other features in the claims. Furthermore, any of the embodiments and features described or depicted herein can be claimed in a separate claim and/or in any combination with any embodiment or feature described or depicted herein or with any of the features of the attached claims.

BRIEF DESCRIPTION OF THE DRAWINGS

FIGS. 31A-31C illustrate schematic side detail views of a helical cutting instrument having a macerating portion, according to particular embodiments.

FIGS. 32A-32C illustrate schematic side detail views of an implementation of the helical cutting instrument, according to particular embodiments.

FIG. 33A illustrates a schematic cross-section of a macerating portion of an implementation of the catheter system, according to particular embodiments.

FIG. 33B illustrates a schematic side detail view of the macerating portion of FIG. 33A, according to particular embodiments.

DESCRIPTION OF EXAMPLE EMBODIMENTS

Particular embodiments are described below. For clarity, not all features of each actual implementation are described in this specification. In the development of an actual device, some modifications may be made that result in an embodiment that still falls within the scope of this disclosure.

Figure 1:
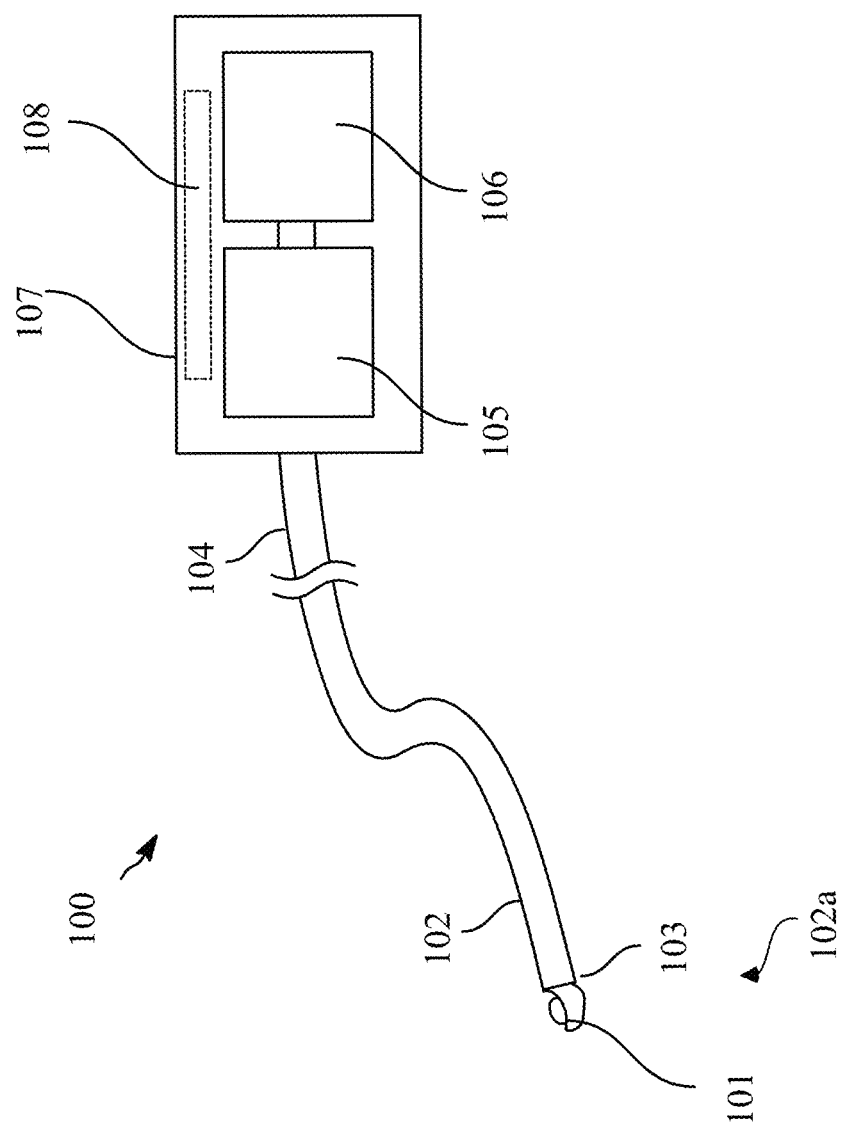
FIG. 1 illustrates a schematic of a thrombectomy system, according to particular embodiments.

FIG. 1 illustrates a schematic of a thrombectomy system 100, according to particular embodiments. In particular embodiments, system 100 may include a catheter 102 attached to base unit 107. By way of example and not limitation, catheter 102 may be a sheath catheter. In particular embodiments, a base unit 107 may house components (e.g., a controller, an aspiration pump, a clot collection container, etc.) that may be operated by a user to effectuate working internal components (not necessarily depicted in FIG. 1) of catheter 102 of system 100. In particular embodiments, a distal end 102a of the catheter 102 may be inserted into a vein, artery, or other passageway, advanced to a treatment site, and then deployed to mechanically disrupt, fragment, and/or aspirate a target substance(s) from the passageway.

In particular embodiments, a cutting instrument 101 may be disposed at or proximal to a distal end 102a of catheter 102. In particular embodiments, a cutting instrument 101 may be referred to as a separator instrument. By way of example and not limitation, cutting instrument 101 may be a helical cutting instrument. In particular embodiments, cutting instrument 101 may extend (e.g., axially) from an opening 103 at the distal end of catheter 102. In particular embodiments, cutting instrument 101 may have a substantially spherical element having a rounded shape at its distal end serving as an atraumatic tip (as will be described in greater detail below). By way of example and not limitation, an atraumatic tip such as described herein may reduce the risk that the passageway or surface of a vessel or tissue may be damaged by advancement of cutting instrument 101 through opening 103 of the catheter 102. In particular embodiments, opening 103 may permit substance(s) from the patient's body to enter an aspiration lumen formed in the catheter 102. In particular embodiments, cutting instrument 101 may separately or additionally extends (e.g., axially) from the opening 103. In particular embodiments, a proximal end 104 of catheter 102 may be coupled to one or more motors, e.g., motor 105. By way of example and not limitation, motor 105 may provide rotational and/or axial motions (e.g., reciprocal motion) to internal components of catheter 102, as will be discussed in greater detail below. In particular embodiments, proximal end 104 of catheter 102 may be provided in fluid communication with an aspiration source. By way of example and not limitation, an aspiration source may comprise a pump, such as pump 106. By way of example and not limitation, an aspiration source may provide a negative pressure gradient (e.g., vacuum suction), which may draw target substance(s) into the aspiration lumen of the catheter 102 (for e.g., through opening 103). Other known aspiration sources that may be used are within the scope of this disclosure. Separately or in combination, the negative pressure gradient and/or the mechanical fragmentation may act to ensure the efficient and effective removal of substances from the body.

In particular embodiments, thrombectomy system 100 may include one or more pumps and/or one or more valves in fluid communication with system 100. In particular embodiments, such pumps and/or valves may provide and/or remove fluids in a way that alters pressure within system 100. In particular embodiments, system 100 may be controlled by an ergonomically shaped handle (not illustrated in FIG. 1) that houses motor 105. In particular embodiments, the handle may house and/or may be in fluid contact with pump 106. By way of example and not limitation, this may allow the user to easily control and manipulate system 100.

In particular embodiments, thrombectomy system 100 may comprise processing and control circuitry 108. In particular embodiments, processing and control circuitry 108 may include one or more components for receiving, processing, and/or transmitting signals and/or data, such as for controlling and/or monitoring one or more of motor 105, catheter 102, or sensors (not necessarily shown) arranged throughout system 100. By way of example and not limitation, processing and control circuitry 108 may be configured to collect data related to different components, for e.g., to determine a modification of operation of one or more of motor 105 or catheter 102. By way of example and not limitation, one form of operation data that may be used by processing and control circuitry 108 may include torque data which, when analyzed according to one or more processes and methods of this disclosure, may be correlated to an engagement or operational state of catheter 102. In particular embodiments, depending on the engagement or operational state determined by processing and control circuitry 108, processing and control circuitry 108 may generate one or more instructions which, when executed, may modify operation of system 100 to change the engagement or operational state.

Aspiration Thrombectomy Systems

Figure 2:
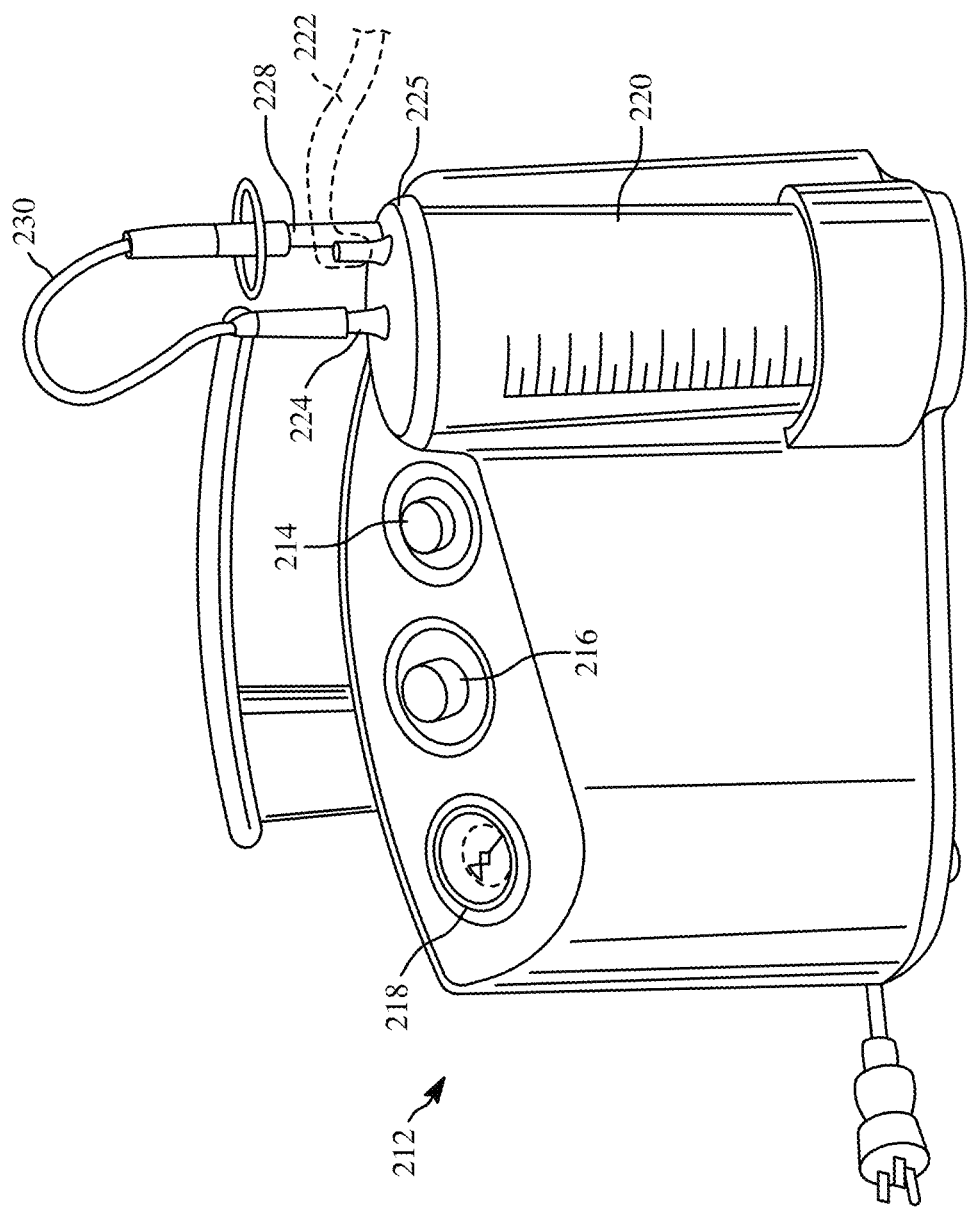
FIG. 2 illustrates a vacuum console and collection canister of an exemplary thrombectomy system, according to particular embodiments.

FIG. 2 illustrates a vacuum console and collection canister of a thrombectomy system 100, according to particular embodiments. As illustrated in FIG. 2, in particular embodiments, a base unit 212 may enclose a vacuum pump (not illustrated), which may operate off of line voltage. In particular embodiments, the base unit may have an on-off switch 214, and/or a separate knob 216 for adjusting the level of vacuum provided by the pump. In particular embodiments, a vacuum level may be read on a pressure gauge 218. In particular embodiments, blood and clot may be drawn into a collection canister 220 from an aspiration tube 222 (illustrated in broken line), which may be connected to a reperfusion catheter (not illustrated) introduced into the vasculature of a patient to aspirate clot.

In particular embodiments, the blood and clot may be drawn into the collection canister by a partial vacuum, which may be provided by a vacuum connector 228 on the base unit 212 which is connected to the vacuum pump (not illustrated). In particular embodiments, vacuum from vacuum connector 228 may be applied to a vacuum port 224 on a removable lid 225. In particular embodiments, vacuum connector 228 may be connected to the vacuum port 224 by an external vacuum tube 230. By way of example and not limitation, vacuum tube 230 may comprise an external tube.

In particular embodiments, clot aspiration using a mechanical thrombectomy apparatus or other a vacuum-assisted thrombectomy systems must sometimes be terminated due to the risk of excessive blood loss by the patient. By way of example and not limitation, terminating clot aspiration due to risk of excessive blood loss may be high when using large aspiration catheters. During aspiration thrombectomy, if the catheter tip falls out of contact with the thrombus or other occlusive material, the tip may be exposed to healthy blood and full flow can ensue. Under such conditions, the blood loss rate may be excessive, and in some cases, may result in premature termination of the procedure. By way of example and not limitation, if the catheter enters healthy blood and full flow ensues during an aspiration procedure, a blood loss rate in the range of 20-25 cc per second may occur, such as with an 8 French size catheter. By way of example and not limitation, assuming a maximum tolerable blood loss of 300-1000 mL for a patient, the catheter may not operate in unrestricted mode for more than approximately 20 to 50 seconds. When a physician operates the system manually, the aggregate blood loss may reach an unacceptable level before sufficient clot is removed during an aspiration procedure. In particular embodiments, reliably identifying whether the tip of the catheter is in contact with clot and/or is undesirably aspirating healthy, clot-free blood can be a significant problem, and manual control may not be optimum.

In particular embodiments, during other procedures such as, for example, neurovascular procedures for treatment of ischemic stroke, excessive removal of blood may be less of a risk, and the primary focus of the procedure may be maximization of removal of occlusive material. Optimizing both technique and aspiration control may be of high importance for successful removal of occlusive material.

In particular embodiments, it can be desirable to provide improved methods and apparatus for controlling the aspiration of thrombus and clot using aspiration catheters in combination with pumping consoles. By way of example and not limitation, it can be particularly useful to provide systems and methods which limit blood loss during such aspiration procedures, such as by automatically stopping aspiration while the aspiration catheter is not in contact with clot or thrombus. Separately or additionally, in particular embodiments, it can be desirable to provide systems and methods which optimize system performance and procedures for removal of occlusive material. Particular embodiments, as will be further described herein, may be designed to meet these requirements and provide corresponding benefits.

Figure 3:
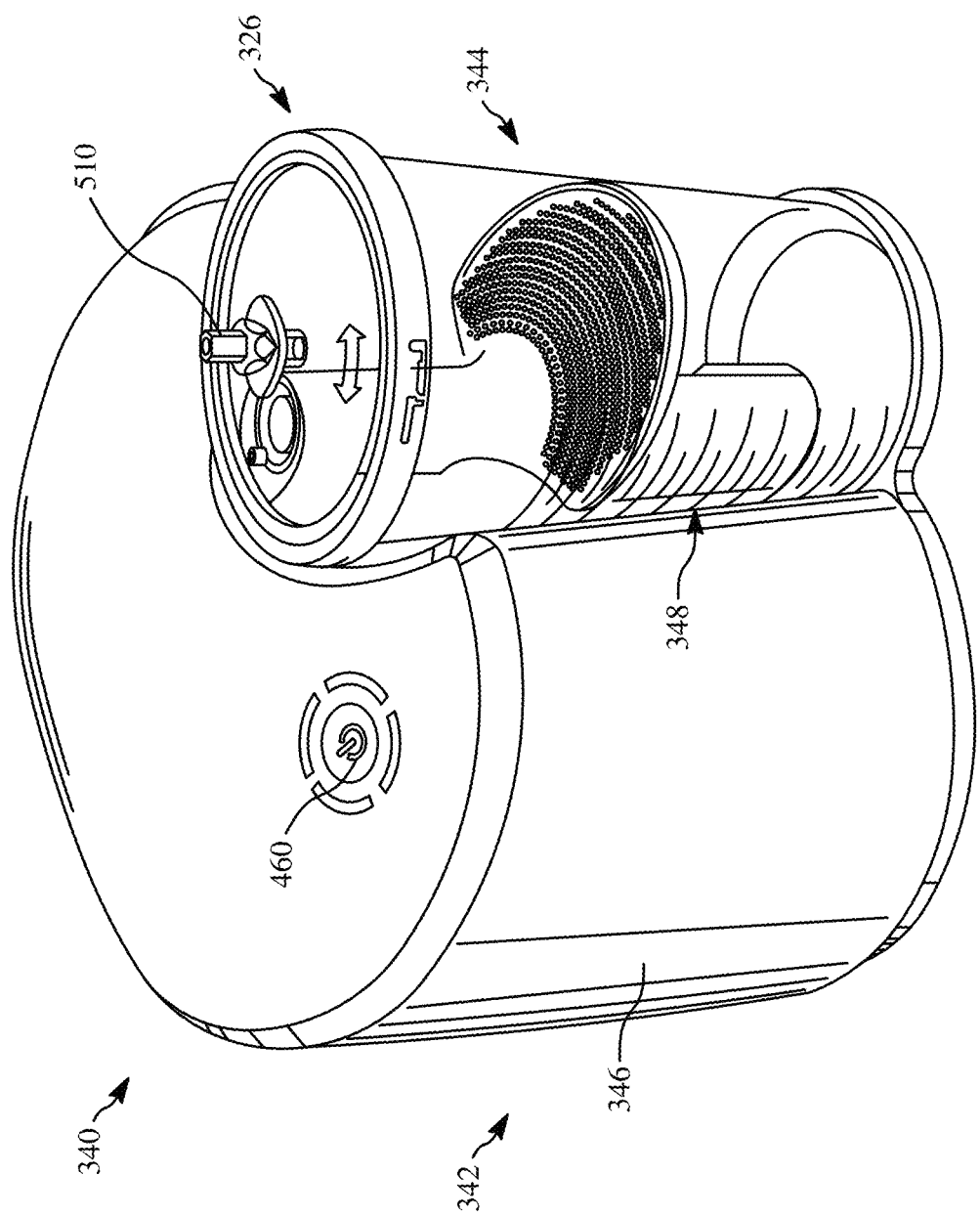
FIG. 3 illustrates a perspective view of a vacuum console and a collection canister of a thrombectomy system, according to particular embodiments.

Referring to FIGS. 3-7, particular embodiments of an apparatus and methods for controlled clot aspiration will be described. FIG. 3 illustrates a perspective view of a vacuum console and a collection canister according to particular embodiments. In particular embodiments, the collection canister may be received in a mounting region of the vacuum console. By way of example and not limitation, the collection canister may be a blood and/or clot collection canister.

In particular embodiments, the vacuum system 340 may include a vacuum console 342, an enclosure 346, and/or a blood/clot collection canister 344 having the lid 326 discussed below in relation to FIGS. 8A, 8B, and 10 (see also, discussion below of lid 580 in relation to FIGS. 5-7). The vacuum console 342 may comprise an enclosure having a recess 348, which may be shaped in particular embodiments to removably receive the collection canister 344, as will be described in more detail below.

Figure 4A:
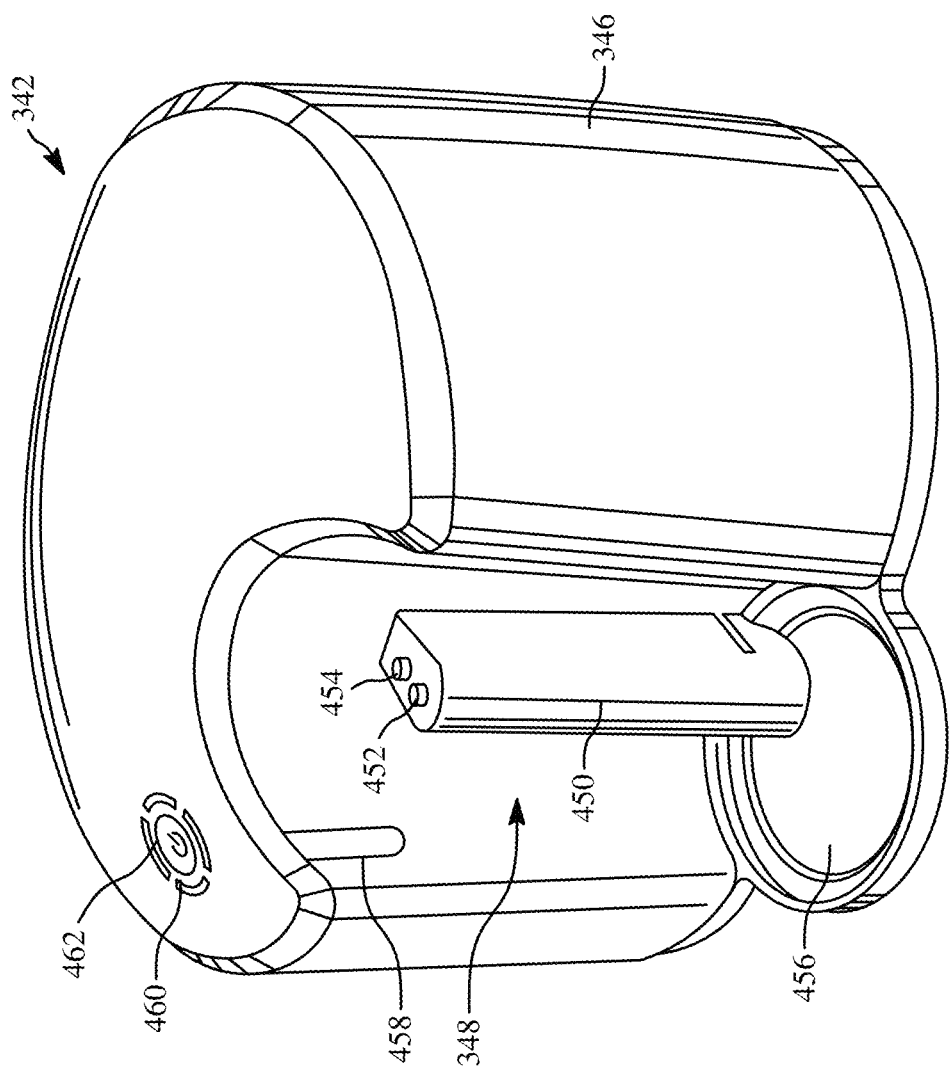
FIG. 4A illustrates a view of the vacuum console of illustrated with the collection canister removed, according to particular embodiments.
Figure 4B:
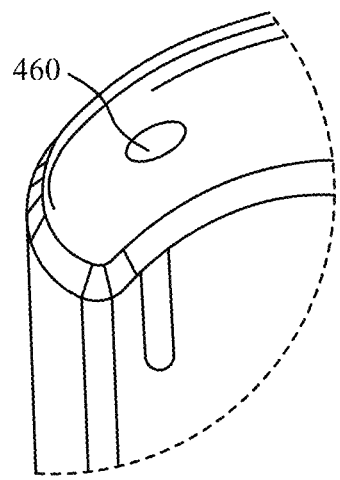
FIG. 4B illustrates a detailed view of the switch and a vacuum display region on a top surface of the vacuum console of FIG. 4A, depicted with the power off, according to particular embodiments.
Figure 4C:
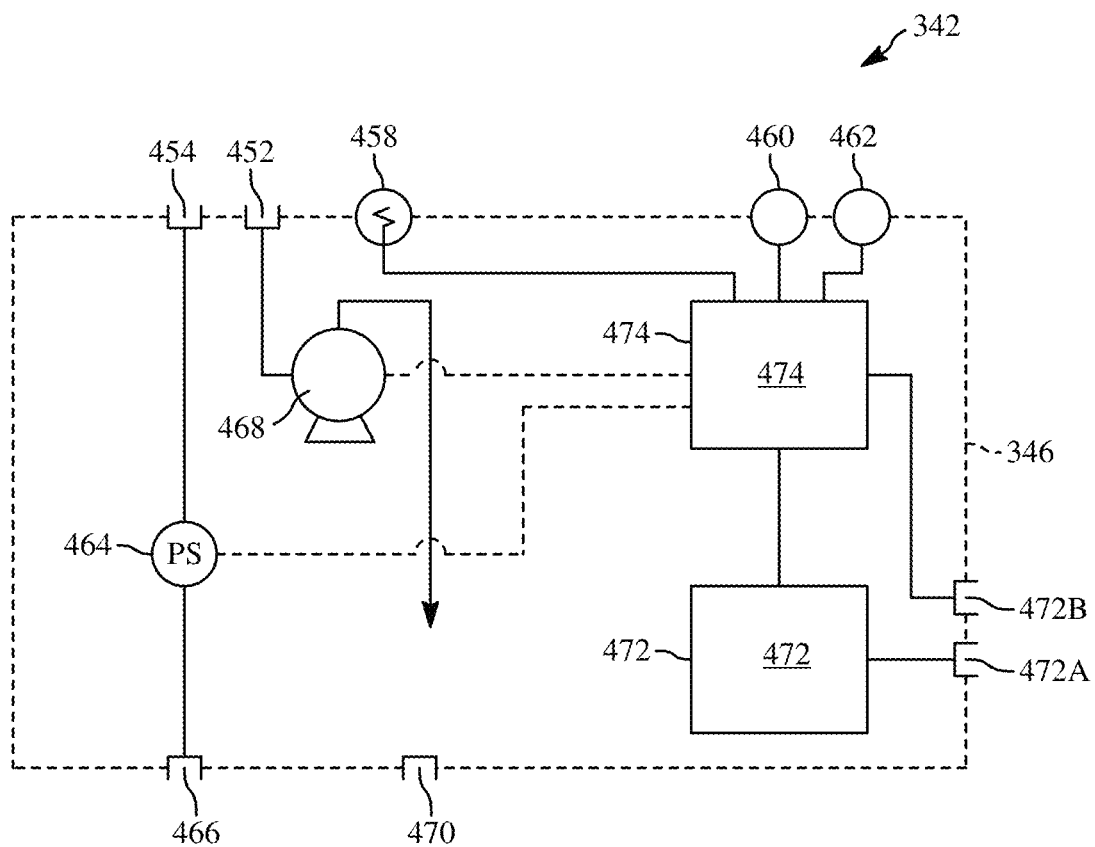
FIG. 4C illustrates a schematic representation of the internal components of a vacuum console, according to particular embodiments.

Referring to the figures, FIG. 4A illustrates a view of the vacuum console of illustrated with the collection canister removed, according to particular embodiments. FIG. 4B illustrates a detailed view of a switch, e.g., an on-off switch, and a vacuum display region on a top surface of the vacuum console of FIG. 4A, depicted with the power off, according to particular embodiments. FIG. 4C illustrates a schematic representation of the internal components of a vacuum console, according to particular embodiments.

In particular embodiments, a post 450, which may form a contiguous portion of the outer surface or wall of the enclosure 346, may be formed within the recess 348 and/or may extend upwardly from a bottom plate 456, which can act as a support for the collection canister 344 when it is received within the recess. In particular embodiments, a vacuum connector 452 and/or a pressure sensing connector 454 may be formed in or on a surface of the post 450, e.g., an upper surface. In particular embodiments, vacuum connector 452 and/or sensing connector 454 may be located so that they may align with a vacuum port 602 and a pressure sensing port 604 (e.g., FIG. 6) on the collection canister 344 when received within the recess 348. By way of example and not limitation, a light 458 may be located on a wall surface of the enclosure 346 within the recess 348. By way of example and not limitation, light 458 may be located to illuminate the contents of the collection canister 344 when the system is in use. By way of example and not limitation, another light (not visible in in FIG. 4A) may be present on the opposite wall of the recess 348. In particular embodiments, vacuum console 342 may have a switch 460 on its upper surface. By way of example and not limitation, switch 460 may be an on-off switch. By way of example and not limitation, switch 460 may illuminate when on (such as illustrated in FIGS. 3 and 4A), and may not illuminate when the system is off (e.g., FIG. 4B). Separately or additionally, in particular embodiments, a display 462 may be provided on the upper surface of the enclosure 346. By way of example and not limitation, display 462 may comprise a pressure display. As illustrated by way of example and not limitation in FIGS. 3 and 4A, the display may comprise a circular light, e.g. having multiple segments, which may be sequentially illuminated as the vacuum level within the canister increases. By way of example and not limitation, each quadrant of an exemplary four-segment display may represent a measured vacuum as a percentage of ambient pressure.

FIG. 4C illustrates a schematic representation of the internal components of a vacuum console, according to particular embodiments. In particular embodiments, primary internal components of the vacuum console may include a pressure sensor 464, a pump 468, a power supply 472, and/or a microprocessor controller 474. In particular embodiments, pump 468 may have an inlet connected to the vacuum connector 452 on the post 450 of the enclosure 346. In particular embodiments, pressure sensor 464 may be connected to the pressure sensing connector 454 on the post 450. By way of example and not limitation, the pump may be turned on by the switch 460, and may draw vacuum through the vacuum connector 452 and release removed gas into an interior of the console. In particular embodiments, the console may be vented by a vent 470 on a bottom surface of the enclosure 346. In particular embodiments, a differential or ambient pressure port 466 may be provided for an enabling pressure sensor 464 to sample a reference measurement, such as ambient pressure measurements.

In particular embodiments, the functions of the pump may be controlled by the microprocessor controller 474. In particular embodiments, the pressure output from pressure sensor 464 may separately or additionally be controlled and/or processed by the microprocessor controller 474. In particular embodiments, one or more of the light 458, switch 460, and/or display 462 may be connected to the microprocessor controller 474, which may be powered by the power supply 472. In particular embodiments, power supply 472 may be powered through line current connector 472A. In particular embodiments, data connector 472B, e.g., a USB connector, may be powered by microprocessor controller 474. By way of example and not limitation, the pump may be plugged into an outlet via a power cord that is supplied with the pump. By way of example and not limitation, the power supply may convert the AC current from the wall outlet to DC current, which the microprocessor controller may use to power one or more of the pump, switch, lights, USB connector, etc.

In particular embodiments, pressure sensor 464 may be connected to the microprocessor controller 474, and may measure vacuum pressure in the canister through the pressure sensing connector 454. In particular embodiments, another pressure sensor (e.g., a second pressure sensor, not illustrated) may be connected to the microprocessor controller 474 to measure ambient pressure outside of the pump enclosure through an internal tube, which may be routed to a vent in the base of the pump. By way of example and not limitation, the microprocessor controller may take the vacuum pressure readings from the pressure sensor 464 and divide it by the ambient pressure reading from the second pressure sensor to calculate the vacuum pressure in the canister as a percent of ambient pressure.

Figure 5:
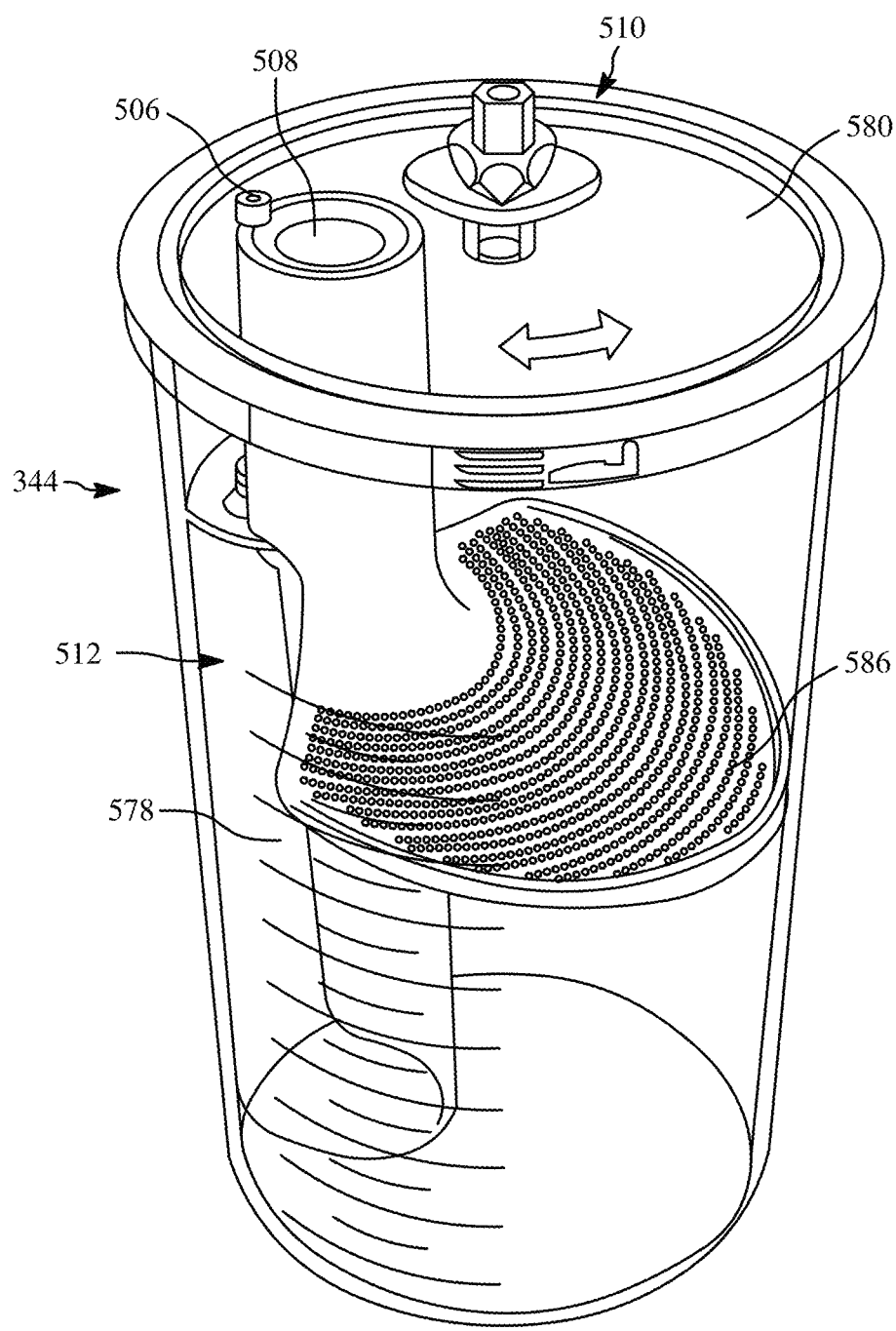
FIG. 5 illustrates a collection canister, according to particular embodiments.
Figure 6:
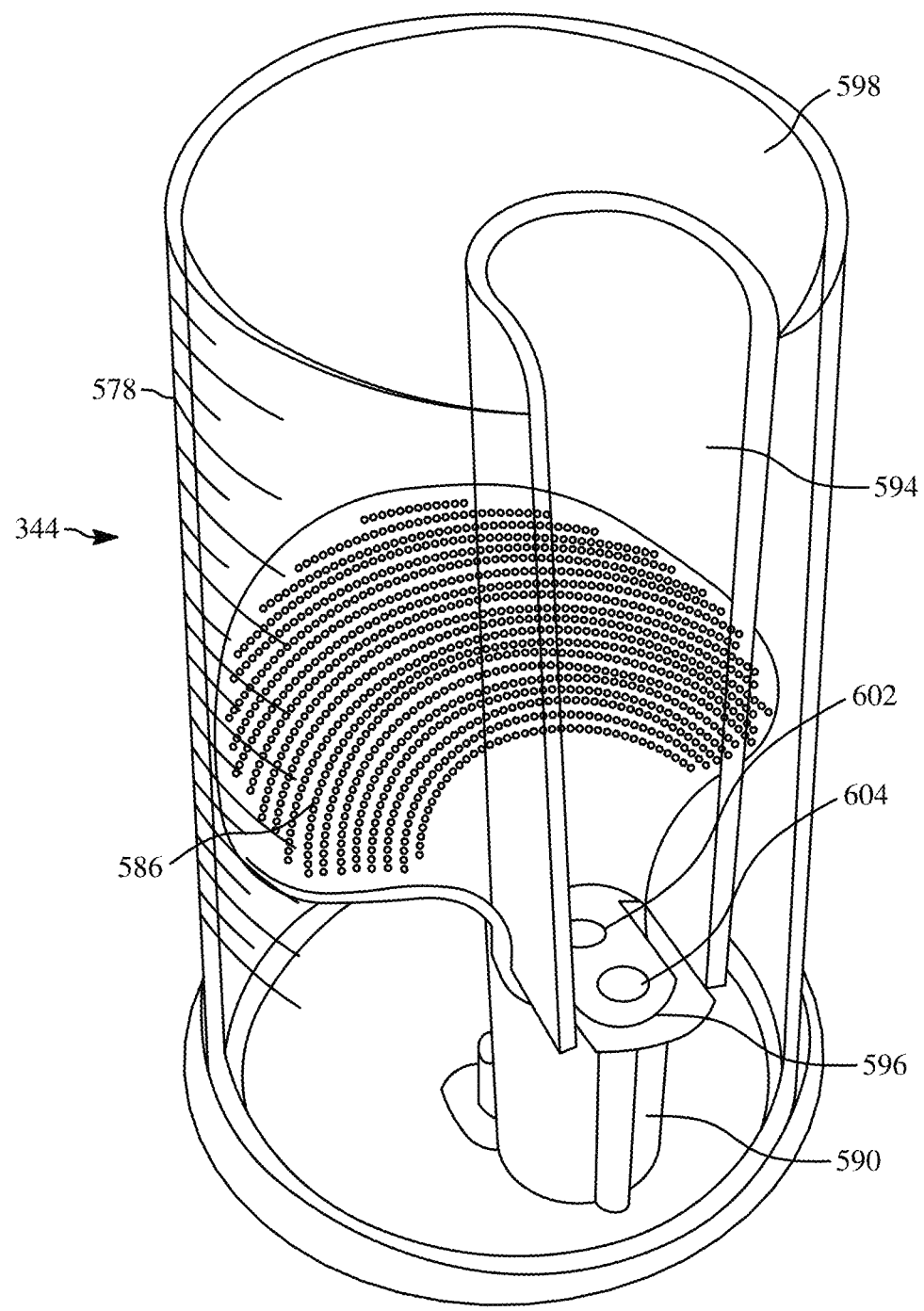
FIG. 6 illustrates an embodiment of the collection canister of FIG. 5, depicted in an inverted or "upside down" view, according to particular embodiments.
Figure 7:
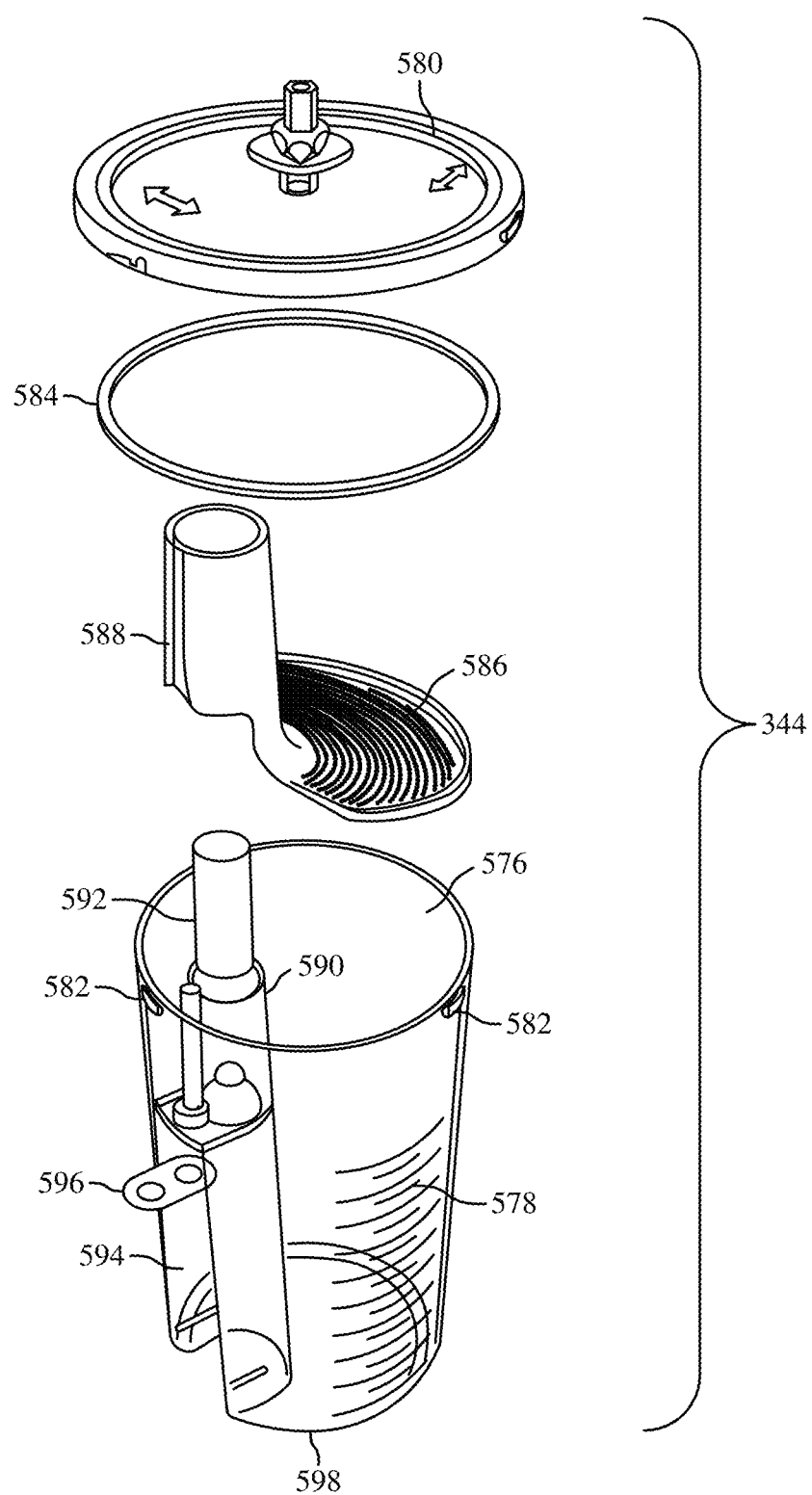
FIG. 7 illustrates an exploded view of the vacuum canister of FIGS. 5 and 6, according to particular embodiments.

Referring now to FIGS. 5-7, particular embodiments of a collection canister 344 may have a main body 578. By way of example and not limitation, main body 578 may be formed from a polished, clear plastic material, and/or may be molded into a suitable shape, e.g., the illustrated shape. FIG. 5 illustrates a collection canister, according to particular embodiments. FIG. 6 illustrates an embodiment of the collection canister of FIG. 5, depicted in an inverted or "upside down" view, according to particular embodiments. FIG. 7 illustrates an exploded view of the vacuum canister of FIGS. 5 and 6, according to particular embodiments.

In particular embodiments, main body 578 may have a bottom 598 and an open upper end 576, which may be covered by a removable clear plastic lid 580. By way of example and not limitation, the clear plastic lid 580 may be attached by a bayonet connector 582, and/or a form or other gasket 584 may seal the lid to the open end of the main body 578.

In particular embodiments, a groove 594 may be formed in one side of the main body 578. By way of example and not limitation, groove 594 may be shaped so that it may be placed over the post 450 in the recess 348 of the enclosure 346 of the vacuum console 342. As illustrated in FIG. 6, in particular embodiments, the pressure sensing port 604 and the vacuum port 602 may be located at the upper end of the groove 594. By way of example and not limitation, they may be so located to align and connect with the vacuum connector 452 and pressure sensing connector 454 on the post 450 when the collection canister 344 is in place in the recess 348.

In particular embodiments, the pressure sensing port 604 may be connected to a tube or lumen, which may extend upwardly in the main body 48 of the collection canister 344 and/or may terminate in an upper opening or aperture 506. In particular embodiments, the vacuum port 602 may extend upwardly through a much larger lumen or tube, and/or may terminate in an open aperture 508 at its upper end. By way of example and not limitation, the apertures 506 and 508 may be located near the top of the interior of the main body 578, but may be below the bottom of the lid 580 when the lid is in place on the collection canister 344. Thus, in particular embodiments, both of the apertures 506 and 508 may be exposed to the interior of the collection canister 344, but may be maintained well above the mid-section and bottom where the clot and blood are collecting. In particular embodiments, the risk of contamination from blood and clot may be minimized based on this arrangement.

In particular embodiments, a filter plate 586, illustrated herein as a perforated screen but which may also be a woven screen or other separating member, may be held in the mid-section of the interior of the main body 578 of the collection canister 344. By way of example and not limitation, clot or occlusive material may be drawn into the interior of the canister through a connector 510, which may be attached to a proximal end of the catheter or other tubing. In particular embodiments, clot and blood may be drawn into the interior of the main body 578 by the vacuum which is drawn through the vacuum port 602 by the vacuum console 342, as previously described. By way of example and not limitation, as clot and blood may fall downward from connector 510 into the collection canister 344, the clot may collect on the upper surface of the filter plate 586 while the blood may flow through the perforations in the plate and collect in the bottom of the canister. As the plate may be inclined downward from a sleeve 588, which may be mounted on a post 590 in the interior of the canister in particular embodiments, excess blood may flow over an open bypass region 512 (FIG. 5) which may be formed on a backside of the plate, and/or may allow the blood to flow directly down to the bottom of the canister.

In particular embodiments, filter body 592 may occupy the interior of post 590 and aperture 508, and may prevent extracted material from contaminating the interior of enclosure 346. By way of example and not limitation, filter body 592 may occupy the interior of post 590, and/or extend to aperture 508. In particular embodiments, the filter body may therefore prevent extracted material from contaminating the interior of enclosure 346.

In particular embodiments, a groove 594 may be formed on a side of the main body 578 of the collection canister 344, and may be received over the post 450 in the recess 348 of the enclosure 346 in order to align the vacuum and pressure sensing connectors and vacuum ports. In particular embodiments, a gasket 596 may be provided at the seal between the vacuum ports and the vacuum connectors.

While particular embodiments of apparatus and methods for controlled clot aspiration for particular embodiments may be used with the vacuum system 340, it will be appreciated that the particular embodiments described and claimed herein are not limited to use with any particular vacuum console, and instead may be useful with any clot or other vascular thrombectomy or aspiration system, such as a thrombectomy or other vascular aspiration catheter in combination with a vacuum pump or other source where there may be a risk of excess blood aspiration, clogging, or both.

Figure 8A:
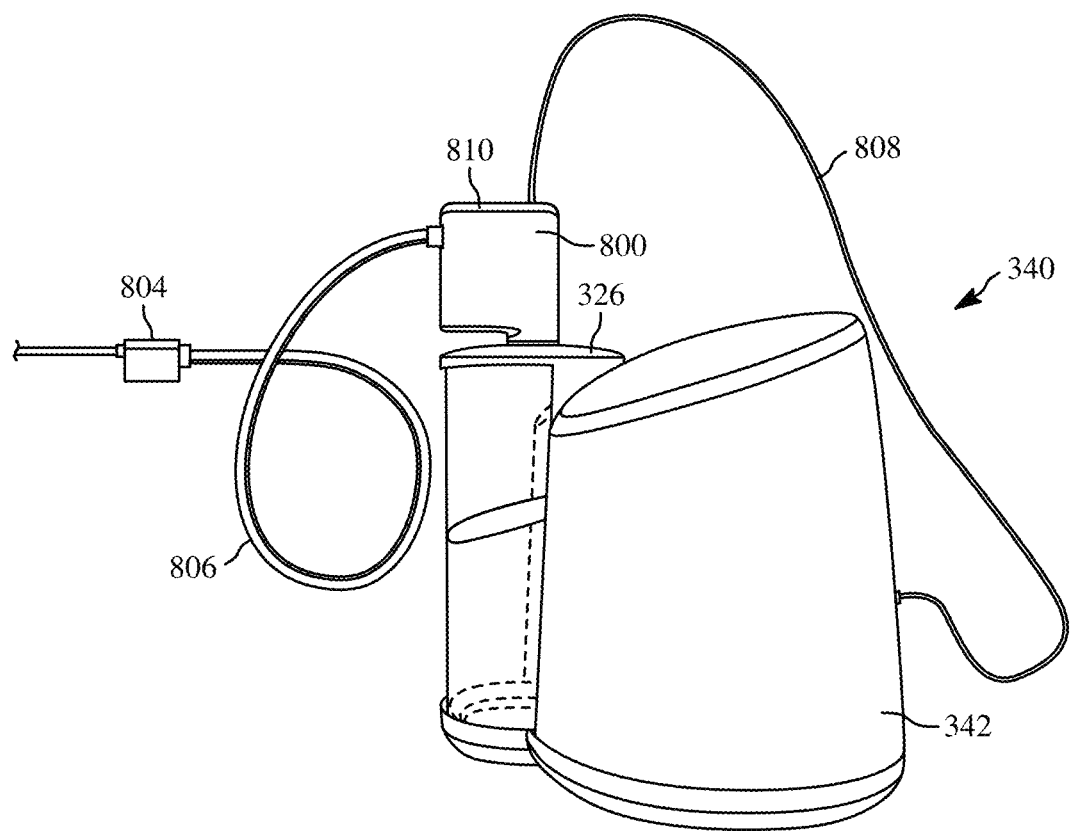
FIGS. 8A and 8B illustrate a vacuum console and collection canister, having a vacuum aspiration control system attached thereto, according to particular embodiments.
Figure 8B:
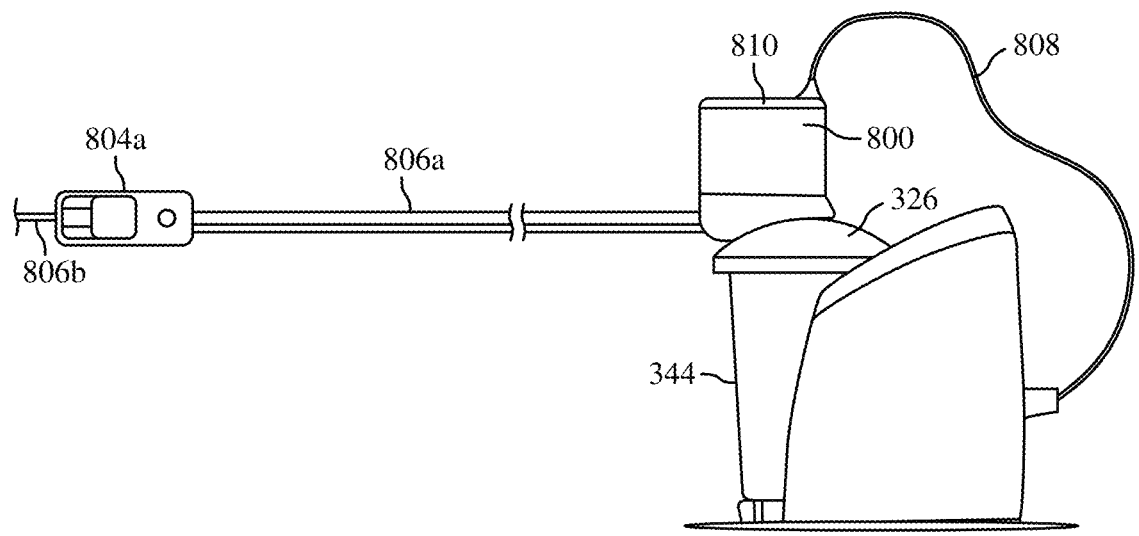

FIGS. 8A and 8B illustrate a vacuum console and collection canister, having a vacuum aspiration control system attached thereto, according to particular embodiments.

In particular embodiments, an exemplary system 800 for performing controlled clot aspiration may comprise a base unit 810 and an external unit, e.g., external unit 804. In particular embodiments, a proximal portion 806a of a connection tubing 806 may be connected to the base unit 810. In particular embodiments, a distal portion 806b of connecting tubing 806 may extend from the external unit, e.g., external unit 804. In particular embodiments, the external unit may be secured on or to the connection tubing at a location spaced apart from the proximal end. By way of example and not limitation, a spacing may be by some distance sufficient to make conclusions about flow. In particular embodiments, external unit 804 may be configured to connect directly to a hub and/or other proximal end of an aspiration catheter, or may be configured to be connected in the middle of the connection tubing. In particular embodiments, the connection tubing may be linear in an unconstrained configuration and/or flexible along its length.

In particular embodiments, the base unit 810 may be configured to sit directly atop the lid 326 on the collection canister 344 of a vacuum console 342. By way of example and not limitation, a communication cable 808 may extend from the base unit 810 through a portion of connecting tubing 806 to a connection receptacle on the vacuum console 342, so that the base unit may be powered by the vacuum console and may optionally communicate data with the controller within the vacuum console.

Figure 9A:
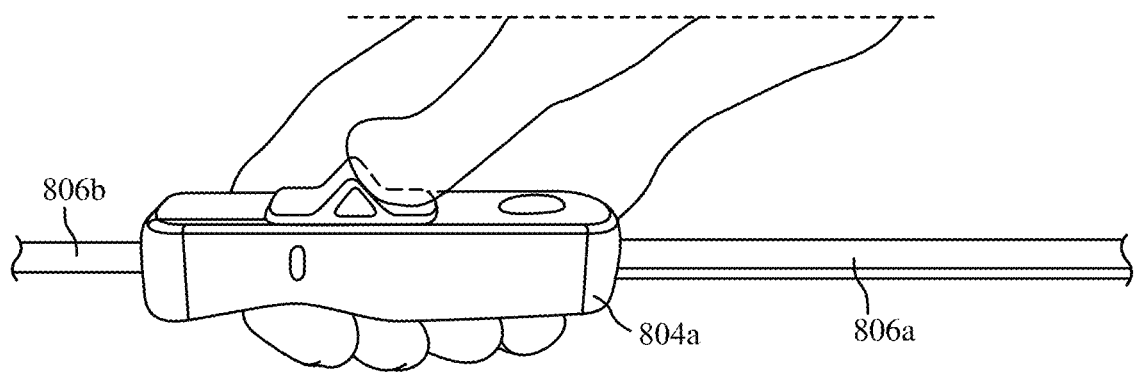
FIGS. 9A and 9B illustrate an external unit, according to particular embodiments.
Figure 9B:
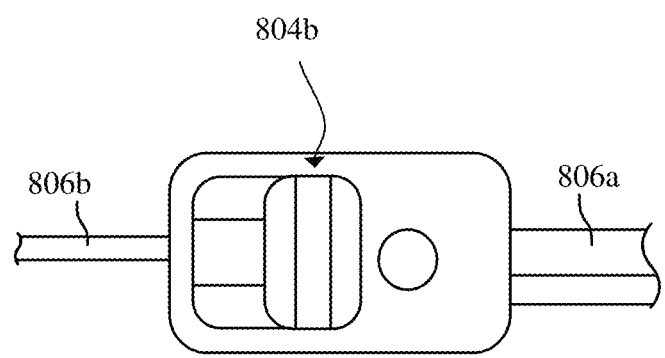

As illustrated in FIG. 8B, in particular embodiments, an external unit 804a may include a switch 804b for initiating treatment using the vacuum console 342 and/or controlled clot aspiration system 800. The switch may also turn off the system, thereby providing a manual override of the algorithm that ensures the system is off with no flow. By way of example and not limitation, when the switch is on, the system may immediately enter an algorithm mode where it decides to remain open, enter a sampling mode, or initiate an extraction cycle in response to pressure sensor readings. Further details of particular embodiments of an external unit 804a are illustrated in FIGS. 9A and 9B.

Figure 10:
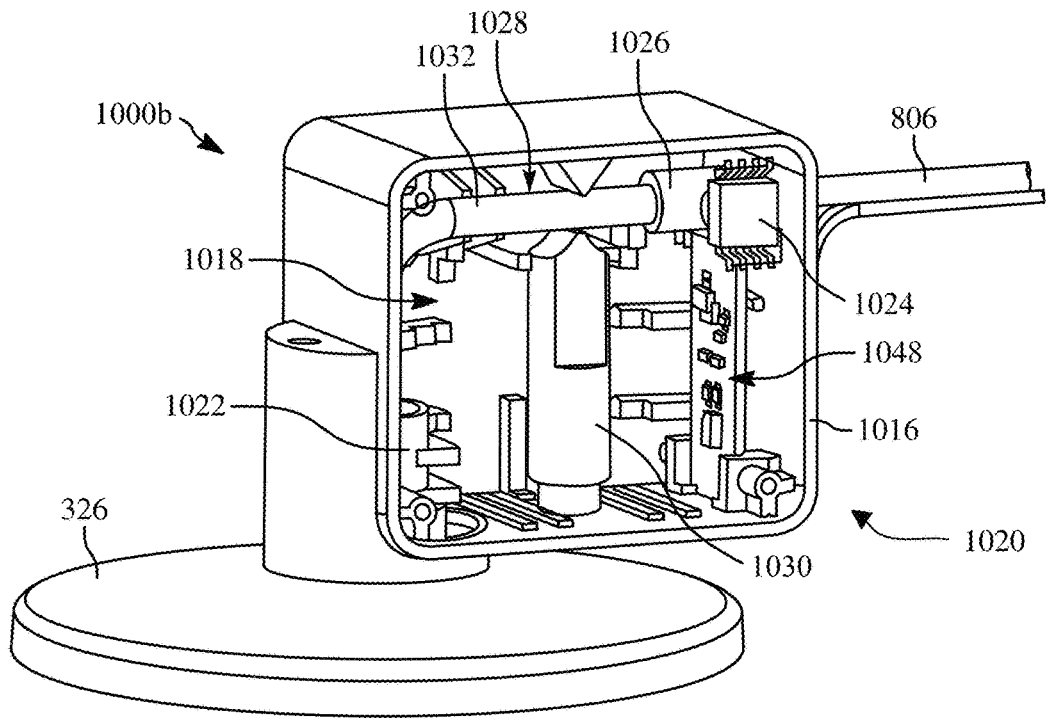
FIG. 10 illustrates an exemplary base unit enclosing an on-off valve and a controller of a type suitable for use in vacuum aspiration control systems, depicted in section, according to particular embodiments.

FIG. 10 illustrates an exemplary base unit enclosing an on-off valve and a controller of a type suitable for use in vacuum aspiration control systems, depicted in section, according to particular embodiments.

In particular embodiments, an exemplary base unit 1000b may comprise a base unit enclosure 1016 having an open interior cavity 1018, which may receive a number of components. By way of example and not limitation, a controller 1020, which may include a microprocessor on a printed circuit board 1048, may be mounted within the cavity 1018. In particular embodiments, a pressure sensor 1024 may be secured between a tube segment 1032 and a proximal end on the connection tubing 806 by a pressure fitting 1026. By way of example and not limitation, tube segment 1032 may be collapsible and positioned in a pinch valve 1028 which is driven by a solenoid 1030. In particular embodiments, pinch valve 1028 may be biased into a closed position by a compressive spring (not visible), unless it is opened by solenoid 1030. In particular embodiments, base unit 1000b may include a connecting fitting 1022, which may be configured to be removably secured to a vacuum fitting (not illustrated) on the lid 326 of the collection canister 344. In particular embodiments, controller 1020 may be configured to open and close the pinch valve 1028, such as to allow and prevent, respectively, the flow of clot and blood through the tube segment 1032 from the aspiration catheter into the collection canister. In particular embodiments, base unit 1000b may optionally include a button (not pictured) in electronic communication with printed circuit board 1048 (for e.g., of controller 1020), such as for advanced user control of various parameters of the system. In particular embodiments, a base unit house and/or be in communication with a pressure chamber, a fluid source, additional on-off valves, and/or a combination thereof.

In particular embodiments, an on-off valve and a controller of the type suitable for use in aspiration control systems may be used to apply mechanical forces on a clot, thrombus, or other occlusive material. In particular embodiments, during a maceration cycle, mechanical action by the on-off valve on the occlusive material may be used for cutting, shearing, chopping, dividing, softening, macerating, or otherwise modifying the form, consistency, and/or deformability of the occlusive material. By way of example and not limitation, modifying the form or consistency of clots, thrombi, or other occlusive material by mechanical action may beneficially enable more effective aspiration of occlusive material through the aspiration catheter. For example, a large thrombus may be divided into smaller pieces for more effective aspiration. For example, a hard or dense thrombus may be mechanically softened or made more pliable by mechanical action to enable more effective aspiration. In particular embodiments, the pinch valve 1028 may be used for applying mechanical forces and action on clots, thrombi, and/or other occlusive material. In particular embodiments, other types of valves, including but not limited to valves specifically designed for improved mechanical action on occlusive material, may be used. In particular embodiments, parameters for selective operation of the valve by the controller, including but not limited to timing, frequency, duty cycle parameters, and/or signal amplitude (which may correspond in particular embodiments to a valve closing-related parameter such as force), may be optimized to provide improved mechanical action by the valve on occlusive material.

Figure 11:
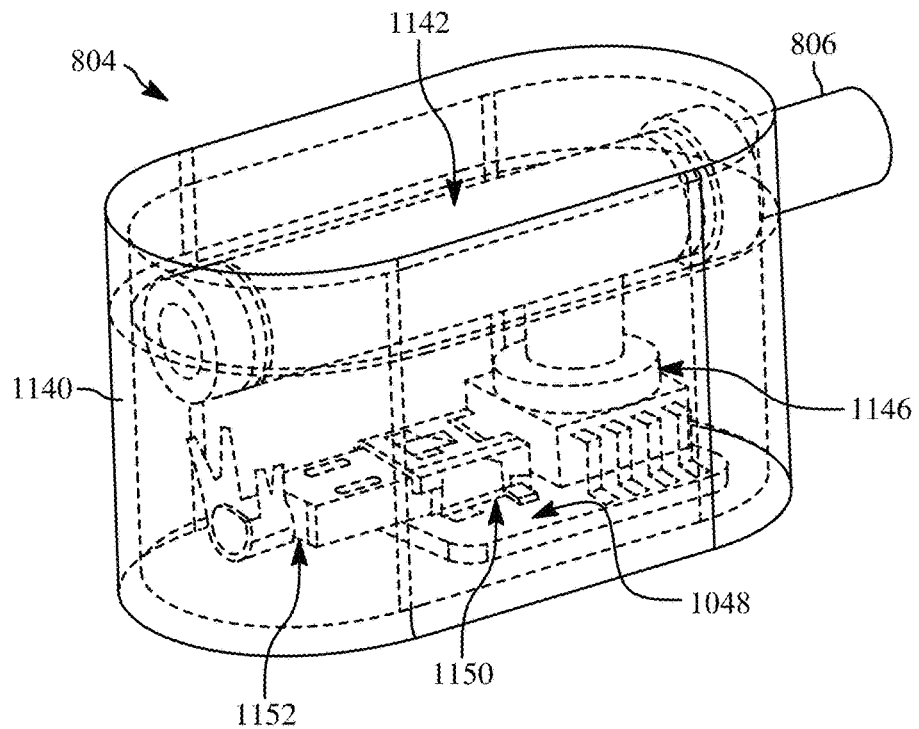
FIG. 11 illustrates an exemplary external unit depicting internal components including a fitting and a pressure sensor, depicted in phantom, according to particular embodiments.

FIG. 11 illustrates an exemplary external unit depicting internal components including a fitting and a pressure sensor, depicted in phantom, according to particular embodiments.

In particular embodiments, an exemplary external unit 804 may include an external unit enclosure 1140 having a flow fitting 1142 in an interior cavity thereof. By way of example and not limitation, the flow fitting 1142 may be connected to portions 806*a* and 806*b* of the connecting tubing 806, such as illustrated with reference to particular embodiments in FIGS. 8B, 9A and 9B. In particular embodiments, a second pressure sensor 1146 may be mounted on a printed circuit board 1048 and/or within an internal cavity of the enclosure 1140. In particular embodiments, the output of one or more pressure sensors may be delivered to the controller 1020 via a connective cable (not illustrated), which may be connected via a signal/power connector 1150 and a mating signal-power connector 1152, which may be, for example, a conventional USB port and plug. In particular embodiments, the connecting cable may have multiple lumens, e.g., dual lumens, as illustrated for particular embodiments in FIG. 10. By way of example and not limitation, one of the lumens may be used to route a communications cable between the external unit and the base unit, while the other lumen may accommodate a fluid flow. In particular embodiments, an external unit may house or be in communication with a pressure chamber, a fluid source, additional on-off valves, or some such combination.

In particular embodiments, by providing a first pressure sensor 1024 in the base unit and a second, axially separated pressure sensor 1146 in the external unit enclosure 1140, the material flow rate through the connection tubing may be calculated. By way of example and not limitation, the material flow rate calculation may be based upon measured differential pressure(s) by the controller. In particular embodiments, the controller may analyze the pressure differentials and flow rate to determine the contents flowing through the aspiration catheter, connective tubing, or both.

In particular embodiments, the controller may characterize the state of a catheter's contents as unrestricted flow, restricted flow, clogged, and/or particular intermediate states. In particular embodiments, a high pressure differential between spaced-apart pressure sensors may indicate unrestricted flow. By way of example and not limitation, unrestricted flow may be comprised of primarily healthy, clot-free blood, or blood free of vessel-obstructing clot. In particular embodiments, healthy blood may be blood with a low enough proportion of cross-linked fibrin such that it is not sufficiently integrated to cause ischemia or other similar vessel occlusions. By way of example and not limitation, aspirating such healthy blood with full aspiration may result in excessive blood loss, which may in particular embodiments require premature termination of the aspiration procedure.

In particular embodiments, a variable and intermediate or low pressure differential may indicate restricted flow. By way of example and not limitation, restricted flow may be comprised of clot, occlusive material, and/or blood. In particular embodiments, restricted flow may benefit from full aspiration. In particular embodiments, a small pressure differential or a pressure differential approaching zero may indicate a clog. In particular embodiments, such flow, or lack thereof, may benefit from an extraction cycle. It will be appreciated that the use of differential pressure for detecting increased flow and occlusions is provided by way of example and not limitation; other flow measurement and/or material property measurement techniques are fully contemplated, and are within the scope of this disclosure.

Figure 12:
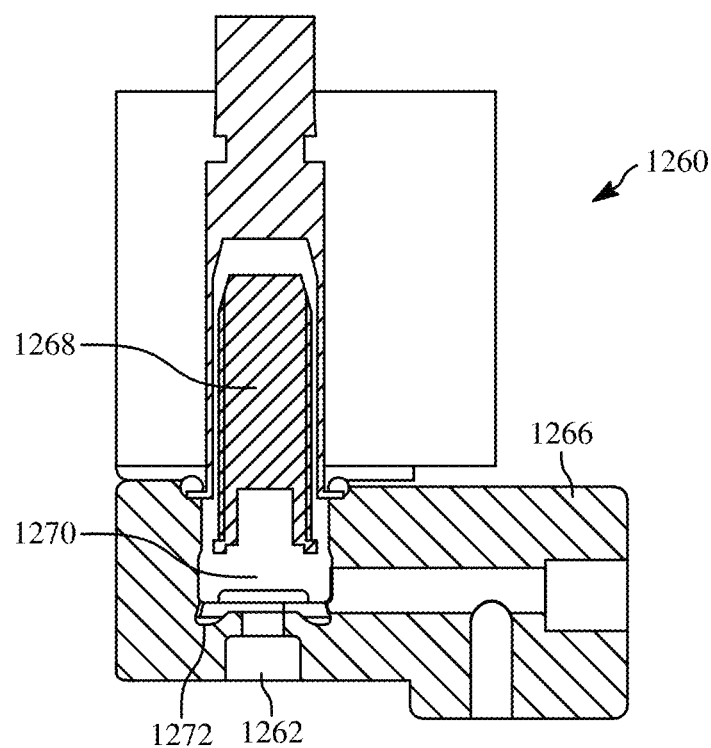
FIG. 12 illustrates an angle valve of a type which may be used as on-off valve in particular embodiments, depicted in section.

FIG. 12 illustrates an angle valve 1260, depicted in section, of the type which may be used as on-off valve in particular embodiments. In particular embodiments, angle valve 1260 may be used instead of a pinch valve 1028. In particular embodiments, an angle valve may be provided with a connector 1262 for being secured to a connector on the vacuum canister (not illustrated), and/or a fitting 1266 that may be connected to the connecting tubing 806, which may in turn be connected to the aspiration catheter. By way of example and not limitation, a solenoid 1268 may be present to open and close valve stem 1270 and valve seat 1272. In particular embodiments, the valves may open to permit aspiration and close to block aspiration. In particular embodiments, the valves may open to allow fluid to enter the aspiration tubing and/or aspiration catheter, and/or may close to block the fluid.

Figure 13:
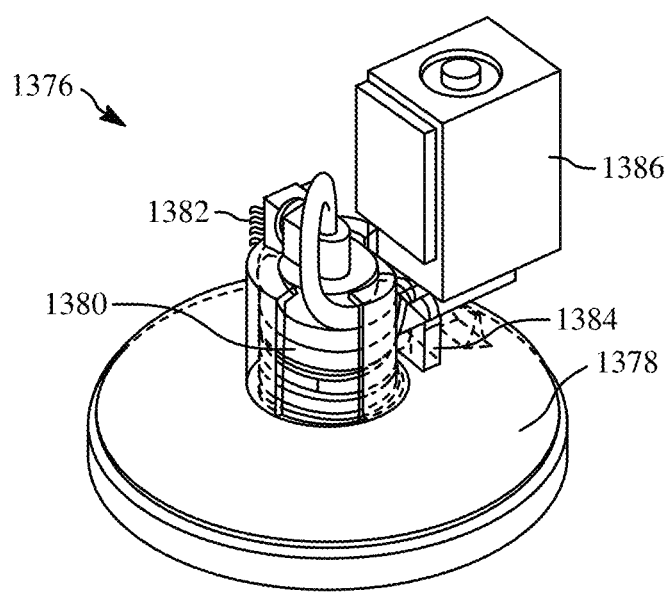
FIG. 13 illustrates an isometric view of an angle valve connected to a coiled tube having pressure sensors at each end thereof mounted on a canister top, according to particular embodiments.

FIG. 13 illustrates an isometric view of an angle valve connected to a coiled tube having pressure sensors at each end thereof mounted on a canister top, according to particular embodiments. In particular embodiments, pressure sensors may be integrated into a single base unit 1376, which may be fixedly attached to a canister cap 1378. By way of example and not limitation, the illustration of FIG. 13 depicts a first pressure sensor 1382 and a second pressure sensor 1384, which may be attached to opposite ends of a coiled flow tube 1380 so that differential pressure may be measured. In particular embodiments, an angle valve 1386 may be secured directly to an outlet of the coiled flow tube 1380, such as to provide for the desired on/off flow control.

In particular embodiments, the controller 1020 may implement an algorithm that may receive and/or analyze pressure sensor data. By way of example and not limitation, such data may be used by controller 1020 to open and close one or more valves, such as an on-off valve. By way of example and not limitation, a valve may be a pinch valve 1028 (e.g., FIG. 10), and/or an angle valve 1386 (e.g., FIG. 13) and/or 1260 (e.g., FIG. 12). In particular embodiments, an algorithm may receive and/or analyze pressure data input at high frequencies or repetition rates. By way of example and not limitation, pressure sensor data may be received and/or analyzed tens, hundreds, or thousands of times per second. In particular embodiments, sensor data, which may not be limited to pressure sensor data, may be compiled to determine particular parameters, such as a diameter of the attached catheter, and/or to determine the contents flowing through the catheter and aspiration tubing, and/or to determine a flow rate.

In particular embodiments, the controller 1020 may implement an algorithm that may use pressure sensor data to analyze the contents flowing through an aspiration catheter, and/or characterizes it as unrestricted flow, restricted flow, or clogged, and/or particular intermediate states. By way of example and not limitation, a catheter with unrestricted flow may be aspirating primarily healthy, clot-free blood, or blood free of vessel-obstructing clot. By way of example and not limitation, a catheter with mixed flow may be aspirating a combination of clot, occlusive material, and blood. By way of example and not limitation, a catheter with little to no flow may be clogged or occluded.

In particular embodiments, if an algorithm determines that an excessive amount of blood may be in the process of being aspirated, as may be the case for a catheter with unrestricted flow, it may restrict aspiration to reduce blood loss. In particular embodiments, if an algorithm determines that a catheter may have restricted flow, it may allow full aspiration. In particular embodiments, if an algorithm determines that a catheter may have little to no flow, it may initiate an extraction cycle, such as to help remove any clogs or occlusions. By way of example and not limitation, as used herein, the term "clot" may be understood to encompass any occlusive material found in vasculature, such as thrombus, embolus, plaque, occlusive material, vessel blockage, or any other obstructive material. "Clot" may be used to reference any combination of such occlusive material in particular instances described here, for brevity's sake.

Figure 14:
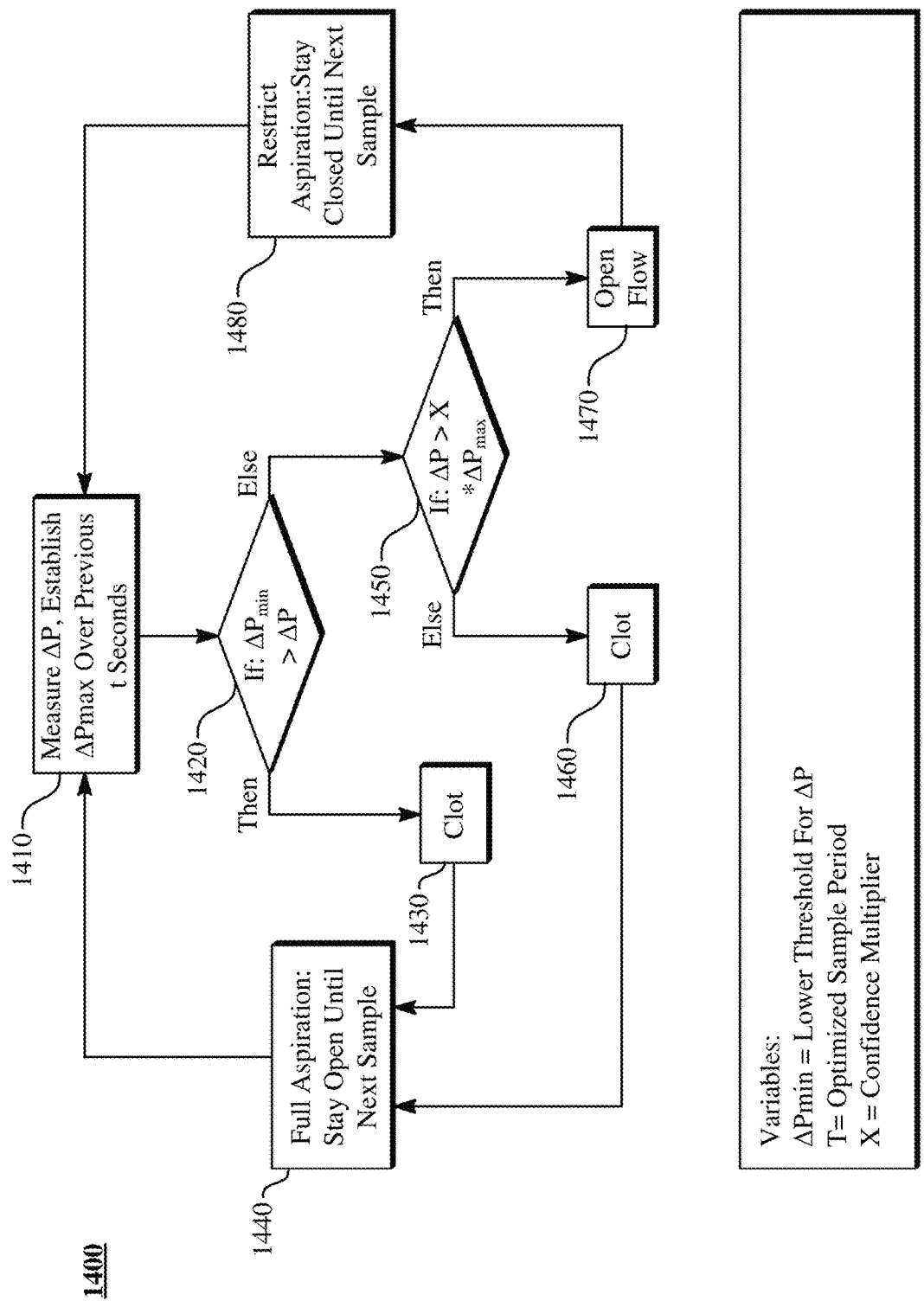
FIG. 14 illustrates an embodiment of an algorithm suitable for use with pressure differentials, according to particular embodiments.

FIG. 14 illustrates an embodiment of an algorithm suitable for use with pressure differentials, according to particular embodiments. By way of example and not limitation, an embodiment 1400 of an algorithm may be suitable for use with pressure differentials ("AP") to determine flowrate, and/or control the one or more valves, for example, based on the determined flowrate.

In particular embodiments, a first step 1410 may be to measure maximum and minimum pressure differential windows over some assessment time period and, after the assessment period, take an instantaneous pressure differential and compare it to such maximum and minimum pressure differential windows. In particular embodiments, the maximum and/or minimum pressure differential windows may be incrementally updated. In particular embodiments, at a step 1420, if the instantaneous pressure differential is determined to be lower than a minimum pressure differential of the assessment period, the algorithm may determine at a step 1430 that the system is in clot, and/or may instruct the system to continue full aspiration, such as by keeping one or more valves (e.g., on-off valves) open until the next sample, at step 1440. On the other hand, according to particular embodiments, if the instantaneous pressure differential is determined to be above the minimum pressure differential, the algorithm may determine at step 1450 whether the instantaneous pressure differential is above a threshold pressure differential. By way of example and not limitation, a threshold pressure differential may be a product of the maximum pressure differential multiplied by a confidence multiplier 'X'. In particular embodiments, 'X' may separately or additionally correspond to or include a correction factor and/or a factor of safety.

In particular embodiments, if the instantaneous pressure differential is not determined to be above the threshold pressure differential at step 1450, the algorithm may determine at step 1460 that the system is in clot, and/or may allow full aspiration. In particular embodiments, if the instantaneous pressure differential is instead determined to be above the threshold pressure differential at step 1450, the algorithm may determine open flow conditions at step 1470, and/or may restrict aspiration to limit blood loss at step 1480, such as by entering a sampling state where aspiration is limited to brief surges to make new instantaneous pressure differential readings. In either case, in particular embodiments, whenever aspiration is allowed, the algorithm may continually take instantaneous pressure differential readings, and/or compare them to the maximum and minimum pressure differentials which may be collected throughout the procedure. In particular embodiments, when unrestricted flow (e.g. open flow) is detected, the algorithm may trigger a sampling state. In particular embodiments, when a clot is detected, the algorithm may initiate full aspiration, or initiate an extraction cycle with pulsed aspiration.

In particular embodiments, a correlation algorithm is utilized that determines whether a catheter has unrestricted flow, restricted flow, or is clogged, e.g. the catheter's state, based on a correlation between flow rate and such states. In particular embodiments, a windowing algorithm may be utilized that may analyze discrete portions of pressure sensor data, such as to establish local minimum and/or local maximum pressure sensor readings. These windowed minima and maxima may be compared to global minima and global maxima across the data set. By way of example and not limitation, for a sudden large change (delta) in pressure readings, the system may preferentially make determinations of a catheter's state according to local minima and/or local maxima. In particular embodiments, pressure readings below minima and above maxima may signify a change in catheter state, e.g. below a minimum may indicate a clogged catheter, and/or above a maximum may indicate an unrestricted flow state.

In particular embodiments, an algorithm may be utilized emphasizing an analysis of standard deviations across a discrete window of data points. In particular embodiments, an ongoing flow rate signal may be compared to a mean flow rate, e.g., a running average. By way of example and not limitation, a small standard deviation may indicate that a catheter is clogged or unrestricted, while a large standard deviation may indicate that a catheter has restricted flow.

In particular embodiments, a learning algorithm may be used to determine the contents flowing through an aspiration catheter. By way of example and not limitation, training data may be formed by collecting pressure readings along the length of catheter in a variety of states, e.g. unrestricted flow, restricted flow, or clogged. Numerous pressure readings may be recorded for each catheter state, and the algorithm may then reference such data sets to interpret never-seen pressure readings, and/or to predict the state of the catheter and/or its flow.

In particular embodiments, an artificial neural network (ANN) may be utilized that may employ a multinomial logistic regression algorithm. In particular embodiments, the ANN may be trained to predict answers by considering numerous training data sets. By way of example and not limitation, the training data may include both observed data as inputs and the actual outputs. In particular embodiments, the inputs may be propagated across the ANN, which may be comprised of layered nodes that may each represent a linear transformation within the solution space. In particular embodiments, the ANN may then "learn" by analyzing differences between the ANN's calculated output and the actual output (e.g., ground truth). In particular embodiments, this difference may be translated into an error function, and/or may be backpropagated across the ANN, whereby the weight of each node may be modified according to its contribution to the error function. Weighting is a process of mathematical optimization that may establish which nodes may optimally map inputs to their correct outputs.

In particular embodiments, numerous sets of training data may be propagated across the ANN iteratively until the error function reaches convergence, i.e. an acceptable and/or predetermined level of tolerance. In particular embodiments, once the nodes have been properly weighted, in that the error function has reached convergence, the ANN may accurately predict the output of previously unseen input. By way of example and not limitation, this may mean that the trained or learned ANN may take novel pressure sensor data inputs and accurately predict catheter size, and/or whether a catheter's contents may be classified as unrestricted, restricted, clogged, and/or particular intermediate states.

In particular embodiments, an algorithm may employ semi-supervised and unsupervised learning to continually update node weights. In particular embodiments, an algorithm may employ clustering, dimensionality reduction, and/or reinforcement learning to improve prediction accuracy. In particular embodiments, an algorithm may accurately interpret pressure fluctuations associated with switching between catheters of different diameters, and/or may filter out pressure fluctuations generated by manual movements of a separator within the aspiration catheter, such as by determining and accounting for the cadence of the movement. Particular embodiments may employ one or more algorithms that may use a combination of the above algorithmic flow analysis techniques.

In particular embodiments, an algorithm may initiate a sampling mode when unrestricted flow is detected. In particular embodiments, an algorithm may detect a change in flow, such as indicating unrestricted flow, within a short period of time. By way of example and not limitation, such a short time interval may span milliseconds. In particular embodiments of the sampling mode, the algorithm may cycle off aspiration, and/or may open and close the on-off valve at a predetermined frequency. In particular embodiments, a sampling state may conduct an aspiration surge when the valve is briefly opened, and/or may make an assessment of the pressure sensor readings. By way of example and not limitation, based on such an aspiration surge, an algorithm may determine whether the system should revert to full aspiration, such as with an on-off valve in the open position, or remain in the sampling state. By way of example and not limitation, such sampling surges may occur over a millisecond order of magnitude, and/or may ensure that full aspiration occurs only when the system is engaging clot, and may thereby minimize blood loss.

In particular embodiments, upon being powered on, the system may have a brief delay before the algorithm assesses flow in the aspiration tubing. By way of example and not limitation, if the sensors indicate an unrestricted flow, then an appropriate delay of time may be calculated for which one or more valves, such as an on-off valve, may remain closed. In particular embodiments, after a brief delay, one or more valves, such as an on-off valve, may be opened to briefly allow aspiration, and/or to sample pressure readings in the aspiration tubing. By way of example and not limitation, by doing so, the system may assess whether the system may still have unrestricted flow, or if it may have been positioned into clot, and/or other occlusive material. In particular embodiments, if the sampling detects unrestricted flow, a new delay may be calculated. In particular embodiments, such a new delay may be determined to be incrementally longer for each consecutive reading, up to a threshold. In particular embodiments, if the sampling detects a restricted flow, for example, due to a clog, an appropriate delay of time may be calculated for which one or more valves, such as an on-off valve, may remain open. While open, in particular embodiments, the system may assess pressure sensors readings, such as at a regular frequency, to determine whether the system may have been positioned such to cause unrestricted flow. In particular embodiments, some, all, or a combination of these processes may repeat until the procedure is finished.

In particular embodiments, an extraction cycle may be useful to clear occlusions in an aspiration catheter, and/or to facilitate aspiration of clot that may be too large, or otherwise difficult to aspirate. In particular embodiments, an extraction cycle may establish pressure differentials between the aspiration catheter and the vacuum source. In particular embodiments, pressure differentials may be alternated or cycled in time, such as to generate pressure pulses. In particular embodiments, pressure pulses may employ multiple mechanisms to facilitate thrombus ingestion into an aspiration catheter. By way of example and not limitation, according to a mechanism, a pressure pulse may introduce an acceleration component, which may facilitate the extraction of occlusive material. By way of example and not limitation, according to a mechanism, a pressure pulse may create a force impulse, which may break static friction momentarily, which may in turn allow a lower dynamic friction to ingest thrombus. By way of example and not limitation, according to a mechanism, a pressure pulse may move a thrombus away from the distal tip of the catheter, and/or subsequently rapidly force contact between the thrombus and the catheter, which may macerate the thrombus.

In particular embodiments, an extraction cycle may alternate between providing vacuum aspiration and relative positive pressure. In particular embodiments, an extraction cycle may be initiated when an aspiration catheter is already under full vacuum. In particular embodiments, when an extraction cycle is initiated, a vacuum on-off valve between the catheter and the aspiration source may be closed, and the pressure in the aspiration catheter may be increased. By way of example and not limitation, this may cause a positive pressure pulse and establish a pressure differential between the vacuum source and the catheter. In particular embodiments, when the on-off valve is opened, the contents and the distal tip of the aspiration catheter may experience the pressure differential as a negative pressure pulse. By way of example and not limitation, a negative pressure pulse may negatively impact the structural integrity of any occlusions, such as to a degree that a static force may only achieve with a greater supply of energy. In particular embodiments, an amplitude, or magnitude, of pressure pulses may be directly correlated to a pressure differential between an evacuated catheter and a pressure source (e.g., for positive pressure pulses), and a pressurized catheter and a vacuum source (e.g., for negative pressure pulses). In particular embodiments, a frequency or timing with which one or more valves, such as an on-off valve, may open and/or close may be predetermined, or responsive to pressure sensor data, or any combination thereof. By way of example and not limitation, an extraction cycle's pressure pulses may have an amplitude, frequency, and/or other parameters optimized to extract thrombus and/or other occlusive material from vasculature.

Pressure differentials in a catheter may be generated in a number of ways. By way of example and not limitation, in particular embodiments, pressure, pressure waves, and/or pressure differentials may be generated by closing off a catheter's access to a vacuum source. In particular embodiments, pressure, pressure waves, and/or pressure differentials may be generated by introducing a fluid medium into the catheter (e.g., FIGS. 15-18). By way of example and not limitation, a fluid medium may be introduced at a pressure between full vacuum and ambient pressure, or at an ambient pressure, or at a systolic pressure of a patient, or above a systolic pressure, or at any other pressure suitable for one or more purposes disclosed herein. In particular embodiments, pressure differentials may be generated by mechanical displacement of a pressure chamber (e.g., FIG. 19).

In particular embodiments, an extraction cycle may be automatically initiated when an algorithm of the controller 1020 detects a clogged catheter, an occluded catheter, or a catheter positioned in clot. By way of example and not limitation, a catheter may be identified as being in a clogged state when the pressure differentials approach zero. In particular embodiments, the controller may automatically initiate an extraction cycle after the system has detected a clog lasting for more than a predetermined time interval. By way of example and not limitation, such as 5 seconds. Alternatively, an extraction cycle may be initiated, and/or terminated, on demand by a user. In particular embodiments, an extraction cycle may provide pressure pulses for a predetermined time period. Additionally or alternatively, in particular embodiments, an extraction cycle may assess pressure sensor data each time one or more valves, such as an on-off valve, open to assess or sample flow, and/or to determine whether the extraction cycle should continue or end. By way of example and not limitation, if an extraction cycle is initially unsuccessful at clearing a clog, it may vary the amplitude, frequency, and/or other parameters of pressure pulses. In particular embodiments, an algorithm on the controller 1020 may consult a library of different pressure pulses, and may select one or more pressure pulses or pulse parameters from among the contents of a library. In particular embodiments, if specific parameters, such as a specific amplitude and/or frequency, starts to clear a clog, the algorithm may continue to generate pressure pulses of those parameters, such as that frequency and/or amplitude, until the clog is cleared.

Figure 15:
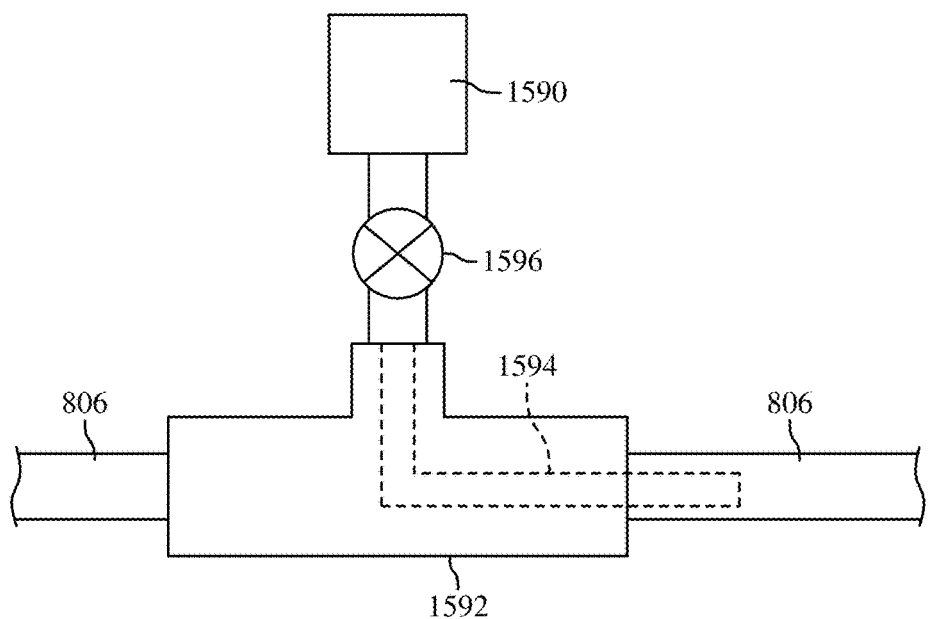
FIGS. 15-19 illustrate exemplary pulsed fluid injection assemblies suitable for use in particular embodiments.

FIGS. 15-19 illustrate exemplary pulsed fluid injection assemblies suitable for use in particular embodiments. FIG. 15 illustrates a fluid system that may be used in particular embodiments to generate pressure differentials, and thus pressure pulses. In particular embodiments, a fluid introduction unit 1590 may be attached along a length of the connection tubing 806 having a three-way or three-point junction 1592. In particular embodiments, three-point junction 1592 may be positioned between base unit 810 and external unit 804, or may be positioned distal to both the base unit 810 and the external unit 804. In particular embodiments, three-point junction 1592 may be positioned in close proximity to an attached aspiration catheter. In particular embodiments, a fluid injection on-off valve 1596 may control the flow of fluid (either liquid or gas) to inject pressure pulses. By way of example and not limitation, such introduction of pressure pulses into the flow path of a clot may facilitate the dislodging, extraction, and/or removal of clot or other occlusive substances. In particular embodiments, the flow of a fluid medium may be introduced directly into connection tubing 806. In particular embodiments, the flow of a fluid medium may first traverse an injection tubing 1594 before entering the connection tubing 806. In particular embodiments, injection tubing 1594 may direct pressure pulses towards the catheter, which may optimize the pressure pulse. In particular embodiments, the three-point junction 1592 may have a T-joint structure, such as illustrated in FIG. 14 by way of example and not limitation. Alternatively, in particular embodiments, a three-point junction may have a Y-joint structure (not illustrated). By way of example and not limitation, a Y-joint may beneficially direct fluid from the fluid introduction unit towards the catheter, which may optimize the pressure pulse in a similar manner to the injection tubing of the prior example.

Figure 16:
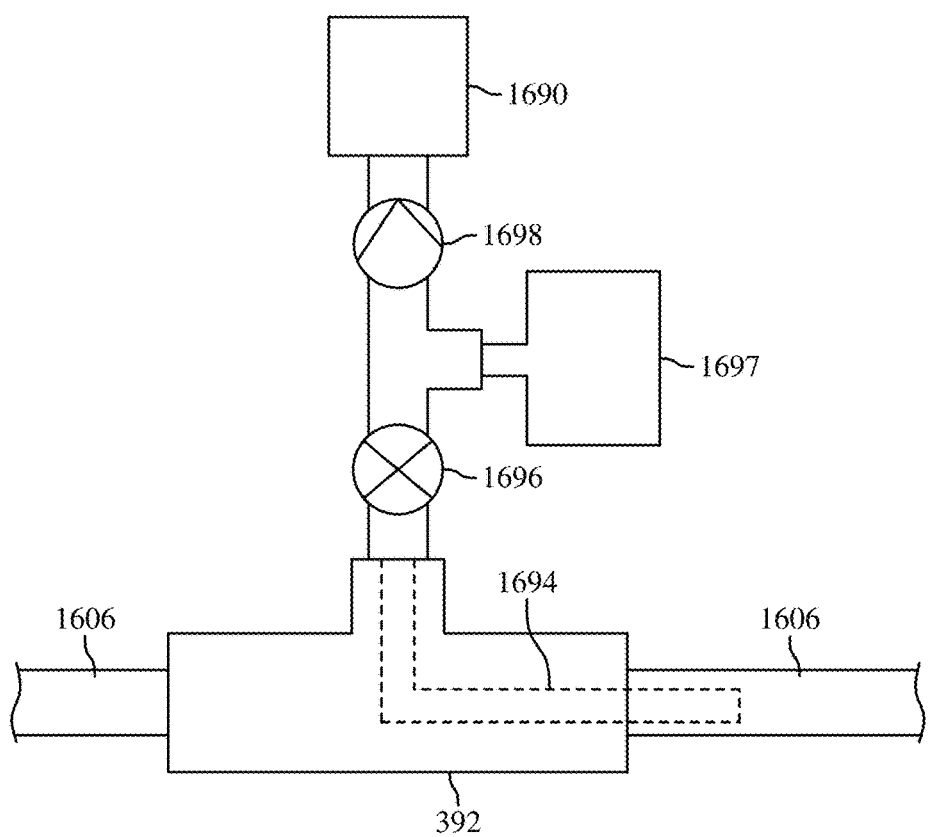

FIG. 16 illustrates a fluid system that, in particular embodiments, may use a pump 1698. In particular embodiments, pump 1698 may be connected between a fluid reservoir 1690 and an injection valve 1696. In particular embodiments, the pump 1698 may cycle on when injection valve 1696 opens. By way of example and not limitation, the pump may provide work by forcefully injecting a fluid medium from a fluid reservoir 1690, for example, through an injection valve 1696 (e.g., an on-off valve), into an injection tube 1694 and/or connection tubing 1606. In particular embodiments, a magnitude of the positive pressure of a pressure pulse may be directly correlated to a throughput (e.g., size) of the pump 1698. In particular embodiments, a pressure chamber 1697 may be positioned between pump 1698 and injection valve 1696. In particular embodiments, a pressure chamber 1697 may allow pump 1698 to provide work even when the injection valve 1696 is closed. By way of example and not limitation, while injection valve 1696 is closed, the pump 1698 may forcefully inject a fluid medium from reservoir 1690 into pressure chamber 1697, whereby pressure chamber 1697 may become pressurized. In particular embodiments, when injection valve 1696 opens, pressure may be released from pressure chamber 1697 into injection tube 1694 and/or connection tubing 1606. In particular embodiments, since the pump 1698 may build up pressure over time, a magnitude of the positive pressure of a pressure pulse may not be directly correlated to a throughput (e.g., size) of the pump 1698, which may allow for a smaller pump in some particular embodiments. To provide even greater control over the duration or magnitude of positive pressure pulses, in particular embodiments, the opening and closing of the injection valve may be throttled or otherwise manipulated to modulate a rate of injection. In particular embodiments, a pressure sensor may be included in pressure chamber 1697 to monitor and control the buildup of pressure.

Figure 17:
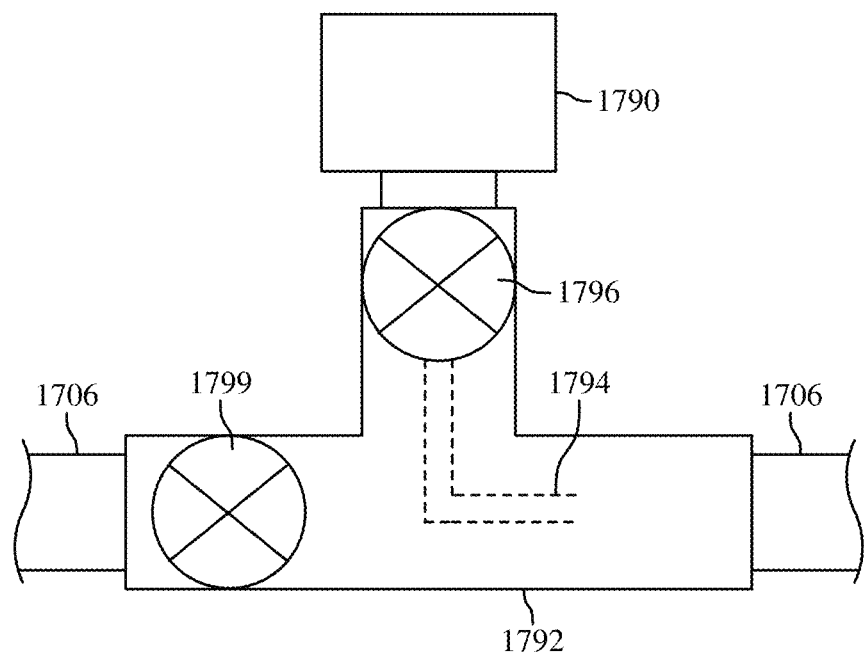

FIG. 17 illustrates another three-point junction 1792 attached along connection tubing 1706, according to particular embodiments. In particular embodiments, a three-point junction 1792 may be positioned between the base unit 810 and external unit 804. In particular embodiments, three-point junction 1792 may be positioned distal to both the base unit 810 and the external unit 804. In particular embodiments, a pressure valve 1796 may control the generation of positive pressure pulses from fluid chamber 1790. By way of example and not limitation, fluid from the fluid chamber 1790 may flow directly into connection tubing 1706, or may first traverse an injection tube 1794 before entering the connection tubing 1706. In particular embodiments, an aspiration valve 1799 may control application of vacuum aspiration from an attached vacuum source.

In particular embodiments, three-point junction 1792 may be provided with one or more valves, for example, to control one or both of vacuum forces and positive pressure pulses. By way of example and not limitation, such a configuration may allow three-point junction 1792 to alternate between applying vacuum aspiration and pressure pulses, wherein a pressure of a pressure pulse may be above that of the vacuum source. In particular embodiments, aspiration valve 1799 and pressure valve 1796 may be opened alternatively, simultaneously, with a delay, in some overlapping sequence, or in a combination thereof. By way of example and not limitation, in an overlapping sequence, one valve may start to open when another valve is starting to close, whereby there may be a brief period wherein both valves may be at least partially open. By way of example and not limitation, in an overlapping sequence, sometimes multiple (e.g., two) valves may be open, and/or multiple (e.g., two) valves may be closed for at least short periods of time.

In particular embodiments, an aspiration valve 1799 may be positioned between a catheter and an aspiration source to modulate aspiration. In particular embodiments, a pressure valve 1796 may be positioned between the catheter and fluid source, for example, to modulate fluid injection. In particular embodiments, both aspiration valve 1799 and pressure valve 1796 may be selectively opened and closed, for example, to create pressure differentials within the catheter and/or aspiration tubing. By way of example and not limitation, selective opening and closing of both aspiration valve 1799 and pressure valve 1796 may be tailored to provide pressure pulses of a desired amplitude and frequency.

Figure 18:
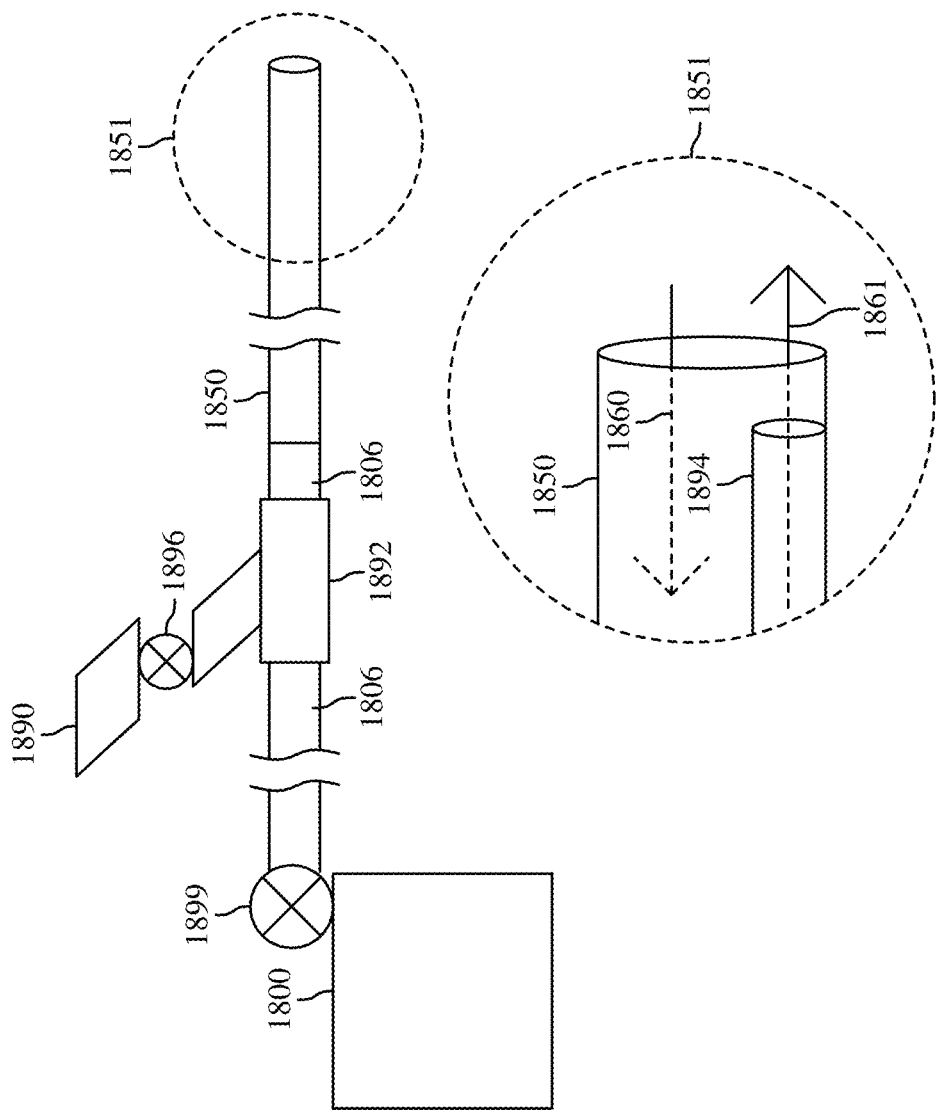

FIG. 18 provides a perspective view of a three-way joint and the components it connects, according to particular embodiments. In particular embodiments, a connection tubing 1806 may act as a common conduit between a vacuum source 1800, a pressure source 1890, and an aspiration catheter 1850. In particular embodiments, connection tubing 1806 may have a first end configured to attach to, and/or be placed in fluid communication with, a vacuum source. In particular embodiments, connection tubing 1806 may have a second end configured to attach to, or be placed in fluid communication with, an aspiration catheter. In particular embodiments, the second end may be attached to the aspiration catheter with a rotating hemostasis valve. In particular embodiments, a three-way joint 1892 may be positioned proximate to the second end, for example, to provide pulses of relative positive pressure near the aspiration catheter 1850. In particular embodiments, three-way joint 1892 may be an angled joint or a Y-joint, whereby fluid from the pressure source may be directed towards the aspiration catheter 1850. In particular embodiments, three-way joint 1892 may include injection tubing 1894, which may direct fluid from the pressure source towards the aspiration catheter 1850. In particular embodiments, the injection tubing 1894 may extend from the three-way joint into the aspiration catheter, whereby fluid may flow from the pressure source into the aspiration catheter 1850. In particular embodiments, the injection tubing 1894 may extend from the three-way joint to a position proximate a distal end of the aspiration catheter 1850, for example, as depicted in perspective 1851, which illustrates a schematic zoomed-in perspective of the distal end of the aspiration catheter 1850. In particular embodiments, the pressure source may cause fluid to flow according to directional arrow 1861, and the vacuum source may cause fluid to flow according to directional arrow 1860. In particular embodiments, the controller may modulate a vacuum valve 1899 and a pressure valve 1896, whereby a closing of vacuum valve 1899 and an opening of the pressure valve 1896 may result in a relative increase in pressure at a distal tip of an aspiration catheter.

Alternatively, in particular embodiments, an opening of vacuum valve 1899 and a closing of pressure valve 1896 may result in a relative decrease in pressure at the distal tip of the aspiration catheter 1850. In particular embodiments, these changes in pressure may be transmitted along a length of the aspiration catheter as a pressure pulse. In particular embodiments, a controller may close vacuum valve 1899 and open pressure valve 1896 for a small period of time. By way of example and not limitation, this may allow a minimal volume of fluid from the pressure source 1890 to be introduced into a proximal end of aspiration catheter 1850, such as to increase the relative pressure at a distal end of the aspiration catheter 1850, before reverting to vacuum by re-opening vacuum valve 1899 and closing pressure valve 1896.

In particular embodiments, a controller may close vacuum valve 1899 and open pressure valve 1896 for a longer period of time, for example, allowing a larger volume of fluid from the pressure source 1890 to be introduced into the aspiration catheter 1850. By way of example and not limitation, this may facilitate a movement of obstructive material away from the distal end of aspiration catheter, before reverting to vacuum by re-opening vacuum valve 1899 and closing pressure valve 1896. In particular embodiments, connection tubing 1806 may have multiple lumens, e.g., dual lumens, along a portion of its length, whereby one lumen, for example, may accommodate fluid, and a second lumen may accommodate connection wiring, which may enable the controller to modulate the vacuum valve 1899 and/or the pressure valve 1896.

Figure 19:
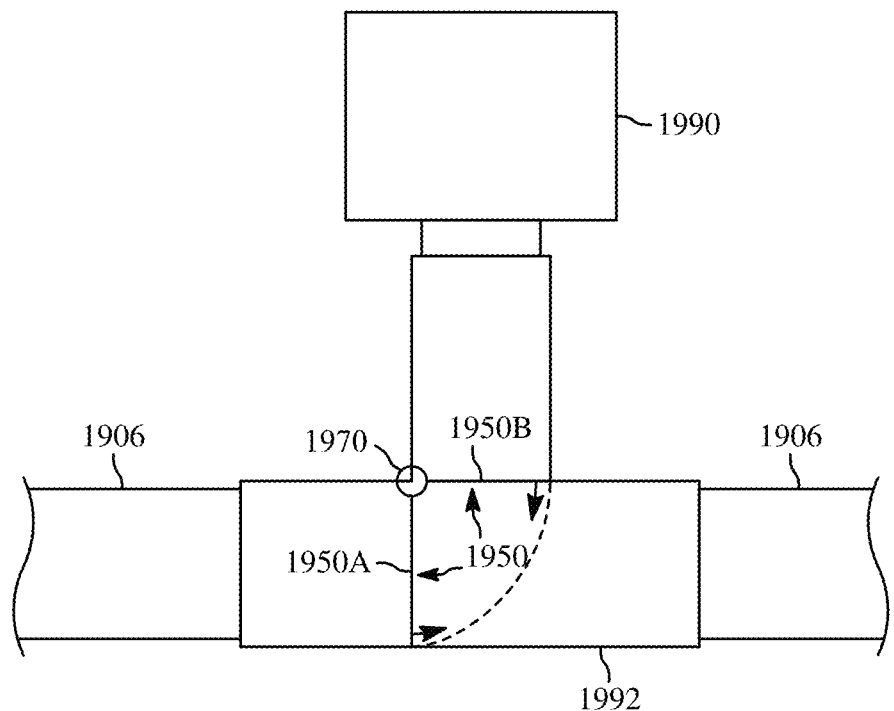

FIG. 19 illustrates a valve structure that controls both aspiration forces and positive pressure pulses, according to particular embodiments. In particular embodiments, a three-point junction 1992 may attach to connection tubing 1906 and pressure chamber 1990. In particular embodiments, a gate valve 1950 (illustrated, without limitation, as being in positions 1950A or 1950B) may translate and/or rotate, e.g. at or about axis 1970, to block aspiration in a 1950A position, and/or to block fluid introduction in a 1950B position. In particular embodiments, gate valve 1950 may provide pulsed aspiration. By way of example and not limitation, gate valve 1950 may oscillate back and forth at a predetermined and/or responsive frequency, such as may be controlled by an algorithm in the controller 1020. In particular embodiments, the three-way gate valve may be provided at a juncture between the aspiration source, the pressure source, and the catheter. In particular embodiments, gate valve 1950 may translate between blocking the aspiration source and blocking the pressure source, for example, to effect pressure pulses of desired parameters, such as a desired amplitude and/or frequency.

In particular embodiments, fluid injection may not occur at a three-point juncture, but may rather occur at a more distal region closer the catheter tip. By way of example and not limitation, a location of relative pressure injection may be used to optimize a pressure pulse variation, in order to facilitate clot removal. In particular embodiments, a distal region of an aspiration catheter may include a valve that may be opened and closed, for example, a distal valve. In particular embodiments, an aspiration valve may be closed, and the distal valve may be opened to allow blood to enter the catheter, which may increase pressure in the catheter and/or amplify a pressure differential between the catheter lumen and the vacuum source. By way of example and not limitation, the distal valve may be then closed, and the aspiration valve may be opened, wherein the pressure differential between the vacuum source and the catheter may result in a pressure pulse. In particular embodiments, fluid may be transferred into an aspiration catheter from another adjacent catheter. By way of example and not limitation, an inner catheter may deliver fluid to an outer aspiration catheter. In particular embodiments, an outer catheter may deliver fluid to an inner aspiration catheter through a valve structure. In either case, for example, a fluid medium may be delivered along the length of the aspiration catheter, rather than through a proximal end. In particular embodiments, an adjacent catheter may offer an alternative or additional connection to a vacuum source.

Figure 20:
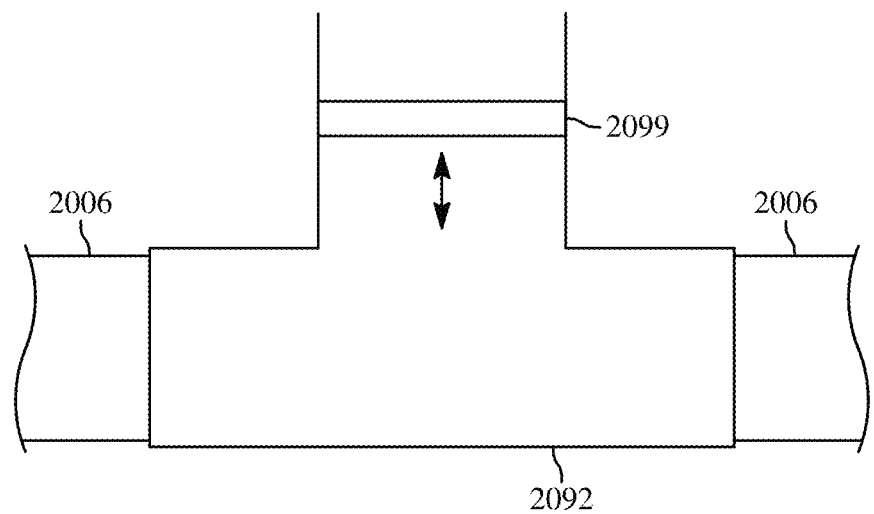
FIG. 20 illustrates a mechanical displacement assembly for manipulating pressure in particular embodiments.

FIG. 20 illustrates a mechanical displacement assembly for manipulating pressure, according to particular embodiments. In particular embodiments, a mechanical piston 2099 may supplement or replace the injection valves previously described herein, as well as pressure chambers, pumps, and/or fluid reservoirs. By way of example and not limitation, a stroke of the piston 2099 or alternative mechanical device may be controlled to adjust the volume of the catheter, which may result in generation of a negative pressure on one stroke, and/or generation of a positive pressure during a stroke with an opposite direction. In particular embodiments, a mechanical actuation device may actuate back and forth, for example, to alternately increase and decrease an overall volume of the system. By way of example and not limitation, when the device may actuate to increase volume, pressure may decrease, and/or when the device may actuate to decreases volume, pressure may increase. In particular embodiments, such pressure changes may create, amplify, and/or assist pressure pulses of an extraction cycle. In particular embodiments, piston 2099 may be provided in conjunction with a three-point juncture 2092. By way of example and not limitation, a three-point juncture 2092 may attach to connection tubing 2006. By way of example and not limitation, other mechanical means of controlling volume, or pressure, of the catheter may include linear motors, stepper/servo motors, cam follower actuators, solenoids, audio exciters, voice coil actuators, diaphragms, peristaltic pumps, rotary vanes, gears, screws, syringes etc., or any combinations thereof.

In particular embodiments, pressure pulses, e.g., high frequency pressure pulses, may be enabled by a mechanical method, such as that illustrated in FIG. 20. By way of example and not limitation, to provide high frequency pressure pulses, a catheter must be rapidly pressurized and/or rapidly evacuated. In particular embodiments, the fluid injection systems of FIGS. 15-19 may readily provide a rapid influx of pressure; however, in particular embodiments, it may take a non-insignificant amount of time for a vacuum source to reduce a catheter pressure back to full, or near full, vacuum. By way of example and not limitation, if a subsequent influx of pressure were to occur too early, a catheter may not have sufficient time to reach full vacuum, or near full vacuum. In such a scenario, in particular embodiments, a pressure differential between the not-quite-evacuated catheter and the pressure source may be lower, and the resulting pressure pulses may have a lower amplitude. In particular embodiments, lower pressure differentials and/or lower amplitude pressure pulses may be suboptimal in some scenarios. In particular embodiments, to avoid low amplitude pressure pulses, which may be caused, for example, by a high frequency, a vacuum recovery system may be utilized. In particular embodiments, a vacuum recovery system may reduce the time required to return a catheter to full vacuum, for example, after an influx of positive pressure. In particular embodiments, with a vacuum recovery system, pressure pulses may be enabled having both a high amplitude and a high frequency.

FIG. 20 illustrates a device that may function as a vacuum recovery system by generating pressure differentials, according to particular embodiments. In particular embodiments, a vacuum recovery system may utilize a syringe, an evacuated chamber, a second aspiration pump, or some combination of these or other suitable options. By way of example and not limitation, a syringe may be a piston actuated device, which may retract to increase a system's volume (and thereby decrease pressure). By way of example and not limitation, a syringe may advance to decrease a system's volume (and thereby increase pressure). In particular embodiments, a syringe-like device may beneficially assist not only vacuum recovery, but may also assist positive pressure pulse generation. In particular embodiments, a syringe may be used during an extraction cycle. In such embodiments, a catheter may start at full, or near full, vacuum. By way of example and not limitation, as the vacuum source may close, the syringe may advance (for example, to reduce system volume), and, optionally, a fluid medium may be injected. In particular embodiments, one or more of such measures may facilitate the formation of a positive pressure pulse. By way of example and not limitation, next, the vacuum source may open, and the syringe may retract (for example, to increase system volume) to generate a negative pressure pulse, whereby the syringe may speed the catheter's return to near full vacuum. In particular embodiments, an aspiration pump may be configured to selectively prime an evacuated chamber that is opened to the catheter, alternatively or in addition to an aspiration pump, after each pressure pulse. In particular embodiments, the aspiration pump and the evacuated chamber together may more rapidly return a catheter to full vacuum. By way of example and not limitation, while the aspiration pump may be closed to the catheter, it may be opened to the evacuated chamber, for example, to further prime the evacuated chamber between pressure pulses. In particular embodiments, a secondary aspiration pump may assist a primary aspiration pump, for example, to facilitate vacuum recovery after each pressure pulse.

Figure 21:
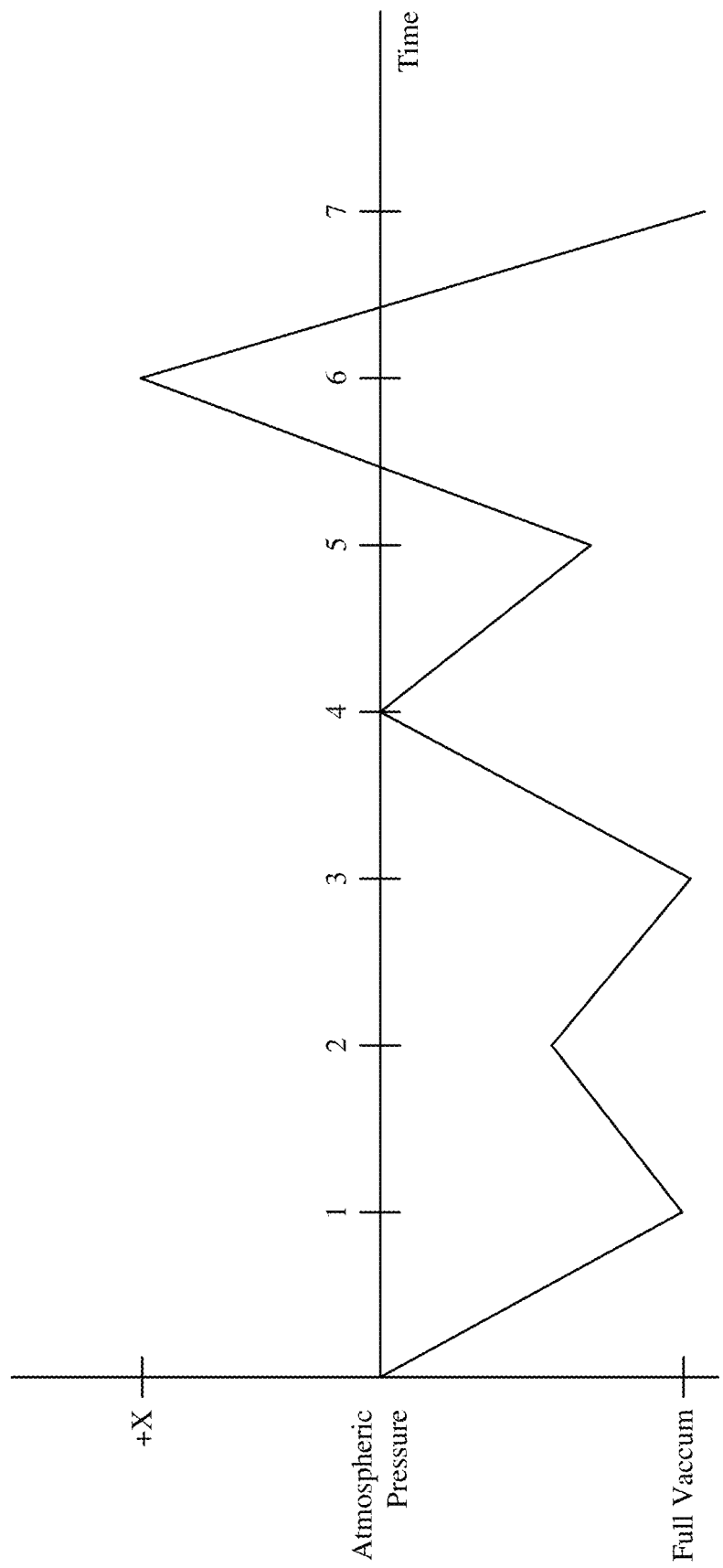
FIG. 21 illustrates a graphical representation of a particular embodiment of pulsed aspiration, where catheter internal pressure is varied over time.

FIG. 21 illustrates a schematic graphical representation of a particular embodiment of pulsed aspiration, where catheter internal pressure may be varied over time. In particular embodiments, an extraction cycle may use a pulsation protocol, for example, to systemically manipulate the amount of pressure within a catheter, and/or to facilitate the extraction of occlusive material.

Pressure in a catheter may be manipulated by a variety of methods. By way of example and not limitation, vacuum aspiration may be used to reduce pressure within the catheter. In particular embodiments, removal of vacuum suction and/or the introduction of fluid may be used to increase pressure within the catheter. In particular embodiments, a mechanically actuating device may alternate between increasing and decreasing pressure within a catheter. In particular embodiments, such as illustrated by FIG. 21, at time 0, the catheter may not have been subjected to any suction forces. By way of example and not limitation, the catheter may be at atmospheric pressure at time 0. From time 0 to time 1, the catheter may have lost pressure, dropping from atmospheric pressure to near full vacuum (i.e., near −29.9 inHg), for example. From time 1 to time 2, the catheter may have gained pressure, which decreases vacuum strength. From time 2 to 3, the catheter may have lost pressure, which may return the catheter to near full vacuum. From time 3 to 4, the catheter may have gained pressure, and returned to ambient pressure, for example. From time 4 to 5, the catheter may have lost pressure, again decreasing from atmospheric pressure to near full vacuum. From time 5 to 6, the catheter may have gained pressure, which may have caused the pressure to rapidly increase from near full vacuum to above ambient pressure. From time 6 to 7, the catheter may have lost pressure, such as rapidly dropping from a pressurized state above atmospheric pressure to near full vacuum.

In particular embodiments, a pulsation protocol, such as illustrated in FIG. 21 by way of example and not limitation, may be executed once, or may be repeated several times. In particular embodiments, the pulsation protocol may include one or more time periods with additional pressure variations and/or pressure patterns. In particular embodiments, the system's pressure may vary from between near vacuum to above average systolic pressure. In particular embodiments, a duration of a pulsation protocol may be predetermined, and/or may be adaptive to pressure sensor readings. In particular embodiments, the controller may prolong or shorten a pulsation protocol, for example, based on pressure sensor readings. In particular embodiments, the system may remain at a stable pressure state across one or more time periods. By way of example and not limitation, the controller may cause the system to dwell at near full vacuum. In particular embodiments, a dwell time in each pressure state, and/or a frequency with which the system transitions between pressure states, may be optimized to ingest, dislodge, macerate, and/or remove different clot or occlusive material compositions. Although FIG. 21 illustrates a pulsation protocol with a particular frequency, such as a stable and consistent frequency, in particular embodiments the frequency of a pulsation protocol may be variable, and/or some combination of partially stable and partially variable frequency.

In particular embodiments, high amplitude (or high magnitude) pressure pulses may be generated by generating large pressure differentials. By way of example and not limitation, FIG. 21 illustrates a high amplitude pressure pulse between times 5 and 7. In particular embodiments, lower magnitude pressure pulses may be generated, for example, by oscillating between less extreme high pressures and low pressures. By way of example and not limitation, a low end of the pressure pulse may not reach near full vacuum, a high end of the pressure pulse may not reach ambient pressure, or both. In particular embodiments, such a reduced pressure range may result in a lower magnitude pressure pulse, which may be desirable in some scenarios. By way of example and not limitation, the time units of FIG. 21 may be in seconds, milliseconds, microseconds, or a different time scale.

In particular embodiments, an extraction cycle may use a predetermined series of pressure pulses, for example, with near full vacuum aspiration before the extraction cycle, between individual pulses of relative positive pressure, and/or after the extraction cycle. In particular embodiments, pressure pulses may be selected from a library of pressure pulses having parameters, for example amplitudes and/or frequencies, that may facilitate the extraction of clot and/or other occlusive material. In particular embodiments, a series of pressure pulses may vary from one another in terms of frequency, amplitude, or both. By way of example and not limitation, a pulsation protocol may use a series of pressure pulses with a trend wherein one or more pressure parameters, such as amplitude and/or frequency, may rise while another diminishes. By way of example and not limitation, a pulsation protocol may comprise a series of pressure pulses where both the amplitude and frequency rise or diminish, or where one of the amplitude or frequency rises or diminishes while the other remains constant.

In particular embodiments, an extraction cycle may provide specific pressure pulses, for example, based on pressure sensor readings. By way of example and not limitation, a responsive extraction cycle may measure pressure within the catheter, and then may select one or more pressure pulses optimized for a catheter with those pressure readings. By way of example and not limitation, in another responsive extraction cycle, the system may cycle through a library of pressure pulse protocols, such as with time periods of static or full aspiration and occlusion detection after each individual pressure pulse. In particular embodiments, after the library has been cycled, the system may repeat the pressure pulses that were measured or otherwise determined to be most successful. By way of example and not limitation, a degree of success of a specific pressure pulse may be commensurate with an amount of increased flow rate after the pressure pulse. In particular embodiments, the system may continue to cycle down until only a few pressure pulse protocols remain in the loop. In particular embodiments, if the efficacy of a loop begins to diminish, the system may return to the full library and initiate a fresh cycle.

In particular embodiments, a responsive extraction cycle may have three modes: cycling up, wherein successive pressure pulses may be stronger in terms of amplitude and/or frequency; cycling down, wherein successive pressure pulses may be weaker in terms of amplitude and/or frequency; and maintenance pressure pulses, wherein pressure pulses may have a consistent frequency and/or amplitude. In particular embodiments, when the system detects a clogged state, it may enter a cycling up mode. In particular embodiments, when the system detects a restricted flow state, it may enter a maintenance mode. In particular embodiments, when the system detects an unrestricted flow state, it may enter a cycling down mode.

In particular embodiments, in situations where maximizing the removal of occlusive material may be more important in particular cases than concerns of blood loss, such as particular cases during neurovascular stroke procedures, an alternative embodiment may be useful. Under such circumstances, in particular embodiments, an optimal technique may include positioning the distal end of a catheter in clot, applying full vacuum, and waiting a predetermined period of time before advancing to a next step. In particular embodiments, an objective may be complete, or nearly complete, catheter tip engagement of a mass of occlusive material. By way of example and not limitation, such engagement may essentially clog the distal end of the catheter, and is sometimes referred to as "corking the catheter." By way of example and not limitation, if a clinician has successfully "corked the catheter" in particular situations, the catheter system may be removed from the vessel, thereby withdrawing the mass of clot or occlusion with it. Alternatively, in particular embodiments, an extraction cycle may be used to draw an occlusion through the catheter lumen, and/or cause the clot to become deeply latched, or corked, within the catheter. After completion of an extraction cycle, in particular embodiments, the clot may be removed, or corked, in the attached catheter, so that the catheter together with the clot may safely be removed from the patient.

In particular embodiments, an extraction cycle may automatically stop, and/or be manually stopped, when a clot or other occlusive material clogs a catheter, and corks it. By way of example and not limitation, the clot or occlusive substance may be too large and/or too tough to traverse an aspiration catheter, but nonetheless may become partially entrained in the aspiration catheter. In particular embodiments, the system may transition to full aspiration to allow the user to remove the corked catheter while dragging the clot or other occlusive material out with the catheter. In some instances, once an extraction cycle is initiated, the clot or occlusive material may still clog the catheter. In particular embodiments, the controller may then revert to full aspiration, and/or notify the user of the corking event, whereby the system may prompt the user to remove the catheter. In particular embodiments, the user may manually turn off an extraction cycle, and/or otherwise cause the system to return to full vacuum, and then remove the catheter.

In particular embodiments, the system may transition to a maceration cycle to allow a valve, such as a pinch valve or a different type of valve, to apply mechanical forces on a clot or other occlusive material. By way of example and not limitation, such mechanical action may be applied to sufficiently modify the form and/or consistency of a clot or other occlusive material, such as to enable more effective aspiration.

In particular embodiments, to indicate a status or operation of work to remove clots or other occlusive material, visual and/or auditory signals may be included that indicate the progress of a given extraction cycle. In particular embodiments, the start of an extraction cycle may be signaled by a flashing light, such as a flashing blue light, which may flash until the cycle is completed. In particular embodiments, at completion, the light may turn to a different color to indicate completion, such as green. In particular embodiments, base unit 1000b or base unit enclosure 1016 may include a light bar. By way of example and not limitation, the light bar may fill or light up incrementally, whereby the light bar may progressively "fill up" with light in proportion to a cycle's progress. Additionally or alternatively, base unit 1000b or base unit enclosure 1016 may include a screen for displaying images. In particular embodiments, a small screen may display an animation indicative of loading. By way of example and not limitation, loading animations may execute a repetitive pattern (for example, a spinning circular object), and/or may execute a single cycle of a prolonged animation (for example, a slowly filling circle). In particular embodiments, either in conjunction with visual progress indication or as an alternative to visual progress indication, the system may use auditory cues in particular embodiments to signify the extraction cycle's initiation, pulsating phase, and/or completion. By way of example and not limitation, auditory cues may include musical notes, beeps, and/or speech. In particular embodiments, auditory cues may include updates (e.g., "extracting"), and/or suggestions (e.g., "advance/retract the catheter").

In particular embodiments, an algorithm may also control a lighting mechanism, e.g., an indicator light, to convey to the user whether the system is in a full aspiration state, an unrestricted flow state, a restricted flow state, a clogged state, a sampling state, and/or an extracting state. In particular embodiments, specific lights may be illuminated to indicate bubbles, and/or that the override switch has been triggered. In particular embodiments, the algorithm may control an acoustic chip, such as a piezo acoustic chip. By way of example and not limitation, the acoustic chip may convey audible information to the physician, such as regarding the state of the effluent and override switch. In particular embodiments, the piezo acoustic chip may be surface mounted. By way of example and not limitation, the piezo acoustic chip may selectively produce a 4 kHz single tone, for example, at 65 dB at 10 cm. By way of example and not limitation, the signals may include sounds and/or phrases such as tone/pitch changes, beeping patterns, "clogged," "occluded," "clot," "blood," "open flow," etc. Particular embodiments may utilize a dynamic beeping cadence. By way of example and not limitation, a beeping pattern may steadily increase when an unrestricted flow state is increasing in duration. In particular embodiments, a speed of the beeps may indicate a length of time the system has been in a particular state, such as unrestricted flow, and/or may alert the physician to the increasingly problematic nature of the system's positioning or status. In particular embodiments, the system may additionally or alternatively include a multi-position switch or button, for example, to specifically activate different algorithms, mute audio cues, and/or to prime the system with fluid. By way of example and not limitation, such a feature may be activated by inserting a pin in the base unit 810, which may activate this customizable feature.

In particular embodiments, the system may be manually powered on and conduct aspiration for a predetermined period of time. By way of example and not limitation, if the system detects unrestricted flow, one or more valves, such as an on-off valve, may be turned off to stop flow. The attending physician may then reposition the catheter tip into clot, and/or manually trigger a mechanism (such as a foot pedal or manual switch) to initiate further aspiration. By way of example and not limitation, such a manual trigger may override the algorithm, and may allow aspiration to continue. In particular embodiments, once a manual trigger is released, the algorithm may again monitor flow to allow aspiration, for example, as long as the flow is acceptable and/or within particular parameters. In particular embodiments, if and when the system may again detect unrestricted flow, one or more valves, as such an on-off valve, may again be closed, for example, until a physician repositions the aspiration catheter and/or manually overrides the controller. In particular embodiments, such a protocol may be repeated until the physician completes the procedure.

In particular embodiments, before an aspiration catheter can be used to remove clot and other occlusive material, it may need to be primed with an incompressible fluid. In particular embodiments, a catheter may be filled with a suitable fluid, such as a saline fluid, to remove all the air from the lumen of the catheter. In particular embodiments, a catheter may be automatically primed, whereby the catheter may be filled with a suitable fluid to expel all compressible fluids (e.g., air). In particular embodiments, one or more sensors may monitor catheter contents during use. By way of example and not limitation, if compressible fluids are detected (e.g., air or bubbles or other gases), the system may alert the user. In particular embodiments, the system may indicate that the procedure needs to stop, for example, so that the catheter may be again primed to remove air bubbles.

Cutting Instrument

In particular embodiments, a catheter, e.g., a thrombectomy catheter, for use in a subject's vasculature may include a rotatable and/or axially movable cutting instrument. In particular embodiments, the cutting instrument may be a spiral-shaped, e.g., helical-shaped, cutting instrument. In particular embodiments, the cutting instrument may include a rounded, e.g., spherical, substantially spherical or partially spherical, element at its distal end. In particular embodiments, the rounded element may be connected to a body having a twisted shape, e.g., a spiral and/or helical shape. In particular embodiments, the cutting instrument may be disposed in a lumen of the catheter, and/or may be configured for axial and/or rotational motion within the lumen.

Figure 22A:
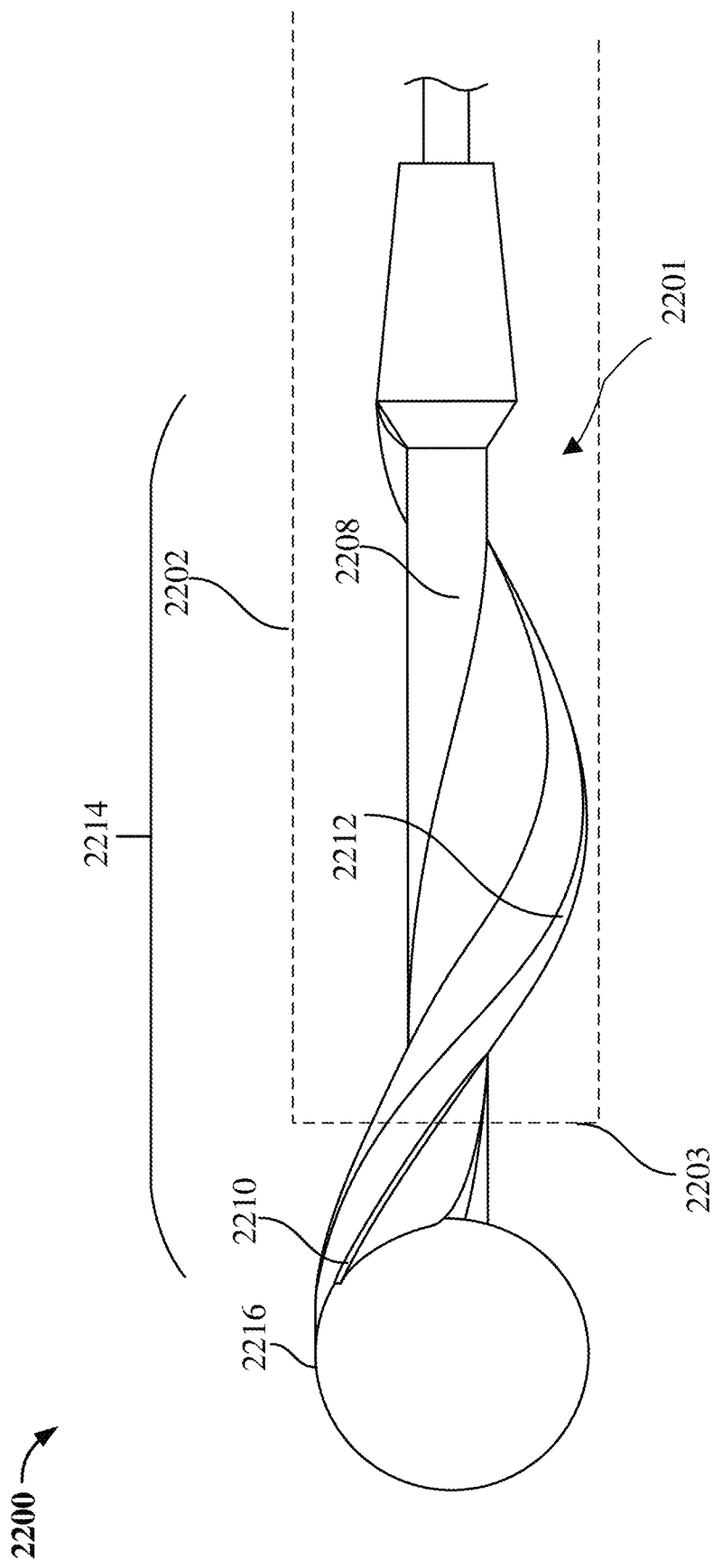
FIG. 22A illustrates a schematic side view of a helical cutting instrument at a distal most segment of a thrombectomy system, according to particular embodiments.

FIG. 22A illustrates a schematic side view of a helical cutting instrument at a distal most segment of a thrombectomy system, according to particular embodiments. By way of example and not limitation, catheter 2202 of distal region 2200 is illustrated as transparent (dashed lines) in order to facilitate an understanding of internal components. By way of example and not limitation, catheter 2202 may be a sheath catheter. In particular embodiments, distal region 2200 of catheter 2202 may have an opening 2203 from which the cutting instrument 2201 may axially extend. In particular embodiments, cutting instrument 2201 may include a helical body 2214 connected to a substantially spherical element 2216, which may serve as an atraumatic tip. By way of example and not limitation, a helical body 2214 of cutting instrument 2201 may have a twisted, spiral shape, like a corkscrew, which may surround a shaft, e.g., a central cylindrical shaft 2208, such as illustrated in FIG. 22A. In particular embodiments, helical body 2214 may include multiple edges, e.g., a pair of edges 2210 and 2212, on the twisted spiral shape surrounding the central cylindrical shaft 2208. In particular embodiments, the pair of edges 2210 and 2212 may be each substantially sharpened, or otherwise configured to promote cutting of the target substance upon coming in contact. In particular embodiments, one of the edges 2210, 2212 may be substantially sharpened while the other of the edges 2210, 2212 may remain substantially blunt. By way of example and not limitation, in this configuration, when the helical body 2214 is rotated, the substantially blunt edge may be configured to gently pull on or draw in the target substance, while the substantially sharp edge may be configured to slice or cut a small portion of the target substance upon coming in contact with the target substance.

Figure 22B:
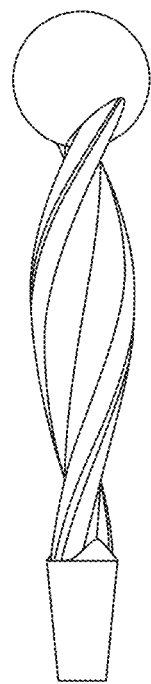
FIGS. 22B-22D illustrate schematic side views of the helical cutting instrument, according to particular embodiments.
Figure 22C:
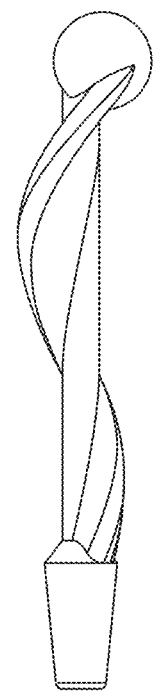
Figure 22D:
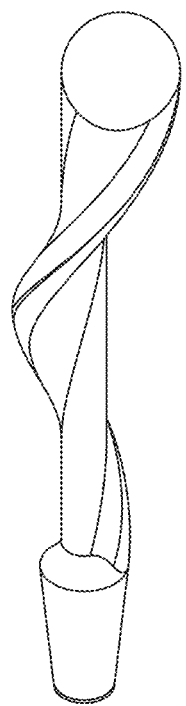

FIGS. 22B-22D illustrate schematic side views of the helical cutting instrument, according to particular embodiments. FIG. 22B illustrates a schematic front view of the cutting instrument 2201 of FIG. 22A. In particular embodiments, as illustrated in FIG. 22B, the helical body 2214 of cutting instrument 2201 may have a double helix shape which includes the two edges 2210, 2212, running opposite to each other and twist together. Although the example illustrated in FIG. 22B may not include cylindrical shaft 2208 in particular embodiments, the double helical structure may be twisted around the cylindrical shaft 2208 in certain embodiments. FIG. 22C illustrates a schematic side view of the helical cutting instrument of FIG. 22A, FIG. 2D illustrates a schematic isometric view of the cutting instrument 2201 for FIG. 22A, according to particular embodiments of the disclosure.

Figure 22E:
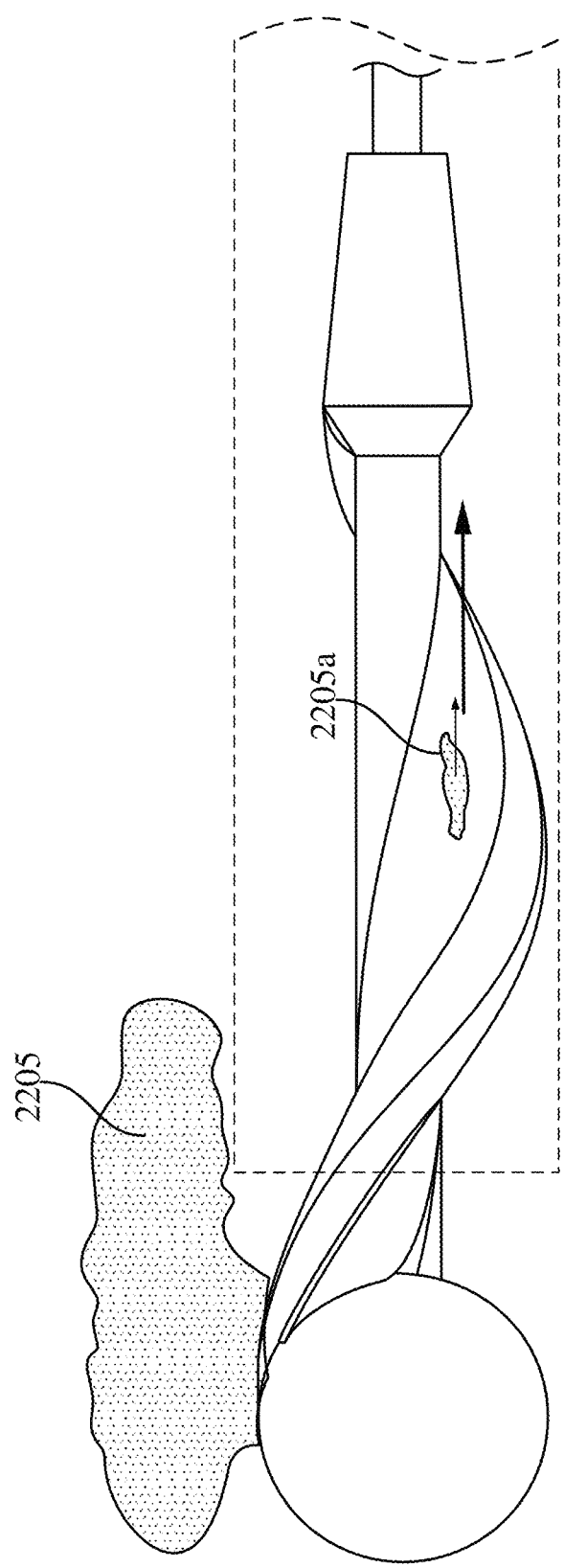
FIG. 22E illustrates a schematic side, transparent, detail view of the helical cutting instrument of FIG. 22A in operation, according to particular embodiments.

FIG. 22E illustrates a schematic side, transparent, detail view of the helical cutting instrument of FIG. 22A in operation, according to particular embodiments. As illustrated in FIG. 22E by way of example and not limitation, distal end of catheter 2202 may be positioned proximal to a target substance 2205. In particular embodiments, one or more motors, e.g., motor 105, may selectively provide rotational and/or axial motion to the cutting instrument 2201. By way of example and not limitation, once catheter 2202 is positioned adjacent to a target substance, motor 105 may operate to distally advance (e.g., while simultaneously rotating or rotationally oscillating) the cutting instrument 2201 to extend from the distal end of catheter 2202. In particular embodiments, a spherical or substantially spherical element 2216 may serve as an atraumatic tip, for e.g., upon contact with the target substance 2205. Specifically, in particular embodiments, the rounded, atraumatic distal spherical or substantially spherical element 2216 may allow for safe advancement of the cutting instrument 2201 through a vessel or a targeted tissue.

In particular embodiments, in operation, once the substantially spherical element 2216 of cutting instrument 2201 is past the target substance 2205, the target substance 2205 may come in contact with the pair of rotating edges 2210, 2212 of helical body 2214. By way of example and not limitation, in particular embodiments, one or more edges, e.g., the pair of edges 2210 and 2212, may be each substantially sharpened and/or may be configured to cut a piece of target substance 2205 upon coming in contact as they rotate. In particular embodiments, the target substance 2205 may be subjected to shearing forces by edges 2210, 2212, as the helical body 2214 may be rotated and/or rotationally oscillated to cut and/or slice the target substance 2205. In particular embodiments, one of the edges 2210, 2212 may be substantially sharpened while another of the edges 2210, 2212 may remain substantially blunt. By way of example and not limitation, in this configuration, when the helical body 2214 is rotated, the substantially blunt edge may be configured to gently pull on or draw in the target substance 2205, while the substantially sharp edge may be configured to slice or cut a small portion 2205a of the target substance 2205 upon coming in contact.

In particular embodiments, the resulting fragments may be then drawn into the lumen of catheter 2202 using one or more mechanisms working individually and/or cooperatively. By way of example and not limitation, such as further illustrated in FIG. 22E, as the double helical structure of helical body 2214 is rotated, the distal end (i.e., the end connected to the substantially spherical element 2216) may scoop up the cut portion 2205a of target substance 2205 and move it along the surface of helical body 2214, for e.g., towards a proximal end of the cutting instrument 2201. By way of example and not limitation, the helical surface of the helical body 2214 may provide a sliding channel for the cut portion 2205a of the target substance 2205, for e.g., to be deposed from the distal section to the proximal section of the catheter 2202. In particular embodiments, the helical surface of the helical body may include a grooved portion configured to provide a sliding channel for the cut portion 2205a of the target substance 2205. In particular embodiments, the cut portion 2205a of target substance 2205 may be further drawn into the lumen of catheter 2202 by an aspiration source (such as pump 106 in FIG. 1) that may provide a negative pressure gradient within the lumen of catheter 2202. In particular embodiments, the cut portion 2205a of target substance 2205 may be drawn into and through the catheter lumen to a proximal region of catheter 2202, where they may be removed from the body of the patient.

In particular embodiments, target substances (e.g., fragments cut from tissues or clots) may be broken up within the system and ingested, while aspiration may be used to ensure that minimal, if any, residual substance is permitted to escape evacuation. By way of example and not limitation, once the target substance 2205 or portion 2205a thereof is inside the lumen of the catheter 2202, aspiration may draw the substance through the lumen and into a collection chamber (not pictured).

In particular embodiments, a motor may be provided which may axially advance and/or retract the cutting instrument (e.g., cutting instrument 2201) along the lumen of the catheter. In particular embodiments, the same motor or a separate motor may also simultaneously rotate and/or rotationally oscillate the cutting instrument 2201 within the lumen of the catheter. In particular embodiments, one or more motors may be provided at or near a proximal end of a catheter, as illustrated by way of example and not limitation in FIG. 1. In particular embodiments, one or more motors may be housed in a handle of the apparatus, e.g., an ergonomically designed handle. In particular embodiments, an aperture may be formed in a separate structure at the distal end of the catheter, such as in a separate housing. By way of example and not limitation, the separate housing may be a metal or polymeric tube (e.g., a rigid tube) having the aperture formed therein. In particular embodiments, the cutting instrument 2201 may be a separate device from the catheter. In particular embodiments, the cutting instrument 2201 may be rotated as well as axially advanced and/or retracted separately and independently from the catheter. The catheter may act as a sheath to the cutting instrument 2201 in particular embodiments.

While the examples shown in FIGS. 22A-22E illustrate a cutting instrument 2201 having double helix shaped edges, it will be appreciated that the structure of the cutting instrument, e.g., one or more edges. may take any suitable form. By way of example and not limitation, the cutting instrument 2201 may comprise any appropriate number of edges, such as a single edge, or any multiple number of edges, e.g., depending on the configuration of the cutting instrument 2201 and/or its intended operational purpose. In particular embodiments, the cutting instrument may comprise at least one edge having a varying amount of curvature, e.g., the edge may comprise at least one straight portion (e.g., axially aligned portion) and/or at least one curved portion. In particular embodiments, the edge may be a spiraled edge having a constant or varied pitch. In particular embodiments, the radial height of the edge may be constant or varied along the length of the body 2214. In particular embodiments, the edge may extend radially outwards, e.g., perpendicularly, from a longitudinal axis of the body 2214, e.g., for at least a portion of a length of the edge. In particular embodiments, the edge may be raked forwards or backwards, e.g., inclined to or from, a longitudinal axis of the body 2214, e.g., for at least a portion of a length of the edge. The term "helical", when applied to the examples described herein, is not intended to be limiting and is used for the sake of example. Indeed, the present disclosure fully contemplates that the benefits of embodiments of the cutting instrument described herein may be achieved with any appropriately configured edge or edges of the cutting instrument 2201.

Figure 23A:
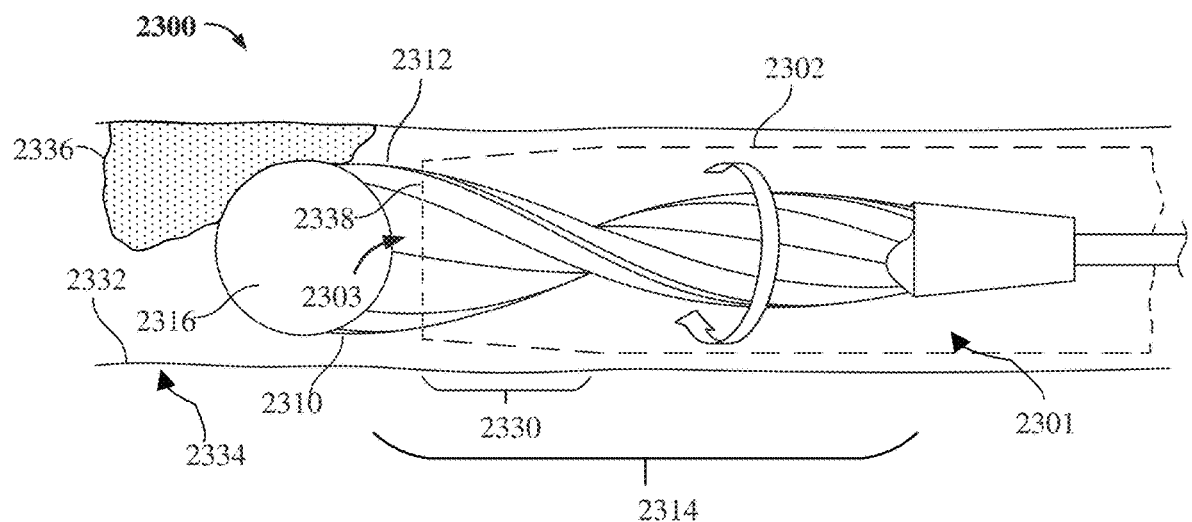
FIGS. 23A-23C illustrate schematic side detail views of a helical cutting instrument in operation, according to particular embodiments.
Figure 23B:
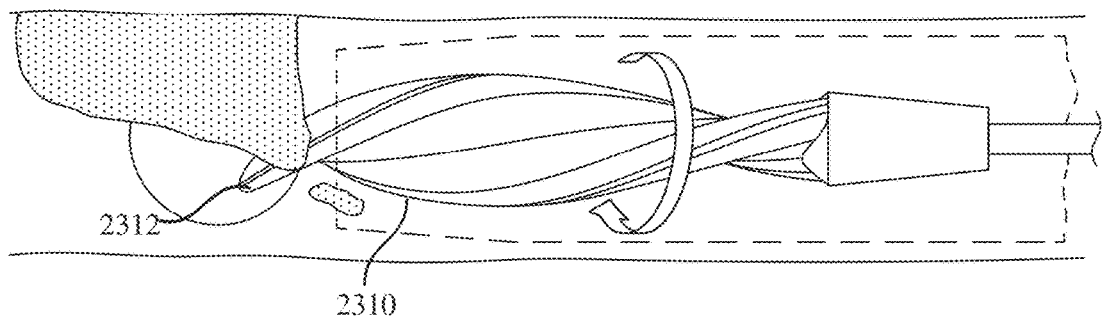
Figure 23C:
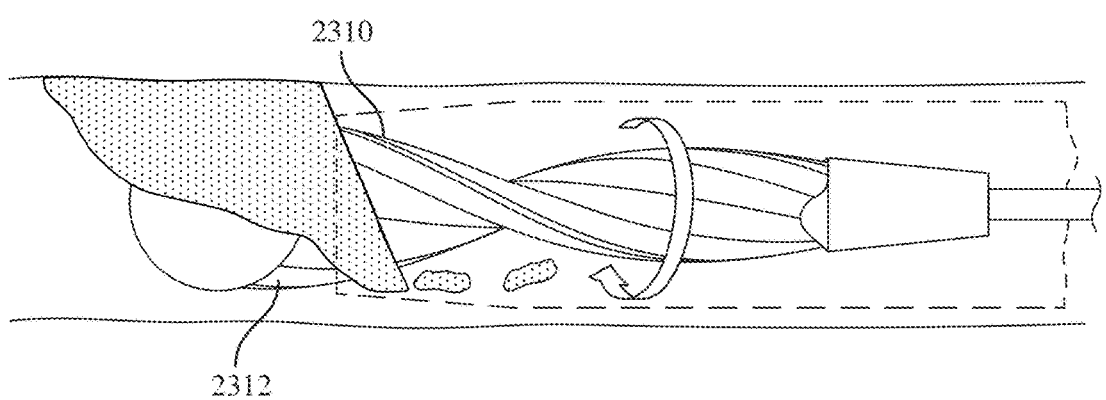

FIGS. 23A-23C illustrate schematic side detail views of a helical cutting instrument having a tapered sheath, in operation, according to particular embodiments. By way of example and not limitation, the catheter may comprise a sheath, such as a tapered sheath. By way of example and not limitation, the catheter 2302 of distal region 2300 is illustrated as transparent (dashed lines) to facilitate, for example, an understanding of internal components. By way of example and not limitation, catheter 2302 may be a sheath catheter. In particular embodiments, distal region 2300 of catheter may have an opening 2303 from which the cutting instrument 2301 may be axially extendable. In particular embodiments, cutting instrument 2301 may include a helical body 2314 connected to a substantially spherical element 2316, which may serve as an atraumatic tip. In particular embodiments, such as in the non-limiting example depicted in FIGS. 23A-23C, catheter 2302 may further comprise a distally tapered portion 2330, causing a radial gap and/or offset between the cutting instrument 2301 and the catheter 2302 to reduce towards opening 2303. In particular embodiments, distally tapered portion 2330 may be configured such that the size of opening 2303 may closely match a characteristic dimension or size of the cutting instrument 2301, e.g., the diameter of the substantially spherical element 2316.

In the non-limiting example illustrated in FIGS. 23A-23C, the distally tapered portion 2330 may taper by a shallow angle, e.g., 2 degrees or 5 degrees. However, in other non-limiting examples, the tapered portion 2330 may taper by any appropriate angle, such as 10 degrees, 30 degrees, or more, and/or may extend over any appropriate length of the catheter 2302 in particular embodiments. In particular embodiments, irrespective of the value of the taper angle of tapered portion 2330, a reduction in the radial size of the distal region 2300 of catheter 2302 may assist in the implantation of the cutting instrument 2301. By way of example and not limitation, a reduction in the radial size of the distal region 2300 of catheter 2302 may help mitigate the distal region 2300 of catheter 2302 becoming snagged and/or otherwise causing damage to an inner wall 2332 of a body lumen 2334, for e.g., during the advancement of the distal region 2300 of catheter 2302 towards a clot 2336. As such, the risk of tissue injury due to cutting instrument 2301, such as illustrated in FIGS. 23A-23C by way of example and not limitation, may be reduced during placement at a clot site by suitable cooperation between substantially spherical element 2316 and tapered portion 2330, for e.g., by substantially matching the diameter of opening 2303 to the diameter of the substantially spherical element 2316. By way of example and not limitation, the radial gap/offset between the substantially spherical element 2316 and opening 2303 of tapered portion 2330 may be approximately 0.1 mm, and increase therefrom proximally along the catheter 2302, e.g., in a liner or non-linear manner.

In particular embodiments, such as the non-limiting example illustrated in FIGS. 22A-22E, a helical body 2314 of cutting instrument 2301 may have a twisted, spiral shape, such as like a corkscrew. In particular embodiments, helical body 2314 may include a pair of edges 2310 and 2312 on the twisted spiral shape. In particular embodiments, such as the non-limiting example illustrated in FIGS. 23A-23C, edge 2310 may be substantially sharpened, and/or otherwise configured to promote cutting of the target substance upon coming in contact; in particular embodiments, edge 2312 may remain substantially blunt. By way of example and not limitation, in such a configuration, when the helical body 2314 is rotated, the substantially blunt edge 2312 may be configured to gently pull on or draw in the target substance while the substantially sharp edge 2310 may be configured to slice or cut a small portion of the target substance upon coming in contact with the target substance, and/or upon interaction with an edge 2338 at least partially forming distal opening 2303 of catheter 2302. By way of example and not limitation, FIGS. 23A-23C illustrate three operational states, e.g., snapshots, which depict a cutting mechanism implemented by cutting instrument 2301.

By way of example and not limitation, in FIG. 23A, cutting instrument 2301 is depicted to have advanced through body lumen 2334 to the site of clot 2336. Cutting instrument 2301 has been distally extended from opening 2303, such that substantially spherical element 2316 may impinge on clot 2336, and edges 2310 and 2312 on the twisted spiral shape may be no longer covered by catheter 2302.

By way of example and not limitation, in FIG. 23B, cutting instrument 2301 is depicted to have rotated clockwise by approximately 90 degrees, as viewed looking onto the distal end of the cutting instrument 2301. As further illustrated by way of non-limiting example, substantially blunt edge 2312 may act to pick up a portion of clot 2336 and/or start to draw clot 2336 into and through opening 2303. In particular embodiments, such an action may cause one or more portions of clot 2336 to break off, e.g., without any interaction between clot 2336 and substantially sharp edge 2310. In particular embodiments, axial reciprocation of cutting instrument 2301 may promote clot 2336 being drawn into opening 2303.

By way of example and not limitation, in FIG. 23C, cutting instrument 2301 is depicted to have rotated clockwise by approximately another 90 degrees, such that edges 2310 and 2312 are shown moved by an approximate half a turn compared to the operational state illustrated in FIG. 23A. As further illustrated in FIG. 23C by way of example and not limitation, substantially blunt edge 2312 may continue to draw clot 2336 through opening 2303 to an extent at which clot 2336 engages edge 2338 of distal opening 2303. In particular embodiments, the action of the pulling of clot 2336 by substantially blunt edge 2312 may urge clot 2336 against edge 2338 in a manner that causes edge 2338 to cut into clot 2336. Additionally or alternatively, in particular embodiments, the action of cutting the clot 2336 using the substantially sharp edge 2310 may be improved as a result of clot 2336 being under tension, owing to the pulling action of substantially blunt edge 2312 (e.g., as shown in FIG. 23C). Additionally or alternatively, in particular embodiments, the action of cutting the clot 2336 using substantially sharp edge 2310 may be improved as a result of a shearing action between the substantially sharp edge 2310 and edge 2338 of the distal opening 2303 of catheter 2302. In particular embodiments, such a shearing action may be promoted by a close operational clearance between the edges 2310, 2312 and the inner diameter of the distal end of the catheter 2302, which may be implemented by tapering, or otherwise reducing the radial size, of the distal end of catheter 2302, as shown in FIGS. 23A-23C.

In particular embodiments, a cutting instrument, e.g., cutting instrument 2201, may be integrated into, or may be considered part of, a progressive cavity pump (hereinafter "PCP") assembly. A PCP is a positive displacement pump that may, for example, transfer fluid as a rotor is turned. A volumetric flow rate of fluid transfer may be proportional to a potentially bidirectional rotational rate of the rotor, assuming reduced levels of shearing being caused by the rotor as applied to the fluid being pumped through the assembly. The rotor of the PCP may, for example, incorporate cutting instrument 2201 to cause the bidirectional rotation within a fluid interfacing with cutting instrument 2201. Ideally, cutting instrument 2201 may be controlled, or actuated, via controls of PCP assembly to ensure minimal variation in net fluid flow in a desired direction (e.g., pulling fluid or other displaced material out of an occluded region of a vascular region).

Figure 24A:
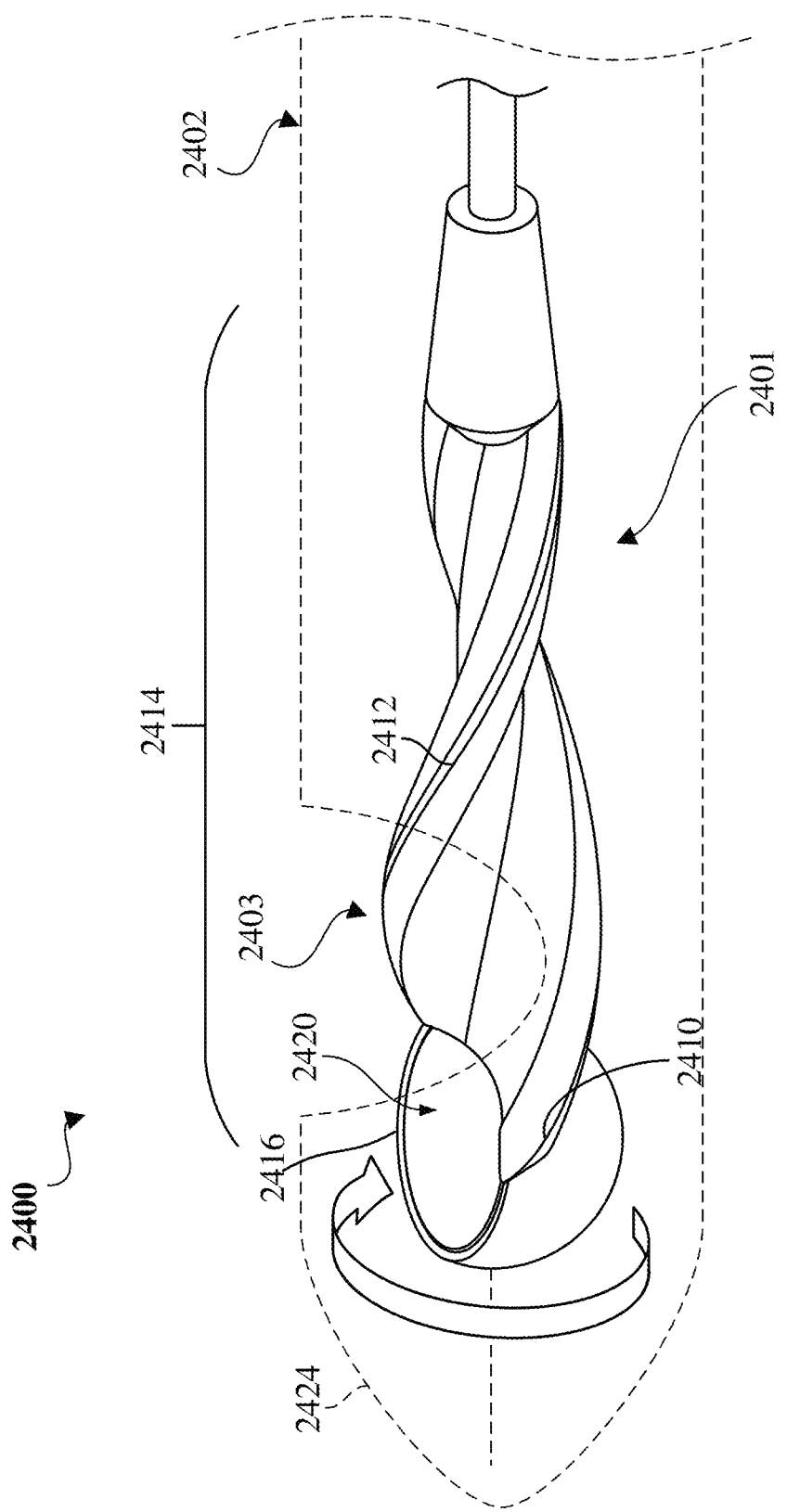
FIG. 24A shows a side detail view of an implementation of the helical cutting instrument, according to particular embodiments.

FIG. 24A illustrates a schematic side detail view of an implementation of a helical cutting instrument, according to particular embodiments. Cutting instrument 2401 of FIG. 24A includes a substantially spherical element 2416 connected to a helical body 2414. In particular embodiments, the operation of helical body 2414 may be similar to that of helical body 2214 discussed above in connection with FIGS. 22A-22E. In particular embodiments, a substantially spherical element 2416 of cutting instrument 2401 may differ from a substantially spherical element 2216 of cutting instrument 2201 in that the substantially spherical element 2416 may include a scooped-out portion 2420. By way of example and not limitation, an edge portion of the scooped-out portion 2420 may be substantially sharpened and/or otherwise configured to promote cutting of the target substance as the substantially spherical element 2416 comes in contact with the target substance, for e.g., while simultaneously being rotated or rotationally and/or laterally oscillated. Moreover, in particular embodiments, such as illustrated in FIG. 24A, the scooped-out portion 2420 may be configured to open into the helical body 2414 of the cutting instrument 2401. By way of example and not limitation, this may allow for any sliced or cut portions of the target substance to be moved proximally along the helical body 2414 (e.g., via a central channel or central surface, which may be substantially flat and/or smooth) by leveraging the helical shape of the helical body 2414.

In particular embodiments, such as illustrated in FIG. 24A, catheter 2402 may include an aperture 2403 and/or an atraumatic tip 2424. By way of example and not limitation, catheter 2402 may be a sheath catheter. In particular embodiments, a distal section of catheter 2402, e.g., comprising aperture 2403 and/or atraumatic tip 2424, may be configured to be softer and/or more flexible relative to the remainder of the catheter 2402. In particular embodiments, the soft and/or atraumatic tip 2424 may allow for the safe advancement of the device through the diseased vessel. In particular embodiments, a substantially sharpened edge of the scooped-out portion 2420 may be serrated or otherwise configured to promote cutting of the target substance as the cutting instrument 2401 is advanced (and optionally rotated and/or rotationally oscillated). In particular embodiments, a substantially sharpened edge of the scooped-out portion 2420 may be configured to promote shearing of the excised portion of the target substance from the remaining mass of target substance as the leading edge engages the target substance.

In particular embodiments, the aperture 2403 may be formed as a "side window" in the distal region of the catheter 2402. In particular embodiments, the cutting instrument 2401 may be advanced and retracted to adjust the size of a gap between the cutting body and the distal end of the window. By way of example and not limitation, aspiration may pull the target substance, such as clot material, to the open window, and the rotating cutting instrument 2401 may fragment the clot as it enters the window. In particular embodiments, a motor which may rotate and/or rotationally oscillate the cutting instrument 2401 may be attached to a proximal end of the catheter, such as illustrated by way of example and not limitation in FIG. 1. In particular embodiments, a motor may be housed in an ergonomically designed handle. In particular embodiments, the aperture may be formed in a separate structure at the distal end of the catheter, such as in a separate housing. By way of example and not limitation, the separate housing may be a metal or rigid polymeric tube having the aperture formed therein. In particular embodiments, both the catheter and the helical cutting instrument may be substantially flexible and pliable.

Figure 24B:
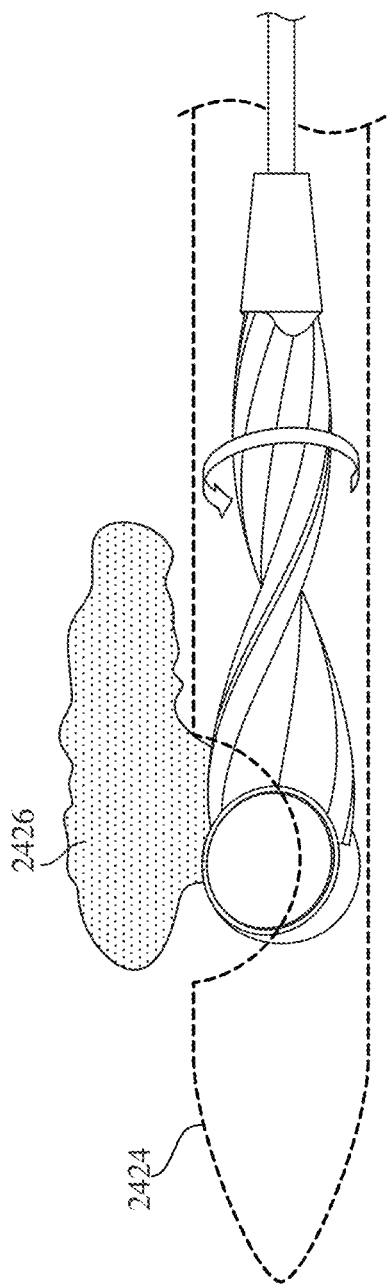
FIGS. 24B-24E illustrate schematic side, transparent, detail views of the helical cutting instrument of FIG. 24A in operation, according to particular embodiments.
Figure 24C:
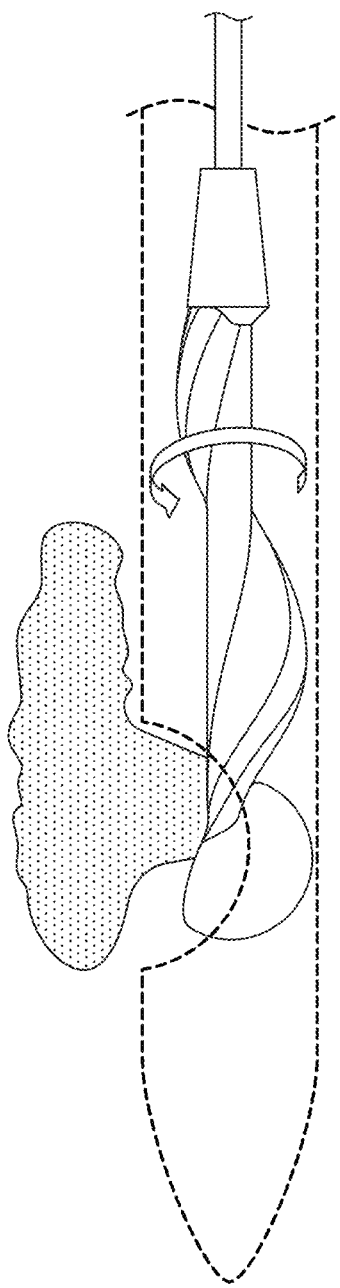
Figure 24D:
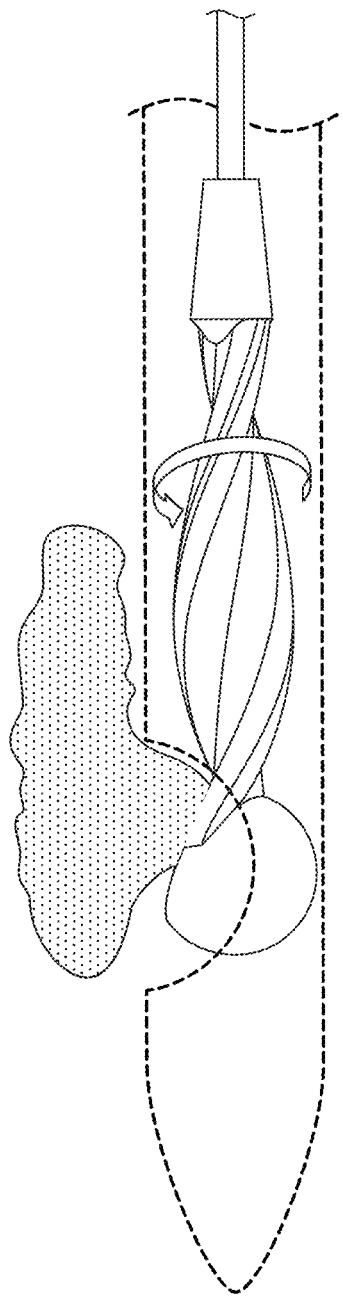
Figure 24E:
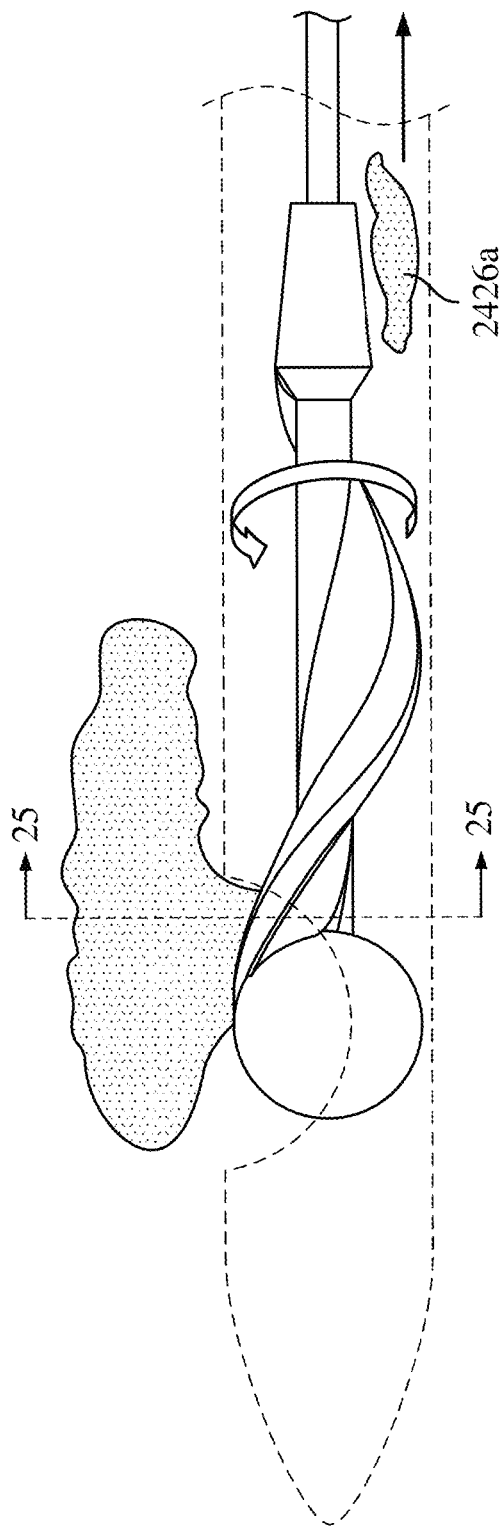

FIGS. 24B-24E illustrate schematic side, transparent, detail views of the helical cutting instrument of FIG. 24A in operation, according to particular embodiments. FIG. 24B illustrates an exemplary system 2400 at a first point in time, when system 2400 may be in a first configuration, prior to beginning the rotational movement of the cutting instrument 2401. FIG. 24C illustrates system 2400 at a second point in time, when system 2400 may be in a second configuration, during a first rotation of the helical cutting instrument by thirty degrees from its initial position shown in FIG. 24B. FIG. 24D illustrates system 2400 at a third point in time, when system 2400 may be in a third configuration, during a second rotation of the helical cutting instrument by an additional thirty degrees from its position shown in FIG. 24C. FIG. 24E illustrates system 2400 at a fourth point in time, when system 2400 may be in a fourth configuration, during a third rotation of the helical cutting instrument by an additional thirty degrees from its position shown in FIG. 24D. For clarity, not all features of a system according to the invention may be included in FIGS. 24B, 24C, 24D, and 24E. System 2400 may include a cutting instrument, e.g., cutting instrument 2401.

Turning to FIG. 24B, in particular embodiments, the catheter 2402 may be positioned near the target substance 2426. Specifically, by way of example and not limitation, catheter 2402 may be advanced through the blood vessel with the clot or thrombus until the soft, atraumatic tip 2424 contacts and then pushes past the target substance 2426. In particular embodiments, the catheter 2402 may not include the atraumatic tip 2424 and/or the aperture 2403. Instead, in particular embodiments, the catheter 2402 may have an open distal end from which the helical cutting instrument may be configured to axially extend and retract from. In particular embodiments, a target substance 2426 may be pulled into the aperture 2403 by an aspirating source. Next, in particular embodiments, cutting instrument 2401 may be positioned inside a lumen of the catheter 2402, and may be distally advanced until the substantially spherical element 2416 of cutting instrument 2401 contacts the target substance 2426. As illustrated in FIG. 24B, in particular embodiments, a rounded atraumatic portion of the substantially spherical element 2416 may be provided and/or configured to initially contact the target substance 2426.

Next, such as illustrated in FIG. 24C by way of example and not limitation, the cutting instrument 2401 may be rotated and/or rotationally oscillated such that the target substance 2426 may be pulled inside the scooped-out portion 2420. In other words, in particular embodiments, the rotation of the cutting instrument 2401 (separately or in combination with an aspiration source) may apply a pulling force on the target substance 2426, for example, to draw in the target substance 2426 within the scooped-out portion 2420.

Turning now to FIG. 24D, in particular embodiments, the cutting instrument 2401 may be rotated and/or rotationally oscillated, in order to, for example, apply a shearing force onto the target substance 2426. In particular embodiments, an edge portion of the scooped-out portion 2420 may be substantially sharpened or otherwise configured to promote cutting of the target substance. By way of example and not limitation, when the shearing force is applied onto the target substance 2426 by the substantially sharpened edge of the scooped-out portion 2420, the target substance may be sheared, cut, sliced, and/or fragmented.

FIG. 24E illustrates discrete and/or relatively uniform slicing or shearing of the target substance, such as due to the rotational shearing force applied on the target substance, according to particular embodiments. By way of example and not limitation, the axial and/or rotational motion of the cutting instrument 2401, which may place the cutting edge of the scooped-out portion 2420 and the cutting edges 2410, 2412 of the helical body 2414 in contact with the target substance 2426, may causes the shearing and/or slicing of target substance 2426.

FIG. 24E illustrates system 2400 at a fourth point in time, when system 2400 may be in a configuration a rotation of the helical cutting instrument, according to particular embodiments. As illustrated in FIG. 24E by way of example and not limitation, the discrete and relatively uniform slicing or shearing of the target substance may occur due to the rotational shearing force applied on the target substance. In particular embodiments, axial and/or rotational motion of the cutting instrument 2401, which may place the cutting edge of the scooped-out portion 2420 and/or the cutting edges 2410, 2412 of the helical body 2414 in contact with the target substance 2426, may cause the shearing and/or slicing of target substance 2426.

In particular embodiments, as the cutting instrument 2401 moves axially while simultaneously rotating or rotationally oscillating, target substance 2426 may be sliced into smaller portions. By way of example and not limitation, this slicing may create a discrete and/or relatively uniform fragment, which may be then immediately aspirated in particular embodiments, in part by the helical structure of the helical body 2414. In particular embodiments, as the cutting instrument 2401 slices or cuts the target substance, the cut portion generated may be aspirated along the helical body 2414 (e.g., by way of a channel surface of the helical body) in a proximal direction. In particular embodiments, the relatively uniform fragments 2426a may be then further aspirated in a proximal direction (indicated by the arrow) within the catheter's lumen. By way of example and not limitation, such fragmentation may occur within the catheter's lumen, and may thereby reduce the risk of clot fragment dispersal within the patient's vasculature.

Figure 25:
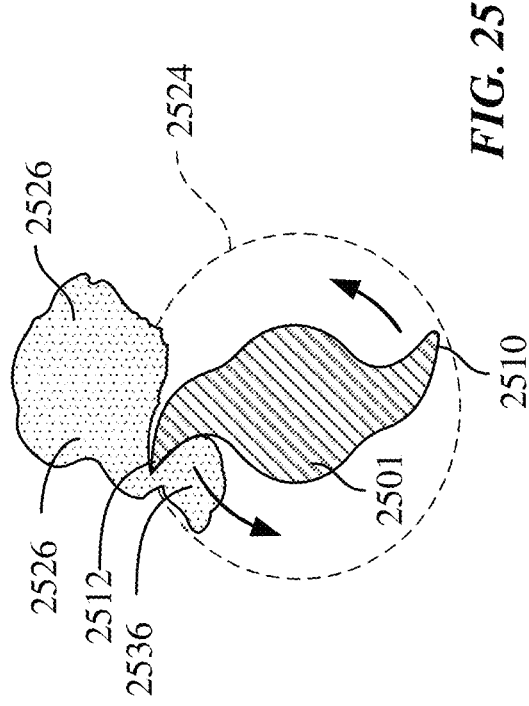
FIG. 25 illustrates a schematic cross-section view of the helical cutting instrument of FIG. 24A, according to particular embodiments.

FIG. 25 illustrates a schematic cross-section of the helical cutting instrument of FIG. 24A (see FIG. 24E along line 25-25), according to particular embodiments. By way of example and not limitation, such as illustrated in FIG. 25, as the helical cutting instrument 2501 is rotated or rotationally oscillated within a lumen of catheter 2524, a shearing force may be applied on the target substance 2526 by edges 2510, 2512 of the helical cutting instrument 2501. By way of example and not limitation, catheter 2524 may be a sheath catheter. In particular embodiments, the shearing force applied by the edges 2510, 2512 of the helical cutting instrument 2501 may cause target substance 2526 to be sliced. By way of example and not limitation, this slicing may create a discrete and relatively uniform fragment 2536. In particular embodiments, such as fragment 2536 may then be aspirated along the helical body of the helical cutting instrument 2501, e.g., in a proximal direction.

Although FIG. 25 depicts an anti-clockwise rotation of the helical cutting instrument 50, in other examples, the helical cutting instrument 2501 may be rotated in a clockwise direction. By way of example and not limitation, edge 2510 of the helical cutting instrument 2501 may be substantially blunt while edge 2512 of the helical cutting instrument 2501 may be substantially sharpened, or otherwise configured to promote cutting of the target substance 2526. In particular embodiments, when the edge 2510 first comes into contact with the target substance 2526, instead of cutting or slicing the target substance, edge 2510 may pull a fragment (e.g., fragment 2536) of the target substance 2526 into the lumen of the catheter. By way of example and not limitation, continued rotation of the helical cutting instrument 2501 may cause substantially sharpened edge 2512 to come into contact with the fragment 2536, which may then proceed to cut or slice that fragment. In this manner, by way of example and not limitation, the two different edges 2510, 2512 may work together to slice small discrete portions of the target substance 2526, while preventing damage to the blood vessels.

Figure 26:
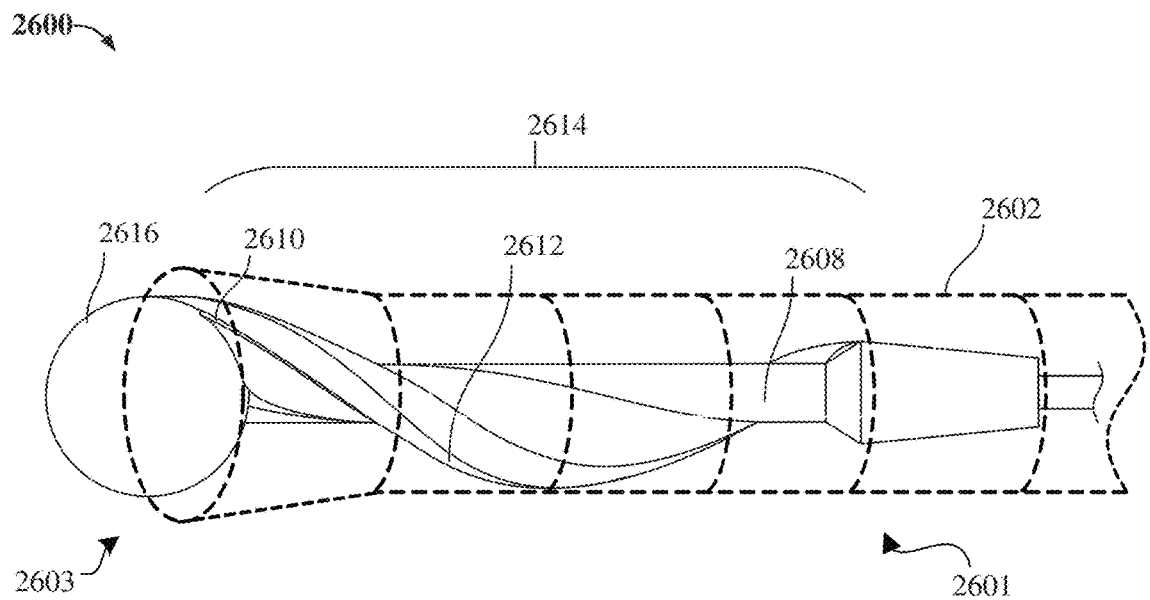
FIG. 26 illustrates a schematic side detail view of a helical cutting instrument at a distal most segment of a thrombectomy system, according to particular embodiments.

FIG. 26 illustrates a schematic side detail view of a helical cutting instrument at a distal most segment of a thrombectomy system, according to particular embodiments. The catheter 2602 of distal region 2600 is depicted as transparent (dashed lines) in order to facilitate an understanding of internal components. By way of example and not limitation, catheter 2602 may be a sheath catheter. In particular embodiments, distal region 2600 of catheter 2602 may have an opening 2603 from which the cutting instrument 2601 may be axially deployable and/or retractable. In particular embodiments, cutting instrument 2601 may include a helical body 2614 connected to a substantially spherical element 2616 which serves as an atraumatic tip. In particular embodiments, the helical body 2614 of cutting instrument 2601 may have a twisted, spiral shape, like a corkscrew in some embodiments, which may surround a central cylindrical shaft 2608 in particular embodiments, such as illustrated in FIG. 26. In particular embodiments, helical body 2614 may include a pair of edges 2610 and 2612 on the twisted spiral shape surrounding the central cylindrical shaft 2608. In particular embodiments, at least one of the pair of edges 2610 and 2612 may be configured to promote removal of the target substance, e.g., by cutting, upon engaging the target substrate. In particular embodiments, at least one of the pair of edges 2610 and 2612 may be configured to sever a portion of the target substance, such as by urging the target substrate against the catheter 2602, e.g., against an inner wall of the catheter 2602 and/or an edge of an opening in a wall of the catheter 2602.

As illustrated in FIG. 26, in particular embodiments, a distal end of catheter 2602 may be flared, e.g., conical in shape, and may be positionable proximal to a target substance. While the flared portion of the catheter 2602 is depicted as a conical portion by way of non-limiting example, the flared portion may be any suitably shaped portion. By way of example and not limitation, the flared portion may be configured in a shape that may result in the transverse area of the catheter 2602 increasing along its length, e.g., toward its distal end. In particular embodiments, this sheath tip may be optimized to maximize force on clot, e.g., given steady vacuum. In particular embodiments, it may also be optimized to protect the vessel wall from the cutting portion of the helical cutting instrument. In particular embodiments, a motor, such as motor 105 of FIG. 1, may selectively provide rotational and/or axial motion to the cutting instrument 2601, e.g., once catheter 2602 may be positioned adjacent to the target substance, to distally advance (optionally while simultaneously rotationally driving) the cutting instrument 2601 to extend from the distal end of catheter 2602. In particular embodiments, the substantially spherical element 2616 may serve as an atraumatic tip upon initial contact with the target substance. By way of example and not limitation, the rounded, atraumatic distal portion of spherical element 2616 may allow for the safe advancement of the cutting instrument 2601 through a diseased vessel or a targeted tissue, e.g., without damaging a wall of the vessel.

In particular embodiments, the flared shape of the distal end of catheter 2602 may comprise an opening 2603. In particular embodiments, this opening may be controllably opened and/or closed. By way of example and not limitation, the opening 2603 (and/or the overall shape of the flared portion) may be controlled by virtue of a shape memory filament (not shown). By way of example and not limitation, catheter 2602 may comprise one or more heat-set filaments that cause the distal end of the catheter 2602 to change from a first state, e.g., where the opening 2603 of the catheter 2602 may be closed, and/or narrowed, compared to a transverse size of the helical body 2614, to a second state, e.g., where the opening 2603 of the catheter 2602 may be open, and/or widened, compared to a transverse size of the helical body 2614. In particular embodiments, the shape of the distal end of catheter 2602 may be changed from a tapered shaped, such as that illustrated in FIGS. 23A-23C, to a flared shape, such as that illustrated in FIG. 26.

In particular embodiments, a change in state, e.g., physical dimensions, of the shape memory filament in the distal end of the catheter 2602 may be caused by removal or retraction of one or more restraint elements (not shown) configured to restrain the shape memory filament, e.g., in the first state, as the catheter 2602 is being advanced through a vessel towards a target occlusion. In particular embodiments, the one or more restraint elements may comprise an outer sheath or band (not shown) extending at least circumferentially around the catheter 2602, e.g., at or towards the distal end of the catheter 2602. In particular embodiments, the outer sheath may axially slidable relative to the catheter 2602, such that retraction of the outer sheath relative to the catheter 2602 causes the shape memory filament to change from the first state to the second state.

In particular embodiments, the catheter 2602 may comprise one or more expandable elements (not shown), e.g., balloon elements, positioned at or towards the distal end of the catheter 2602, which may cause the distal end of the catheter 2602 to radial expand or flare, thus widening opening 2603, upon inflation of the one or more expandable elements. By way of example and not limitation, widening of the opening 2603 may be at least partially caused by the axial movement, e.g., distal extension, of cutting instrument 2601 relative to catheter 2602.

In particular embodiments, such as illustrated in FIG. 26 by way of example and not limitation, the cutting instrument 2601 may be placed in a partially extended position, such that the opening 2603 may be opened to allow the spherical element 2616 to extend beyond the distal end of the catheter 2602. In particular embodiments, the shape of the distal end of the catheter 2602 and/or opening 2603 may be controlled by one or more control wires (not shown), e.g., that may be manipulated to cause opening 2603 to widen, resulting in the transverse cross-sectional area of the catheter 2602 increasing towards its distal end. By way of example and not limitation, in use, the opening 2603 of the catheter 2602, in its expanded state, may be in contact with the inside wall of the of the blood vessel in which it is implanted. By way of example and not limitation, the flared shape of the distal end of the catheter 2602, as illustrated in FIG. 26, may aid in removing the target substance, such as a clot, from the blood vessel wall by funneling the target substance towards the spherical element 2616 and cutting instrument 2601, e.g., as shown in more detail in FIGS. 31A-31C. In addition, in particular embodiments, the flared shape of the distal end of the catheter 2602 may aid in reducing trauma to the vessel walls by the cutting instrument 2601, such as the advancement of the substantially spherical element 2616, by centering the cutting instrument 2601 relative to the vessel walls.

In the non-limiting example shown in FIG. 26, the flared portion is illustrated as extending from the distal end of the catheter 2602. However, in other non-limiting examples, the catheter system may comprise a secondary catheter sheath (not shown) extending around catheter 2602. In such an example, the secondary catheter sheath may comprise a flared portion similar to that described above, either alone, or in combination with a flared portion of catheter 2602.

Figure 27:
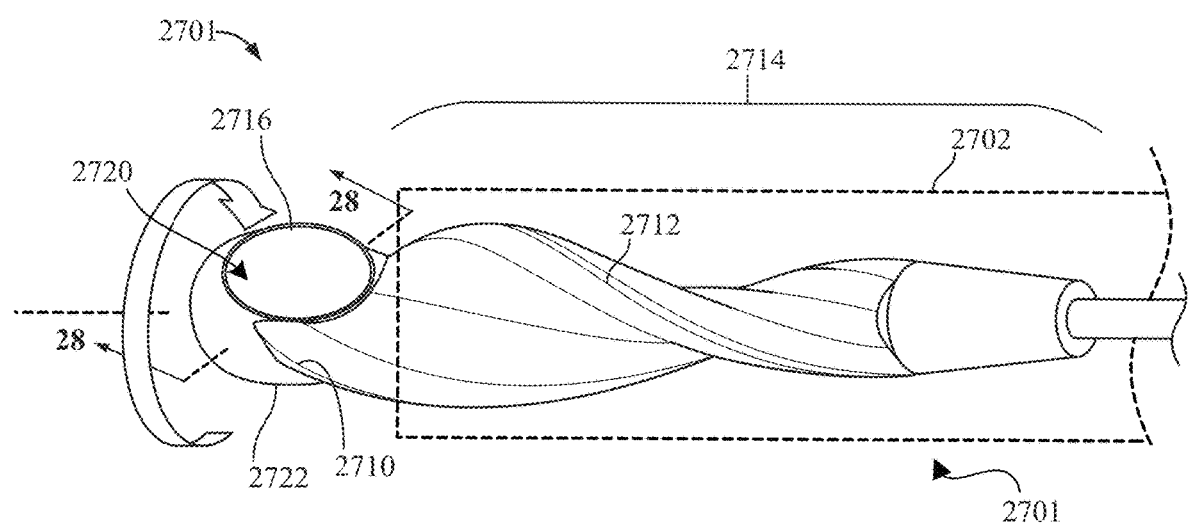
FIG. 27 illustrates a schematic side detail view of an implementation of a helical cutting instrument, according to particular embodiments.

FIG. 27 illustrates a schematic side detail view of an implementation of a helical cutting instrument, according to particular embodiments. By way of example and not limitation, helical cutting instrument 2701 of FIG. 27 may include a substantially spherical element 2716 connected to a helical body 2714 having edges 2710, 2712. In particular embodiments, the operation of helical body 2714 may be similar to that of helical bodies 2214 and 2314 discussed above in connection with FIGS. 22A-22E and 23A-23E. By way of example and not limitation, the substantially spherical element 2716 of helical cutting instrument 2701 may differ from substantially spherical element 2216 of cutting instrument 2201 and/or substantially spherical element 2316 of cutting instrument 2301, in that the substantially spherical element 2716 may include two scooped-out portions 2720, 2722. By way of example and not limitation, the scooped-out portions 2720, 2722 may be on opposite sides of the helical cutting instrument 2701 with a rounded top portion connecting the two scooped-out portions. As illustrated in FIG. 27 by way of example and not limitation, the scooped-out portion 2720 may be designed to open into the helical body 2714 of the helical cutting instrument 2701. By way of example and not limitation, this may allow for any sliced or cut portions of the target substance to be moved proximally along the helical body 2714 by leveraging the helical shape of the helical body 2714. By way of example and not limitation, scooped-out portion 2722 (such as shown in FIG. 28) may similarly open up into an opposite side of the helical body 2714.

By way of example and not limitation, edge portions of the scooped-out portions 2720, 2722 may be substantially sharpened or otherwise configured to promote cutting of the target substance as the substantially spherical element 2716 engages the target substance (for example, while simultaneously being rotated or rotationally oscillated). By way of example and not limitation, only one of the edges of the scooped-out portions 2720, 2722 may be substantially sharpened while the other of the edges of the scooped-out portions 2720, 2722 may be substantially blunt. By way of example and not limitation, such as configuration may allow for one of the scooped-out portions 2720, 2722 with the substantially blunt edge to pull on the target substance to draw the target substance into the cutting path of the other scooped-out portion and the rotating or rotationally oscillating helical body 2714.

Figure 28:
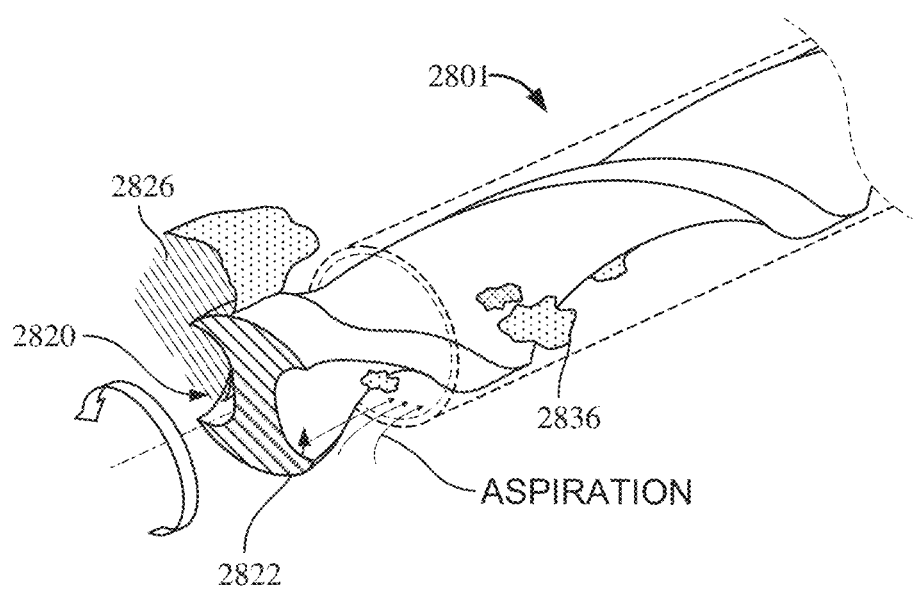
FIG. 28 illustrates a schematic perspective cross-section of the helical cutting instrument of FIG. 27, according to particular embodiments.

FIG. 28 illustrates a schematic perspective cross-section of the helical cutting instrument of FIG. 27, according to particular embodiments. By way of example and not limitation, such as illustrated in FIG. 28, as the helical cutting instrument 2801 is rotated or rotationally oscillated, a shearing force may be applied on the target substance 2826 by the scooped-out portions 2820, 2822 of the helical cutting instrument 2801. By way of example and not limitation, the shearing force applied by the scooped-out portions 2820, 2822 of the helical cutting instrument 2801 may cause target substance 2826 to be sliced. By way of example and not limitation, this slicing may create a discrete and/or relatively uniform fragment 2836, which, in particular embodiments, may then be immediately aspirated along the helical body of the helical cutting instrument 2801, e.g., in a proximal direction. Although FIG. 28 depicts an anti-clockwise rotation of the helical cutting instrument 2801 by way of example and not limitation, the helical cutting instrument 2801 may be rotated in a clockwise direction in other examples. By way of example and not limitation, scooped-out portion 2822 of the helical cutting instrument 2801 may have a substantially blunt edge while scooped-out portion 2820 of the helical cutting instrument 2801 may have a substantially sharpened edge, or may be otherwise configured to promote cutting of the target substance 2826. In particular embodiments, when the scooped-out portion 2822 first comes into contact with the target substance 2826, instead of cutting or slicing the target substance, scooped-out portion 2822 may merely pull onto a fragment (e.g., fragment 2836) of the target substance 2826. By way of example and not limitation, continued rotation of the helical cutting instrument 2801 may cause scooped-out portion 2820 with the substantially sharpened edges to come into contact with the fragment 2836, which may then proceed to cut or slice that fragment. In this manner, in particular embodiments, the two scooped-out portions 2820, 2822 may work together to slice small discrete portions of the target substance 2826, while preventing damage to the blood vessels.

Figure 29A:
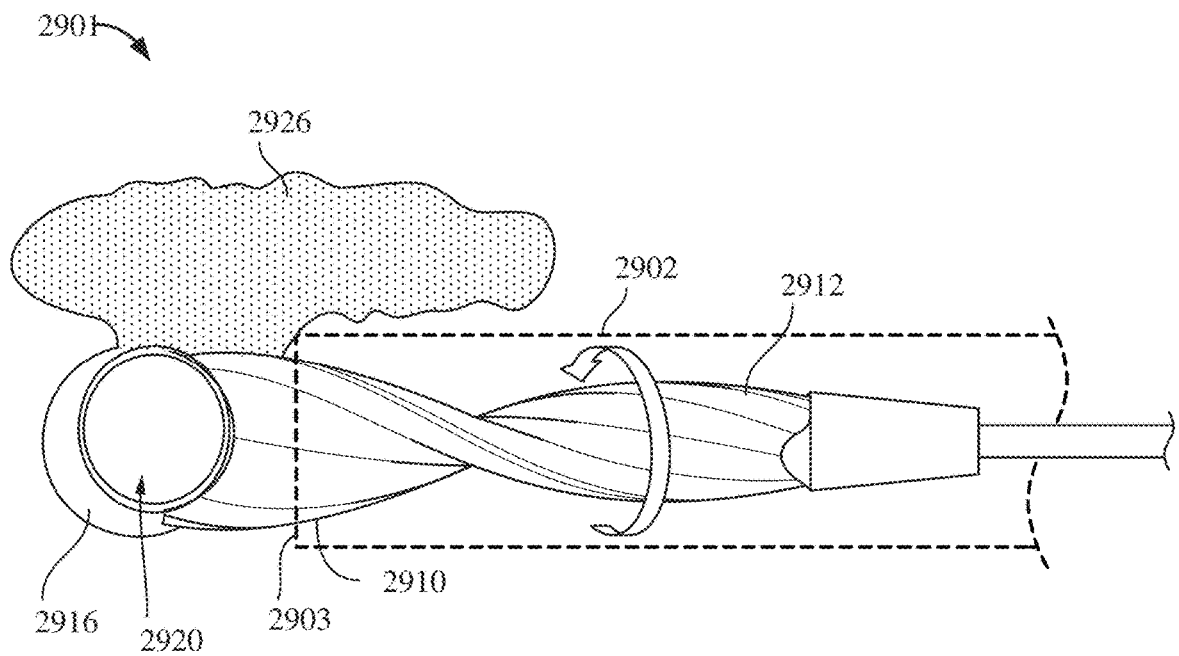
FIGS. 29A-29C illustrate a schematic side, transparent, detail view of the helical cutting instrument of FIG. 27, in operation, according to particular embodiments.
Figure 29B:
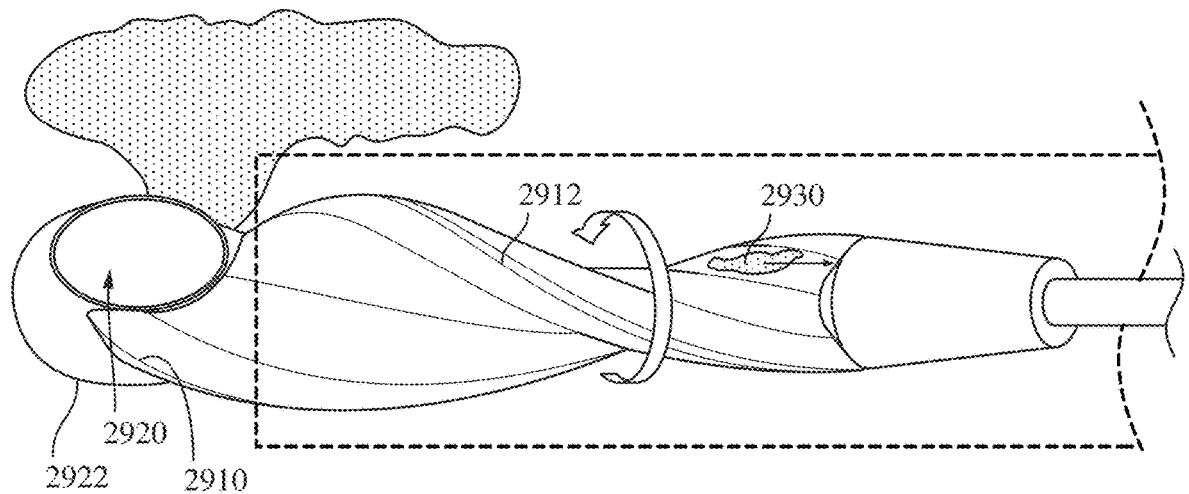
Figure 29C:
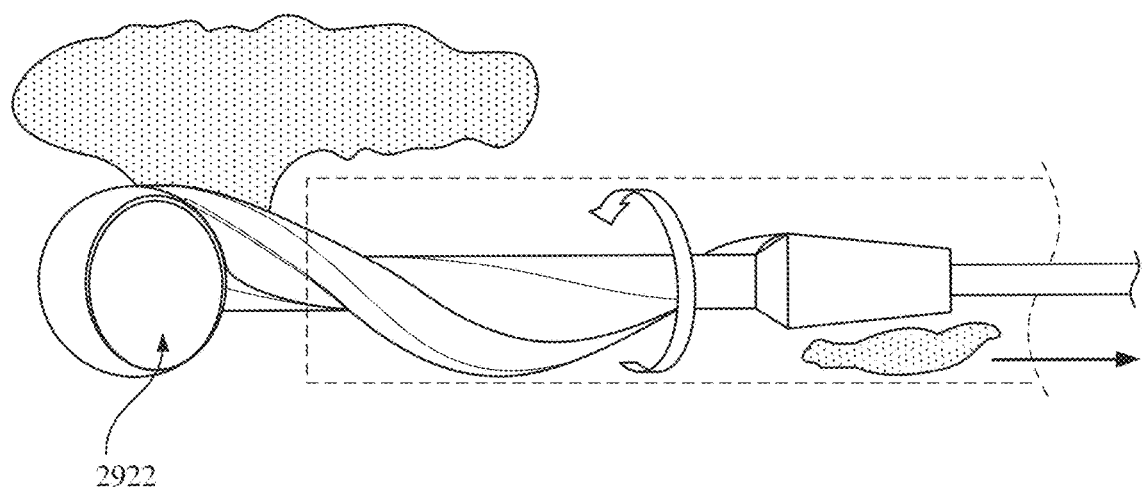

FIGS. 29A-29C illustrate a schematic side, transparent, detail view of the helical cutting instrument of FIG. 27, in operation, according to particular embodiment. By way of example and not limitation, FIG. 29A illustrates a system at a first point in time, when the system may be in a first configuration, such as prior to beginning the rotational movement of the cutting instrument 2901. By way of example and not limitation, FIG. 29B illustrates the system at a second point in time, when the system may be in a second configuration, such as during a first rotation of the helical cutting instrument by ninety degrees from its initial position shown in FIG. 29A. By way of example and not limitation, FIG. 29C illustrates the system at a third point in time, when the system may be in a third configuration, such as during a second rotation of the helical cutting instrument by an additional ninety degrees from its position shown in FIG. 29B. For clarity, not all features of an embodiment of the system need be included in FIGS. 29A, 29B, and/or 29C. By way of example and not limitation, the system includes the cutting instrument 2901. By way of example and not limitation, edges 2910 and 2912 are additionally illustrated.

Turning to FIG. 29A, in particular embodiments, the catheter 2902 may be positioned near the target substance 2926. By way of example and not limitation, catheter 2902 may be a sheath catheter. By way of example and not limitation, catheter 2902 may be advanced through the blood vessel with the clot or thrombus until the catheter opening 2903 may be adjacent to the target substance 2926. Next, cutting instrument 2901 may be distally advanced outside a lumen of the catheter 2902 from opening 2903 until the substantially spherical element 2916 of cutting instrument 2901 contacts the target substance 2926. By way of example and not limitation, as illustrated in FIG. 29A, a rounded atraumatic portion of the substantially spherical element 2916 may make the initial contact with the target substance 2926 so as to prevent any damage to the blood vessels while the cutting instrument 2901 may be being positioned. At this time, in particular embodiments, the scooped-out portion 2922 may face the target substance 2926 such that rotation of the helical cutting instrument may impart a shearing force onto the target substance 2926.

Next, such as illustrated in FIG. 29B by way of example and not limitation, the cutting instrument 2901 may be rotated and/or rotationally oscillated such that the target substance 2926 may be sliced by the scooped-out portion 2922. In other words, in particular embodiments, the rotation of the cutting instrument 2901 (in combination with an aspiration source) may apply a pulling force on the target substance 2926, for e.g., to draw it inside the scooped-out portion 2922, and in particular embodiments may then applies a shearing force by an edge of the scooped-out portion 2922 as the cutting instrument 2901 continues its rotation. In particular embodiments, application of shearing force by the edge of the scooped-out portion 2922 may cause shearing or slicing of the target substance 2926, resulting in smaller fragments 2930 being collected in the scooped-out portion 2922. As discussed above, by way of example and not limitation, the scooped-out portion 2922 may open up into the helical body of the cutting instrument 2901 which allows the fragment 2930 to be moved proximally into the lumen of the catheter (e.g., by way of a channel surface of the helical body), from which it may be further aspirated in a proximal direction in particular embodiments.

Turning now to FIG. 29C, by way of example and not limitation, the cutting instrument 2301 may be rotated and/or rotationally oscillated an additional ninety degrees such that it may be rotated 180 degrees from its position in FIG. 29A. In particular embodiments, at this point of time, the scooped-out portion 2920 may face the target substance 2926 such that rotation of the helical cutting instruments may impart a shearing force onto the target substance 2926, while the scooped-out portion 2922 may face away from the target substance 2926. Accordingly, in particular embodiments, additional rotation of the cutting instrument 2901 may cause an edge of the scooped-out portion 2920 to slice the target substance 2926. By way of example and not limitation, rotation of the cutting instrument 2901 (for e.g., in combination with an aspiration source in particular embodiments) may apply a pulling force on the target substance 2926 to draw it inside the scooped-out portion 2920, and may then applies a shearing force by an edge of the scooped-out portion 2920 as the cutting instrument 2901 continues its rotation. By way of example and not limitation, application of the shearing force by the edge of the scooped-out portion 2920 may cause fragmenting of the target substance 2926, and/or may result in smaller fragments 2930 being collected in the scooped-out portion 2920. As discussed above by way of example and not limitation, the scooped-out portion 2920 may open up into the helical body of the cutting instrument 2901, which may allow the fragment 2930 to be moved proximally into the lumen of the catheter, from which it may be optionally further aspirated in a proximal direction in particular embodiments.

By way of example and not limitation, each of the scooped-out portion 2920, 2922 may include a leading substantially blunt edge portion which may first contacts the target substance 2926, and/or may apply a pulling force onto the target substance 2926. By way of example and not limitation, the scooped-out portion 2920, 2922 may also each include a trailing substantially sharp edge portion which may contact the target substance 2926 after the leading substantially blunt edge, and may apply a shearing or cutting force onto the target substance 2926. Thus, in particular embodiments, the leading substantially blunt edge and the trailing substantially sharp edge may work together to pull a fragment of the target substance 2926 and/or perform a cutting action, in a particular sequence.

Figure 30:
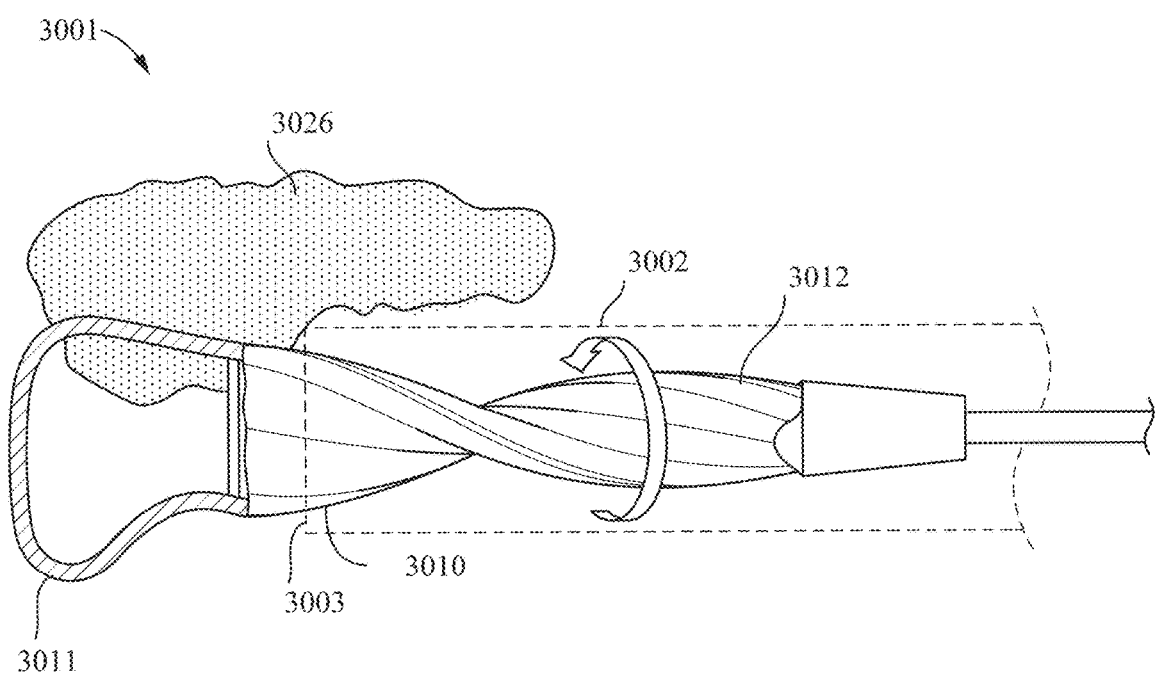
FIG. 30 illustrates a schematic side detail view of an implementation of a helical cutting instrument having a looped tip, according to particular embodiments.

FIG. 30 illustrates a schematic side detail view of an implementation of a helical cutting instrument having a looped tip (e.g., an atraumatic wire element 3011), according to particular embodiments. While FIG. 30 depicts wire element 3011 as replacing substantially spherical element, it is understood that wire element 3011 may be used in combination with substantially spherical element in particular embodiments. As illustrated in FIG. 30 by way of example and not limitation, distal end of catheter 3002 may be positioned proximal to a target substance 3026. By way of example and not limitation, catheter 3002 may be a sheath catheter. In particular embodiments, a motor, such as motor 105, may selectively provide rotational and/or axial motion to the cutting instrument 3001, for e.g., once catheter 3002 may be positioned adjacent to the target substance to distally advance (e.g., while simultaneously rotating or rotationally oscillating in particular embodiments) the cutting instrument 3001 to extend from the distal end of catheter 3002 through an opening 3003. In the non-limiting example depicted in FIG. 30, the wire element 3011 extends from edge 3010 to edge 3012. In particular embodiments, the wire element 3011 may comprise a loop, a loop of coiled wire, and/or a hook that serve as an atraumatic tip as the cutting instrument 3001 may be advanced through a body vessel toward a clot site, e.g., in a similar manner to the substantially spherical element. Specifically, in particular embodiments, wire element 3011 may allow for the safe advancement of the cutting instrument 3001 through a diseased vessel or a targeted tissue, e.g., by virtue of its flexibility and/or resilience, but may still enable pulling, cutting and/or slicing of a target substance 3026, and/or otherwise promote removal of a target substance 3026 from a body vessel. In particular embodiments, the choice of material of the atraumatic wire element 3011 could include shape memory material that would offer an appropriate balance of flexibility and/or resilience, or a tunable flexibility and/or resilience. For the avoidance of doubt, the example atraumatic wire element 3011 may be compatible with any of the examples as described herein.

By way of example and not limitation, in operation, the rotating atraumatic wire element 3011 of cutting instrument 3001 may come into contact with the target substance 3026. Specifically, in particular embodiments, target substance 3026 may be subjected to shear force when engaged by the atraumatic wire element 3011, for e.g., as the helical body is rotated or rotationally oscillated. By way of example and not limitation, such forces may act to help draw target substance 3026 away from an inner wall of a vessel to which the target substance 3026 may be adhered. In particular embodiments, the atraumatic wire element 3011 may act to entangle the target substance 3026 upon rotation of the cutting instrument 3001, such that the target substance 3026 may be drawn into catheter 3002 upon retraction of cutting instrument 3001. Additionally or alternatively, in particular embodiments, wire element 3011 may be configured to cut into the target substance 3026 upon rotation of the cutting instrument 3001. By way of example and not limitation, the resulting fragments may be then drawn into the lumen of catheter 3002 as described in relation to the above examples.

Figure 31C:
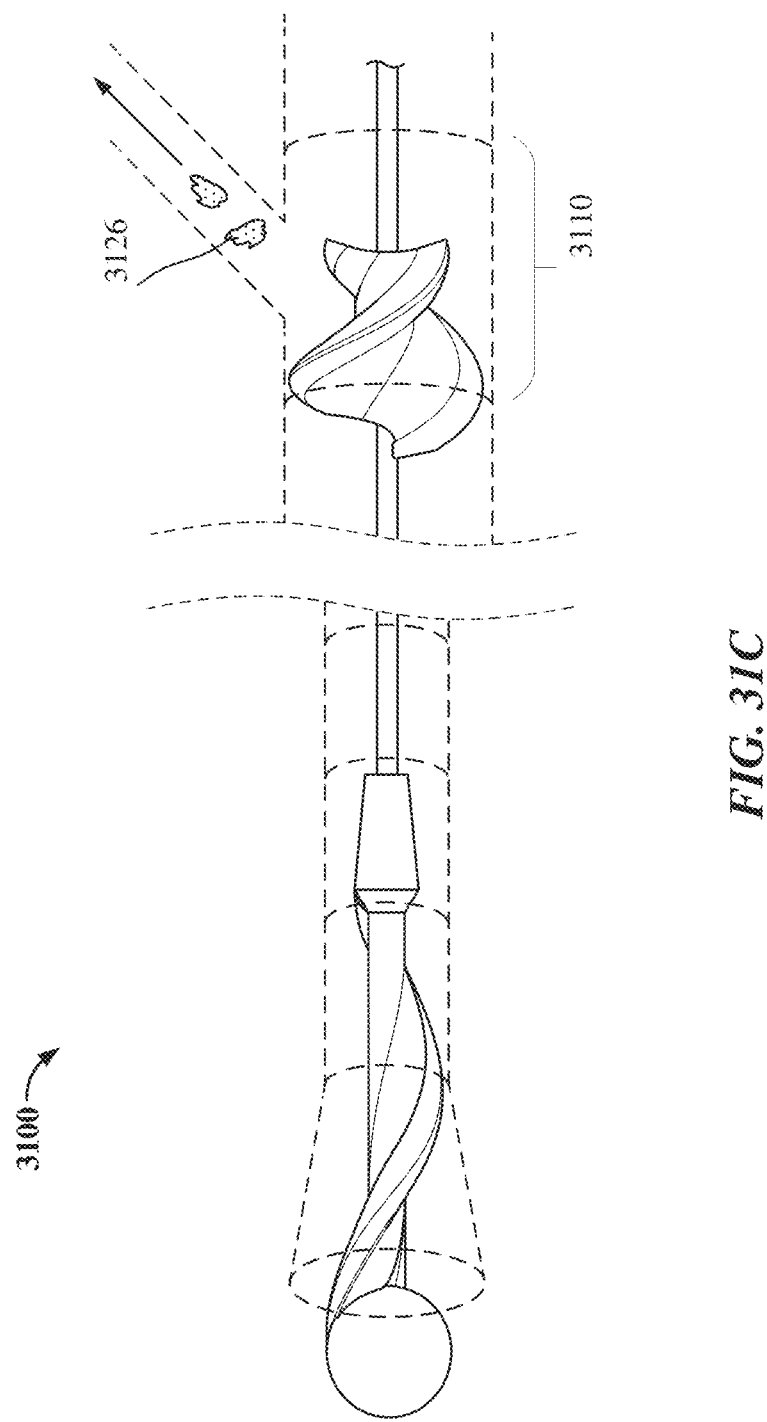

FIGS. 31A-31C illustrate schematic side detail views of a helical cutting instrument having a macerating portion, according to particular embodiments. In particular embodiments, such as illustrated in FIG. 31A, an opening 3103 in the distal portion 3100 of catheter 3102 may be closed or narrow, and/or the cutting instrument 3101 may be in a retracted position. By way of example and not limitation, catheter 3102 may be a sheath catheter. By way of example and not limitation, FIGS. 31A-31C also depict a macerating portion 3110 of the catheter system. In particular embodiments, a macerating portion 3110 may comprise a macerating blade that may be coupled to the drive wire and/or drive shaft 3108. In particular embodiments, such as illustrated herein by way of example and not limitation, a drive wire and/or drive shaft 3108 may also drive the cutting instrument 3101. As such, the rotational and axial position of the cutting instrument 3101 and the macerating blade may be synchronized in particular embodiments. In particular embodiments, a macerating portion 3110 may be configured to aid in the breaking apart portions of the target substance 3126. In particular embodiments, one or more portions of target substance 3126 may be aspirated through the catheter 3102. In particular embodiments, such as illustrated in FIGS. 31A-31C by way of example and not limitation, the macerating portion 3110 may be disposed adjacent to an aspiration tube, such that aspirated portions of the target substance 3126, for e.g., moving proximally through the catheter 3102, may be broken up into smaller pieces to aid entry into and passage through aspiration tube 3120.

In particular embodiments, the size of catheter 3102 of may vary along its length. In particular embodiments, such as illustrated in FIGS. 31A-31C by way of non-limiting example, the distal portion 3100, comprising the cutting instrument 3101, may be smaller in diameter than the proximal end 3150, comprising the macerating portion 3110. In particular embodiments, such a variation in size may be permitted by several reasons. By way of example and not limitation, the macerating portion 3110 of catheter system may be configured for ex-vivo operation, and, as such, may not need to be constrained by factors affecting the portion of the catheter system configured for in-vivo operation (size, heat, toxicity, etc.) in particular embodiments. As such, in particular embodiments, the macerating blade of macerating portion 3110 may be configured to break up the aspirated portions 3126 of the target substance in a more aggressive manner than cutting instrument 3101. By way of example and not limitation, the macerating blade may be larger, e.g., 0.5 inch in diameter, and/or may have a more aggressive blade angle, e.g., a steeper lead-in angle, than the cutting instrument 3101. In particular embodiments, such as illustrated in FIGS. 31A-31C, the macerating blade may comprise a spiral-shaped blade. While particular configurations are disclosed herein to provide a better understanding, it will be appreciated that the macerating blade may have any suitable shape, size, features, and/or configuration for breaking up aspirated portions 3126 of the target substance.

In particular embodiments, such as illustrated in FIG. 31B by way of example and not limitation, the drive shaft 3108 may be distally advanced, which may cause cutting instrument 3101 and macerating portion 3110 to advance also. Notably, in particular embodiments, macerating portion 3110 may have advanced, but may still be adjacent the aspiration tube 3120. That is to say, in particular embodiments, the macerating portion 3110, in the most distally advanced position and most proximally retracted position of the drive shaft 3108, may at least partially overlap with the entry to aspiration tube 3120. Also illustrated in FIG. 31B by way of example and not limitation, is a portion of the target substance 3126, which may be removed from the blood vessel and/or aspirated towards aspiration tube 3120 and macerating portion 3110 by virtue of operation of the cutting instrument 3101 and aspiration pressure. In particular embodiments, such as illustrated in FIG. 31C, the target substance 3126 may be broken into smaller target substance pieces after passing through macerating portion 3110.

Figure 32C:
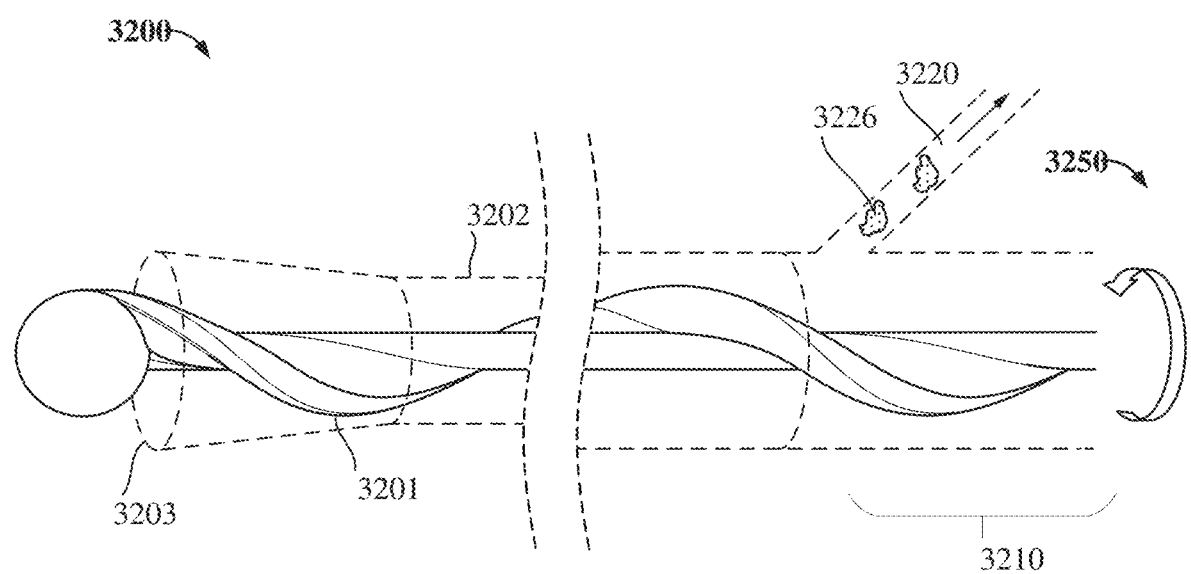

FIGS. 32A-32C illustrate schematic side detail views of an implementation of the helical cutting instrument, according to particular embodiments. By way of example and not limitation, such as illustrated in FIGS. 32A-32C, distal end 3200, cutting instrument 3201, catheter 3202, opening 3203, aspiration tube 3220, and/or proximal end 3250 may be similar to those described for corresponding features in FIGS. 31A-31C. By way of example and not limitation, catheter 3202 may be a sheath catheter. In particular embodiments, however, macerating portion 3210 may be different from macerating portion 3110. By way of example and not limitation, macerating portion 3210 may comprise a macerating blade having the same, or similar, configuration to the helical body of cutting instrument 3201. In particular embodiments, the helical body of the cutting instrument 3201 may extend, e.g., continuously, from the distal end 3200 to macerating portion 3210. As such, in particular embodiments, the outer diameter of catheter 3202 may remain constant, e.g., between a distal portion of the catheter system configured for in-vivo operation and a proximal portion of the catheter system configured for ex-vivo operation. In particular embodiments, the pitch, rake, and/or the outer dimensions of the helical body of cutting instrument 3201 may vary along its length. By way of example and not limitation, the pitch of the helical body of cutting instrument 3201 may increase and/or the outer diameter of the helical body may decrease along at least a portion of the helical body between the distal end 3200 and the proximal end 3250. In particular embodiments, the removal, aspiration, and/or break-up of target substance 3226 may occur in a similar manner to that described for the example of FIGS. 31A-31C.

FIG. 33A illustrates a schematic cross-section of a macerating portion of an implementation of the catheter system, according to particular embodiments. FIG. 33B illustrates a schematic side detail view of the macerating portion of FIG. 33A, according to particular embodiments. In particular embodiments, such as depicted in FIGS. 33A and 33B by way of example and not limitation, the distal end 3300 may be similar to the distal end of any of the above-described examples. In particular embodiments, such as depicted by way of example and not limitation in FIGS. 33A and 33B, macerating portion 3310 may comprise a macerating blade that may be mounted on or around drive shaft 3304 in a manner that may transfer rotational drive from the drive shaft 3304 to the macerating blade, and/or may allow for axial movement of the drive shaft 3304 relative to the macerating blade. By way of example and not limitation, the macerating blade may be supported by one or more support structures 3340 within a housing 3342 of macerating portion 3310. By way of example and not limitation, FIG. 33B shows two support structures 3340, each having a hub and three equally spaced support legs arranged circumferentially around the hub.

In particular embodiments, such as illustrated in FIG. 33A by way of example and not limitation, the support structures 3340 may carry the macerating blade such that the macerating blade may be axially restrained within housing 3342, and/or may rotate about a longitudinal axis. In particular embodiments, drive shaft 3304 may extend from motor 3305 and base unit 3307, through a wall of housing 3342 and central openings in the support structures 3340 and the macerating blade. In particular embodiments, the drive shaft 3304 and macerating blade may be rotationally coupled, e.g., by virtue of a key feature or spine, that may transfer rotational drive from the drive shaft to the macerating blade. In this manner, in particular embodiments, the macerating blade may spin at the same or correlated rotational speed as the drive shaft 3304 (and thus the cutting instrument). Separately or additionally, in particular embodiments, the coupling between the drive shaft 3304 and macerating blade may allow for the drive shaft 3304 to slide, e.g., distally and/or proximally, relative to macerating blade and housing 3342. By way of example and not limitation, such as illustrated in FIG. 33A, drive shaft 3304 may be placed in a distally extended position, such that the cutting instrument may protrude from distal end 3300. In particular embodiments, the key feature and/or spine may be moved to a distal extent of its travel within the macerating portion 3310. In particular embodiments, base unit 3307 and housing 3342 may be configured for ex-vivo operation, and/or may be fixable to a benchtop in a manner that may allow catheter 3302 to be removably secured to an inlet to housing 3342. By way of example and not limitation, base unit 3307 and housing 3342 may be reusable and/or serviceable portions of the catheter system, whereas any portions of the catheter system coupled distally to the housing 3342 may be single use items in particular embodiments.

Figure 34:
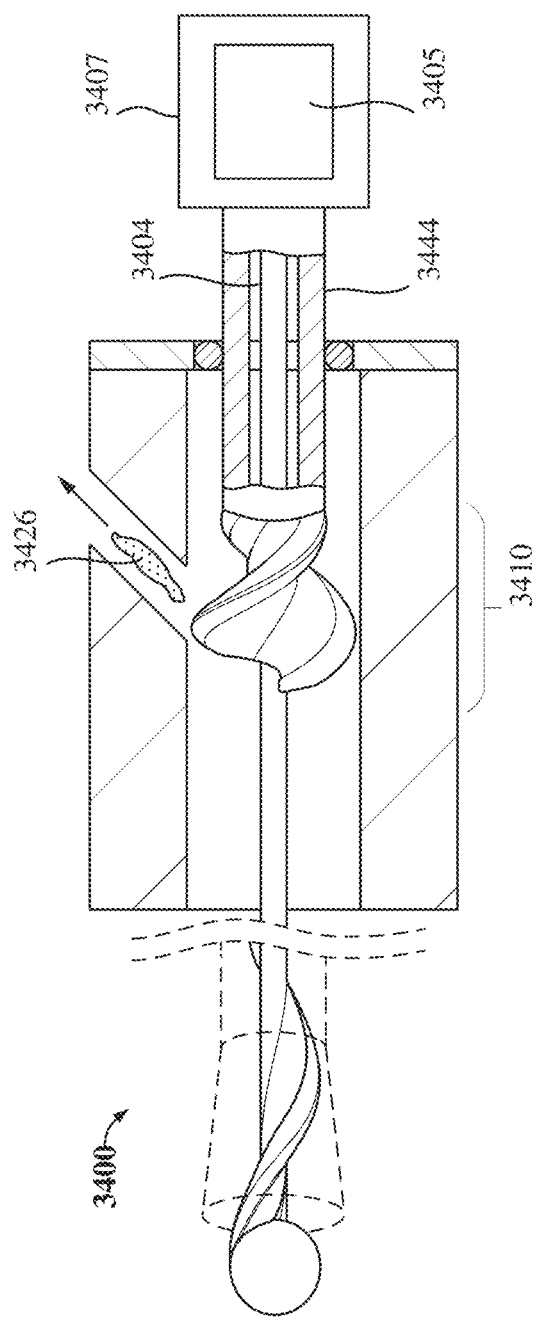
FIG. 34 illustrates a schematic cross-section of a macerating portion of an implementation of the catheter system, according to particular embodiments.

FIG. 34 illustrates a schematic cross-section of a macerating portion of an implementation of the catheter system, according to particular embodiments. In particular embodiments, such as depicted in FIG. 34 by way of example and not limitation, distal end 3400 may be similar to the distal end of any of the above-described examples. However, in particular embodiments, such as the non-limiting example illustrated in FIG. 34, macerating portion 3410 may comprise a macerating blade that may be mounted on drive shaft 3444, which may be separate from drive shaft 3404. In particular embodiments, such as the non-limiting example depicted in FIG. 34, drive shaft 3404 and 3444 may be arranged in a coaxial arrangement such that drive shaft 3404 may extend through the macerating blade, and/or drive shaft 3444. In this manner, in particular embodiments, the helical cutter and the macerating blade may be controlled independently from each other, e.g., so that they may be driven at different rotational speeds. In particular embodiments, such an implantation may be beneficial as it may allow for the speed of the macerating blade to be greater than the speed of the helical cutter, which may preserve the gentle action of the helical cutter against a wall of a vessel, and/or may allow for high shear forces to be generated in the macerating housing. In particular embodiments, such an implementation may be separately or additionally used to optimize aspiration of target substance 3426 through the aspiration tube.

In particular embodiments, such as the non-limiting example depicted in FIG. 34, drive shaft 3404 and drive shaft 3444 may be coupled to motor 3405 and base unit 3407. However, according to one or more non-limiting examples, drive shaft 3404 and drive shaft 3444 may be coupled to respective motors and/or drive units (controllers). In particular embodiments, an apparatus contemplated herein may include one or more catheters adapted for intraluminal introduction into the target body lumen. In particular embodiments, the dimensions and other physical characteristics of the catheter may vary significantly, such as depending on the body lumen which may be accessed. In particular embodiments, such as in the case of catheters intended for intravascular introduction, the catheter may be flexible, and/or may be compatible with introduction over a guidewire to a target site within the vasculature. In particular embodiments, catheters may be intended for "over-the-wire" introduction, such as when a guidewire lumen may extend fully through the catheter body, and/or for "rapid exchange" introduction wherein the guidewire lumen may extend only through a distal portion of the catheter body.

Dynamic System State Detection

Figure 35:
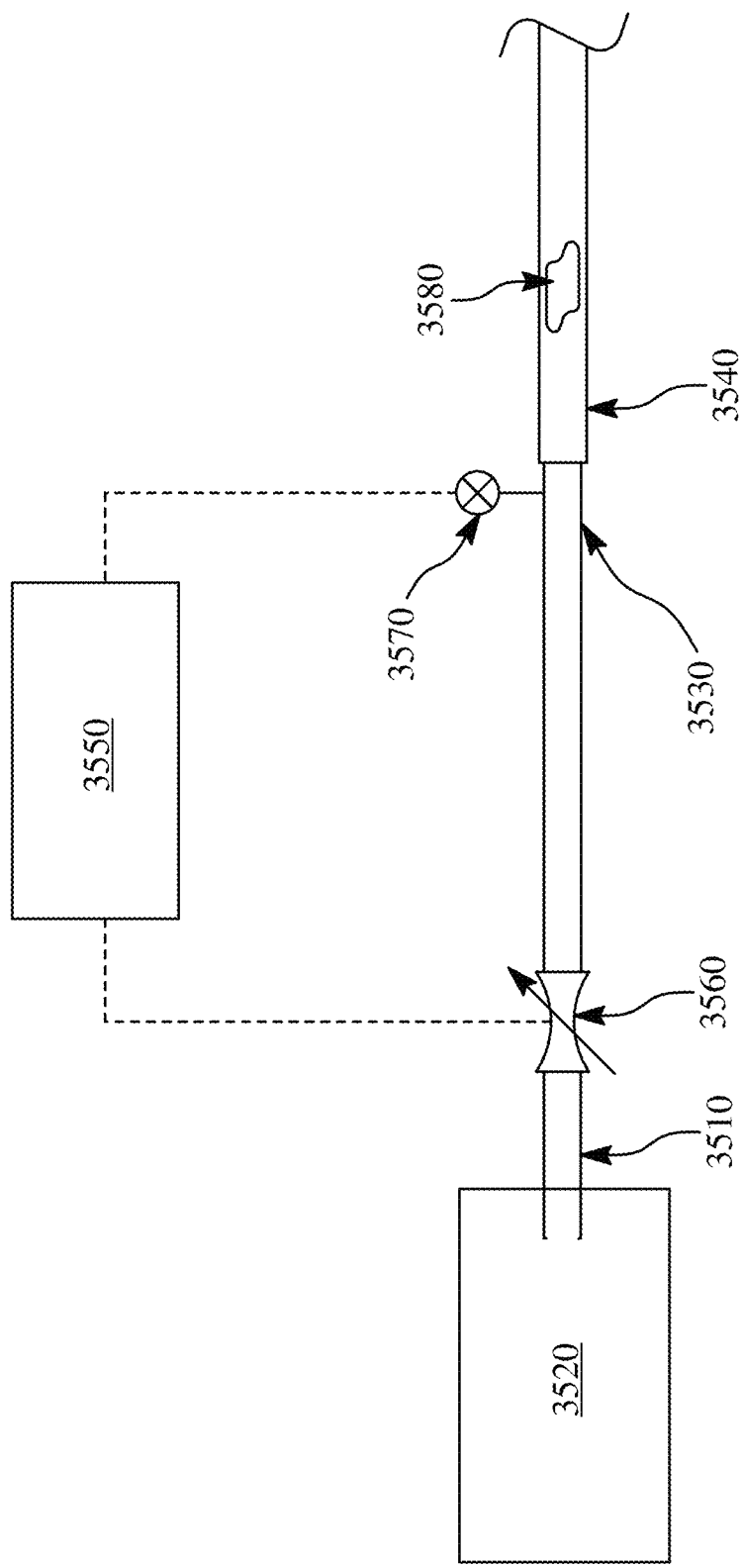
FIG. 35 is a schematic representation of a particular embodiment configured for dynamic system state detection.

FIG. 35 is a schematic representation of a particular embodiment configured for dynamic system state detection, illustrating an alternative approach for detecting one or more system states in a thrombectomy system, for e.g., unrestricted flow or occluded flow in an aspiration catheter. With reference to FIG. 35, a proximal end of connection tubing 3510 may be connected in fluid communication with a vacuum source 3520. The distal end 3530 of the connection tubing may be connected in fluid communication with the proximal end of aspiration catheter 3540. In FIG. 35, the distal end of the aspiration catheter is depicted truncated, i.e., not illustrated in the schematic. By way of example and not limitation, an occlusion, such as clot 3580, is depicted within the lumen of aspiration catheter for illustration.

In particular embodiments, the controller 3550 may selectively open and close vacuum valve 3560 to control fluid communication or corresponding isolation of the connection tubing relative to the vacuum pressure of the vacuum source. Based on the parameters used for operating the vacuum valve, such as the number, sequence, frequencies, and/or duty cycles of triggering the open/closed valve states, many operational states of operating the vacuum valve are possible. A distal pressure sensor 3570 may be located proximate the distal end of the connection tubing. In particular embodiments, an external unit, such as a unit previously described and illustrated in FIGS. 9A, 9B, and/or 11, may be present as a connecting module between the distal end of the connection tubing and the proximal end of the aspirating catheter. In particular embodiments, the external unit may additionally comprise the distal pressure sensor.

In particular embodiments, the controller may operate the vacuum valve to generate one or more pressure level changes in the connection tubing, and thereby into the contents of the connection tubing and/or the aspiration catheter system. Further, the controller may detect pressure levels at the distal end of the connection tubing using the distal pressure sensor, wherein changes in the detected pressure levels are correlated with the pressure level changes generated by operating the vacuum valve.

In particular embodiments, based on the detected pressure profile, wherein a profile comprises a time-dependent sequence of detected pressure levels, the controller may dynamically determine one or more system states in the aspiration catheter and/or connection tubing. Based on the determination of one or more flow states, the controller may further initiate one or more actions.

The generalized approach of the specific implementation of FIG. 35 and as discussed above may be considered dynamic detection of system states. Some particular embodiments of this approach will be further discussed herein. It should be appreciated that specific implementations of dynamic detection of system states may vary across embodiments, and may be tailored based on particular configurations and applications.

Figure 36:
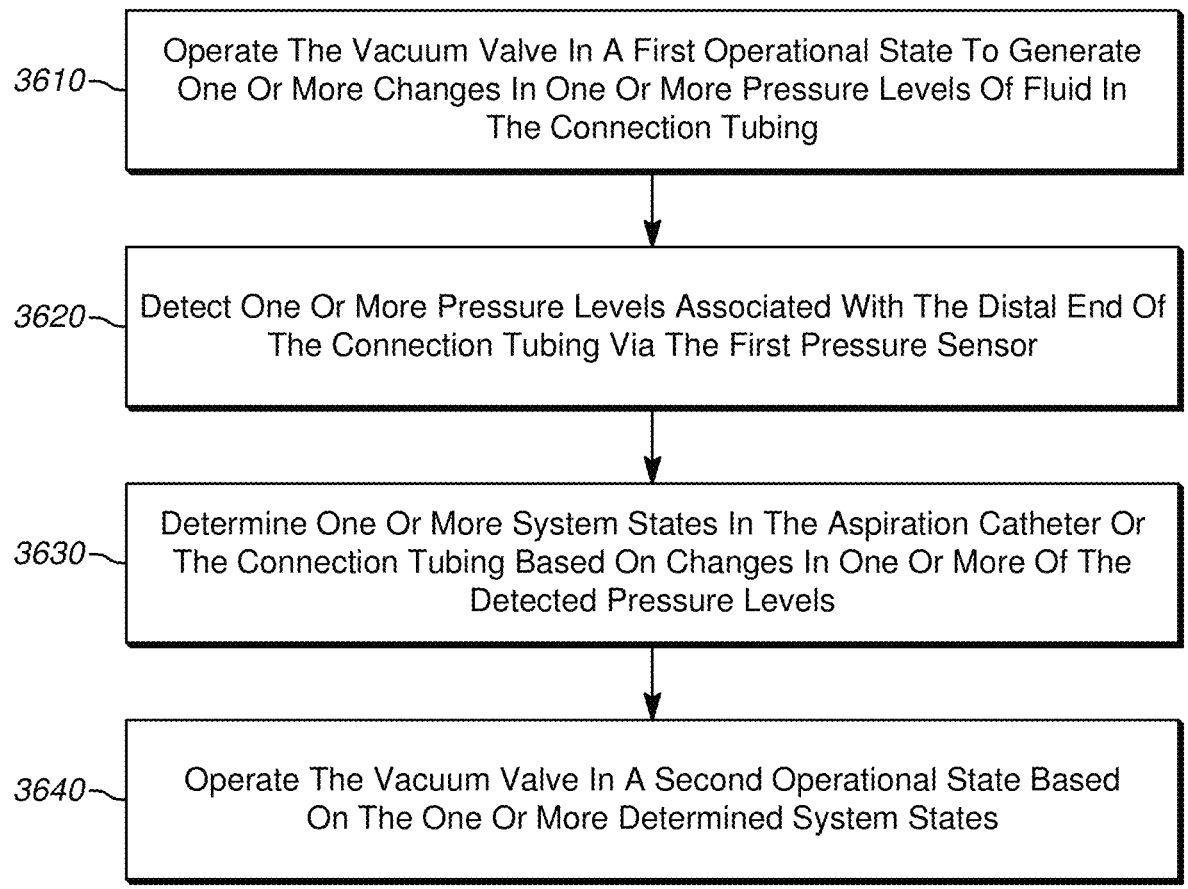
FIG. 36 illustrates a particular embodiment of an algorithm suitable for implementing dynamic system state detection in an embodiment.

FIG. 36 illustrates a particular embodiment of an algorithm suitable for implementing dynamic system state detection and detecting system states in the aspiration catheter or the connection tubing of an aspiration thrombectomy system. In a first step 3610 of the illustrated algorithm, the controller may generate one or more pressure level changes in the connection tubing by operating the vacuum valve in a first operational mode, such as by selectively opening and closing the vacuum valve. In a second step 3620, the controller may detect one or more pressure levels associated with the distal end of the connection tubing via the first pressure sensor. In a third step 3630, the controller may determine one or more system states in the aspiration catheter or the connection tubing based on changes in one or more of the detected pressure levels. In a fourth step 3640, the controller may operate the vacuum valve in a second operational state based on the one or more determined system states.

In particular embodiments or cases, based on the system state inferred to exist in the aspiration catheter or connection tubing based on the detected pressure profile, the controller may determine that no additional vacuum valve operation is immediately required. For instance, the controller may generate a pressure level change in the connection tubing by opening, and then closing, the vacuum valve. In particular embodiments, if the controller were to subsequently determine that presence of unrestricted or open flow in the aspiration catheter, it may continue to keep the vacuum valve closed, until the next action step is required.

System states may comprise qualitative and/or quantitative descriptions of flow states within the aspiration catheter and/or connection tubing. In particular embodiments, the flow state may be an unrestricted or open flow state, wherein the distal end or tip of the aspiration catheter may be in contact with healthy blood, and there may be little or no occlusive material in the catheter and/or connection tubing. In particular embodiments, an occluded flow state may exist in the aspiration catheter, such as due to a clot 3580 of FIG. 35. As will be further discussed, in particular embodiments, flow states may also include "in-between" states, such as partially occluded flow, which may require specific action(s) to follow determination of that system state.

System states may further comprise qualitative and/or quantitative descriptions of the presence of specific fluids and/or other materials in the aspiration catheter and/or connection tubing. In particular embodiments, the presence or absence of a flushing or priming fluid, such as saline, may define one or more system states. In particular embodiments, the presence or absence of gases, such as trapped air, may define one or more system states.

System states may still further comprise qualitative and/or quantitative descriptions that are related to the presence, absence and/or other characteristics of components of the aspiration thrombectomy system. In particular embodiments, as will be discussed further, the disclosed methodology may be used to detect when an aspiration catheter is not attached to the thrombectomy system. In particular embodiments, system states may also comprise qualitative and/or quantitative descriptions that are related to specific aspects of operational importance for the aspiration thrombectomy system. In particular embodiments, as will be discussed further, the disclosed methodology may be used to detect when a clot has been engaged by the distal end of the aspiration catheter. In particular embodiments, such a determination may be used to further automatically initiate modulated aspiration. In particular embodiments, such a determination may be used to further automatically initiate a maceration cycle.

The contents of the system comprising the connection tubing and/or aspiration catheter may include blood, including healthy blood, and clots and other occlusive material found in vasculature, such as thrombus, embolus, plaque, occlusive material, and/or vessel blockage material. Additionally, the contents of the system may include other fluids and materials used for preparing and for operating the aspiration thrombectomy system. In particular embodiments, a saline fluid may be used for flushing and/or priming the aspiration thrombectomy. In particular embodiments, gas bubbles, such as air bubbles, may be trapped in the connection tubing and/or aspiration catheter, and may be part of the contents of this system. In particular embodiments, the generation of pressure level changes via operating the vacuum valve may be considered the creation of a pressure wave in the system comprising the contents of the connection tubing and/or aspiration catheter.

Although this disclosure describes using particular sensors and/or valves for detecting particular system states in a particular manner, this disclosure contemplates providing any suitable sensors, actuators or methodologies for detecting system states or taking further action in any suitable manner.

Particular embodiments of a dynamic system state detection methodology may separately or additionally use pressure sources and/or valves other than the vacuum source and vacuum valve described above. In particular embodiments, as has been previously disclosed, a pressure source may be connected in fluid communication with the connection tubing via a controllable pressure valve, wherein a reference pressure level of a pressure source may vary from vacuum (i.e., a very low absolute pressure) to absolute pressures that are significantly higher than ambient pressures or systolic blood pressures. As an example and not by way of limitation, in particular embodiments, a saline supply system may be used as such a pressure source. These separate or additional pressure sources and/or pressure valves may be used in different combinations for generation of pressure level changes, and/or for initiating action as a consequence of determining specific system states.

Particular embodiments of this dynamic system state detection methodology may separately or additionally use sensors other than the distal pressure sensor described above. In particular embodiments, as has been discussed previously, a vacuum pressure sensor monitoring the level of vacuum at the canister may be used. In particular embodiments, a saline pressure sensor monitoring the pressure level of the saline fluid may be used. Furthermore, sensors used in particular embodiments of this methodology may not be limited to pressure sensors. In particular embodiments, data may be sourced from a variety of sensors, including, for instance, sensors for detecting pressures, sonic energy, ultrasonic energy, and flow rates.

In particular embodiments, one or more system scores may be determined for determining system states, wherein each system score, independently or in combination with other system scores, may indicate a likelihood of specific system states in the aspiration catheter or the connection tubing. In this respect, system scores may function as metrics for quantifying the corresponding likelihood of specific system states.

System scores may be directly or indirectly derived from sensor data, such as the detected pressure profiles discussed above. In particular embodiments, system score determination may be based on automatically identifying specific features from the detected pressure profiles, extracting pressure parameters based on values and trends derived from those specific features, and calculating one or more system scores based on the pressure parameters of those features. In particular embodiments, system scores may be determined as summations of specific parameter indicators, such as pressure parameters. By way of example and not limitation, one or more pressure parameters indicating a system state of open flow may return a system score of 1, or 2, or 3, for instance, depending upon the specific pressure parameter(s) and specific threshold values used in the system combination, application, and/or embodiment, which may be directly summed for computing quantitative values of one or more system scores, such as an open flow score. In particular embodiments, determining system scores may involve further processing. In particular embodiments, determining system scores based on pressure parameters may further comprise appropriate weighting of the parameters, and/or use of correction factors. By way of example and not limitation, weighting of pressure parameters may be determined empirically. Maximum and minimum values, thresholds, and other characteristics relevant to system scores may be determined and/or adjusted based on specific system combinations and/or applications. For instance, specific thresholds of system scores may be varied based on specific combinations of catheter and aspiration systems. Several examples and particular embodiments with specific features involving detected pressure profiles and corresponding system scores will be further discussed. It should be appreciated that derivation of system scores from sensor data may vary across embodiments, and may be tailored for the specific configuration and application.

In particular embodiments, system scores may be determined based on machine learning. In particular embodiments, intermediate quantities used toward determining system scores may be determined based on machine learning. By way of example and not limitation, intermediate quantities of interest may include thresholds and/or weighting factors. In particular embodiments, training data sets may be assembled from detected pressure profile data taken over a broad range of scenarios, incorporating statistical variations, and corresponding to system states of interest. Trained machine learning models may be then used to make predictions of system state for novel situations. In particular embodiments, machine learning algorithms may employ semi-supervised and/or unsupervised learning. The algorithms may employ clustering, dimensionality reduction, and/or reinforcement learning to further improve prediction accuracy. Additionally, an algorithm that uses a combination of the above algorithmic flow analysis techniques may be employed in particular embodiments.

It is noted that particular sensor parameters and profiles, such as pressure profiles, choices of parameters, thresholds, and other criteria, and/or all other quantities such as valve states that are illustrated in this document are exemplary, and not limiting. For example, illustrations in FIGS. 37-84, which are further discussed below, are provided as examples, and not by way of limitation.

Figure 37:
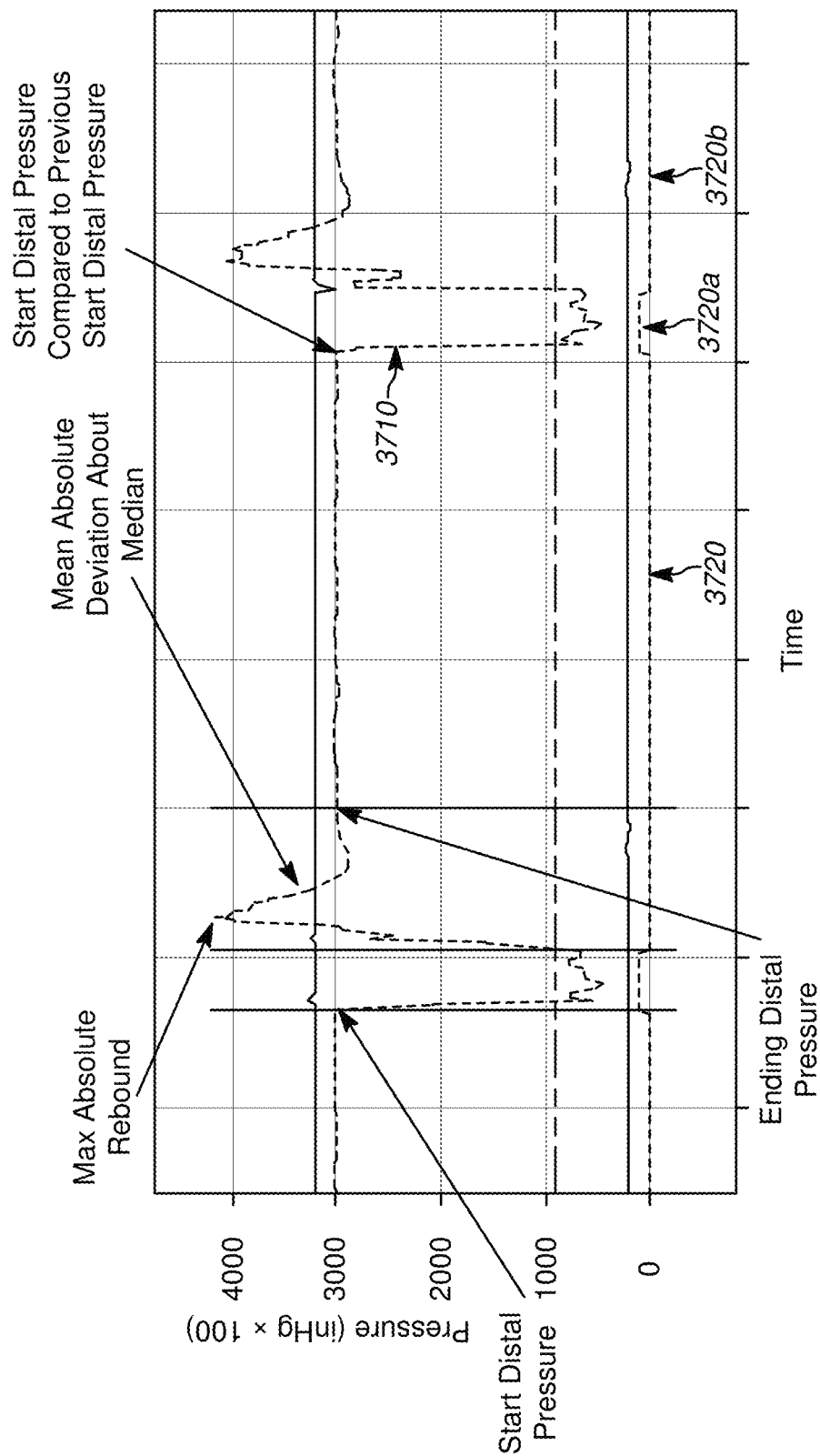
FIG. 37 illustrates a particular embodiment of a distal pressure profile detected over time, illustrating some pressure parameters.

FIG. 37 illustrates a distal pressure profile detected over time, for a particular embodiment, illustrating some pressure parameters. A distal pressure profile 3710 is based on the time-varying pressure detected by the distal pressure sensor. A corresponding vacuum valve profile 3720 indicates the time-varying state of the vacuum valve, where an open state of the vacuum valve is indicated as a relatively elevated steady level on the y-axis, such as in 3720*a*, and the closed state of the vacuum valve as a relatively lowered steady level, such as in 3720*b*. As with the vacuum valve states described above, the open or closed states of vacuum valves or other valves in other figures and illustrations herein may also be indicated by the relative levels of the respective valve profiles on the y-axis.

As a result, in particular embodiments, it may be possible to observe in a detected pressure profile (such as illustrated in FIG. 37) the response of the system to pressure level changes generated by cycling (i.e., the rapid opening and closing) of the vacuum valve. FIG. 37 further illustrates some specific exemplary features of a detected pressure profile, previously mentioned as pressure parameters.

For instance, in particular embodiments, such as illustrated by FIG. 37 and corresponding to a generally unrestricted or open flow scenario, when the vacuum valve is first opened, the distal pressure may experience a large decrease in pressure as the contents of the connection tubing and aspiration catheter become exposed to the very low absolute pressure levels of the vacuum source, and accelerate toward the lower pressure.

For example, a value of the distal pressure corresponding to its starting value prior to the sudden distal pressure decrease may be identified as a Start (or Starting) Distal Pressure, as illustrated. For instance, in particular embodiments, a Starting Distal Pressure may be indicative of a patient's blood pressure, as well as of time history of the system state. Further, in particular embodiments, rates of change of Starting Distal Pressure may be correlated with blood viscosity, and/or the presence of clots in the catheter. In particular embodiments, following the subsequent closing of the vacuum valve, the contents of the connection tubing and aspiration catheter may experience an abrupt deceleration, and an eventual return to the new pressure equilibrium in the system disengaged from the vacuum source.

In particular embodiments, one or more peak pressure levels may be pressure parameters of interest for determining system scores, and/or system states. In particular embodiments, the recorded maximum value of the large overshoot of distal pressure corresponding to the vacuum valve closing in this scenario may be identified as the Maximum Absolute Rebound pressure, as illustrated in FIG. 37 by way of example, and not by way of limitation. Maximum Absolute Rebound Pressure may also be correlated with blood viscosity.

In particular embodiments, one or more pressure levels and/or time intervals corresponding to restoration of pressure level equilibria following a pressure change generation event, such as vacuum valve cycling, may be pressure parameters of interest for determining system scores, and/or system states. For instance, a time window may be established based on pressure and/or time metrics that corresponds to the cessation of effects of a pressure disturbance related to an opening and closing sequence of the vacuum valve. In particular embodiments, the value of the distal pressure at such a time instant may be identified as an Ending Distal Pressure, as illustrated. For instance, in particular embodiments, an Ending Distal Pressure may correspond to the distal pressure value at a predetermined time interval, such as 80 ms, after vacuum valve closing, or may also be based on a time interval determined based on other parameters.

It should be appreciated that specific definitions and thresholds for sensor parameters may vary across embodiments, based on the requirements of specific configurations and applications. The following disclosed pressure parameters and related features are intended to be exemplary, and not limiting.

In particular embodiments, measures of pressure variance may be further extracted as pressure parameters. For instance, the pressure variance between the time instants marking Start and Ending Distal Pressure may be considered for such extraction. In particular embodiments, a Mean Absolute Deviation ("MAD") of pressure about the Median ("Med") pressure, as illustrated, may be identified as a measure of pressure variation between closing of the vacuum valve and the time instant of Ending Distal Pressure. Mean Absolute Deviation of pressure about the Median pressure ("MAD/med") may also be correlated with blood viscosity.

In particular embodiments, differential pressure levels may be pressure parameters of interest for determining system scores, and/or system states. In particular embodiments, for two consecutive vacuum valve cycling sequences, the difference of the second Start Distal Pressure relative to the first Start Distal Pressure may be identified as a differential pressure level of interest, as illustrated in FIG. 37. In particular embodiments, such a Differential Start Distal Pressure may be stable across viscosity.

As previously discussed, system scores may be determined based on detected pressure parameters. In particular embodiments, an Open Score may be determined based on detected pressure parameters. As an example and not by way of limitation, the value of the Open Score may vary between 0 and 7, and may indicate the likelihood of at least an open flow state. Similarly, in particular embodiments, an Occlusion Score may be determined based on detected pressure parameters. As another example and not by way of limitation, the value of the Occlusion Score may vary between 0 and 7, and may indicate the likelihood of at least an occluded flow state. Furthermore, in particular embodiments, various combinations of an Open Score and an Occlusion Score may indicate the likelihood of one or more additional system states of interest, for instance, a partially occluded flow state.

In particular embodiments, thresholds may be established for determining system states based on system scores. As some examples and not by way of limitation, in particular embodiments, the system may be determined to be in an occluded state if the Occlusion Score equals or exceeds 3 (out of a maximum possible score of 7). In particular embodiments, the system may be determined to be in an open flow state if the Open Score equals or exceeds 3 (again, out of a maximum possible score of 7). In particular embodiments, if the Open Score and Occluded Score are both less than 3, the system may be determined to be in a partially occluded state. Such a partially occluded state may, in particular embodiments, suggest the presence of a clot or thrombus that is pliable or deformable enough to be extracted by continuous aspiration, and not necessarily require pulsed or modulated aspiration.

Although this disclosure describes establishing specific thresholds for determining system states based on particular system scores in a particular manner, this disclosure contemplates providing any suitable thresholds for determining system states based on any system scores in any suitable manner.

FIGS. 38-45 illustrate particular embodiments of distal pressure profiles for a range of system state scores. In these examples of particular embodiments, specific parts of the respective detected profiles are highlighted, and an Occlusion Score and an Open Score determined based on detected pressure parameters are indicated corresponding to the highlighted parts of each detected pressure profile. These illustrations are exemplary, and not provided by way of limitation.

Figure 38:
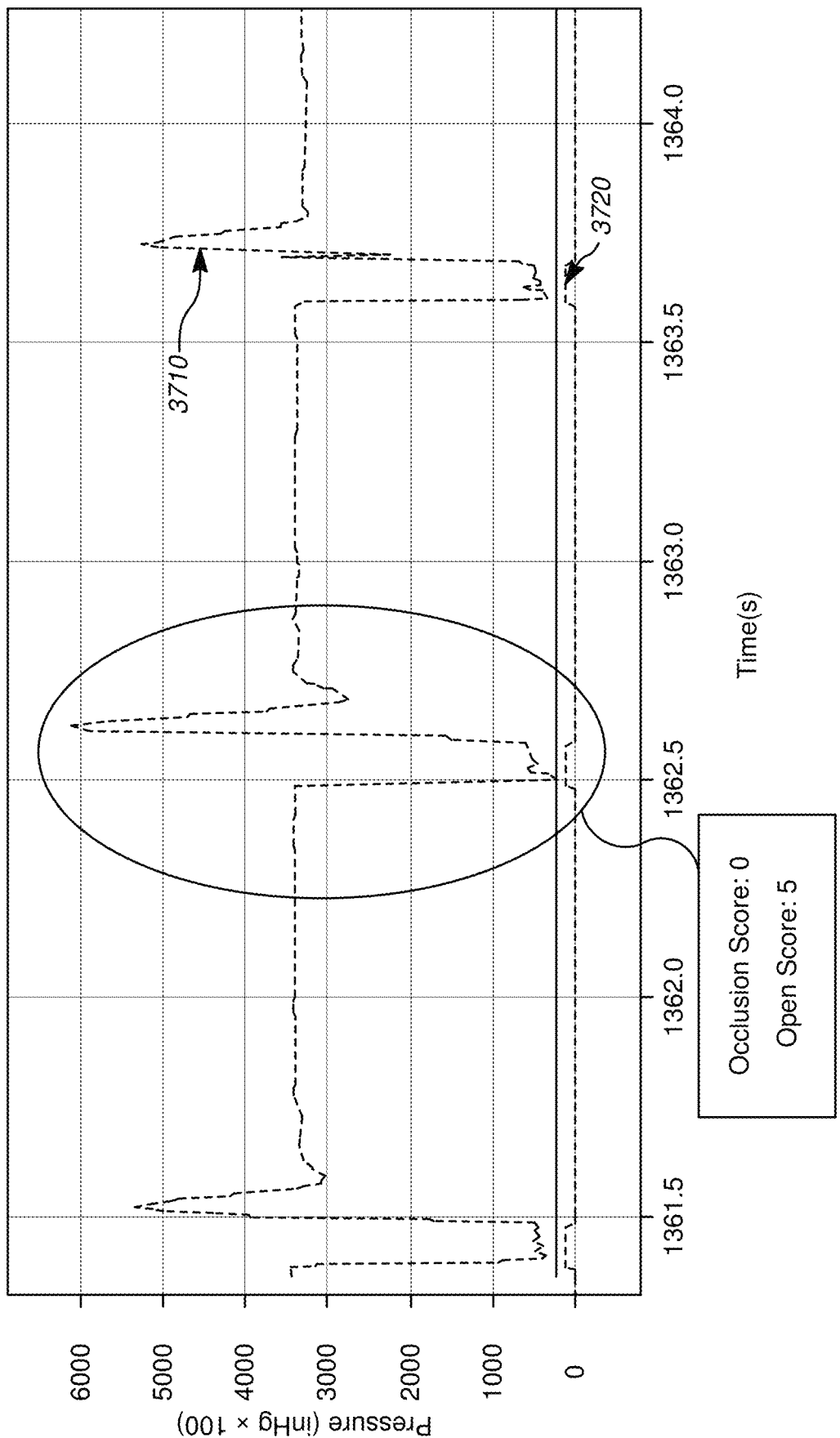
FIGS. 38-45 illustrate particular embodiments of distal pressure profiles for a range of system state scores.

For instance, FIG. 38 illustrates a detected distal pressure profile in a generally open or unrestricted flow scenario, for a particular embodiment. The detected profile of the particular embodiment illustrates relatively rapid pressure changes in distal pressure profile 3710 responsive to vacuum valve state changes depicted by vacuum valve profile 3720. The highlighted zone illustrates a relatively large overshoot or maximum rebound pressure, as well as a high variance of detected pressure immediately flowing vacuum valve closure. Based on at least these pressure parameters, the Occlusion Score in this example is determined to be 0, whereas the Open Score is determined to be 5.

Figure 39:
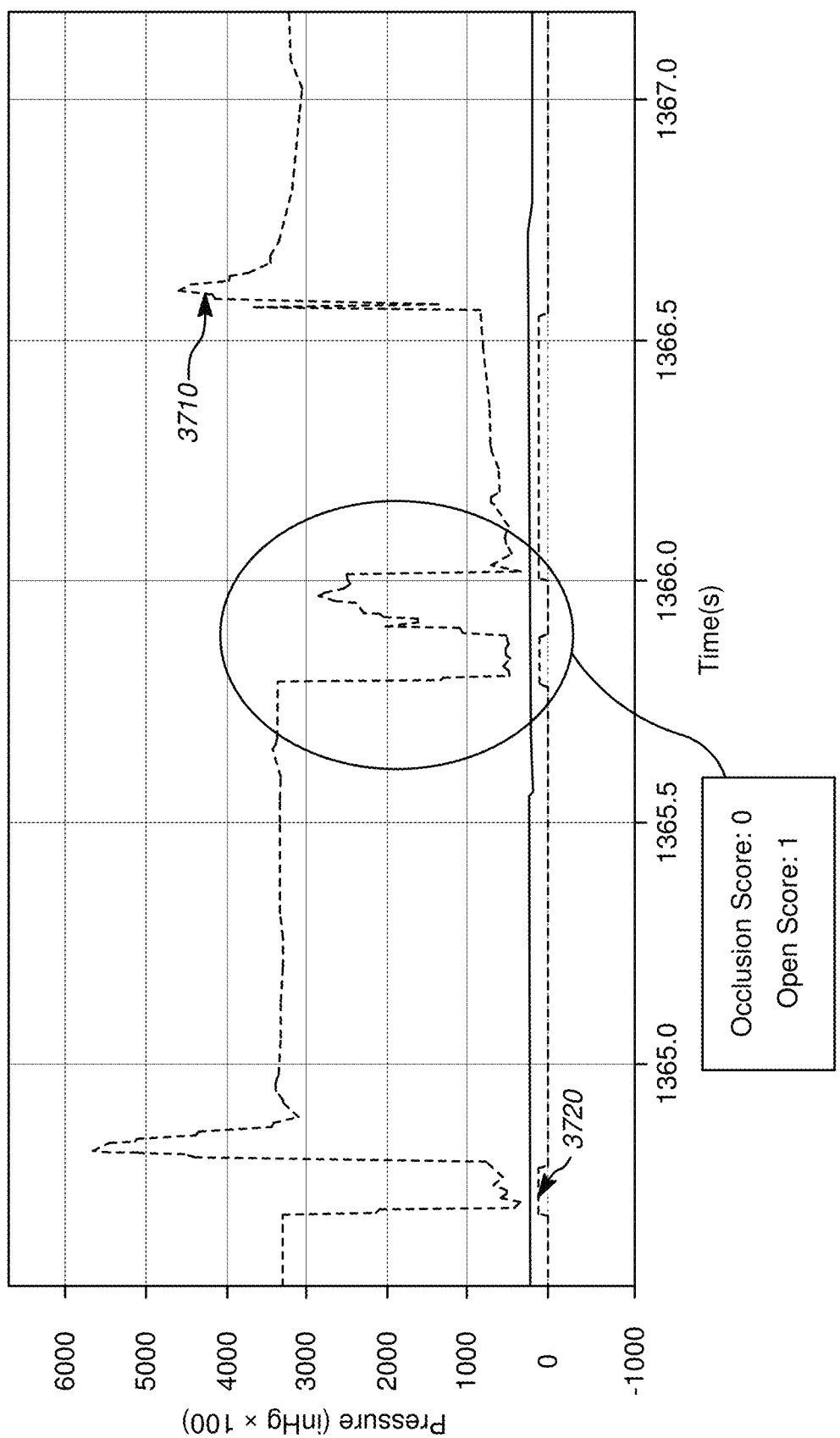
Figure 40:
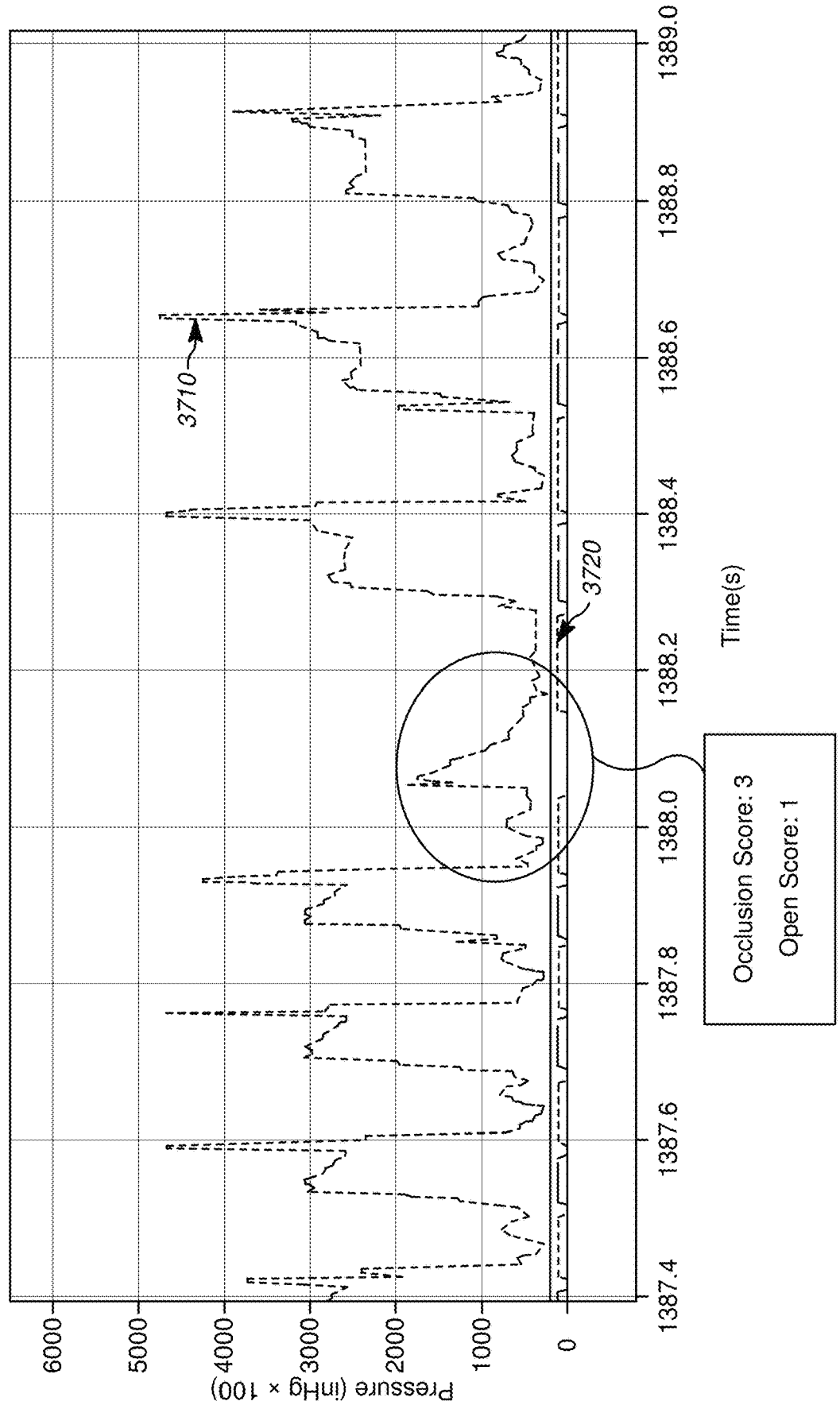

As another example, FIG. 39 illustrates the detected distal pressure profile in a partially occluded flow scenario, for a particular embodiment. The profile illustrates relatively damped rebound, with the detected pressure level not being restored to the levels of its starting distal pressure. Based on at least these pressure parameters, the Occlusion Score in this example is determined to be 0, whereas the Open Score is determined to be 1. FIG. 40 illustrates a particular embodiment where the Occlusion Score is determined to be 3, and the Open Score is determined to be 1.

Figure 41:
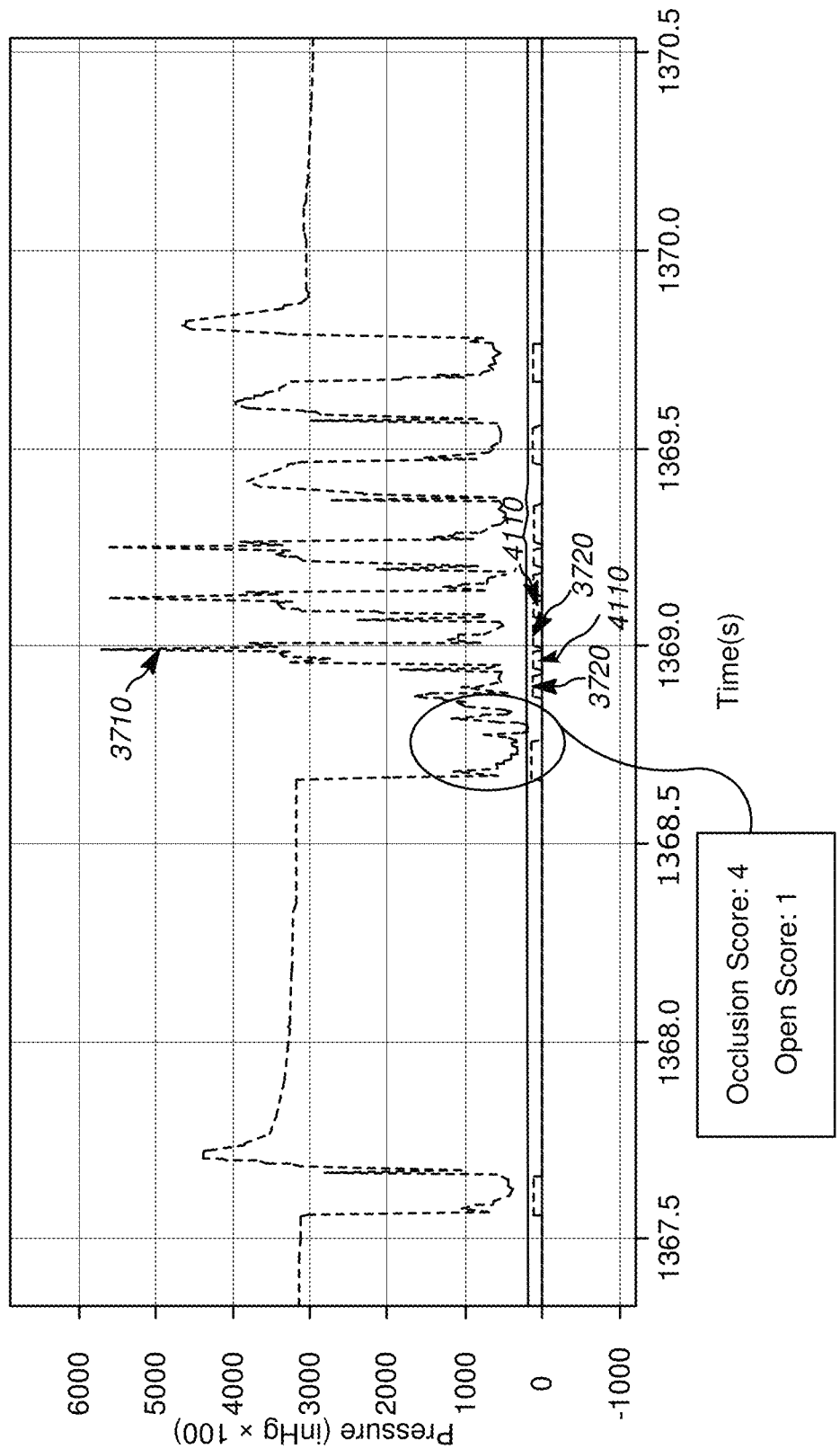

FIG. 41 illustrates an example where the Occlusion Score is determined to be 4 and the Open Score is determined to be 1, for a particular embodiment. In this example, the system may be initially determined to be in an open flow state based on the pressure profile detected in response to the first vacuum valve cycling, starting soon after the 1367.5 s time marker. Based on a determination of open flow, the system may be operated in intermittent aspiration, i.e., the vacuum valve may be held closed for a time interval to prevent aspiration of healthy blood. During this intervening time interval, in some embodiments, the catheter may be repositioned for engagement with a clot. The vacuum valve profile indicates that it was cycled again soon after the 1368.5 s time marker. Based on the corresponding detected pressure profile, the system may be determined to be in an at least partially occluded flow state, which is reflected in the system scores determined in this example. In some embodiments, as illustrated here, the system may trigger modulated or pulsed aspiration in response to this situation. Modulated aspiration may be observed in this particular embodiment as alternately cycling vacuum valve profile (3720) and pressure valve profile (4110), each indicating the time-varying state of the respective valve. In some embodiments, a saline fluid at an elevated pressure may function as a pressure source via a pressure valve. By the end of the sequence, as the distal profile illustrates, the occlusion may be aspirated, and the exemplary pressure profile illustrates indications of the system being in an open flow state again.

Figure 42:
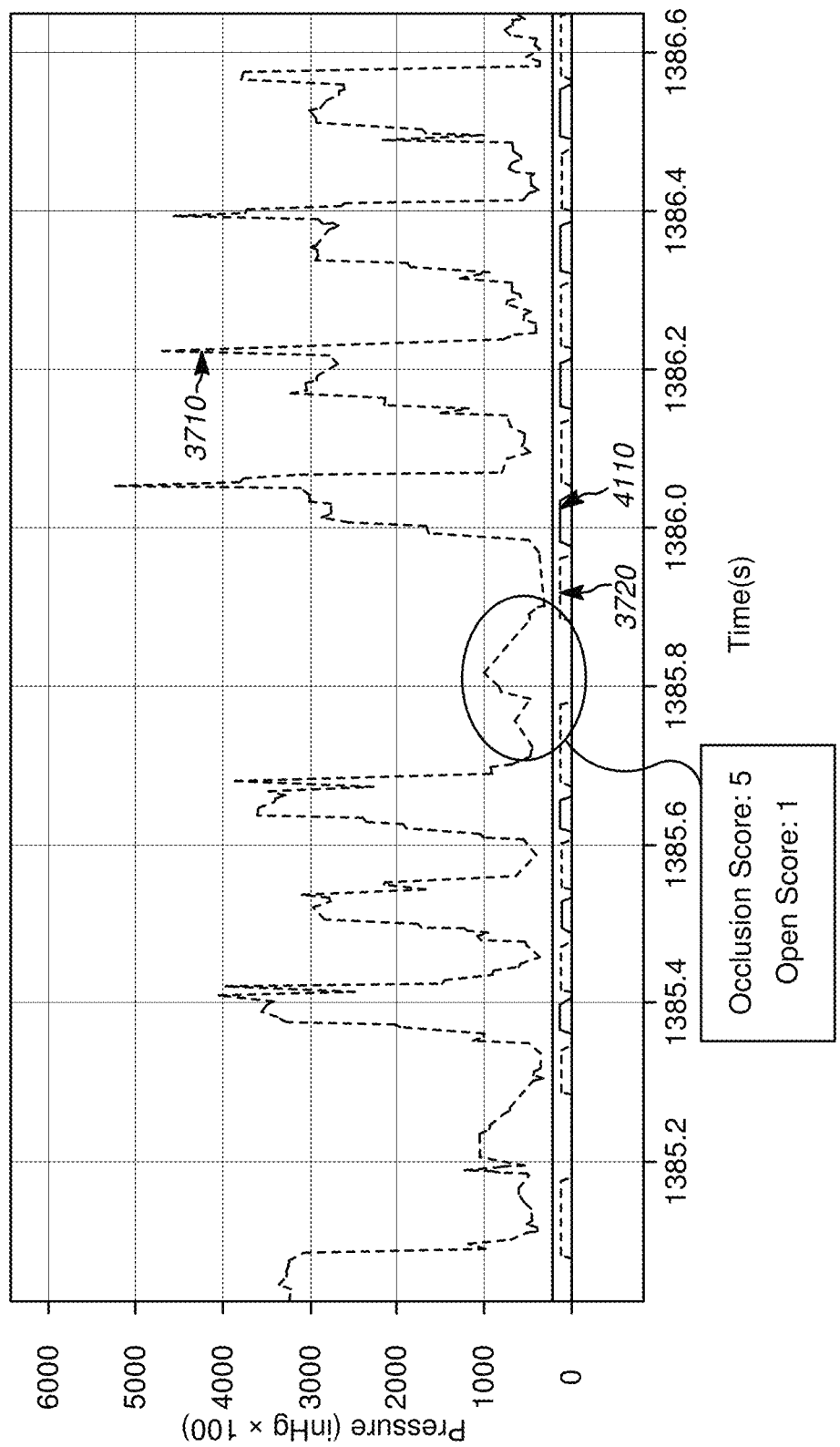
Figure 43:
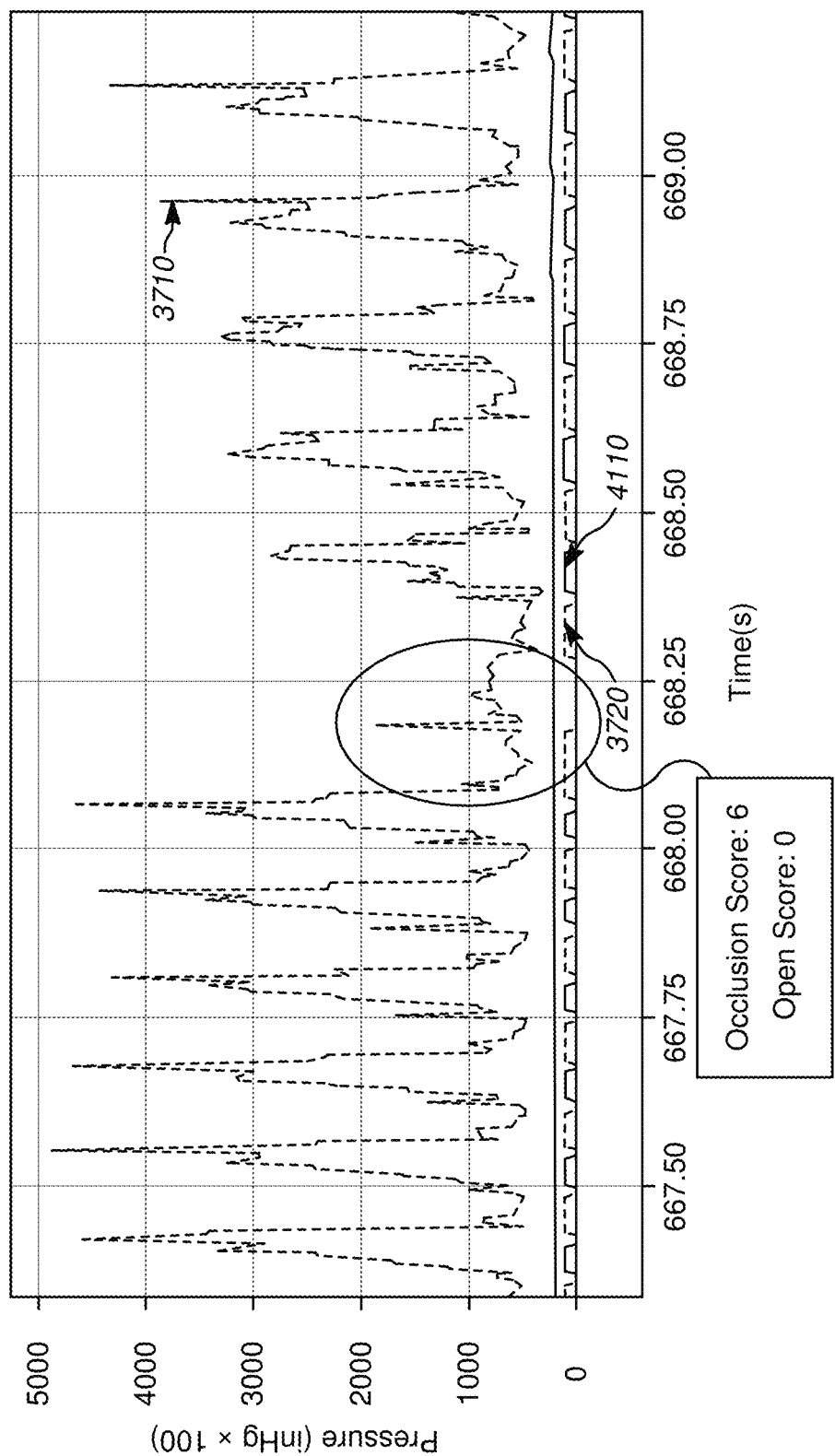
Figure 44:
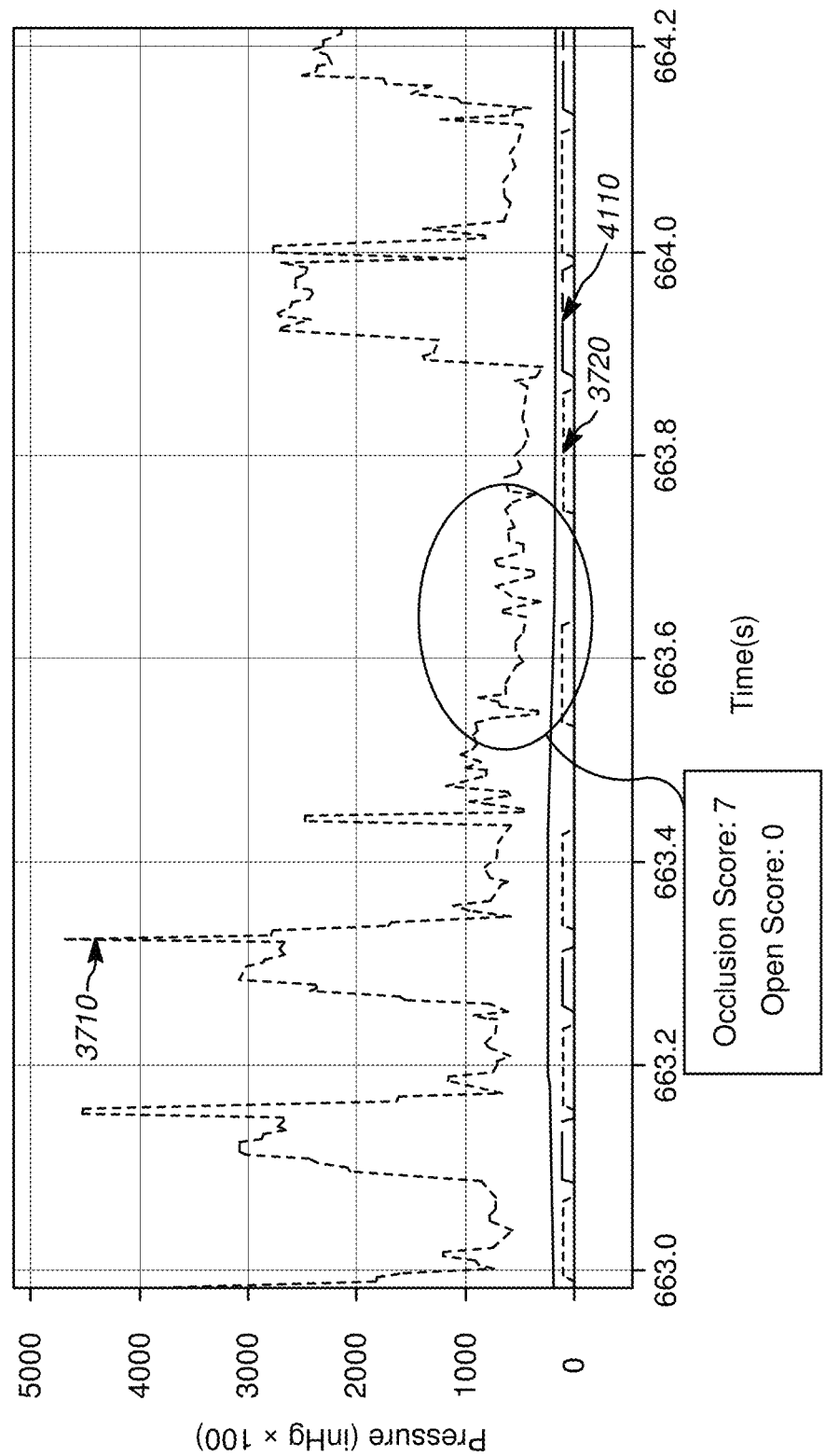
Figure 45:
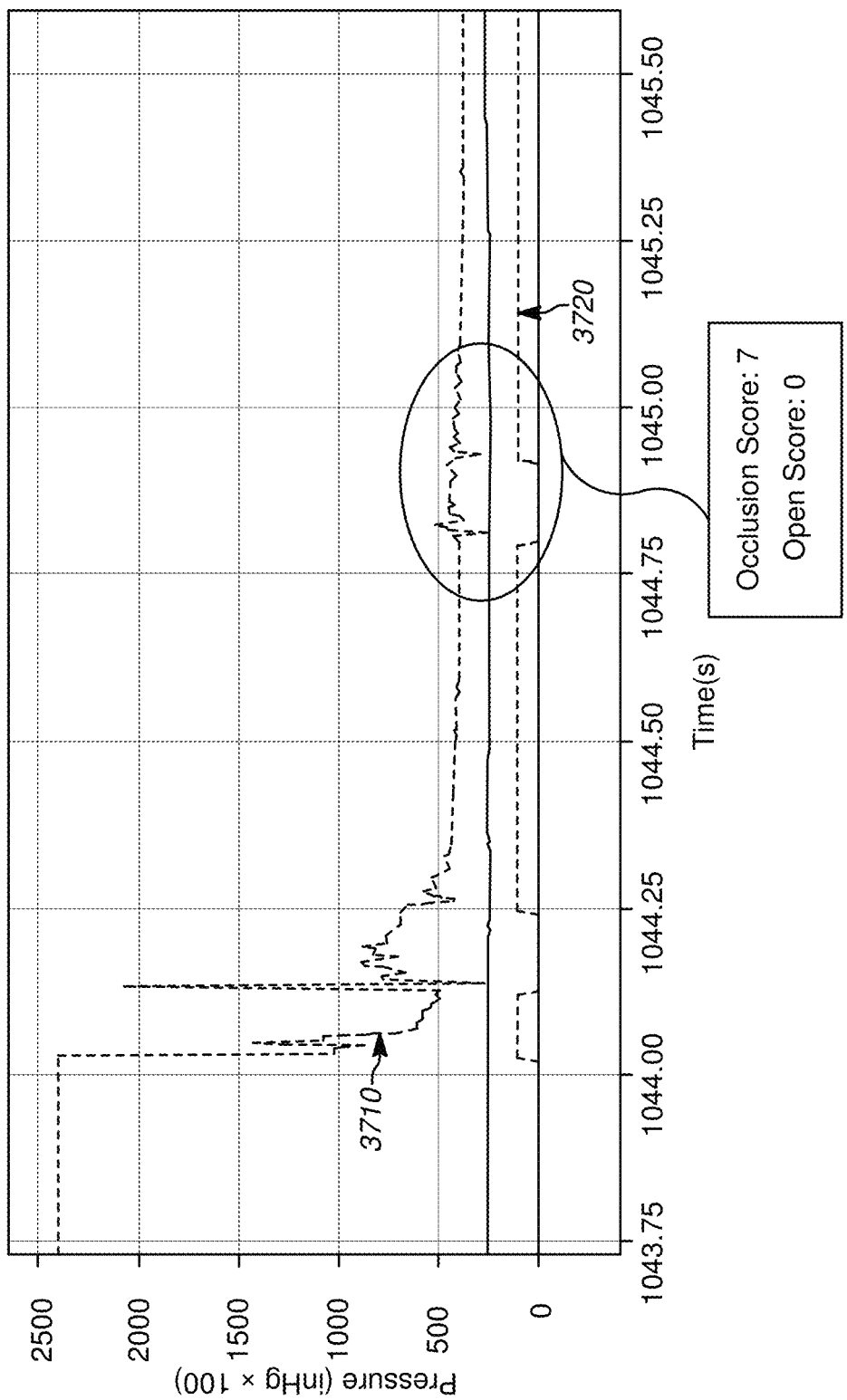
Figure 46:
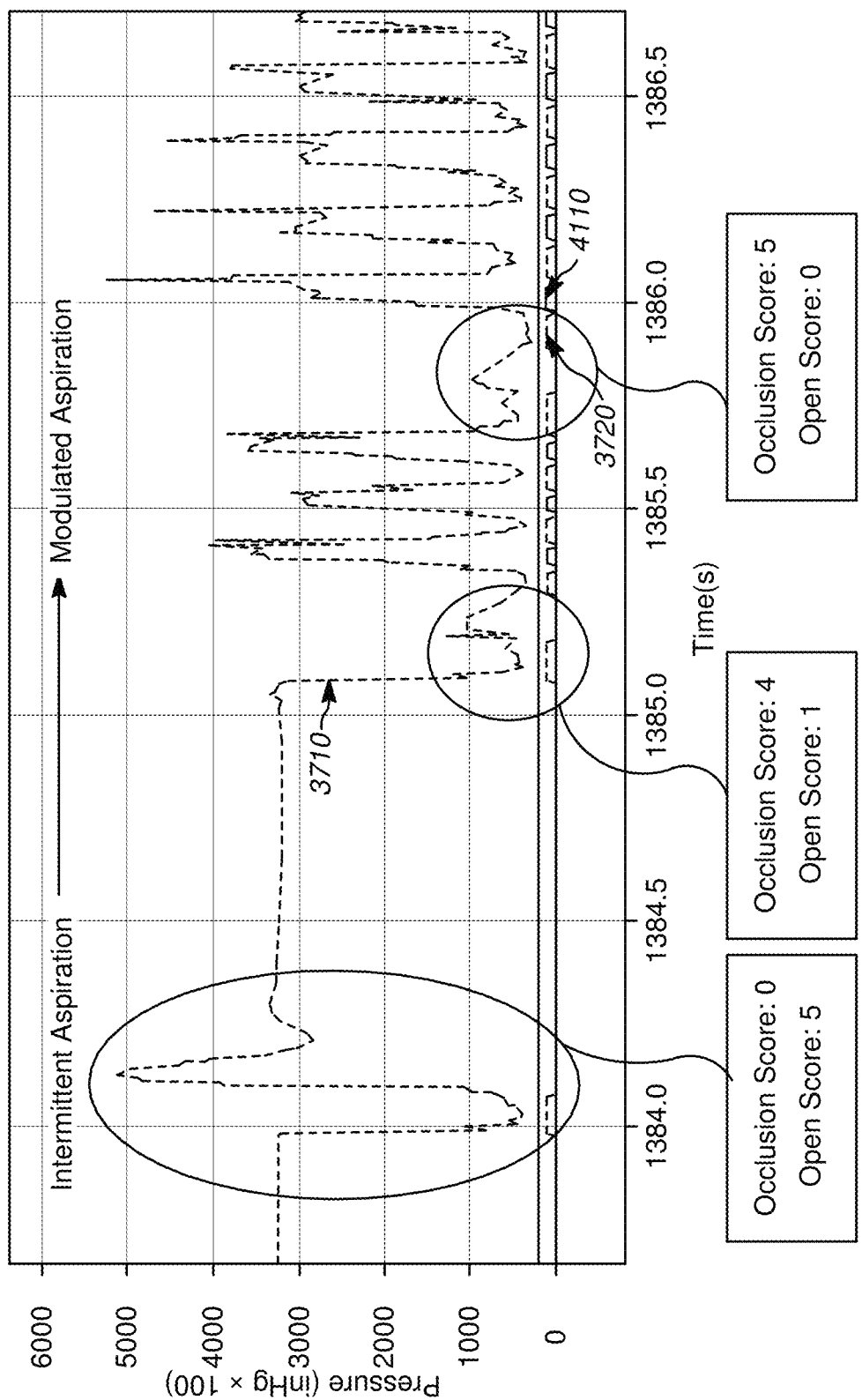
FIG. 46 illustrates a particular embodiment of evolution of distal pressure profile and corresponding system state scores.

FIGS. 42-45 illustrate examples of progressively more pronounced markers that may indicate occlusion in particular embodiments, with correspondingly larger Occlusion Scores, and/or lower (or zero) Open Scores determined by the controller. FIG. 42 illustrates an example with an Occlusion Score of 5, and an Open Score of 1. FIG. 43 illustrates an example with an Occlusion Score of 6, and an Open Score of 0. FIG. 44 illustrates an example with an Occlusion Score of 7, and an Open Score of 0. FIG. 45 illustrates a different example with an Occlusion Score of 7, and an Open Score of 0. FIG. 46 illustrates an open flow and corresponding intermittent aspiration evolving into an occluded or partially occluded flow in a particular embodiment, which may require modulated or pulsed aspiration. These illustrations are exemplary, and not provided by way of limitation.

In particular embodiments, particular combinations of Occlusion Score, Open Score, and/or other system scores may be used to trigger a maceration cycle for applying mechanical forces on occlusive material. Such mechanical action may be applied to sufficiently modify the form and/or consistency of a clot or other occlusive material to enable more effective aspiration.

In particular embodiments, an escalation feature may be used wherein an Escalate Count of consecutive determinations of identical system state is maintained by the controller, and specific action may be taken if the count exceeds a threshold. In particular embodiments, the count may be reset in the iteration following the threshold crossing iteration. In particular embodiments, the action taken if the count exceeds a threshold may be generating a notification, such as a user notification. In particular embodiments, the action taken if the count exceeds a threshold may involve the operation of one or more valves by the controller. In particular embodiments, the parameters for modulated or pulsed aspiration may be adjusted based on a combination of the Occlusion Score and the Escalate Count.

Figure 47:
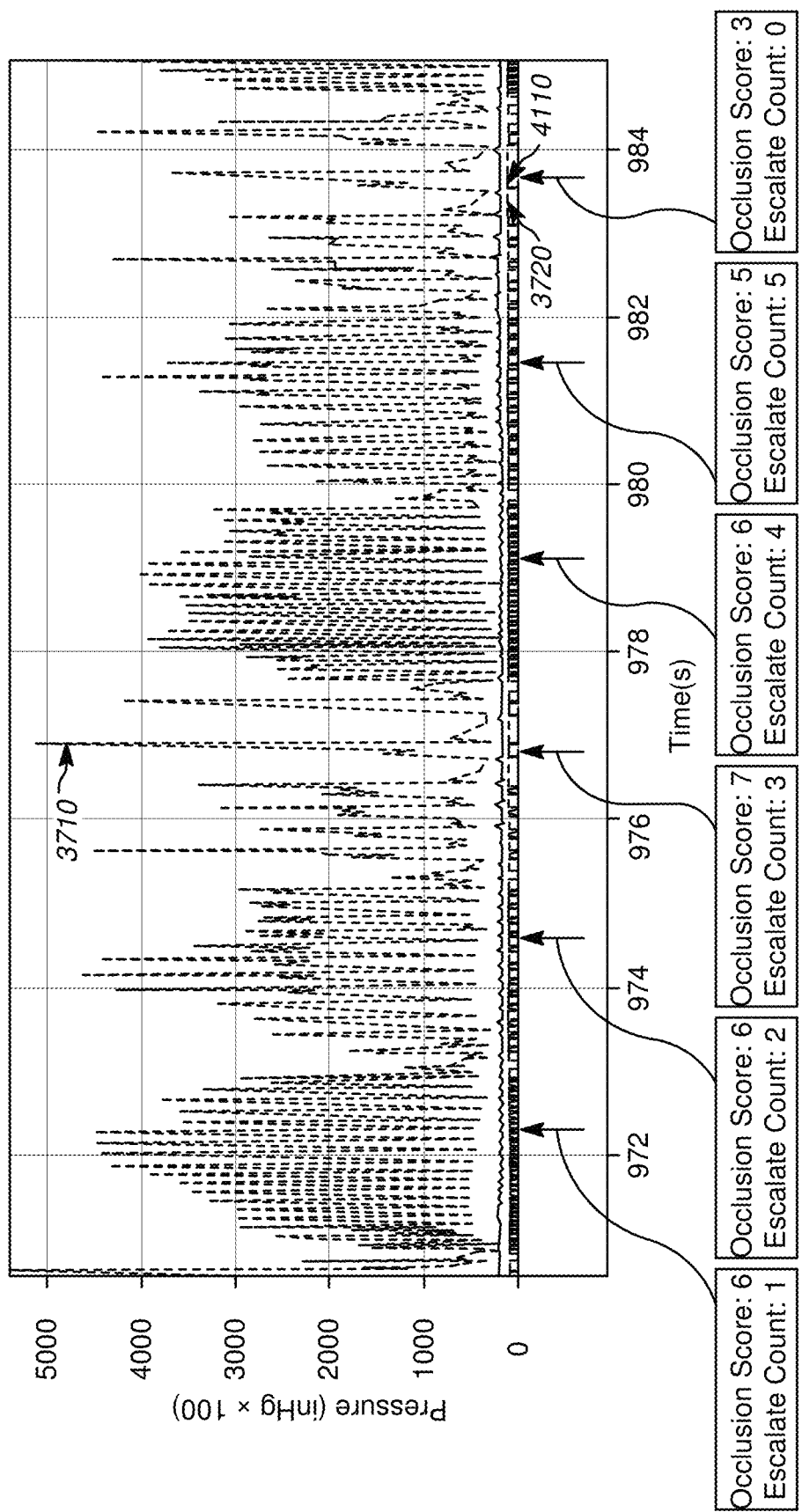
FIG. 47 illustrates a particular embodiment of consecutive system scores, and escalation.

FIG. 47 illustrates the progression of an escalation count scenario, in a particular embodiment. The Occlusion Score determined at the specific time instants indicated by the arrows is illustrated as an example, and not by way of limitation, fluctuating between 5 and 7 during the time interval spanning the first five such instants (arrows), but which may generally be indicating a persisting occluded flow state. Correspondingly, an Escalate Count is illustrated to be incrementing during each consecutive identical determination of occluded flow, until a threshold Escalate Count of 5 is reached, at which time, in particular embodiments, the parameters of the modulated aspiration may be modified based on the combination of the Occlusion Score and Escalate Count. At the next determination of system scores, as illustrated by the last arrow in FIG. 47, the Escalate Count may been reset to zero. In this example, the Occlusion Score is illustrated to have significantly decreased to 3.

In particular embodiments, the values of one or more system scores relative to thresholds may be used to initiate action based on operating one or more valves. Such action taken may additionally depend on prior or current system states and/or modes of aspiration by valve operation.

In particular embodiments of an aspiration thrombectomy system performing intermittent aspiration, an increase of an Occlusion Score beyond a threshold may trigger initiation of a modulated aspiration mode. In particular embodiments of an aspiration thrombectomy system performing intermittent aspiration, an increase of an Open Score beyond a threshold may trigger a mode involving continued intermittent aspiration. In particular embodiments of an aspiration thrombectomy system performing intermittent aspiration, if neither an Open Score nor an Occlusion score increase beyond a threshold, it may trigger initiation of continuous aspiration. In particular embodiments of an aspiration thrombectomy system performing modulated aspiration, a decrease of an Occlusion Score below a threshold may trigger a change of mode to intermittent aspiration.

Figure 48:
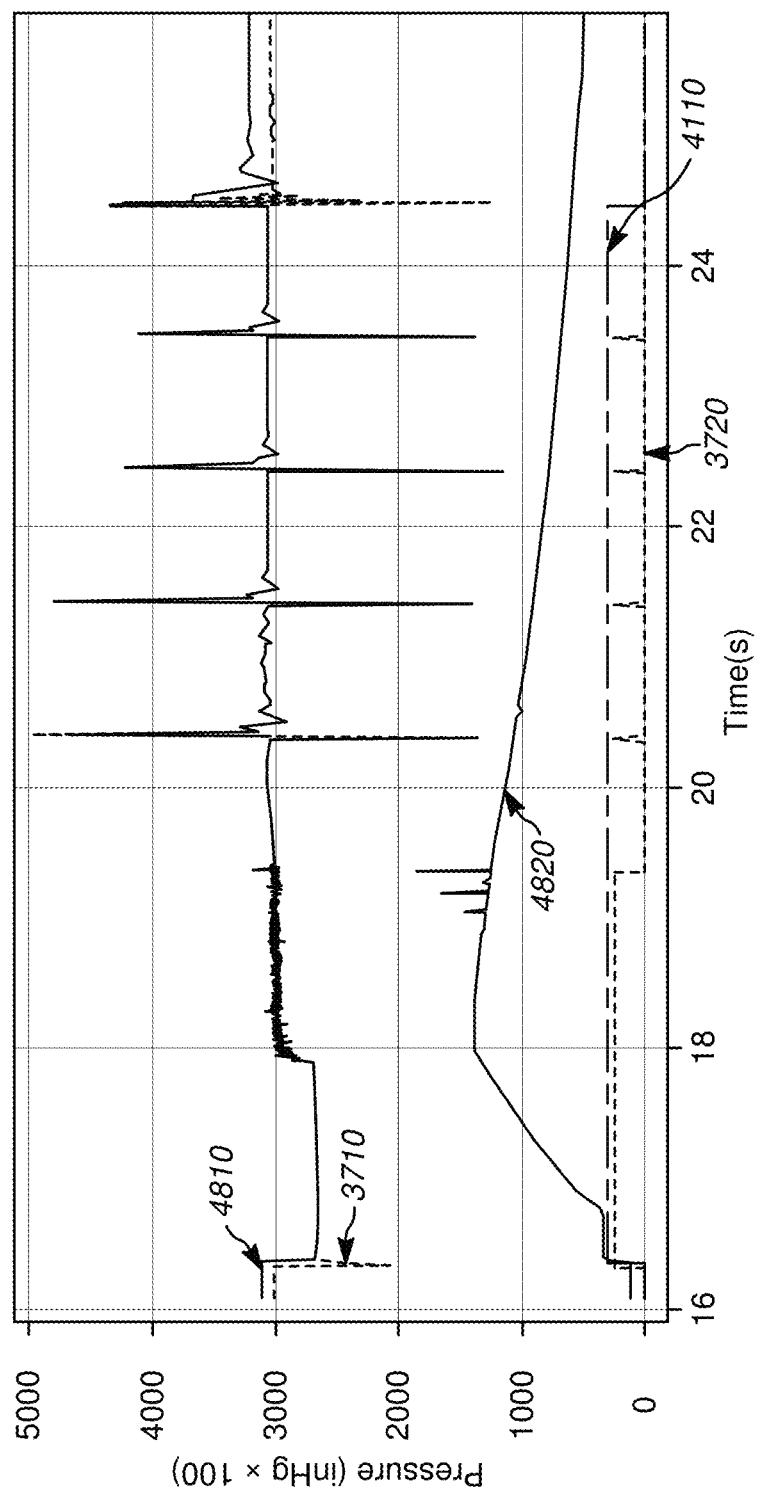
FIGS. 48-49 illustrate pressure profiles of particular embodiments during priming.
Figure 49:
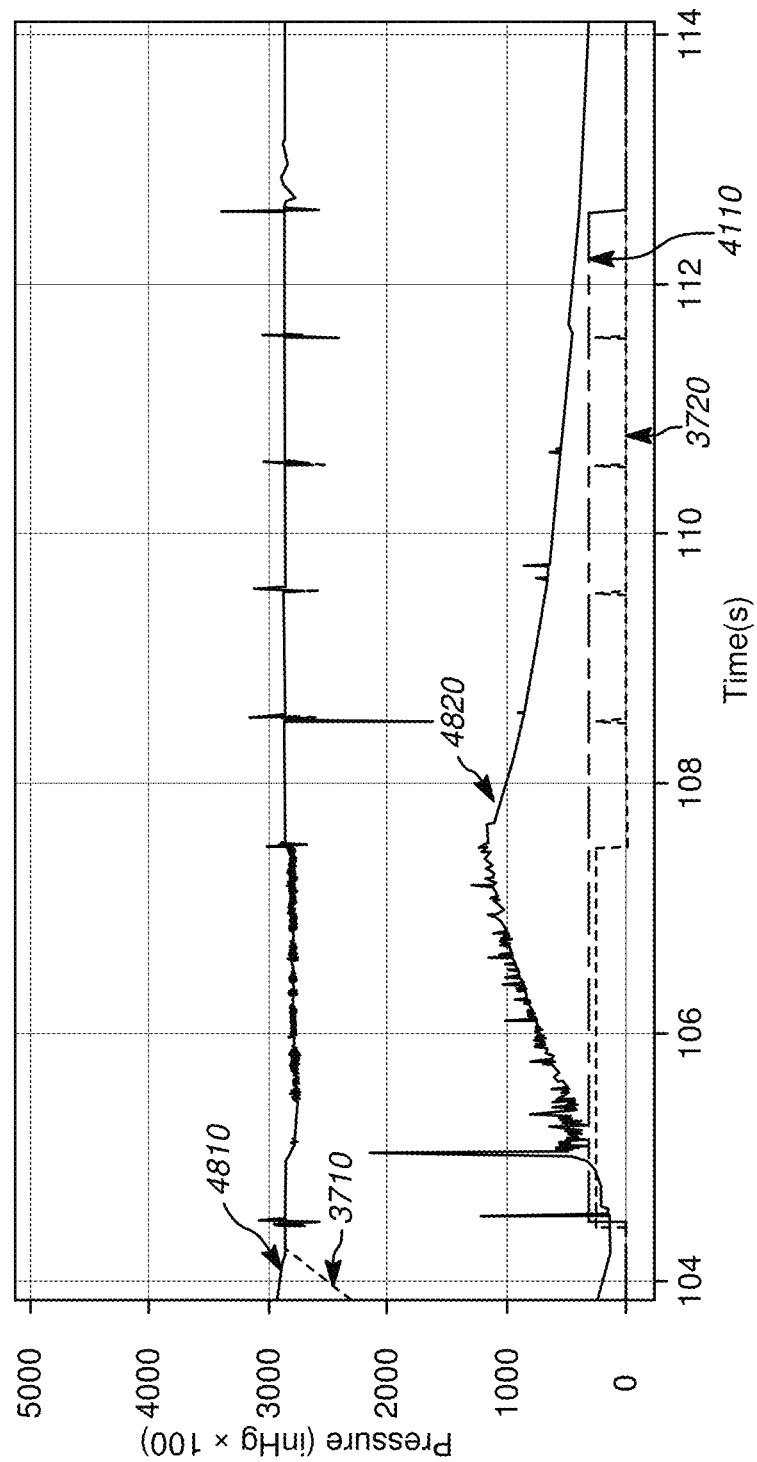

As previously discussed, additional system states may be determined based on detected sensor data correlated with generated pressure level changes. For instance, in particular embodiments, presence of saline and/or air in the system may be detected by such dynamic system state detection. FIGS. 48 and 49 illustrate examples of detecting a successful and an unsuccessful priming operation, respectively, in particular embodiments, by using detected pressure profiles correlated with generated changes in pressure by valve operation. These illustrations are exemplary, and not provided by way of limitation.

FIGS. 48 and 49 illustrate a distal pressure profile 3710, a saline pressure profile 4810 associated with a saline pressure source, and a vacuum pressure profile 4820 associated with a pressure in the vacuum canister, based on particular embodiments. An exemplary vacuum valve profile 3720 illustrates the time-varying open/close operational state of the vacuum valve. An exemplary pressure valve profile 4110, also called a vent valve profile, illustrates the time-varying open/close operational state of the pressure valve for the saline pressure source. Specific features and pressure parameters that may permit detection of saline and/or air will be further discussed.

Figure 50:
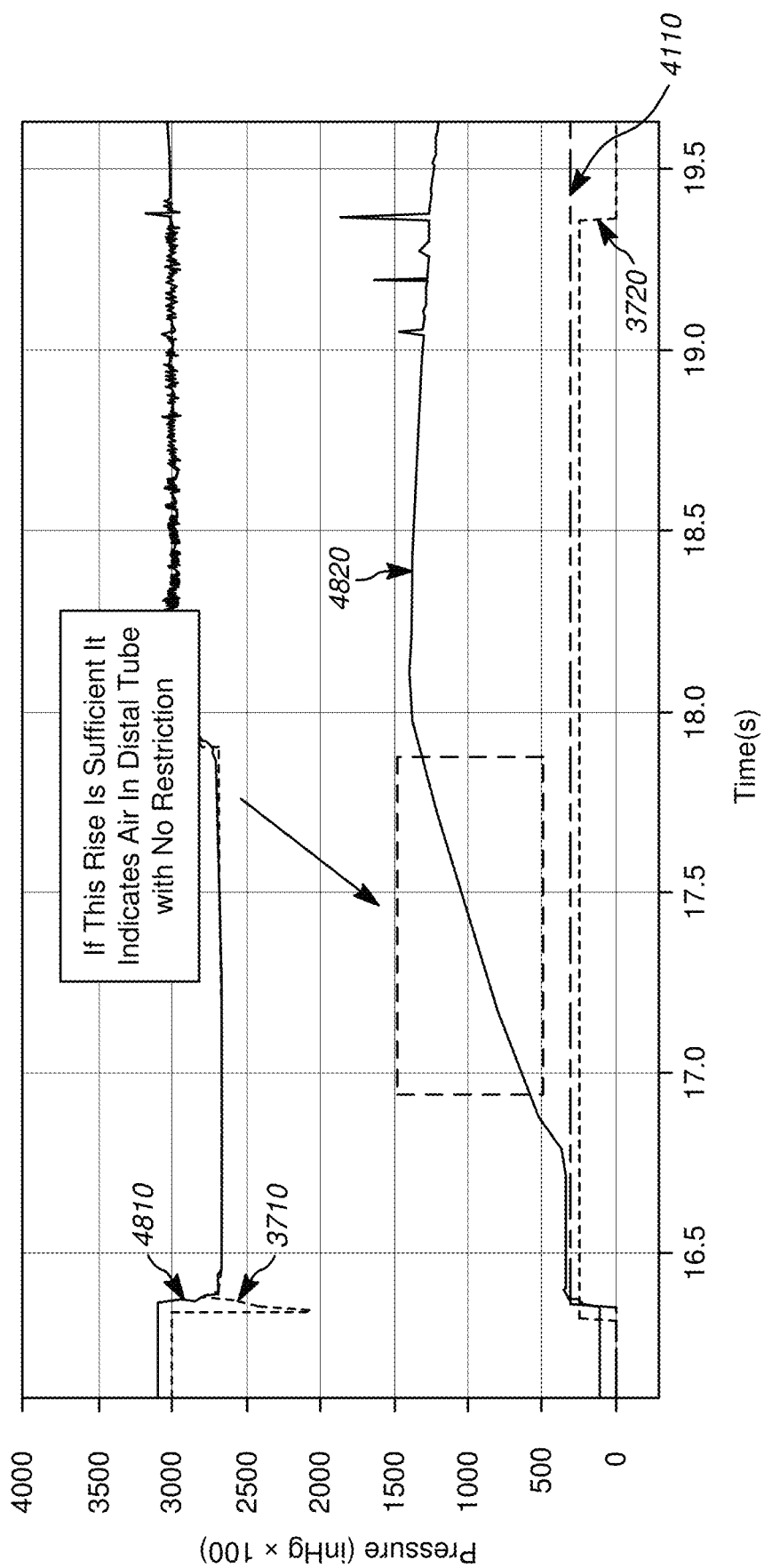
FIGS. 50-64 illustrate pressure profile features of particular embodiments for dynamic system state detection during priming.
Figure 51:
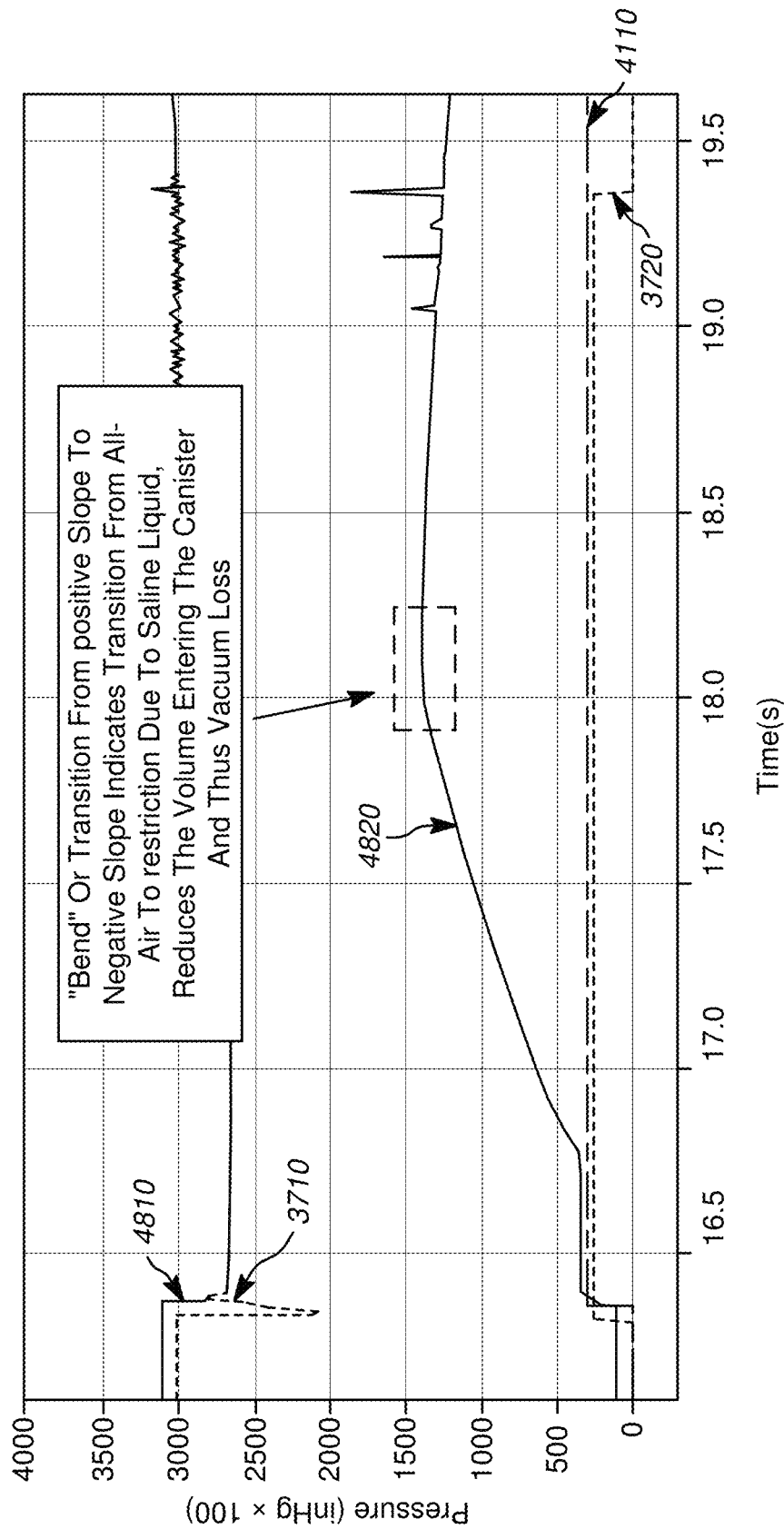
Figure 52:
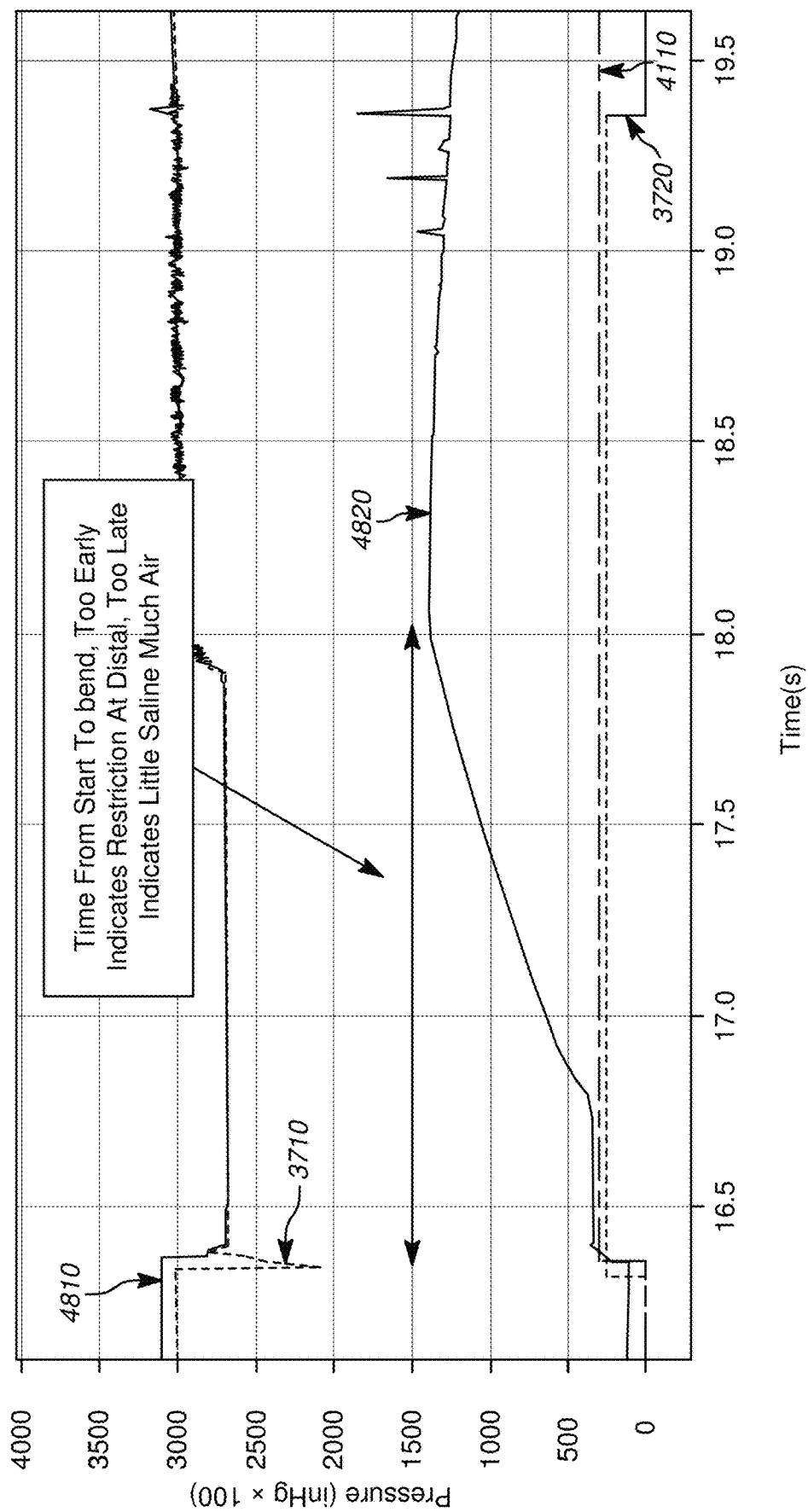

FIGS. 50-64 illustrate pressure profile features of particular embodiments for dynamic system state detection during priming. These illustrations are exemplary, and not provided by way of limitation. FIG. 50 illustrates pressure profiles at the beginning of a priming sequence in particular embodiments, upon opening both the vacuum valve and the saline pressure valve. It illustrates how the slope of a vacuum pressure profile may indicate air in the distal connection tubing, along with the absence of restrictions. FIG. 51 illustrates, still at the beginning of a priming sequence in particular embodiments, how the nature of a transition or change in slope of a vacuum pressure profile, such as a bend from positive to negative slope, may indicate a transition from an air-filled system to restrictions due to a saline liquid entering the vacuum canister. FIG. 52 illustrates how the time interval between the start of priming and identifying a bend, or change of slope, in the vacuum pressure profile, in particular embodiments, may be indicative of relative balance of air and/or saline, as well as restrictions at the distal connection tubing.

Figure 53:
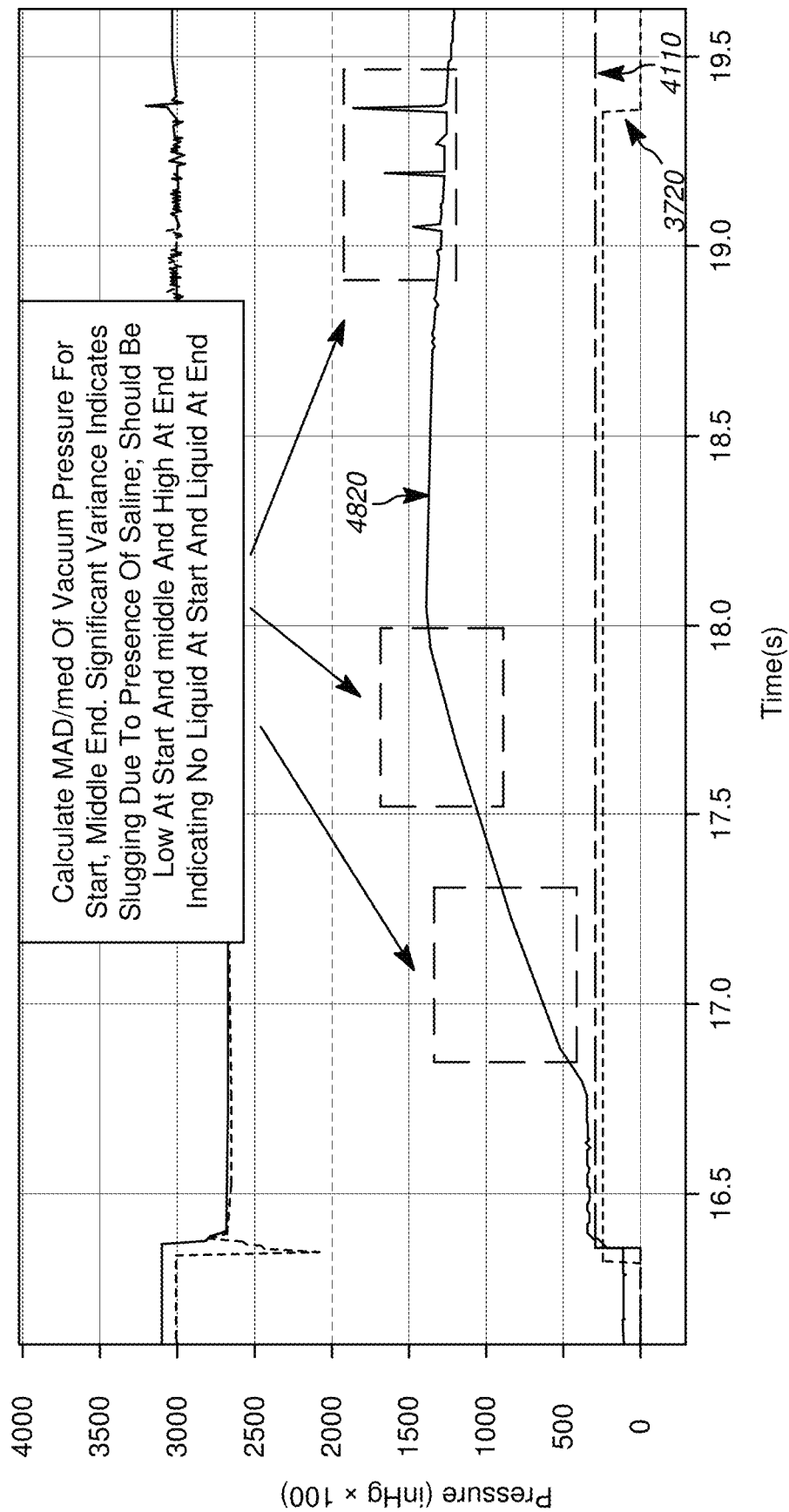
Figure 54:
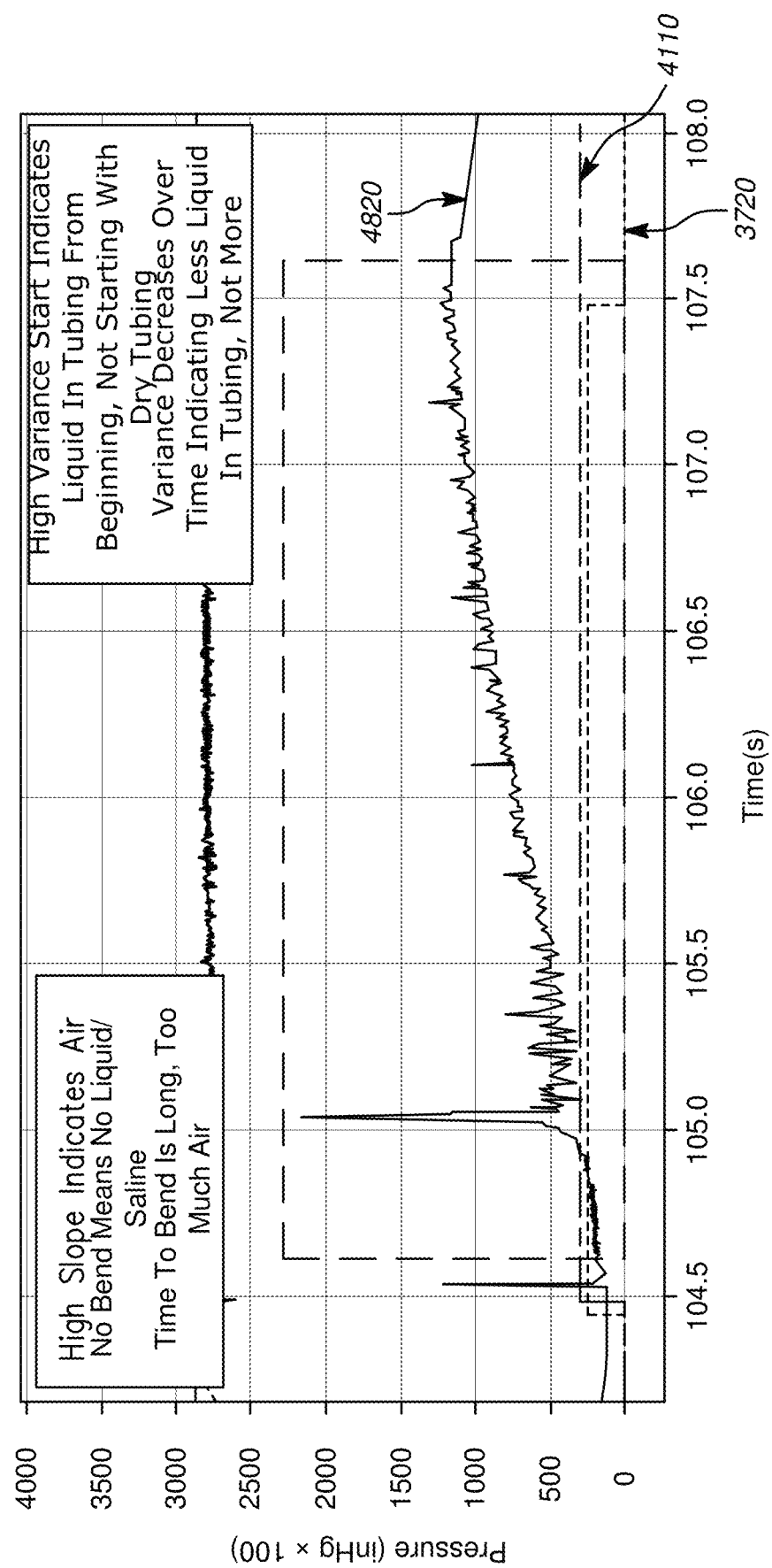

FIG. 53 illustrates how the Mean Absolute Deviation ("MAD") of Vacuum Pressure over the Median ("Med"), which may be denoted as "MAD/med," taken during time windows/intervals at the beginning, middle, and end of the priming operation, may be used to identify saline, and be used to detect successful priming, in particular embodiments. High levels of variance may indicate slugging due to liquid saline; such variance may increase through the evolution of a successful priming operation, indicating progressive replacement of air with liquid. In contrast, FIG. 54 illustrates features of a vacuum profile corresponding to an unsuccessful priming operation, in particular embodiments. During the early stages of priming, a high slope may indicate the presence of air, and the delay or absence of a notable and timely change of slope may be indicative of the absence of liquid saline. The excessive time taken for the slope to change may be indicative of too much air in the system. Furthermore, the levels of variance from the beginning may indicate starting with the presence of liquid in the tubing, rather than with dry tubing. A decrease in vacuum pressure variance over time may be indicative of less liquid in the tubing over time, rather than more.

Figure 55:
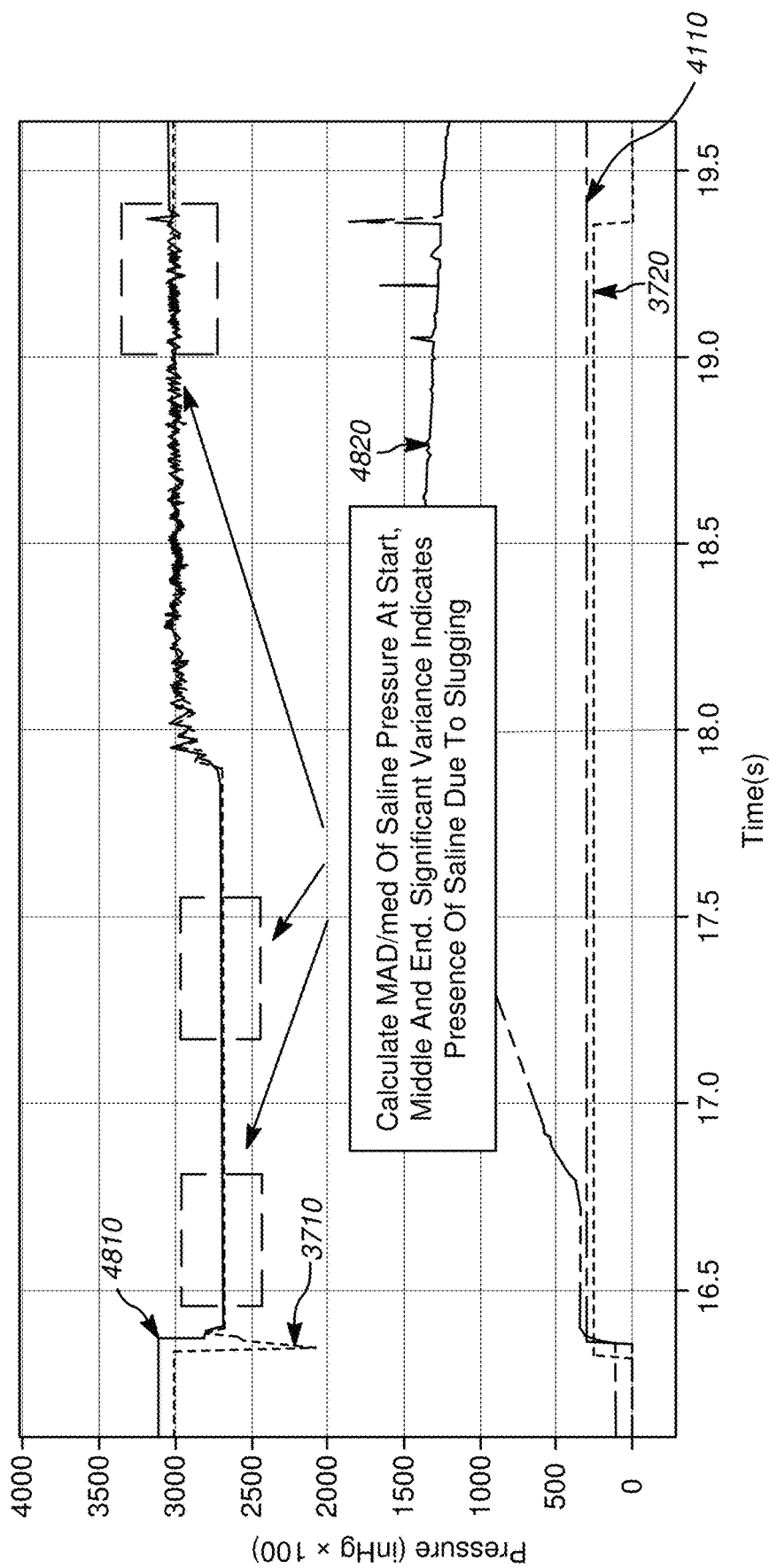
Figure 56:
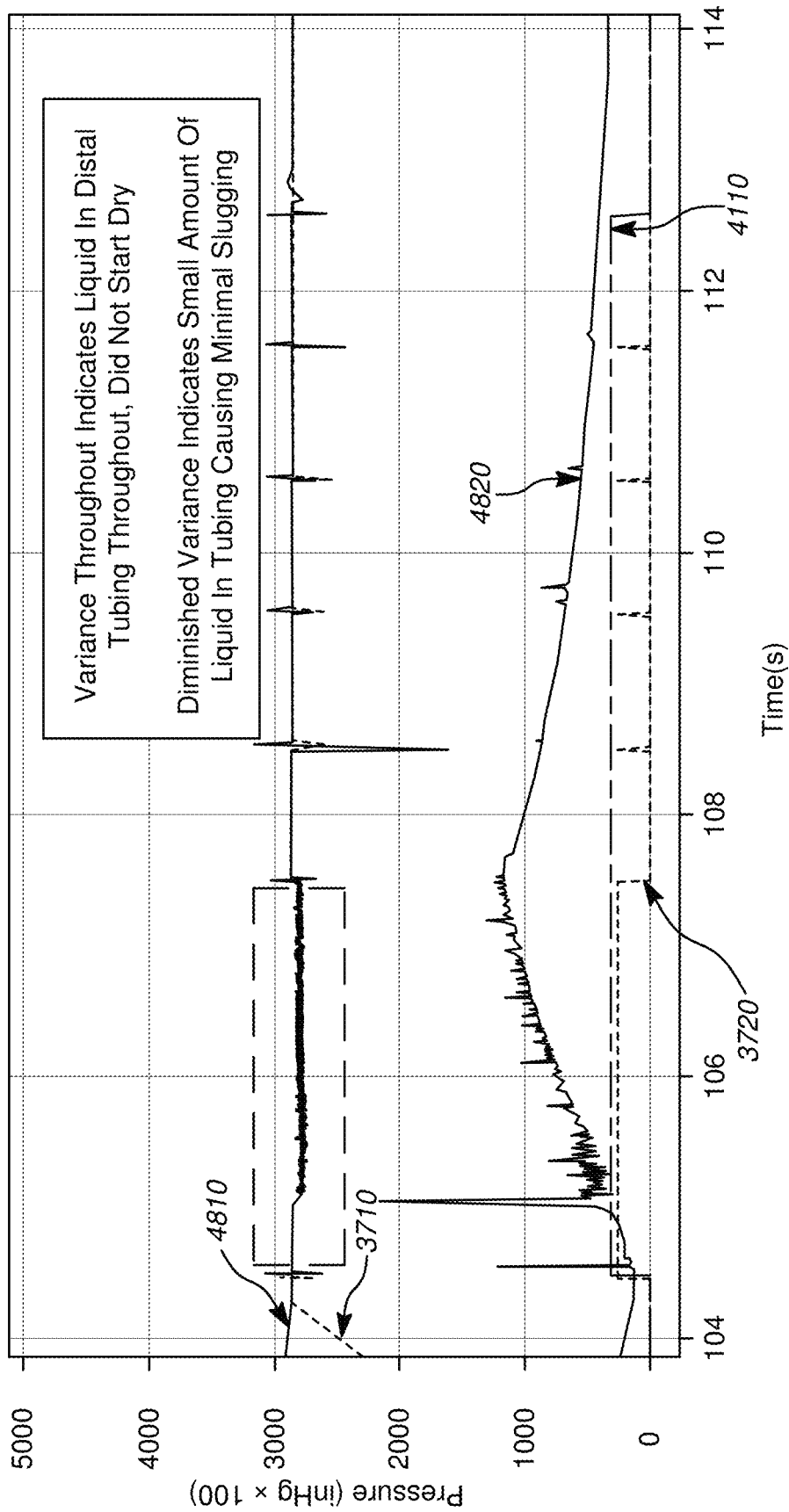

FIG. 55 illustrates the evolution of variance of saline pressure through the beginning, middle, and end of a successful priming operation, in particular embodiments. For instance, the Mean Absolute Deviation of Pressure over the Median, or MAD/med, of each pressure may be used as a metric of variance. Again, high levels of variance may be indicative of slugging due to the presence of saline. For the case of successful priming in this particular embodiment, the low variance at the beginning may be indicative of starting with a dry tube, with the increased and significant pressure variance by the end of the operation indicating potential presence of saline. In contrast, FIG. 56 illustrates significant pressure variance in saline pressure at the beginning of the priming sequence in particular embodiments, indicating that the tube may not have started dry. Diminished variance may indicate a small amount of liquid in the tubing causing minimal slugging.

Figure 57:
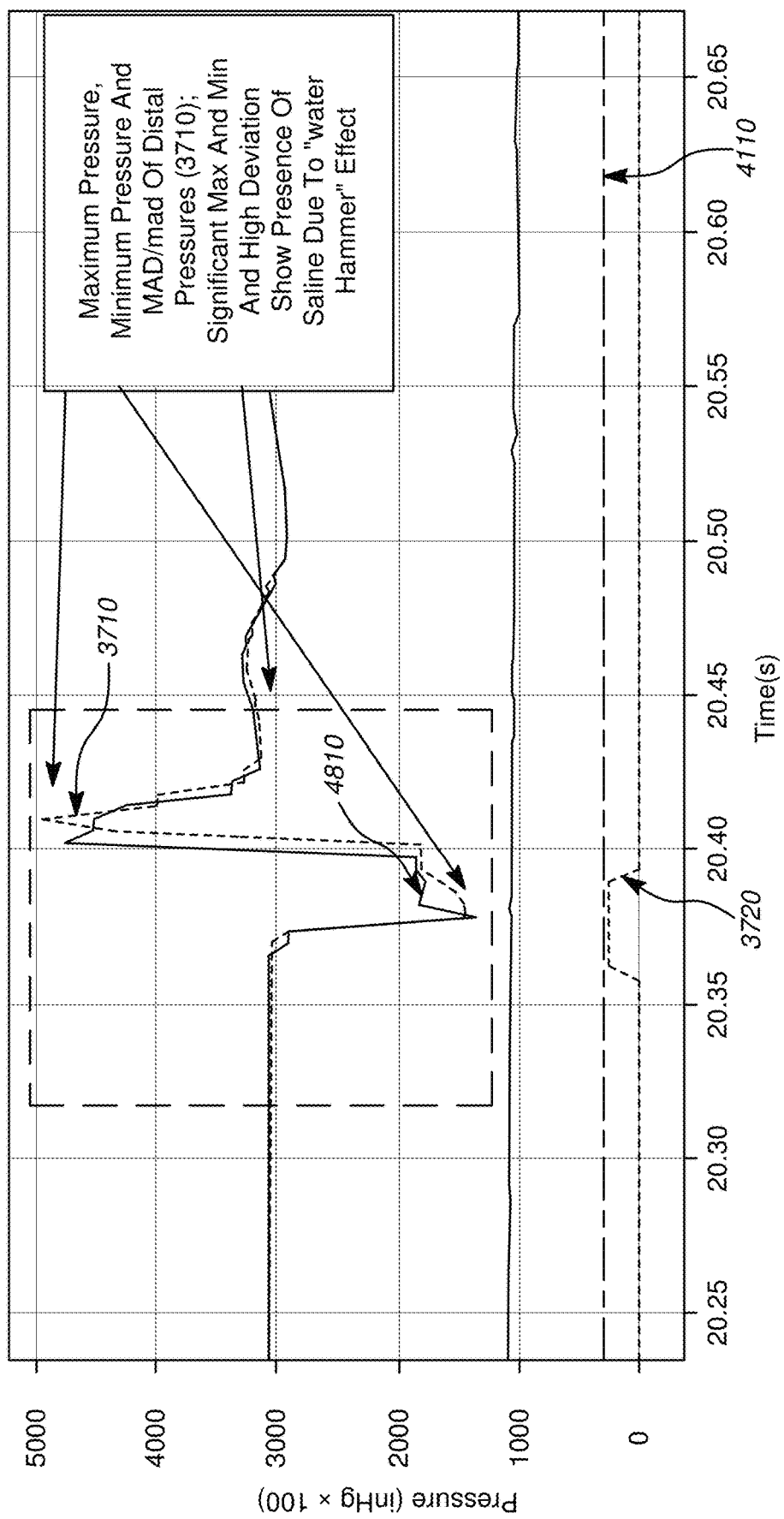
Figure 58:
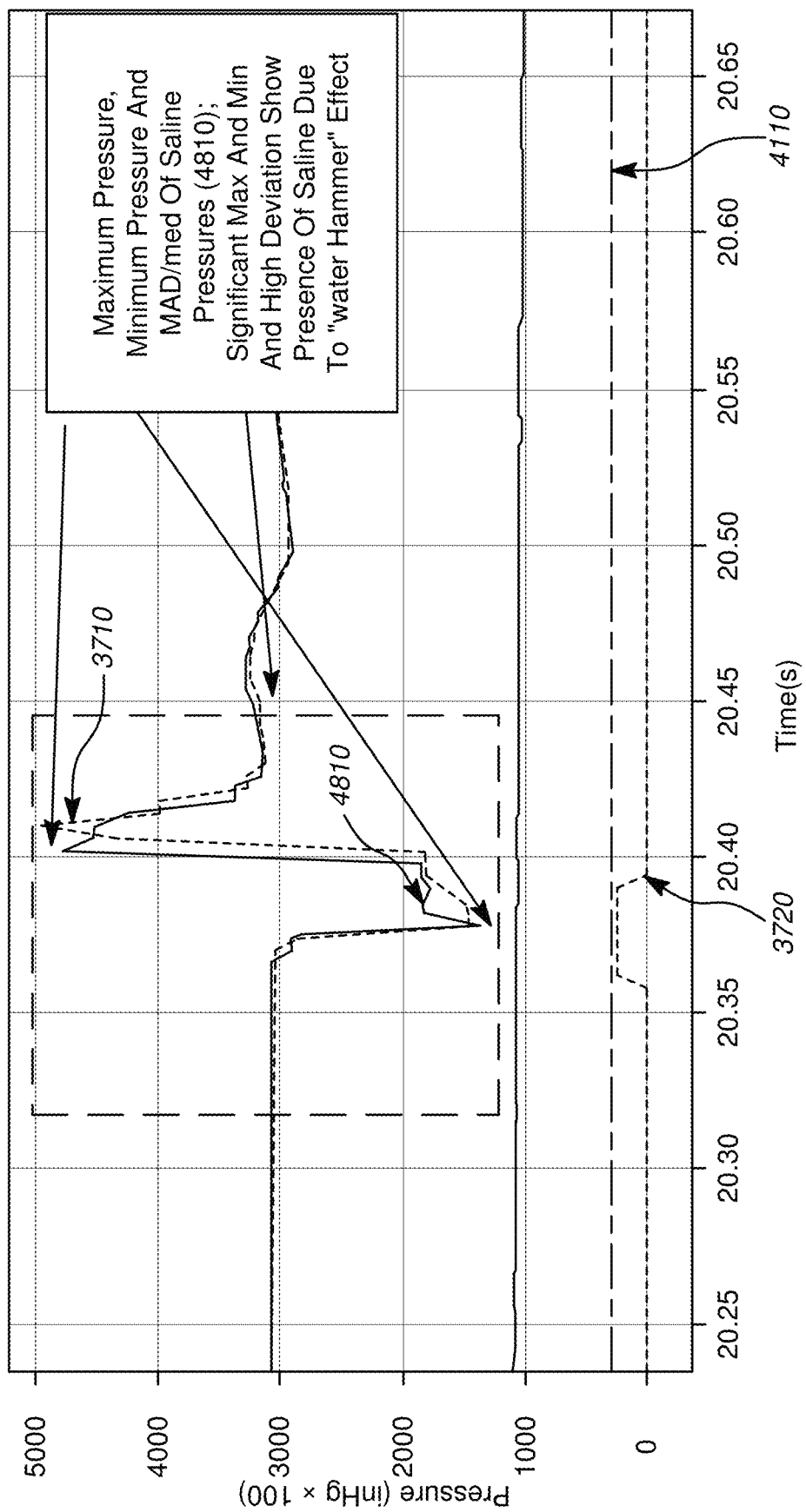
Figure 59:
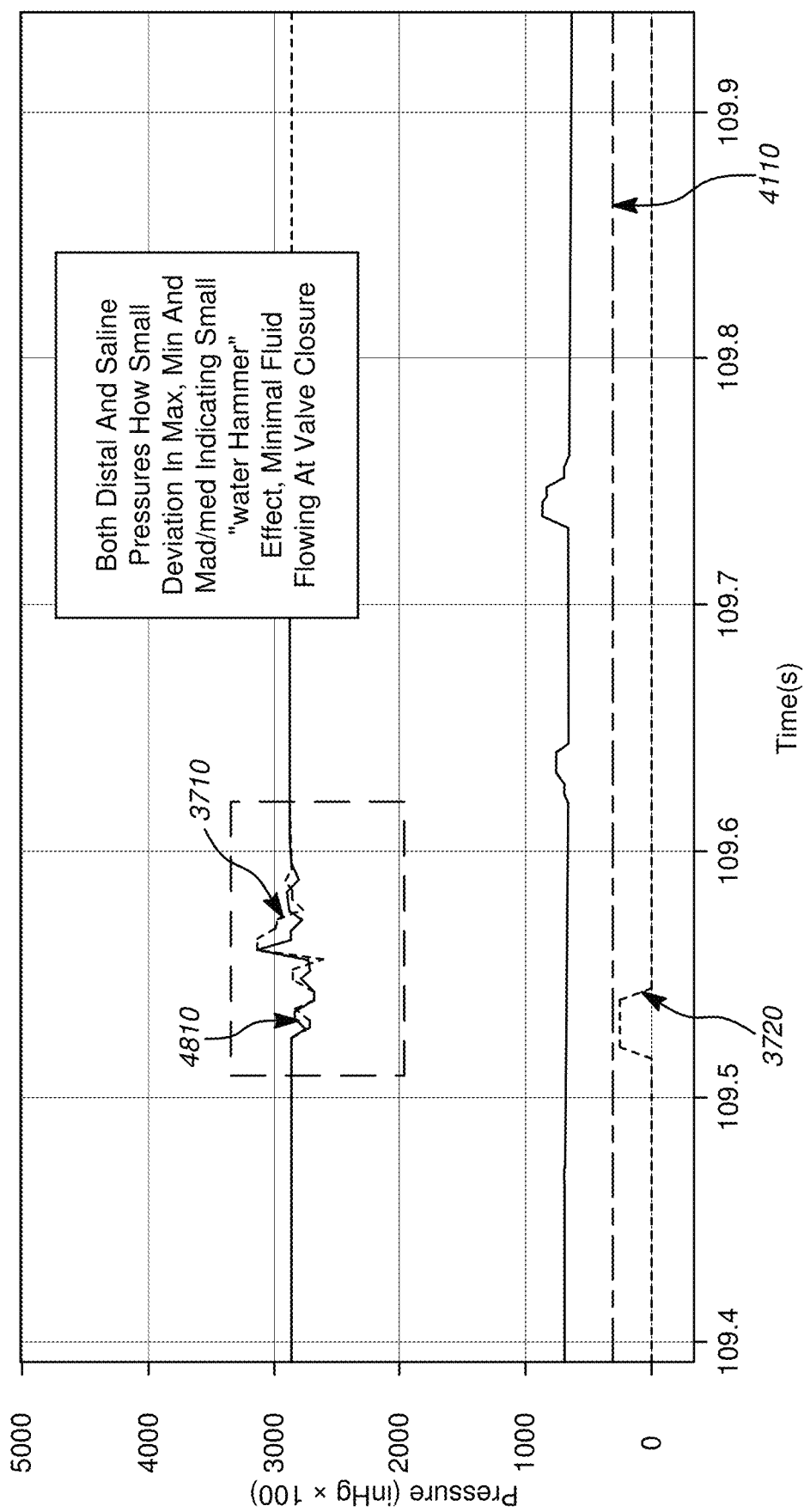

FIG. 57 illustrates a distal pressure profile 3710 taken during the middle of a successful priming sequence, in particular embodiments. Significantly high maximum and low minimum distal pressures, as well as high variances, may indicate inertial "water hammer" effects of the liquid relative to air, which may further indicate the presence of liquid saline. Similarly, FIG. 58 illustrates a saline pressure profile 4810 taken during the middle of a successful priming sequence, in particular embodiments. Significant high maximum and low minimum saline pressures, as well as high variances, may indicate inertial "water hammer" effects of the liquid relative to air, which may further indicate the presence of liquid saline. In contrast, FIG. 59 illustrates distal and saline pressure profiles taken during the middle of an unsuccessful priming sequence, in particular embodiments. Both exemplary pressure profiles illustrate small deviations in maximum and minimum pressures, and low variances, which may indicate low inertial "water hammer" effects and minimal fluid flow at vacuum valve closure.

Figure 60:
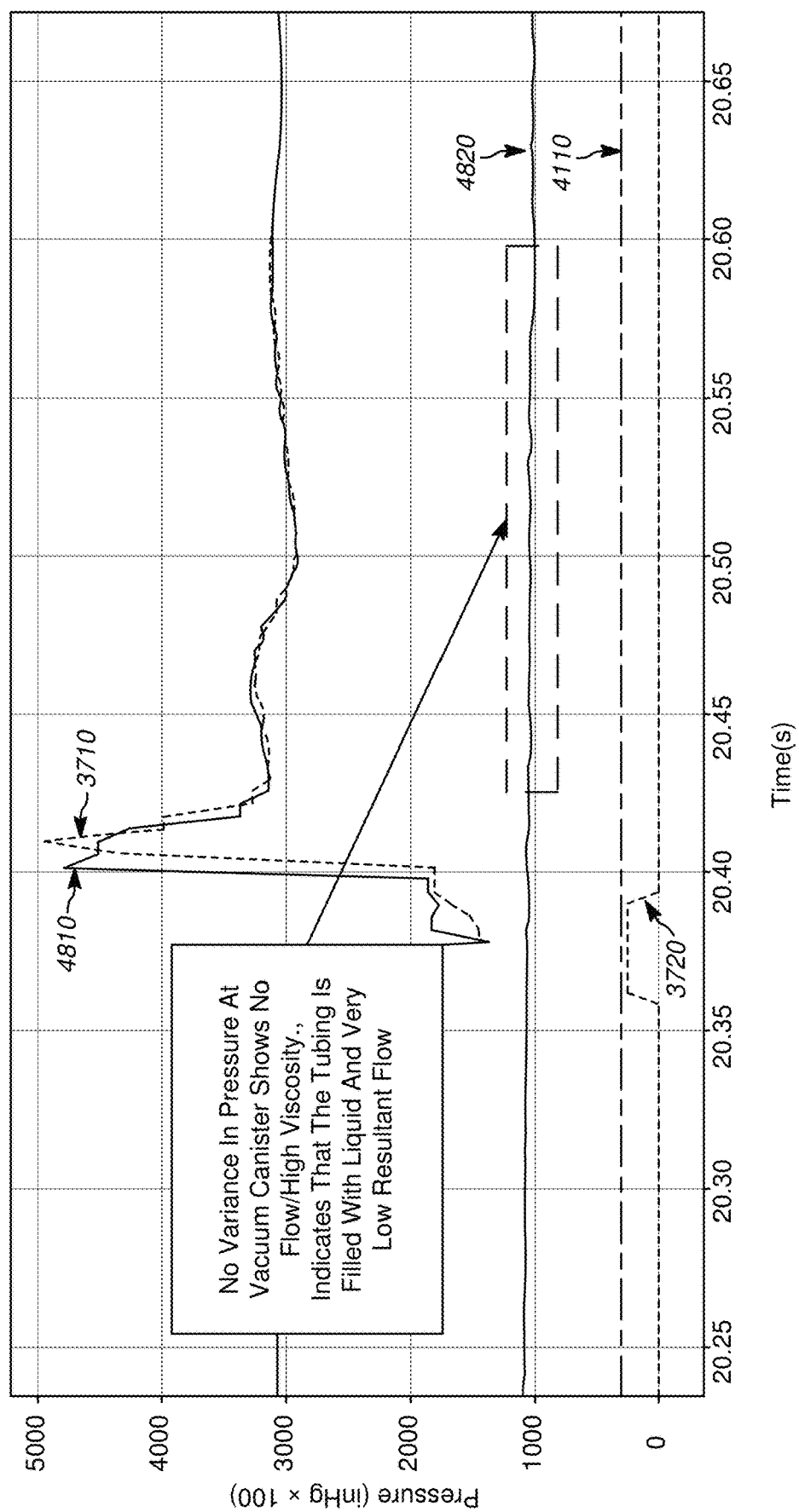
Figure 61:
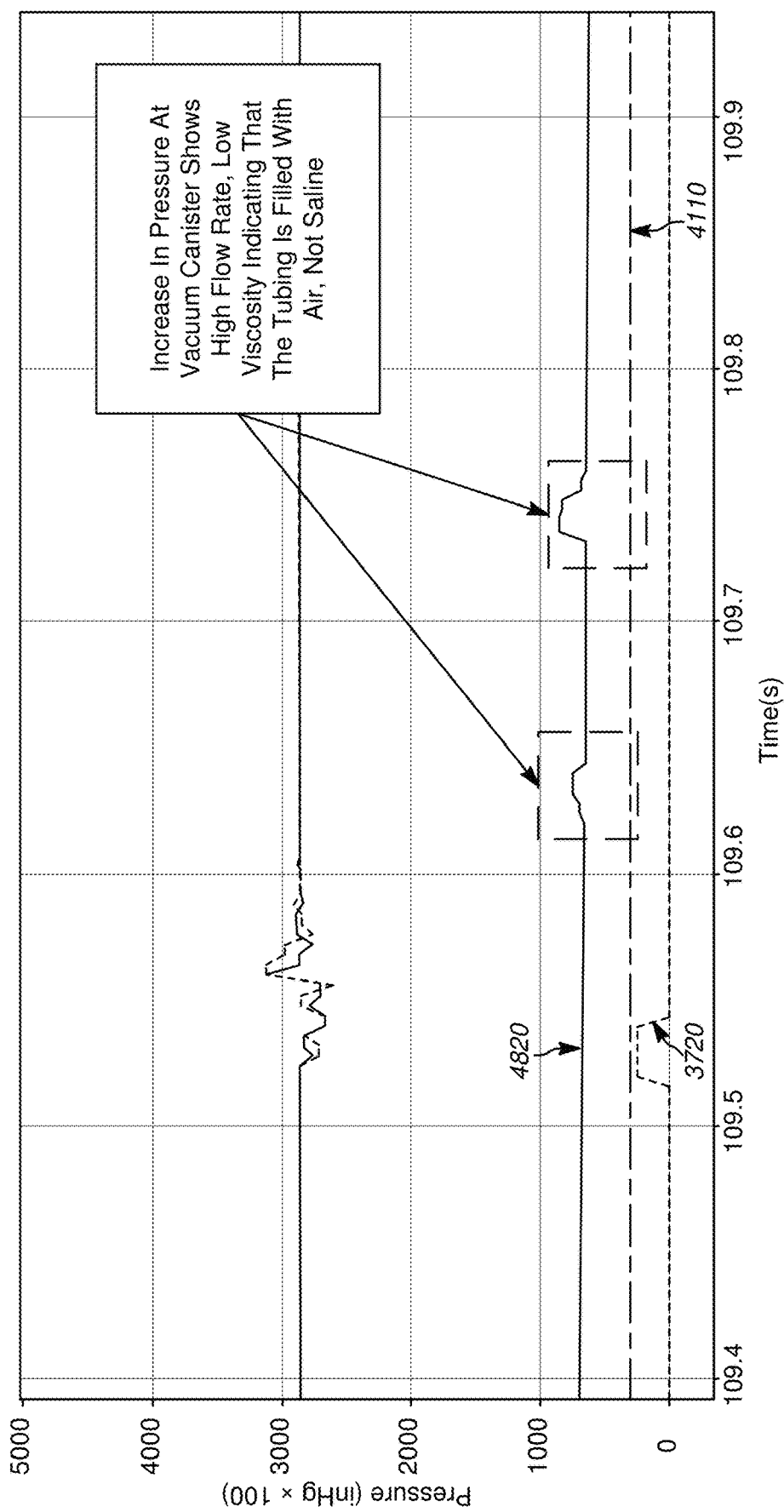

FIG. 60 illustrates a vacuum pressure profile taken during the middle of a successful priming sequence, in particular embodiments. Little or no variance in vacuum pressure may be observed at the vacuum canister, which may indicate no flow and/or high viscosity, further indicating that the tubing may be filled with liquid with very low resultant flow at the vacuum valve. In contrast, FIG. 61 illustrates a vacuum pressure profile taken during the middle of an unsuccessful priming sequence, in particular embodiments. Pressure increases at the vacuum canister may indicate high flow rates and/or low viscosity, indicating that the tubing may be filled with air, not liquid saline.

Figure 62:
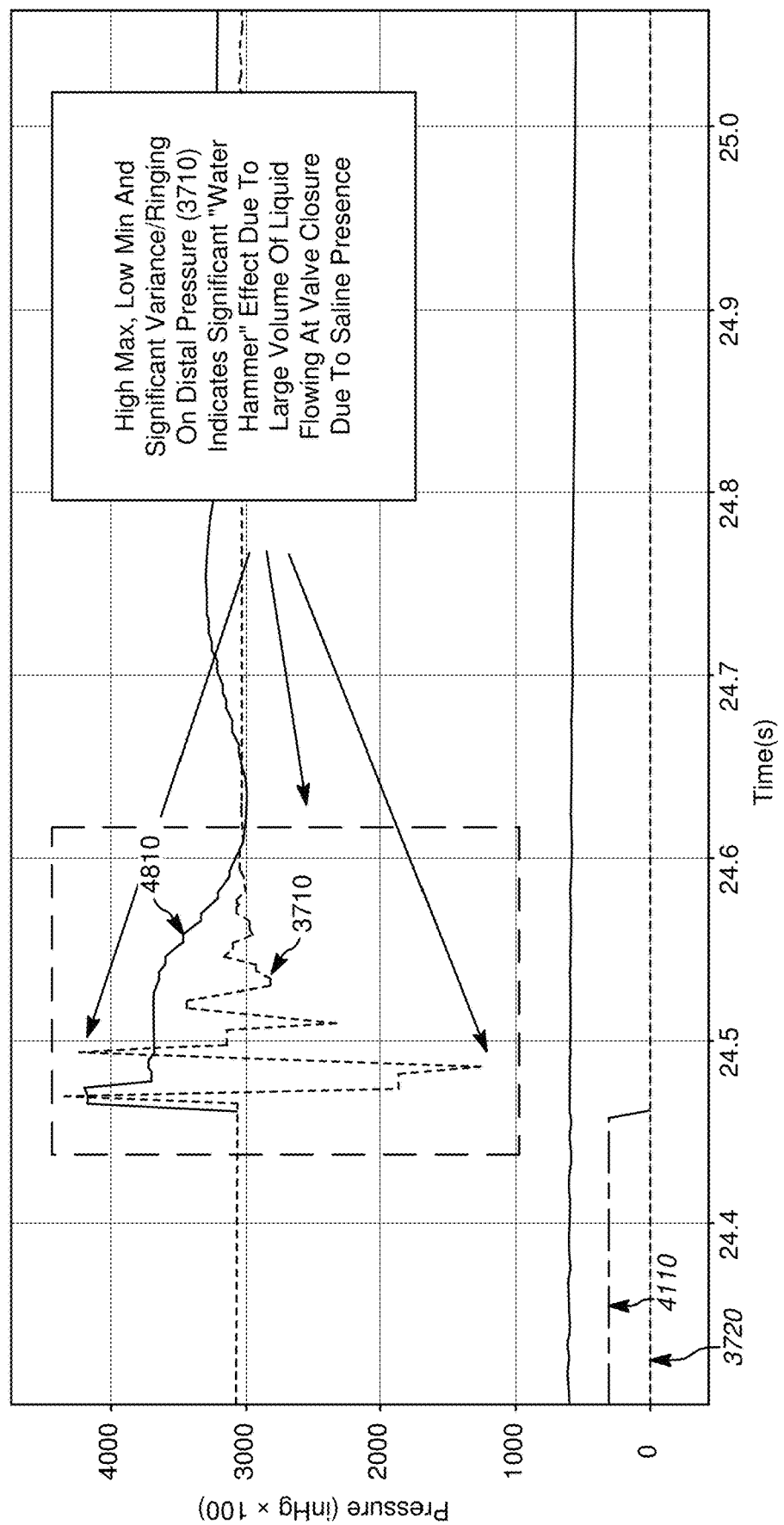
Figure 63:
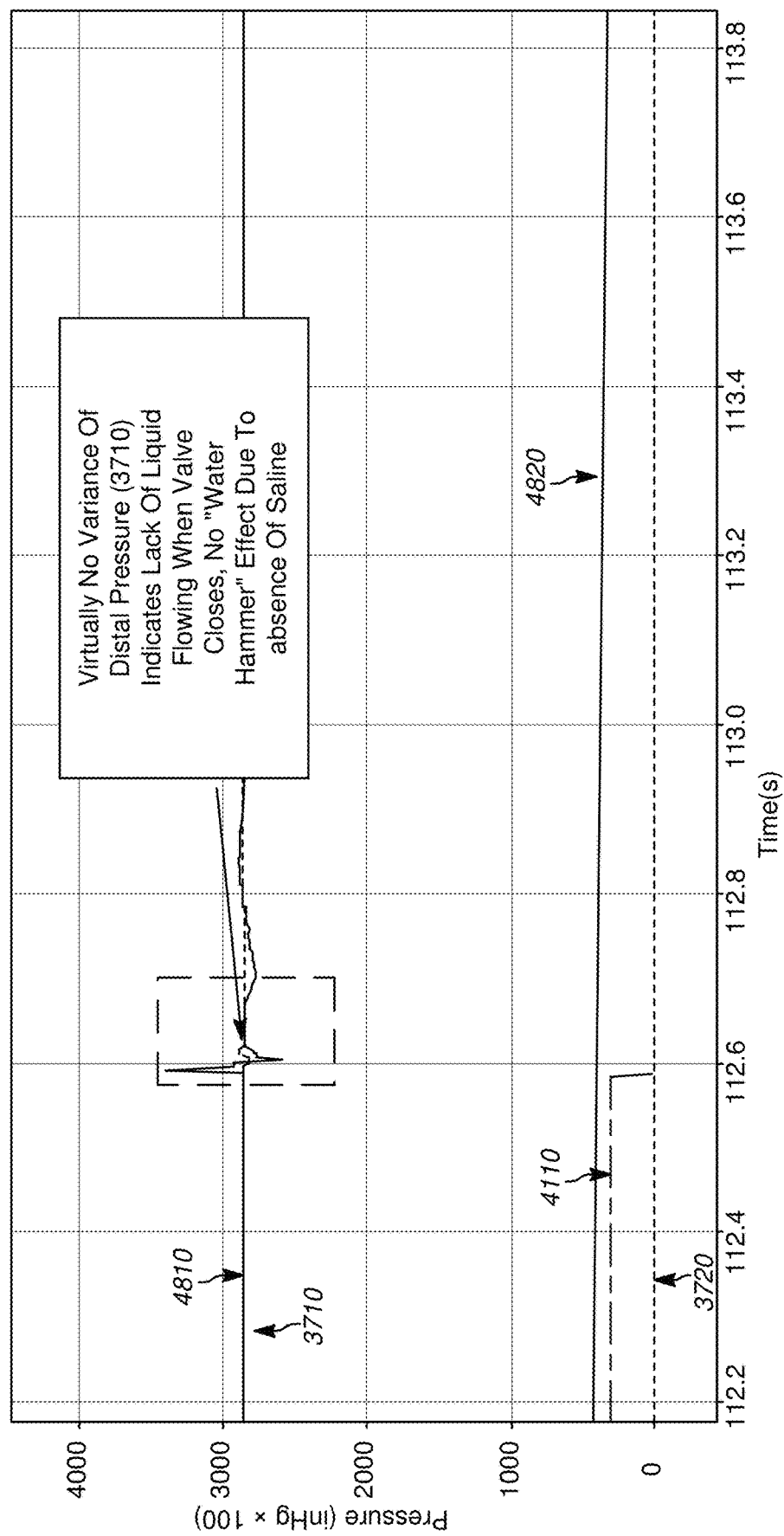

FIG. 62 illustrates a distal pressure profile taken near the end of a successful priming sequence, in particular embodiments. Significantly high maximum and low minimum distal pressures, as well as high variances and ringing or oscillations, may indicate inertial "water hammer" effects of the liquid relative to air due to large volumes of liquid flowing at pressure valve closure, which may be due to the presence of liquid saline. In contrast, FIG. 63 illustrates a distal pressure profile taken near the end of an unsuccessful priming sequence, in particular embodiments. Little or no variance of distal pressure may be observed, which may indicate a lack of liquid flowing when the pressure valve closes, with little or no inertial "water hammer" effects observed due to the relative absence of saline.

Figure 64:
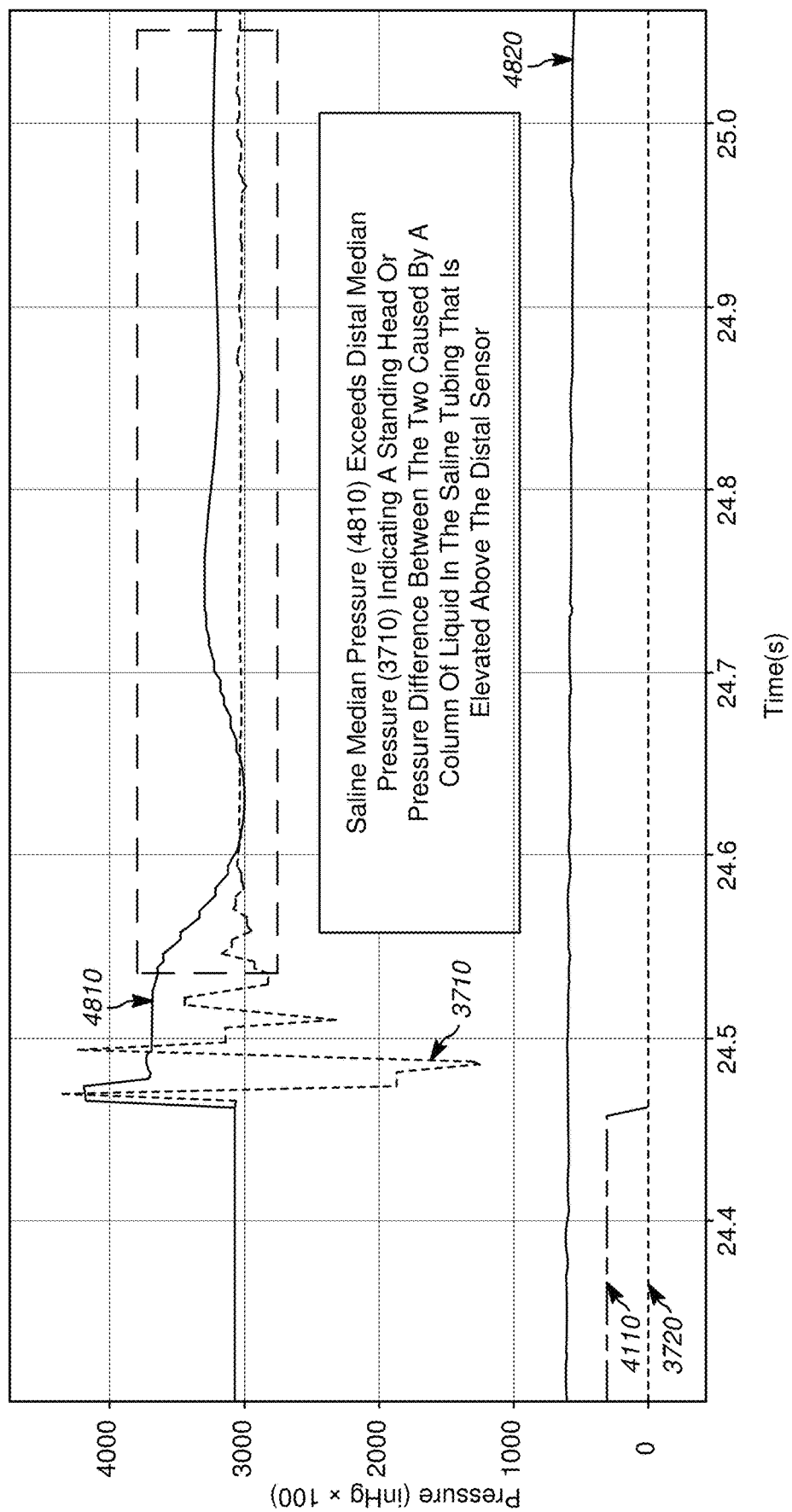

FIG. 64 illustrates a saline pressure profile taken near the end of a successful priming sequence, in particular embodiments. The median ending saline pressure exceeds the median ending distal pressure, which may indicate a standing head or pressure difference between the two pressures. This may be caused by a liquid column in the saline tubing that is elevated above the distal sensor.

Although this disclosure describes using particular sensor profiles, particular parameters and/or particular actuators such as vacuum valves for dynamically detecting system states and/or taking further action based on the determination, this disclosure contemplates providing any suitable providing any suitable sensors, actuators and/or methodologies for detecting system states or taking further action in any suitable manner.

As was previously discussed for determining of system states such as an open flow state, an occluded flow state, or "in-between" states based on system scores such as an Open Score and an Occlusion Score, in particular embodiments, the controller may be configured to detect system states relating to the relative presence or absence of liquid and gas, such as saline and air. For instance, each feature, such as those disclosed above, may be weighted, and the weighted sums of the features may be used to determine one or more corresponding system states. The above and following aspects are exemplary, and not limiting. It should be appreciated that methodologies for dynamic system state detection may vary across embodiments, and may be tailored based on specific configurations and/or applications.

In particular embodiments, dynamic system state detection may be used to determine whether a catheter is attached to the aspiration thrombectomy system. In particular embodiments, for flushing the system with saline, a catheter must not be connected to the system. Additionally, other factors indicating the presence of saline may be used for proceeding. As examples and not by way of limitation, FIGS. 65-66 illustrate pressure profile features of particular embodiments for catheter detection during flushing.

Figure 65:
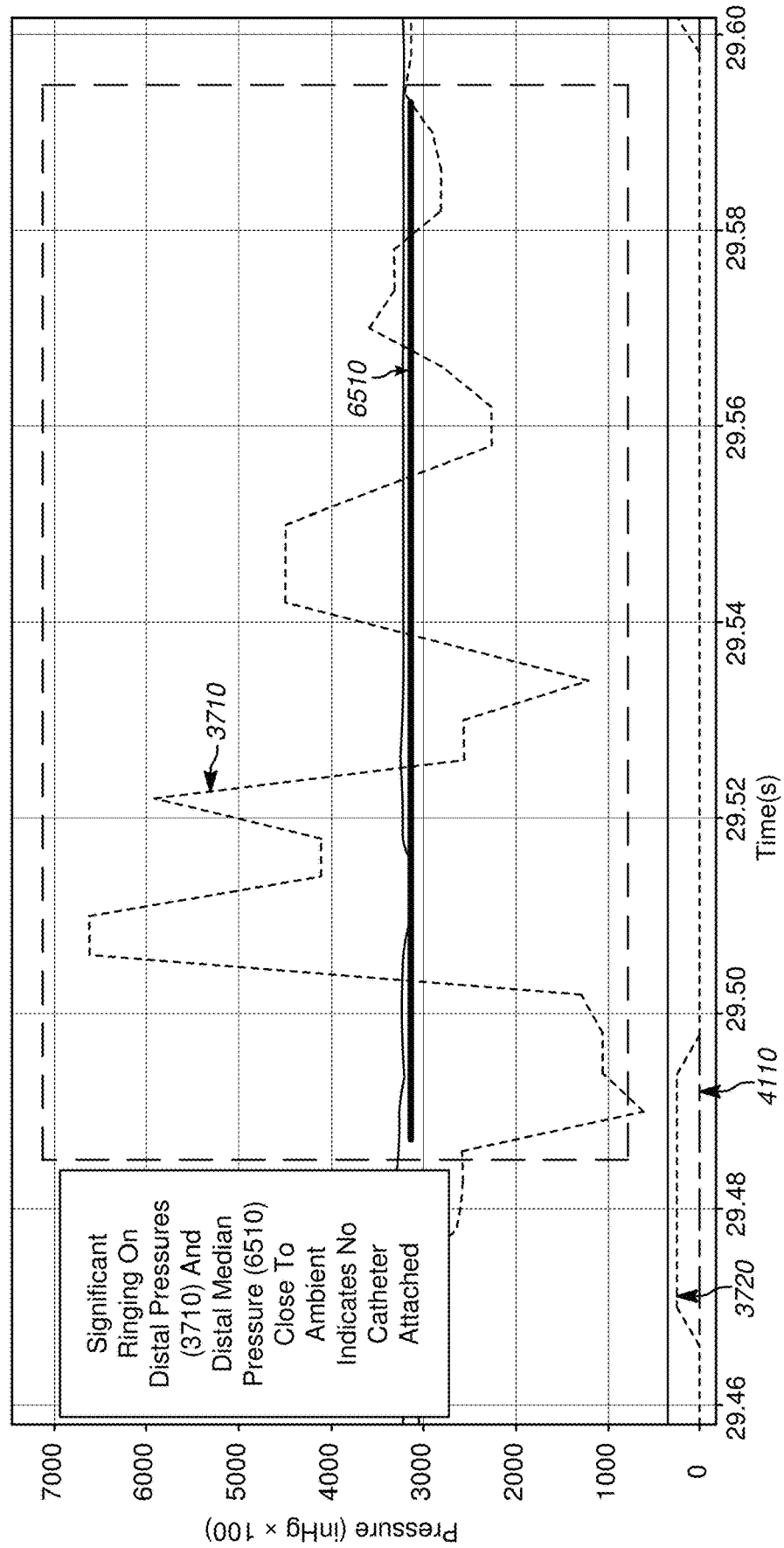
FIGS. 65-66 illustrate pressure profile features of particular embodiments for catheter detection during flushing.
Figure 66:
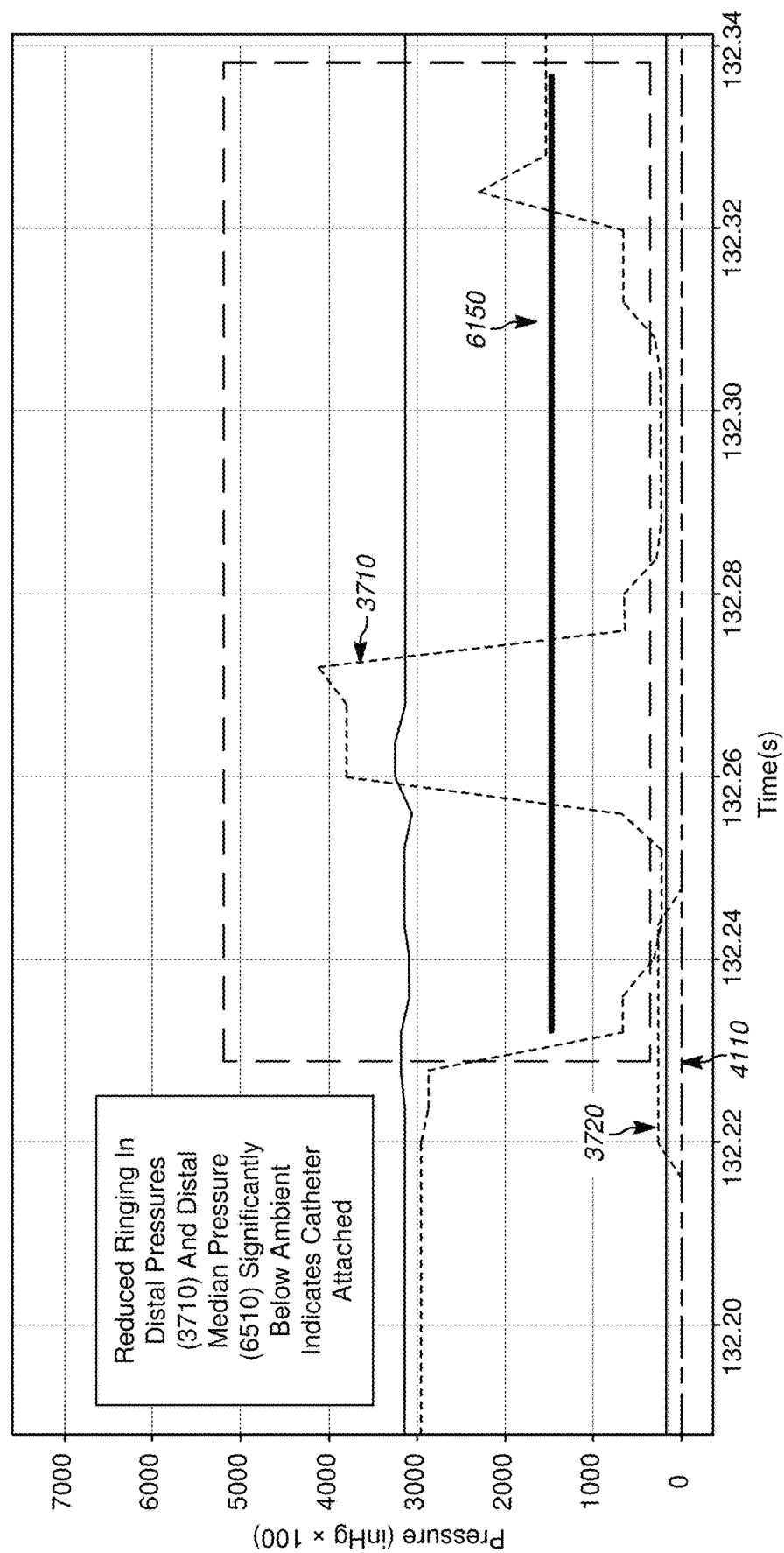

FIG. 65 illustrates a distal pressure profile taken at the start of a flush sequence, with no catheter attached to the system, in particular embodiments. Within the time interval or window of interest, based on cycling the vacuum valve, a large variance, or ringing, of distal pressures may be observed. Additionally, the median of the distal pressure 6510 during this time interval may be determined to be close to the local ambient pressure. This combination of features may indicate that no catheter is attached to the system. In contrast, FIG. 66 illustrates a distal pressure profile taken at the start of a flush sequence, with a catheter attached to the system, in particular embodiments. Based on cycling the vacuum valve, notably reduced variance or ringing of the distal pressure may be observed, along with a median of the distal during this time interval being significantly below the local ambient pressure, indicating that a catheter may be attached to the system.

Figure 67:
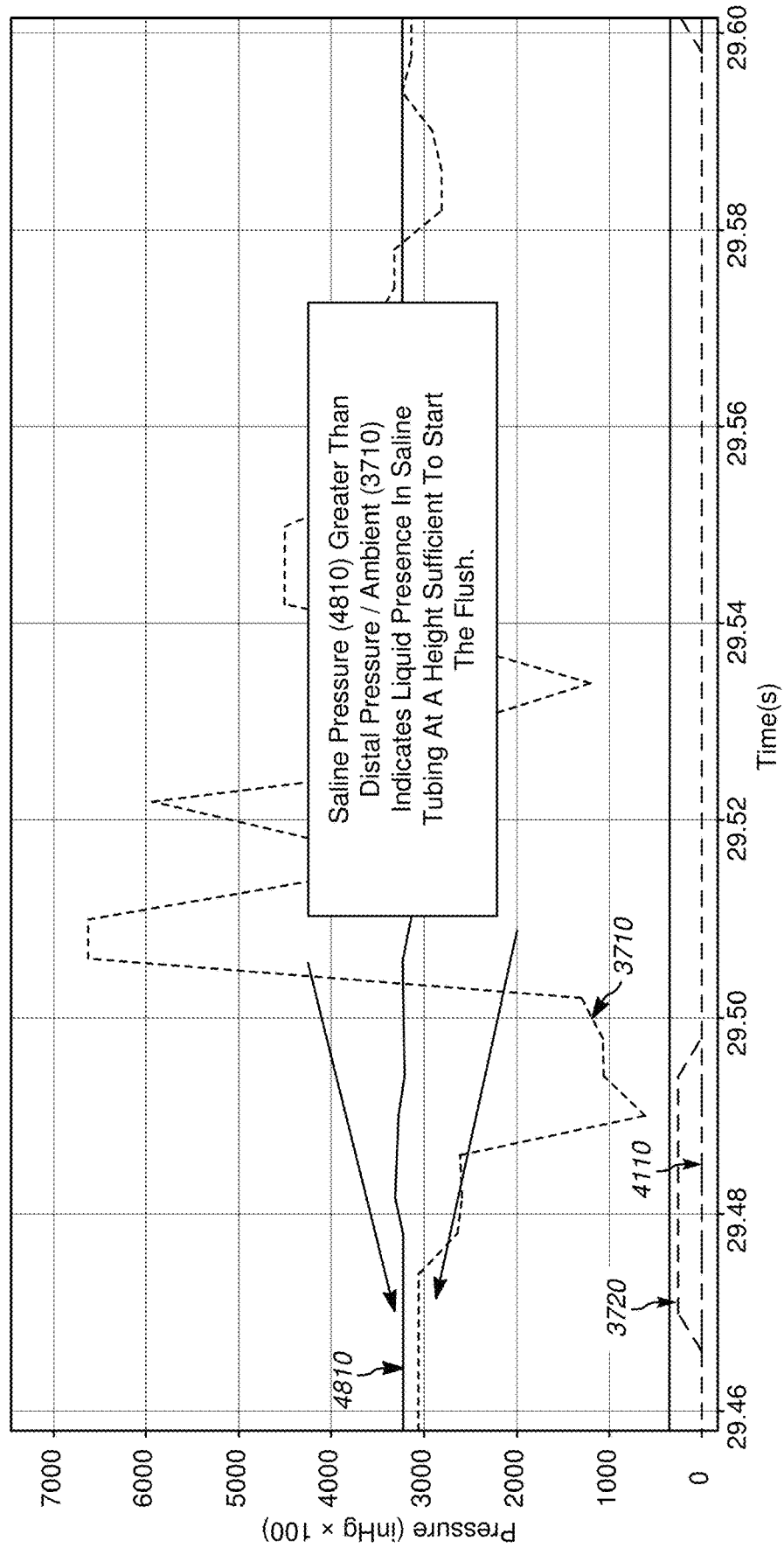
FIGS. 67-69 illustrate pressure profile features of particular embodiments for verifying liquid presence during flushing.
Figure 68:
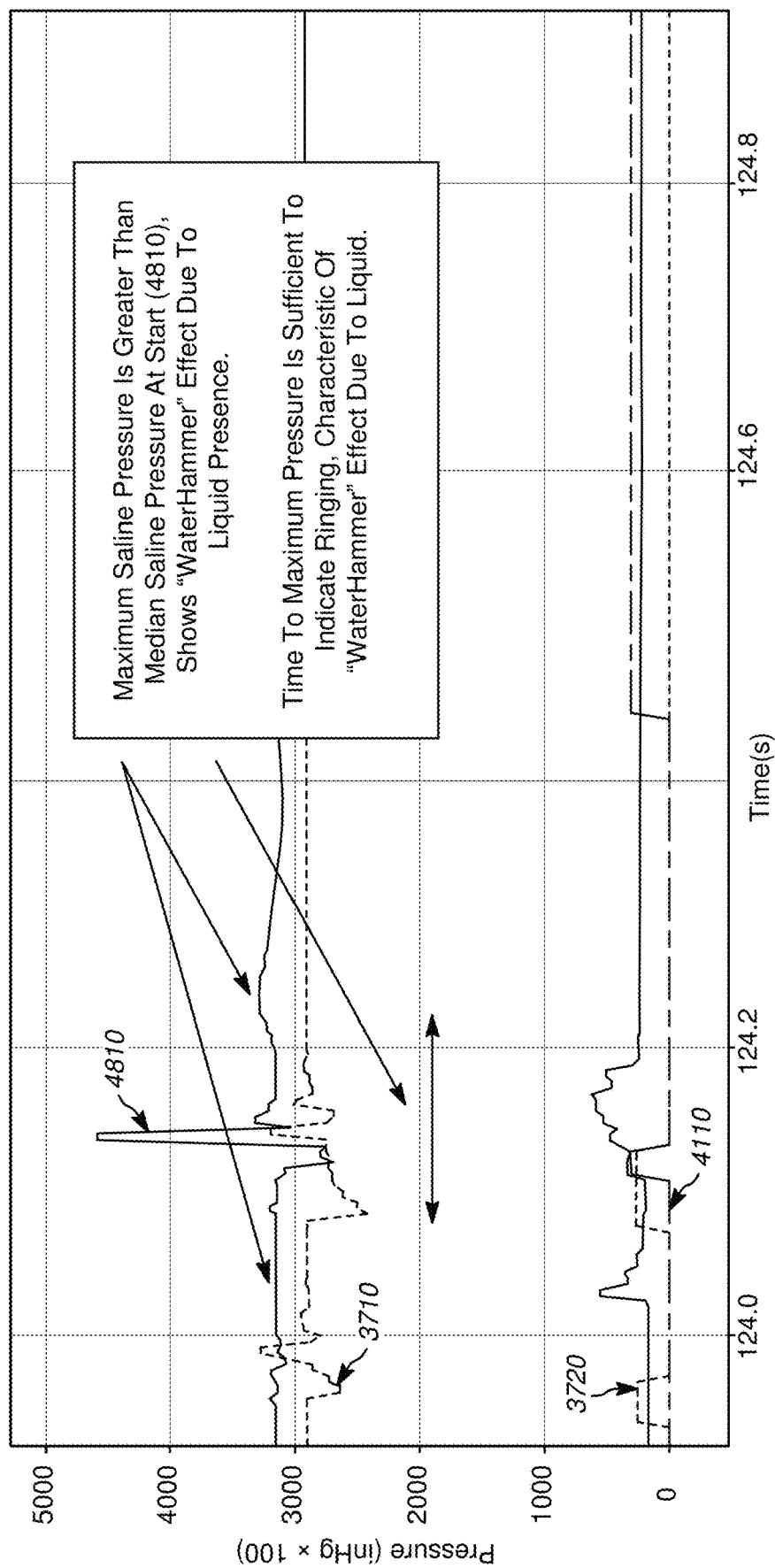
Figure 69:
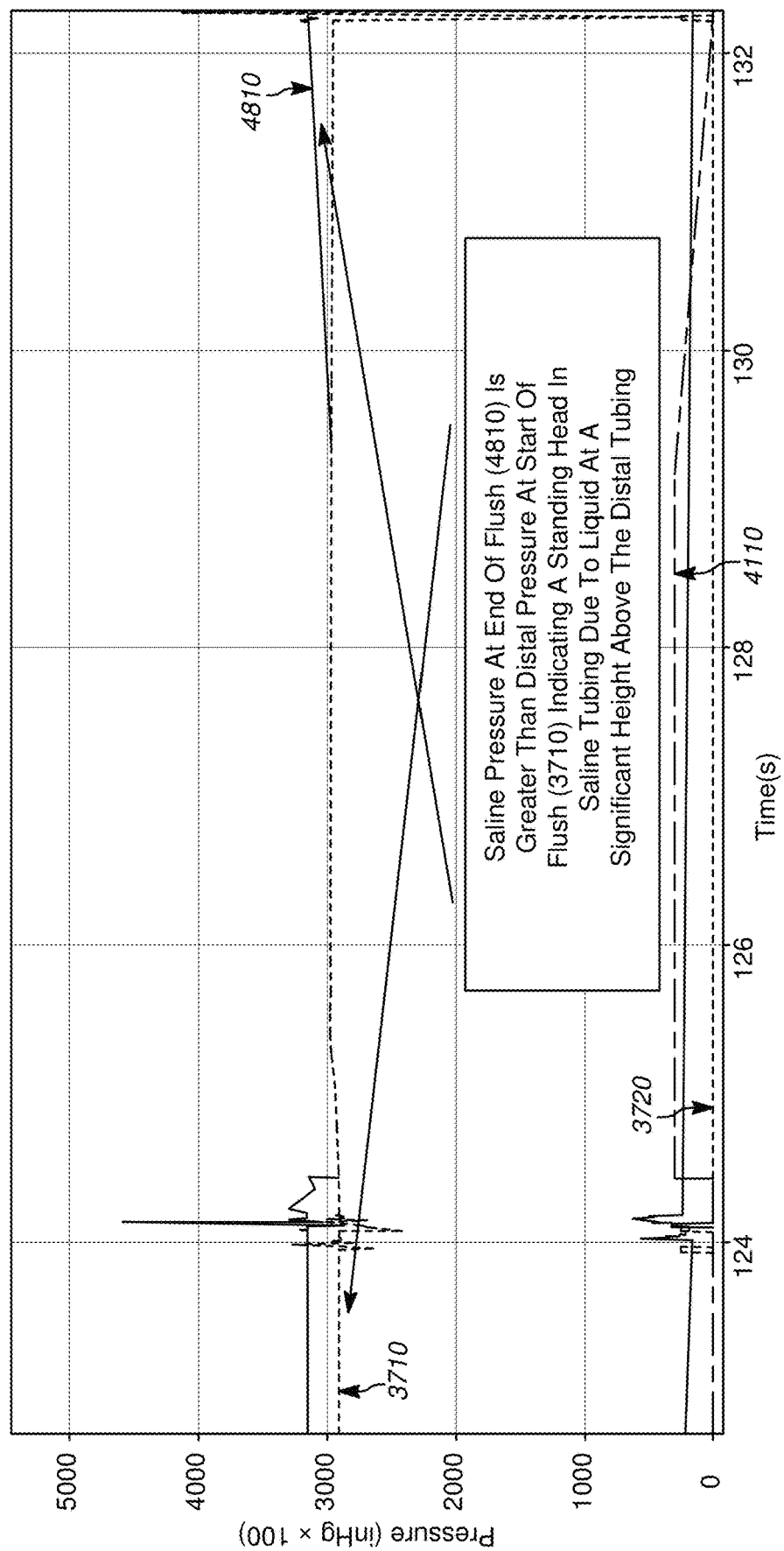

FIGS. 67-69 illustrate pressure profile features of particular embodiments for verifying liquid presence during flushing. FIG. 67 illustrates a saline pressure profile at the start of a flush sequence, in particular embodiments. The higher saline pressure relative to the distal or ambient pressure may indicate the presence of liquid in the saline tubing at a height sufficient to start the flush. FIG. 68 illustrates a saline pressure profile during the middle of a flush sequence, in particular embodiments. The higher maximum saline pressure relative to the median saline pressure at the start illustrates inertial "water hammer" effects due to the presence of liquid. Further, the time taken to reach maximum saline pressure may be sufficient to indicate ringing in this particular example. FIG. 69 illustrates a saline pressure profile during at the end of a flush sequence, in particular embodiments. The saline pressure at the end of the flush is greater than the distal pressure at the start of the flush, which may indicate a standing head in saline tubing due to liquid at a significant height above the distal tubing. These illustrations are provided as examples and not by way of limitation.

Figure 70:
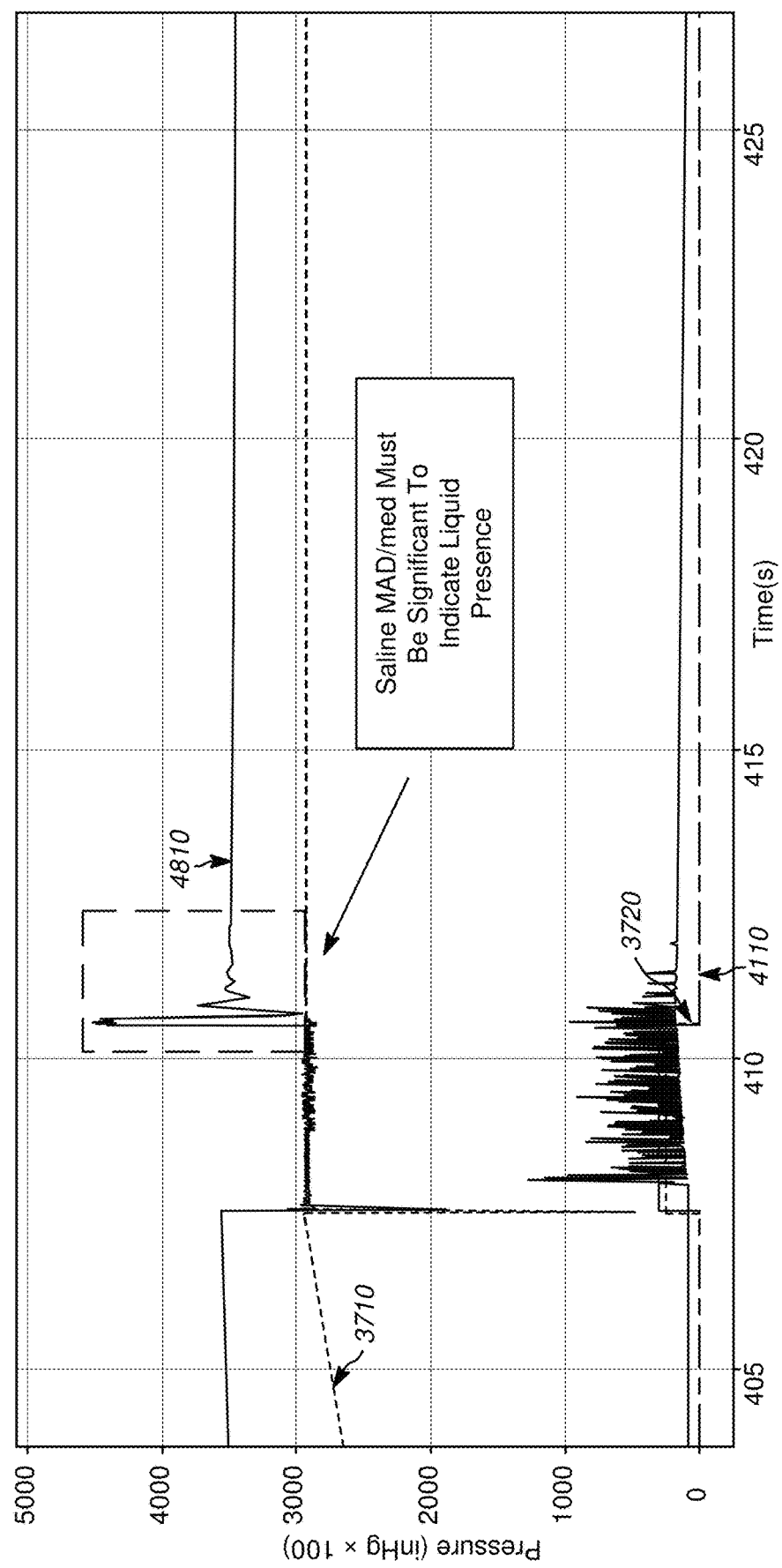
FIGS. 70-72 illustrate pressure profile features of particular embodiments for verifying liquid presence during repriming.
Figure 71:
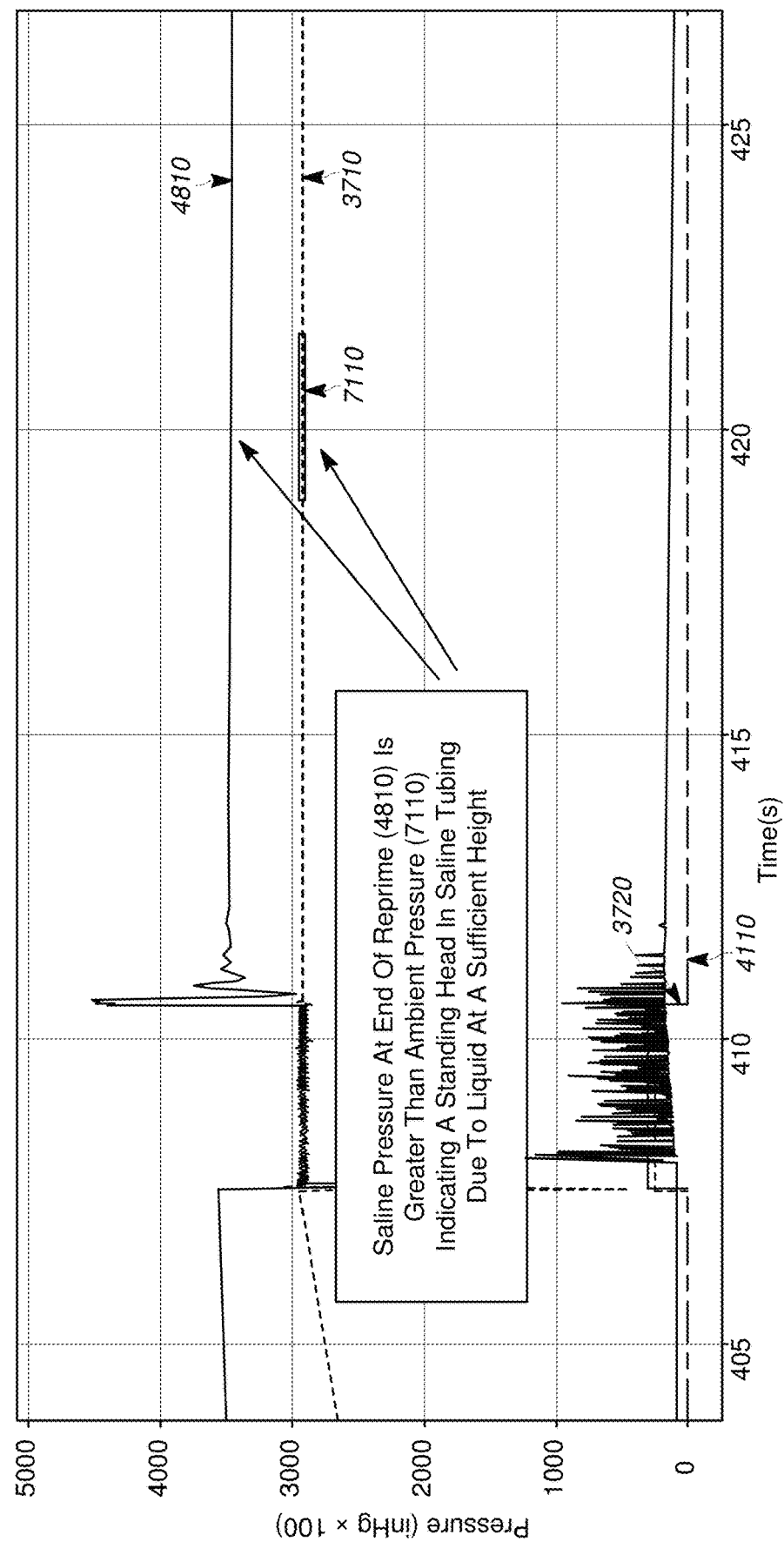
Figure 72:
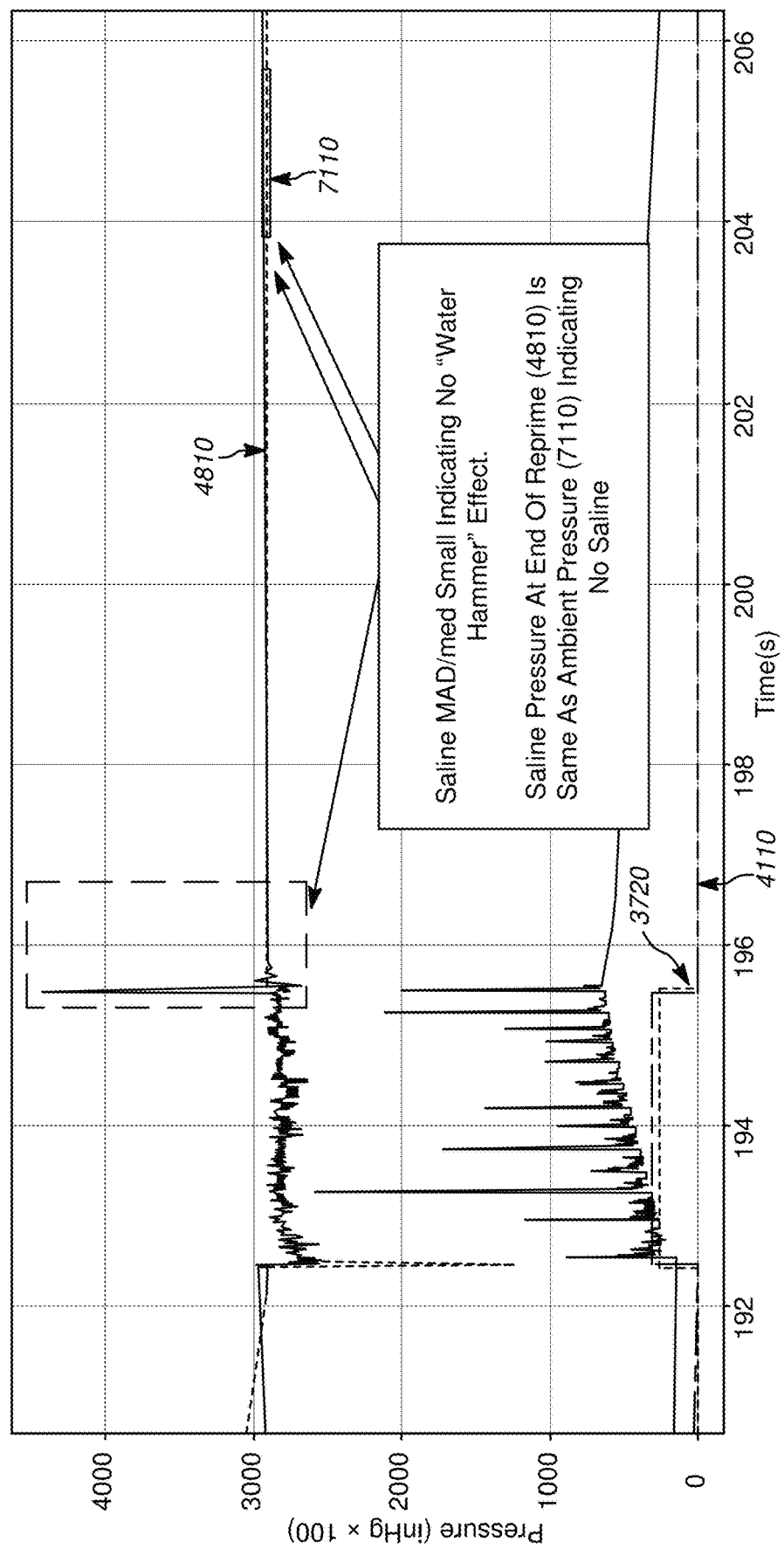

In particular embodiments, dynamic system state detection may be used to determine the presence or absence of saline during a repriming sequence. As examples, and not by way of limitation, FIGS. 70-72 illustrate pressure profile features of particular embodiments for verifying liquid presence during repriming. FIGS. 70 and 71 illustrate a saline pressure profile taken at the end of a successful repriming sequence, in particular embodiments. As illustrated in FIG. 70, a significant variance (using a metric such as a MAD/med) of saline pressure detected during a time interval window following valve closure may be used to verify liquid presence. As illustrated in FIG. 71, a saline pressure at the end of reprime being greater than the ambient pressure level 7110 may be indicative of a standing head in the saline tubing due to liquid at a sufficient height. In contrast, FIG. 72 illustrates a saline pressure profile corresponding to an unsuccessful repriming sequence, in particular embodiments. A low variance (using a metric such as a MAD/med) of saline pressure detected during a time interval window following valve closure may indicate a lack of inertial "water hammer" effects, which may further indicate a lack of liquid saline. Additionally, saline pressure at the end of reprime is observed to be the same as the ambient pressure, which may also indicate a lack of saline.

Figure 73:
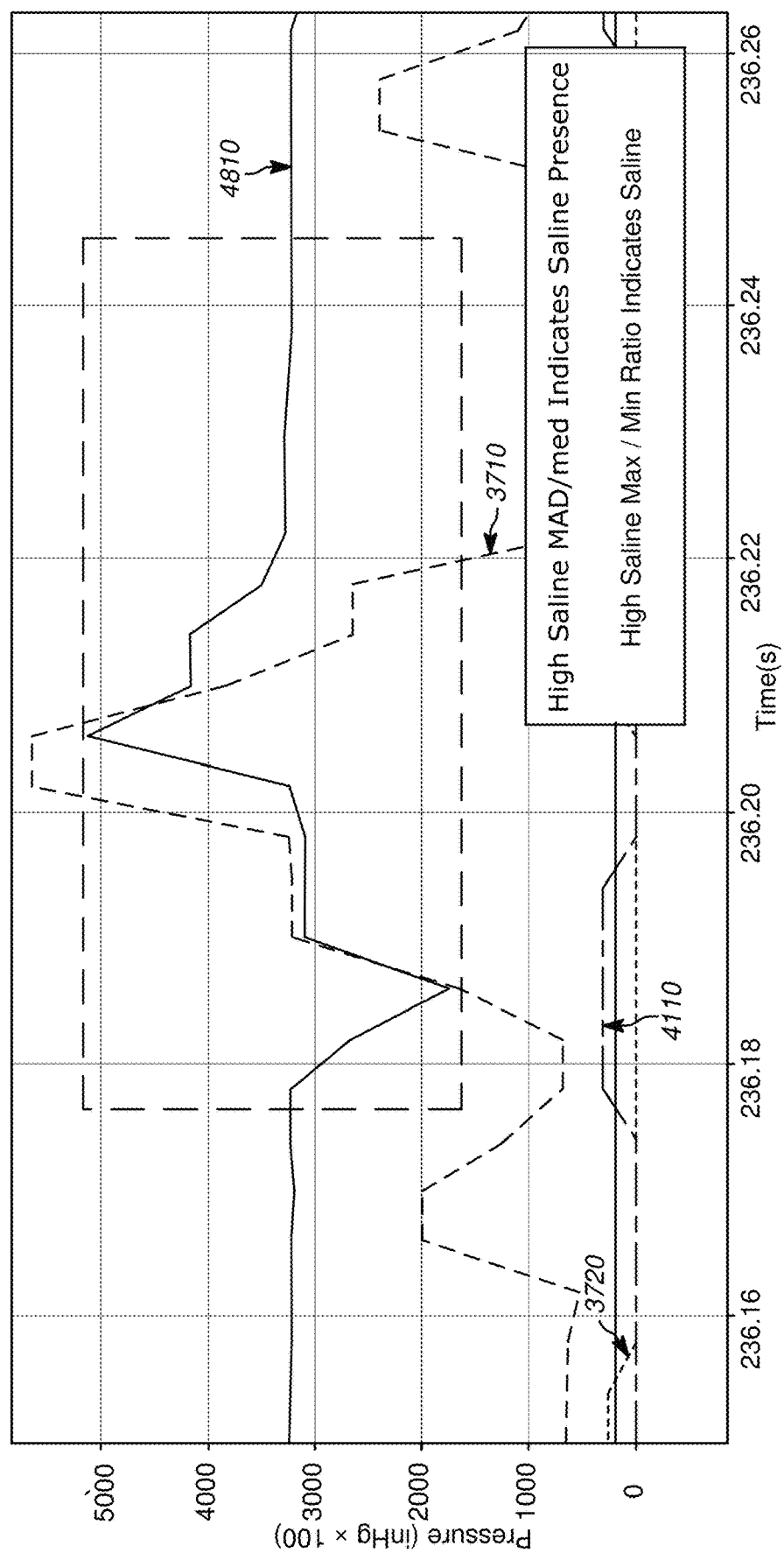
FIGS. 73-74 illustrate pressure profile features of particular embodiments for saline detection during a pulse sequence.
Figure 74:
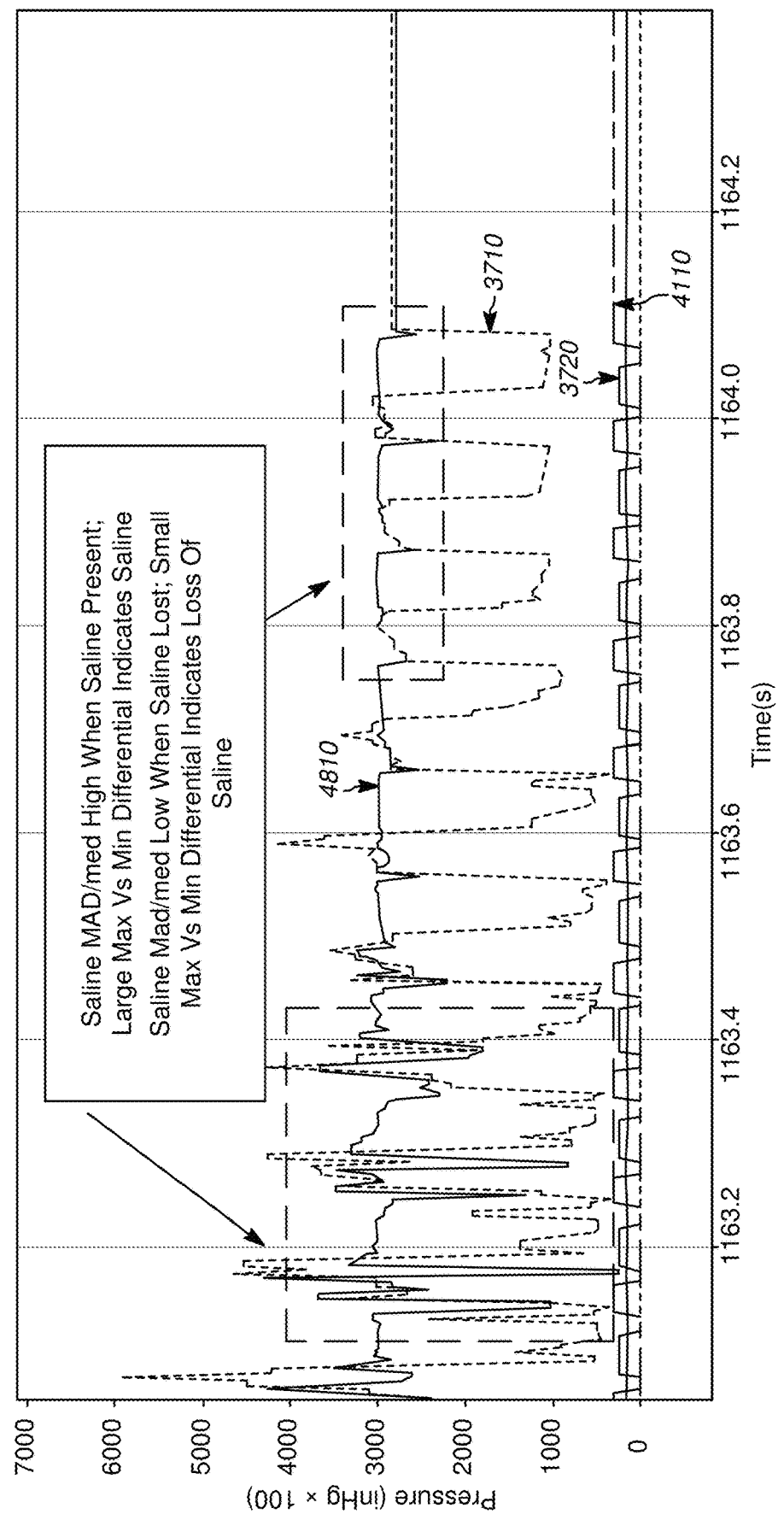

In particular embodiments, dynamic system state detection may be used to determine the presence or absence of saline during a pulse sequence. As examples, and not by way of limitation, FIGS. 73-74 illustrate pressure profile features of particular embodiments for saline detection during a pulse sequence. FIG. 73 illustrates a saline pressure profile during a pulse sequence, in particular embodiments. A high variance of saline pressure (using a metric such as a MAD/med) detected during a time interval window based on operating the pressure valve may indicate saline presence. Additionally, a high ratio of maximum to minimum saline pressures may indicate saline presence. FIG. 74 illustrates detection of loss of saline during pulsing, in particular embodiments. While the early time interval window during pulsing illustrates a high variance of saline pressure, and a large ratio of maximum to minimum saline pressures, all indicating possible saline presence, the later stage time interval window illustrates a significantly lower variance of saline pressure, and a significantly lower ratio of maximum to minimum saline pressures, all indicating possible loss of saline during pulsing.

In particular embodiments, dynamic system state detection may be used to determine whether a clot has been engaged. In particular embodiments, initiation of modulated aspiration may follow such a determination of clot engagement. In particular embodiments, such a determination may be separately or additionally used to initiate a maceration cycle for applying mechanical forces on occlusive material. Such mechanical action may be applied to sufficiently modify the form and/or consistency of a clot or other occlusive material to enable more effective aspiration.

Figure 75:
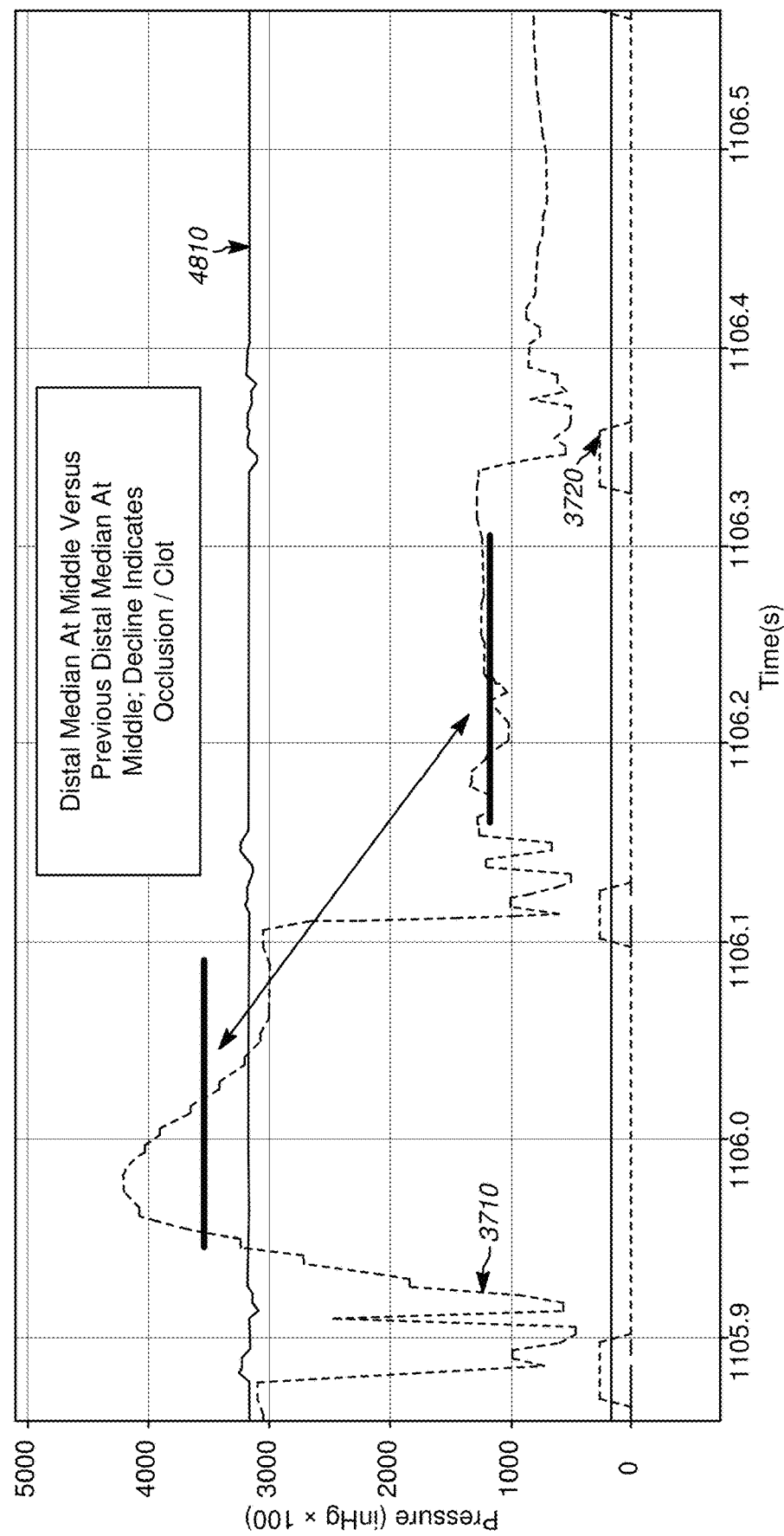
FIGS. 75-79 illustrate pressure profile features of particular embodiments for clot detection corresponding to a pulse sequence.

As examples, and not by way of limitation, FIGS. 75-79 illustrate pressure profile features of particular embodiments for clot detection corresponding to a pulse sequence. FIG. 75 illustrates a distal pressure profile during a pulse sequence, in particular embodiments. A comparison of the median distal pressures taken during the middle of the time intervals between vacuum valve cycling events illustrates a decline in the median value across two consecutive such detections, which may indicate the presence of an occlusion or clot.

Figure 76:
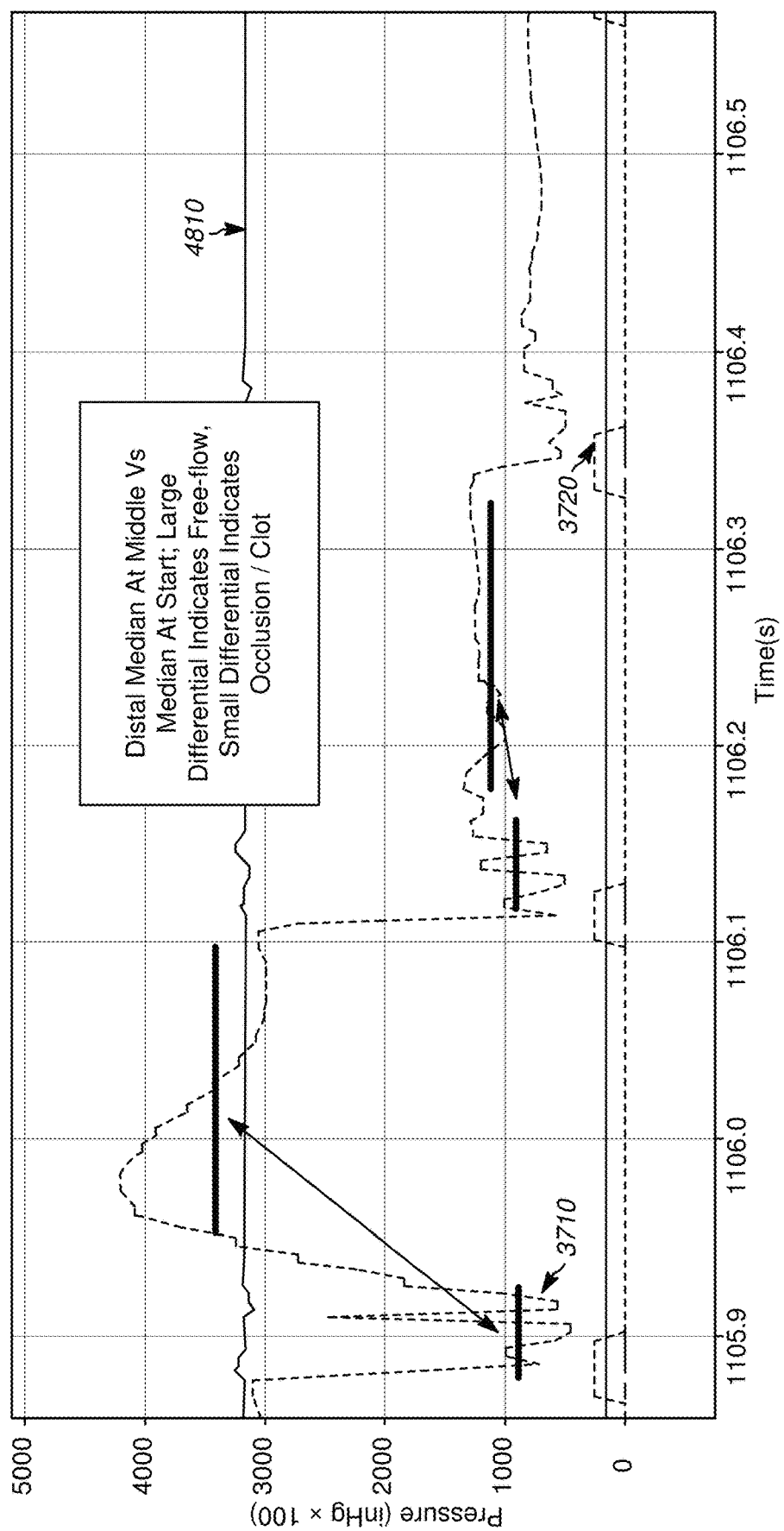

FIG. 76 illustrates a distal pressure profile during a pulse sequence, in particular embodiments. In a first case corresponding to the first cycling of the vacuum valve around the 1105.9 s time marker, the median value of the distal pressure taken at the start is compared to the median value of the distal pressure taken at the middle of the pulsing cycle. A large differential between these median pressures, as observed in the first case, may be indicative of open or unrestricted flow. In a second case corresponding to the second cycling of the vacuum valve that starts around the 1106.1 s time marker, a small differential between the median pressures is observed, which may be indicating the presence of an occlusion or clot.

Figure 77:
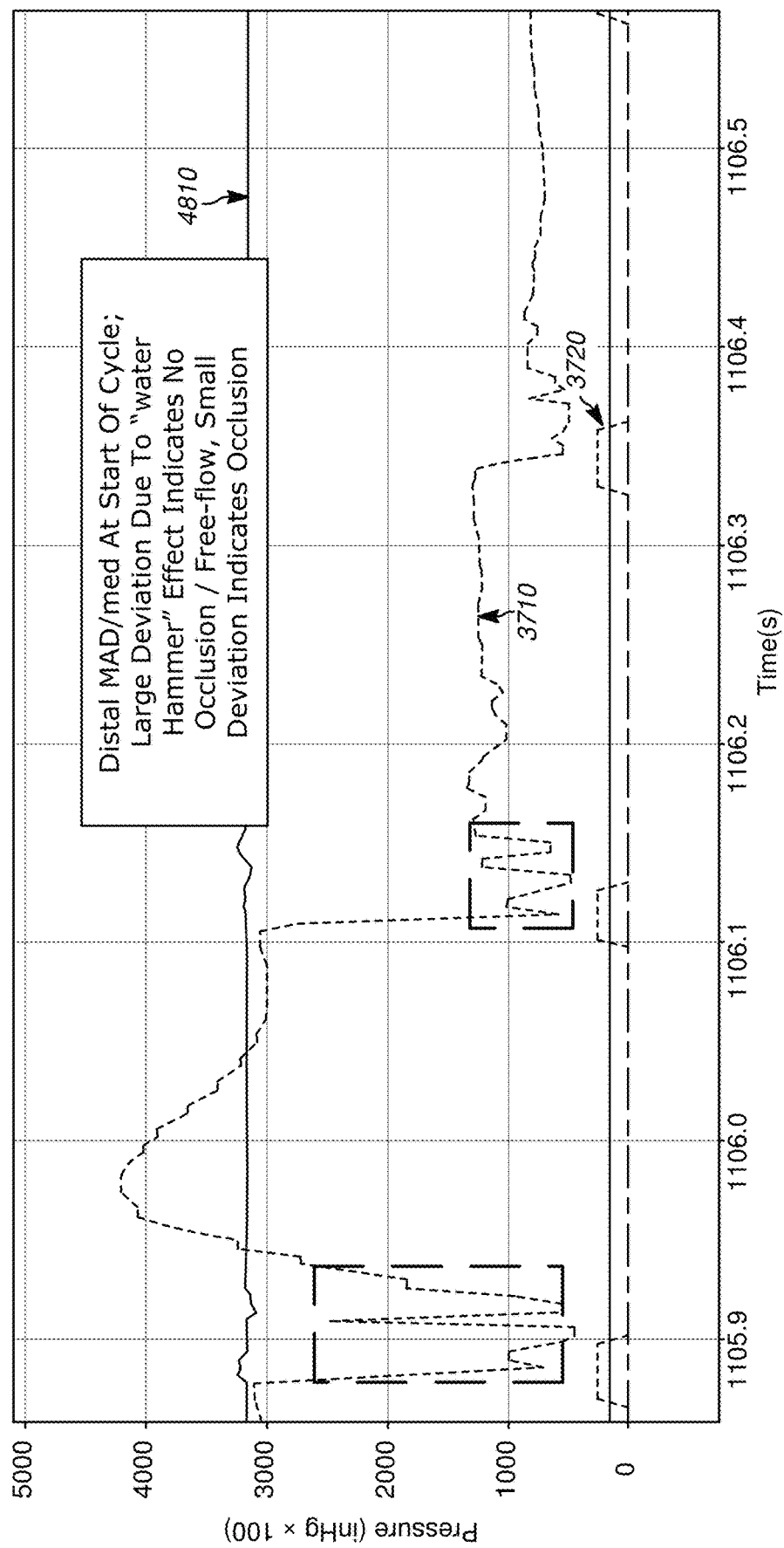

FIG. 77 illustrates a distal pressure profile during a pulse sequence, in particular embodiments. In a first case corresponding to a short time window taken at the start of the first cycling of the vacuum valve around the 1105.9 s time marker, the variance of distal pressure (using a metric such as MAD/med) is large due to inertial "water hammer" effects, which may be indicating open, free, or unrestricted flow. In a second case corresponding to a short time window taken at the start to the second cycling of the vacuum valve that starts around the 1106.1 s time marker, the variance of distal pressure (using a metric such as MAD/med) is small, which may be indicating the presence of an occlusion or clot.

Figure 78:
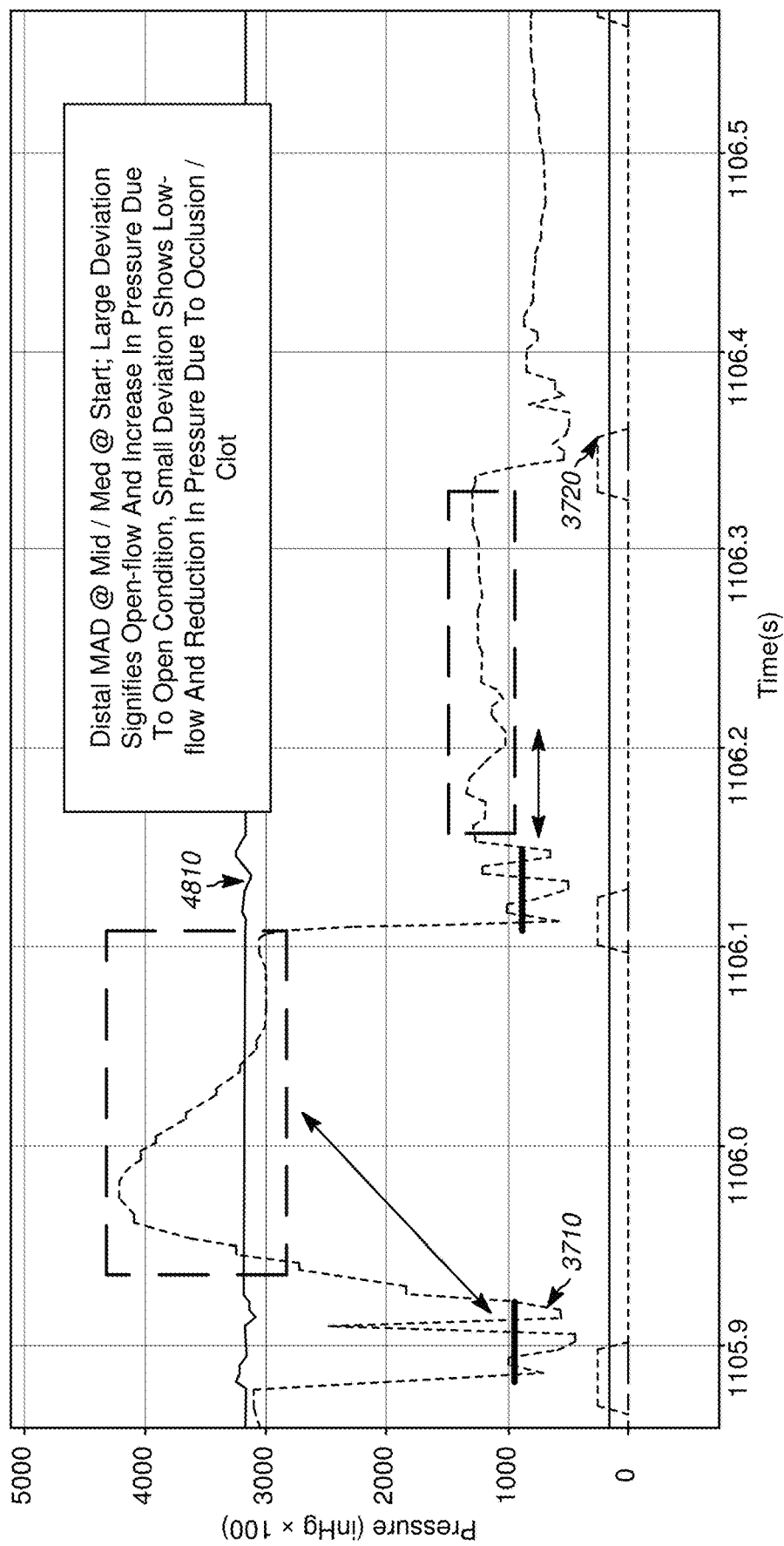

FIG. 78 illustrates a distal pressure profile during a pulse sequence, in particular embodiments. In a first case corresponding to the first cycling of the vacuum valve around the 1105.9 s time marker, the median distal pressure at the start of the pulse cycle is compared to the mean absolute deviation of distal pressure during the middle of the pulse cycle. The large deviation(s) observed may indicate open flow conditions, and corresponding increase in pressure. In a second case corresponding to the second cycling of the vacuum valve that starts around the 1106.1 s time marker, the median distal pressure at the start of the second pulse cycle is again compared to the mean absolute deviation of distal pressure during the middle of the second pulse cycle. Small deviation(s) observed may indicate low flow conditions, and reduction in pressure due to the possible presence of an occlusion or clot.

Figure 79:
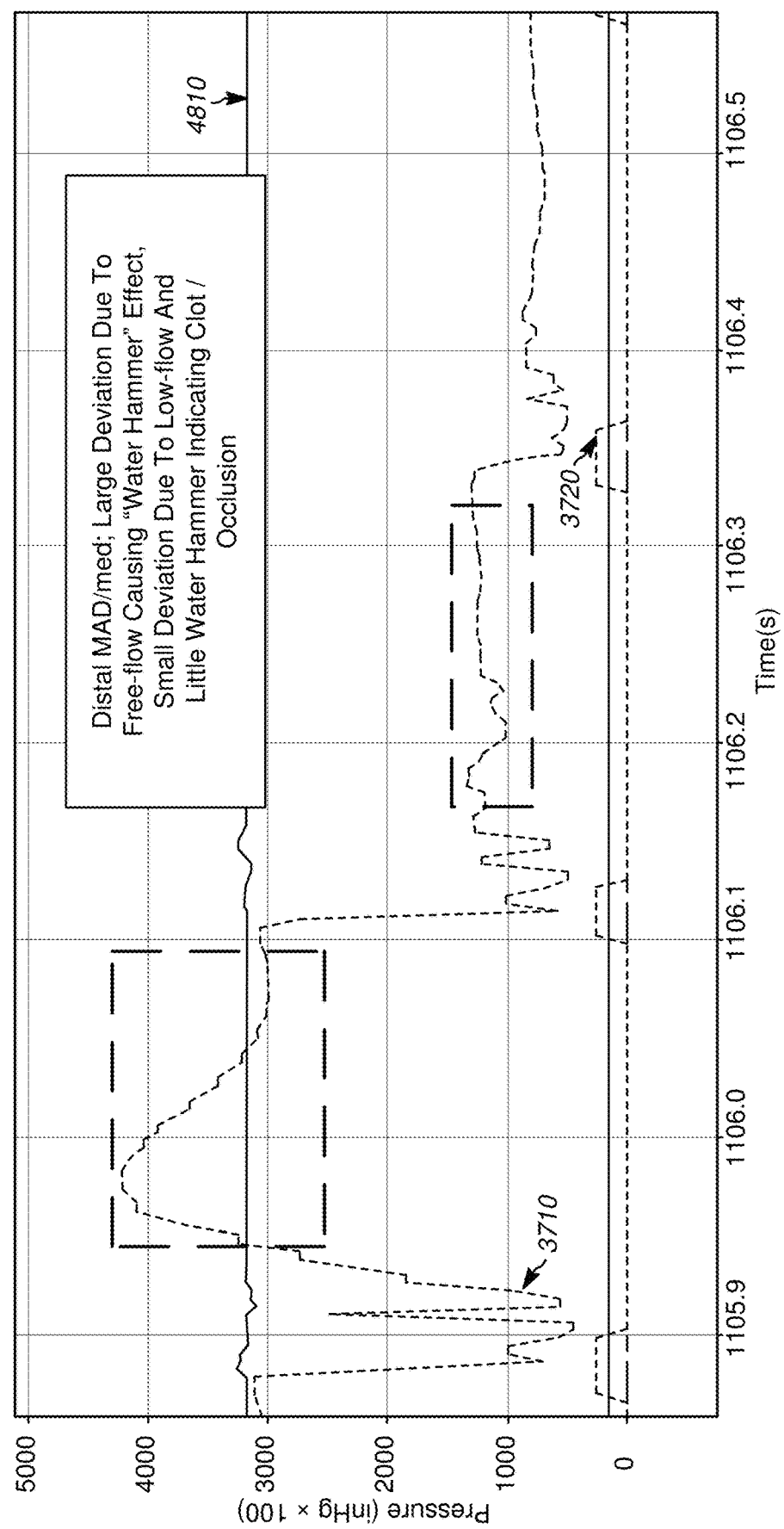

FIG. 79 illustrates a distal pressure profile during a pulse sequence, in particular embodiments. In a first case corresponding to a large time interval window taken during the middle of the first cycling of the vacuum valve that start around the 1105.9 s time marker, the variance of distal pressure (using a metric such as MAD/med) is large due to inertial "water hammer" effects, which may indicate open, free, or unrestricted flow. In a second case corresponding to a large time interval window taken during the middle of the second cycling of the vacuum valve that starts around the 1106.1 s time marker, the variance of distal pressure (using a metric such as MAD/med) is small, which may indicate the presence of an occlusion or clot.

In particular embodiments, dynamic system state detection may involve the use of multiple sensors, such as multiple pressure sensors, including interactions between multiple sensors. As examples, and not by way of limitation, FIGS. 66-70 illustrate pressure profiles of particular embodiments detected using multiple pressure sensors, P1 and P2, used for dynamic system state detection. It should be appreciated that using multiple sensors for dynamic system state detection may vary across embodiments, and may be tailored based on specific configurations and/or applications.

Figure 80:
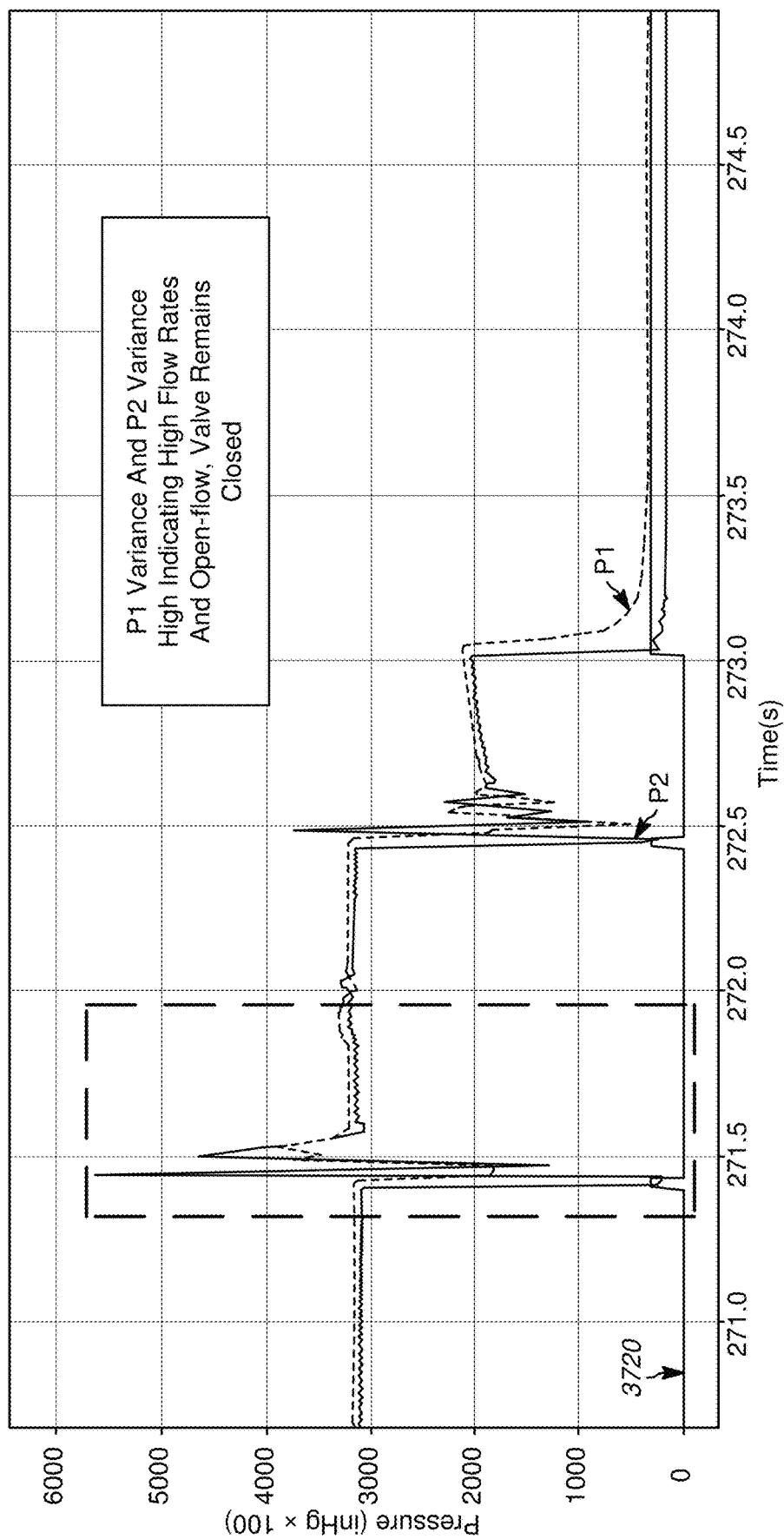
FIGS. 80-84 illustrate pressure profiles of particular embodiments detected using multiple pressure sensors used for dynamic system state detection.

FIG. 80 illustrates detection of open flow conditions using P1 and P2 pressure profiles, in particular embodiments. For instance, for the starting time interval window of FIG. 66 corresponding to a first valve cycling event, both P1 and P2 pressure variances are large based on cycling the valve, which may indicate open flow conditions. Based on that determination, the valve may be kept closed. Separate or additional determinations of open flow may be made, for instance, based on comparing median pressure levels at the start and the end, and/or based on comparing median pressure levels at the end relative to the ambient pressure. In particular embodiments, if P1 variance multiplied by the P2 variance is large, and P1 median pressure at the start is less than the P1 median pressure at the end, and if P1 median pressure at the end is approximately equal to ambient pressure, a determination of open flow may be made. In particular embodiments, if P1 variance multiplied by the P2 variance is large, and P2 median pressure at the start is less than the P2 median pressure at the end, and if P2 median pressure at the end is approximately equal to ambient pressure, a determination of open flow may be made.

Figure 81:
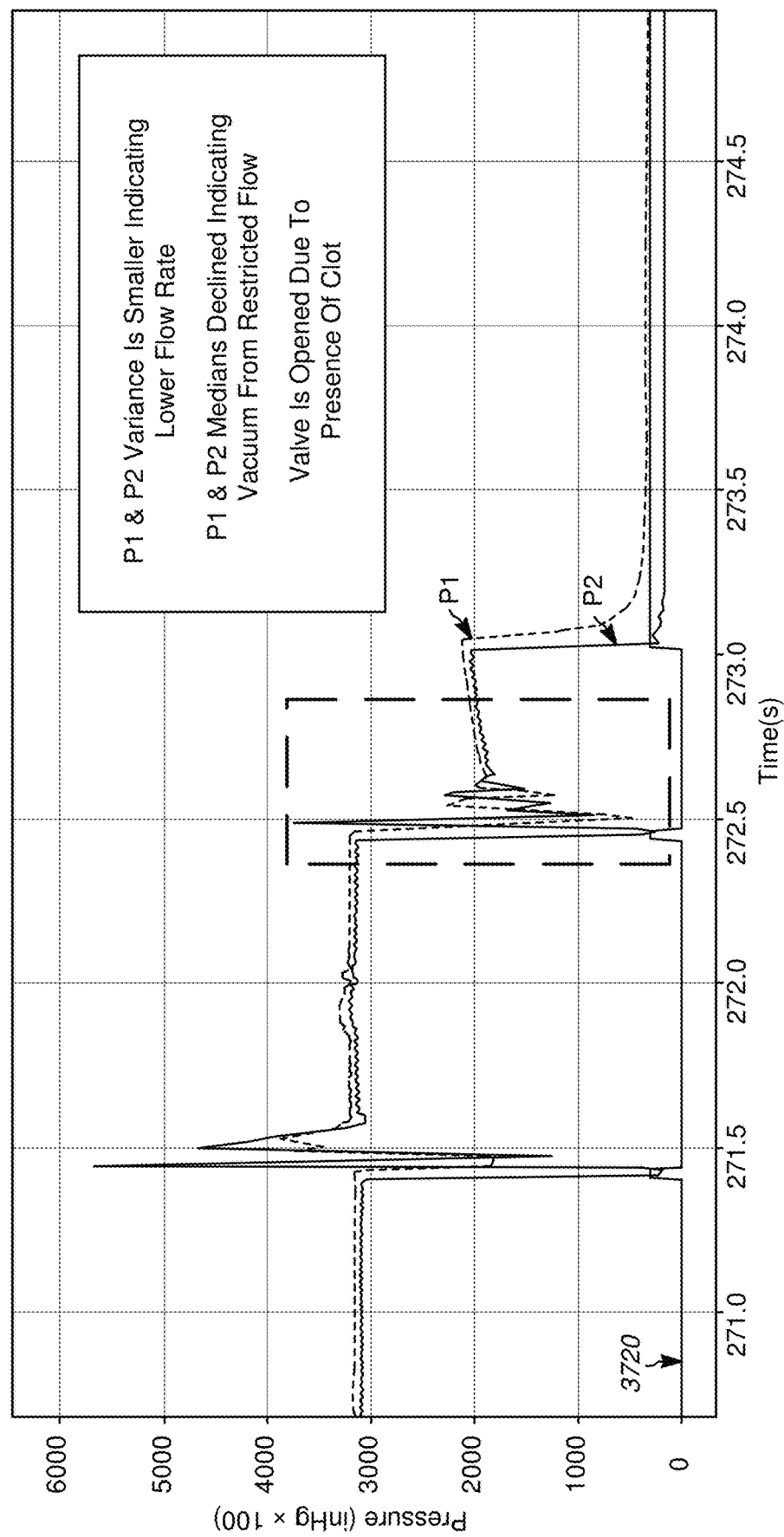

For the middle time interval window of FIG. 81 corresponding, in particular embodiments, to a second valve cycling event, both P1 and P2 pressure variances are relatively reduced, which may indicate lower flow rates. Additionally, the median values of P1 and P2 pressure levels taken during this middle time interval window are also reduced, which may indicate restricted flow due to the presence of a clot. Based on that determination, the valve may be opened. In particular embodiments, if the P1 variance multiplied by the P2 variance were small, lower flow rates may be indicated. In particular embodiments, if the P1 variance multiplied by the P2 variance were large and the system was determined to not be in free flow, lower flow rates and/or restricted flow may be indicated, and the valve may be opened due to presence of a clot.

Figure 82:
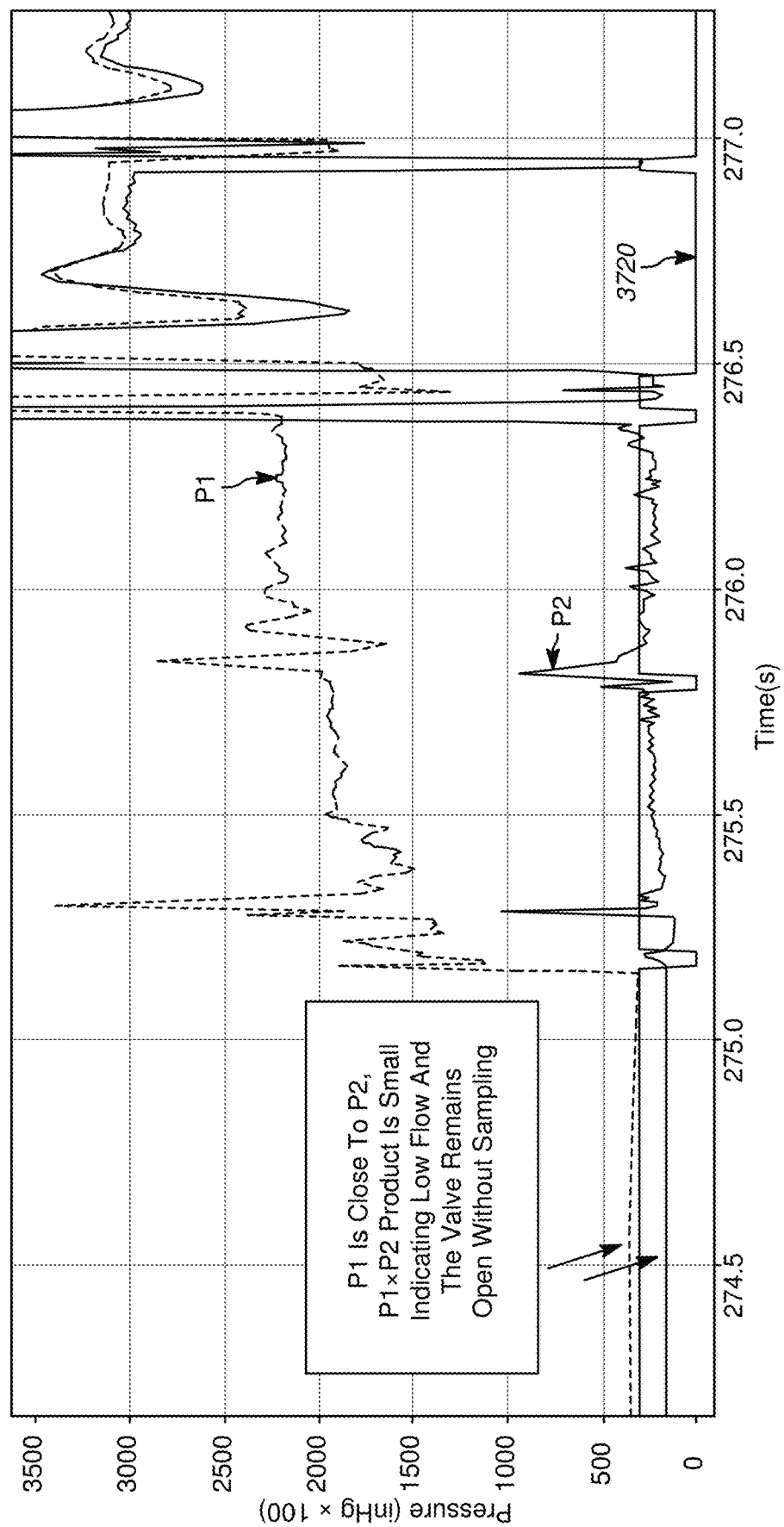
Figure 83:
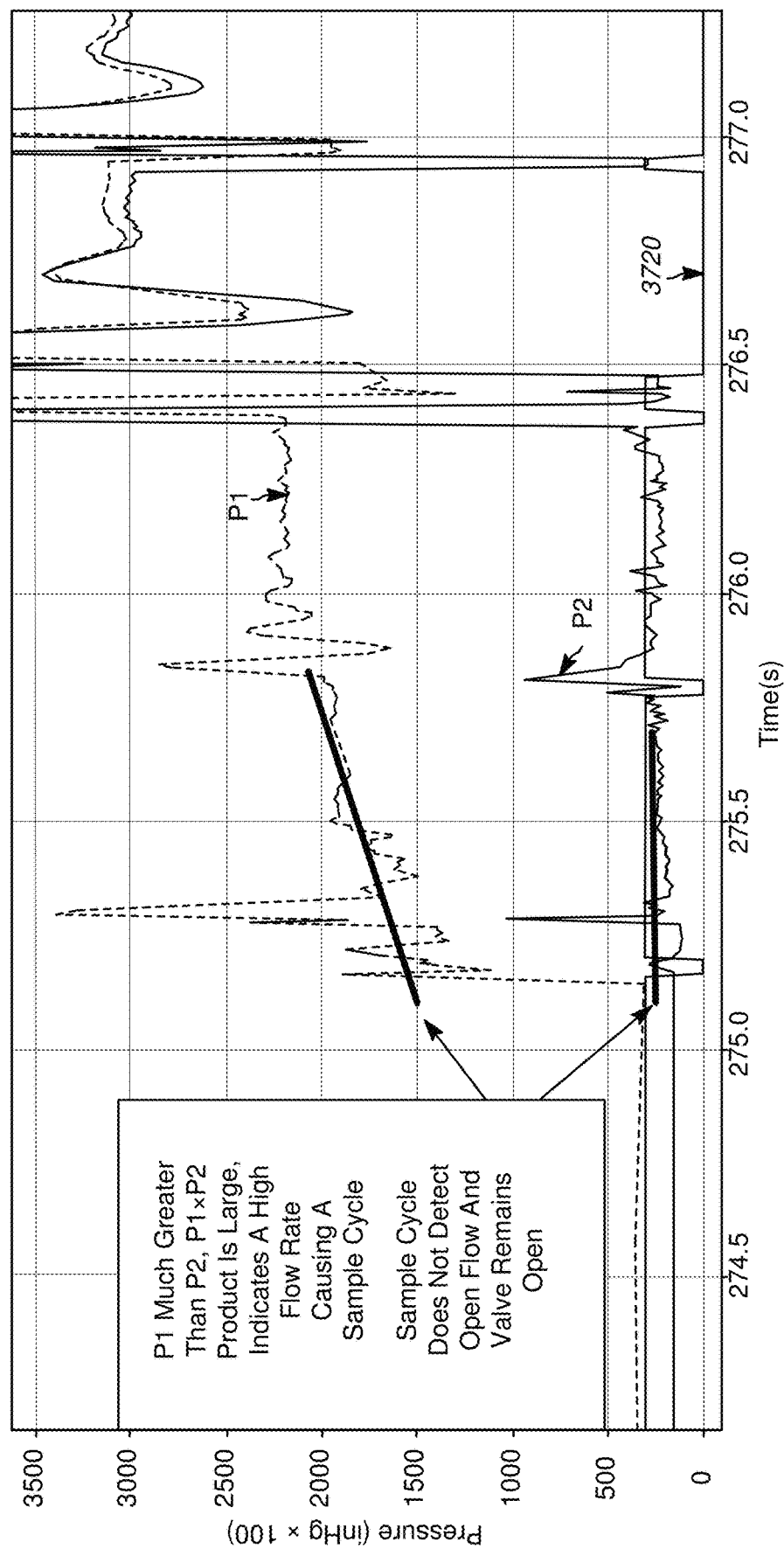
Figure 84:
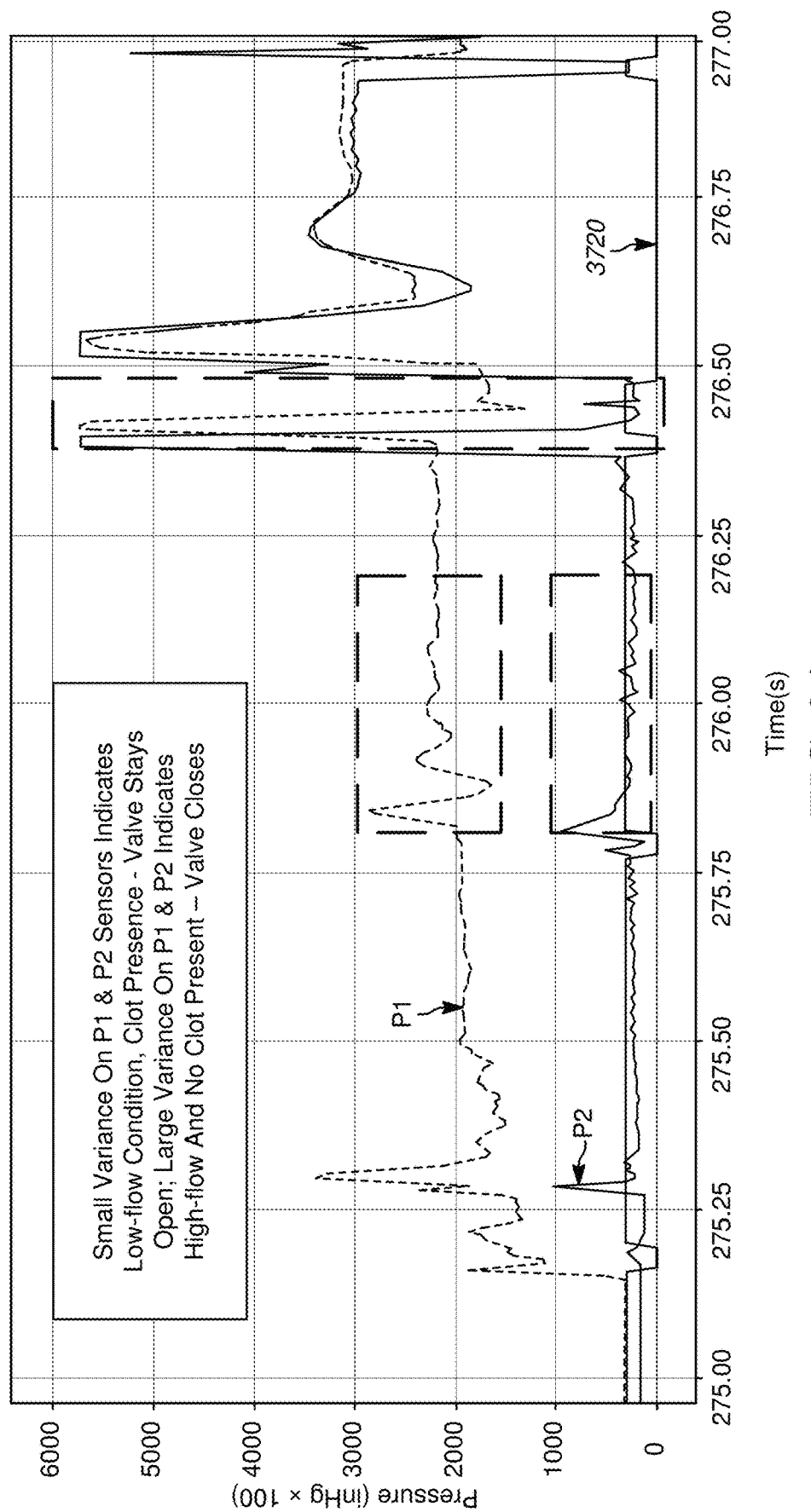

FIG. 82-84 illustrate system state detection using P1 and P2 in an open-valve state without valve cycling, in particular embodiments. As illustrated in FIG. 82, in particular embodiments at the beginning of the open-valve state, P1 pressure is close to P2 pressure, and the product of P1 and P2 is small, which may indicate low flow rates. In particular embodiments, if P1 pressure is approximately equal to P2 pressure, and if P1 pressure is approximately equal to ambient pressure, and if P2 pressure is approximately equal to ambient pressure, and if P1 pressure multiplied by P2 pressure is small, low flow may be indicated. Based on that determination of low flow, the valve may remain open without sampling. FIG. 83 illustrates an increase in flow in particular embodiments. As illustrated in the figure, P1 increases to a value much greater than P2, producing a large product of P1 and P2, which may indicate a high flow rate that may cause a sample cycle, and may cause the valve to operate. As the sample cycle may not detect open flow, the valve may remain open. In particular embodiments, if P1 pressure is greater than P2 pressure, and if P1 pressure multiplied by P2 pressure is large, and if P1 and P2 ambients are usable, a high flow rate may be indicated, causing a sample cycle. As the sample cycle may not detect open flow, the valve may remain open. In particular embodiments, if P1 pressure is much greater than P2 pressure, and if P1 and P2 ambients are not usable, a high flow rate may be indicated, causing a sample cycle. As the sample cycle may not detect open flow, the valve may remain open. In particular embodiments, if P1 pressure multiplied by P2 pressure is large, and if P1 and P2 ambients are not usable, a high flow rate may be indicated, causing a sample cycle. As the sample cycle may not detect open flow, the valve may remain open.

FIG. 84 illustrates a comparison of variances of P1 and P2 pressures observed during time interval windows in the middle and toward the end of the profiles illustrated, in particular embodiments. Small variances in P1 and P2 pressures, such as those observed approximately during the middle of the profile sequence illustrated in this figure, may indicate low flow conditions and possible presence of clot(s). In such cases, the valve may stay open. Conversely, such as observed toward the end of the pressure profile sequence illustrated in this figure, large variances in P1 and P2 pressures may indicate high flow rates and the absence of clots. In such cases, the valve may close. In particular embodiments, if P1 variance squared (i.e., P1 variance multiplied by itself) multiplied by P2 variance is large, a high flow rate may be determined, indicating the absence of clots. Based on this determination, the valve may close.

In particular embodiments, physical parameters may be extracted from sensor data. Specific features and pressure parameters detected during dynamic system state detection may be dependent on, differently dependent on, or independent of, particular physical parameters. For example, as previously discussed, Starting Distal Pressures and/or Maximum Absolute Rebound Pressures may be correlated with blood viscosity in particular embodiments. Differential Starting Distal Pressures, in contrast, may be stable with changes in blood viscosity in particular embodiments. Based on other known parameters, in particular embodiments, on comparison to known databases and/or selectively generating pressure changes in the system, physical parameters such as blood viscosity, clot or thrombus characteristics such as elasticity or deformability, catheter and/or connection tubing dimensions, geometries, configurations and other characteristics may be determined from detecting sensor profiles, such as pressure profiles. In particular embodiments, parameters such as clot or thrombus characteristics determined from detecting sensor profiles may be used to determine the selective application of particular operational modes, such as extraction, modulation, and/or maceration modes.

As has been discussed, system state determination may be based on determining one or more system state scores. Algorithms and thresholds for determining and interpreting system state scores may be adapted, in particular embodiments, based on physical conditions, such as ambient and other temperatures and pressures; based on material parameters, such as elasticity of the connection tubing, or viscosity of the blood; based on geometry and configuration parameters, such as the length or diameter of the aspiration catheter; based on characteristics of the thrombus, such as elasticity or deformability; and/or based on other detected parameters, such as pressure, torque, and/or rotational speed parameters.

Tube and System Flushing

As has been previously disclosed herein, occlusive material may be associated with partial or total blockage related to the catheter's operation, such as a clogged catheter tip, an occluded catheter, or a catheter positioned in clot, during operation of the aspiration thrombectomy system. Separately or additionally, occlusive material may partially or completely block, coat, deposit, or otherwise impede fluid communication, fluid flow, and/or vacuum transfer between a vacuum source and the catheter tip. By way of example and not limitation, occlusive material may deposit or accumulate in the lumen and/or along the walls of fluid flow passages in the system. By way of example and not limitation, such fluid flow passages may comprise the aspiration catheter and the connection tubing, which acts as a fluid conduit between the aspiration catheter and the vacuum source, as well as any other fluid medium sources in the system. Such occlusive material deposits or accumulation along the walls of the aspiration catheter and/or connection tubing may, by way of example and not limitation, decrease available flow area, increase flow passage wall friction, increase pressure drops, reduce flow rates, and/or reduce the ability and efficiency of transferring vacuum to the catheter tip.

In particular embodiments, the aspiration thrombectomy system may be configured to detect, locate, dislodge, and/or operate to displace or remove occlusive material from the tubing and system, such as by flushing with a fluid medium. It will be appreciated that while terms such as "flush" and "flushing" may be used herein to describe related aspects for brevity, this disclosure fully contemplates any and all of the aspects and/or operations described above, and other related aspects and operations. By way of example and not limitation, a flushing fluid medium may comprise air and/or saline.

Figure 85:
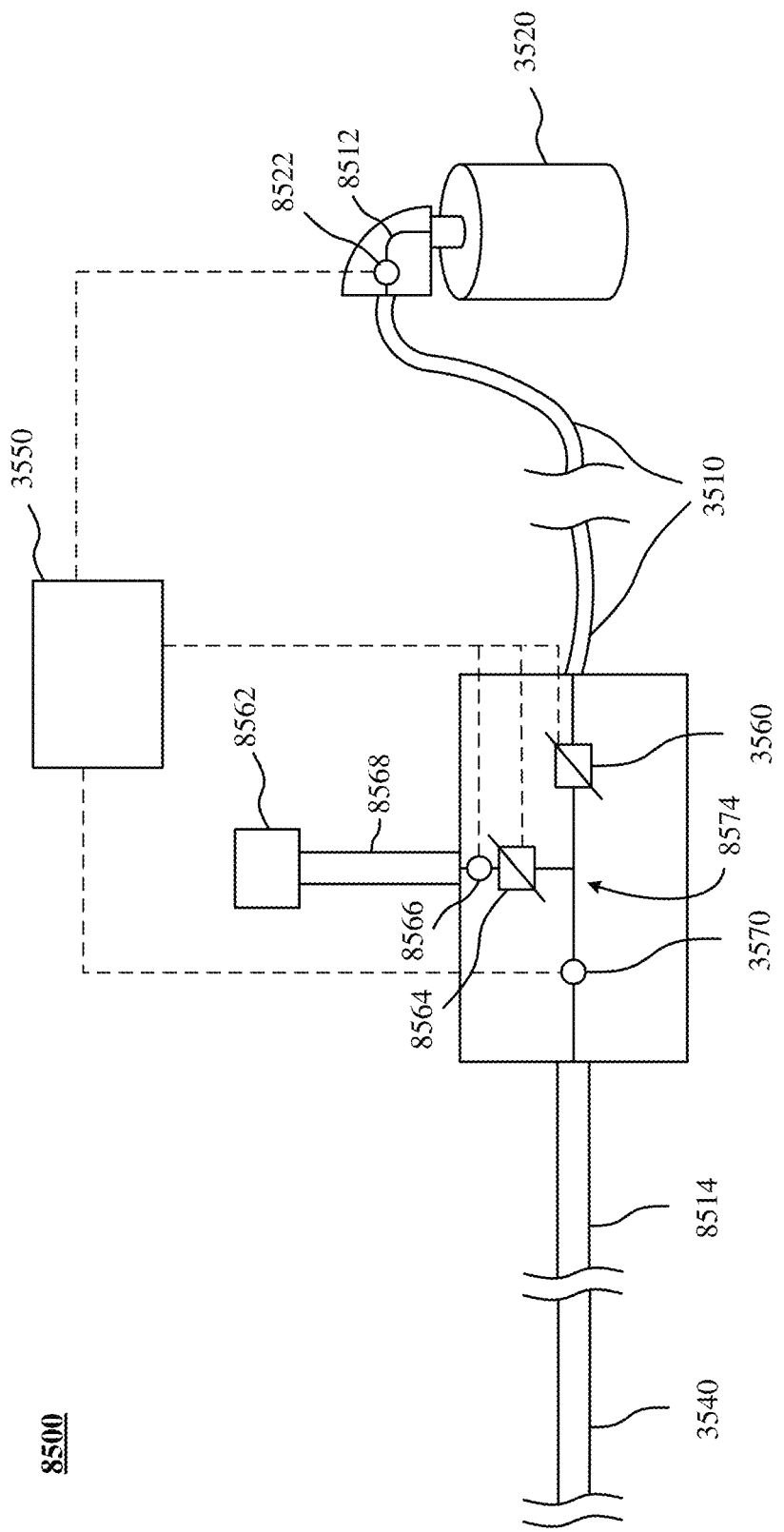
FIG. 85 illustrates a schematic representation of a particular embodiment configured for tube and system flushing.

FIG. 85 is a schematic representation 8500 of a particular embodiment configured for tube and system flushing. Connection tubing 3510, which may comprise paratubing, is illustrated with a proximal end 8512 connected in fluid communication with a vacuum source 3520. A distal end 8514 of the connection tubing 3510 may be connected in fluid communication with the aspiration catheter 3540.

In particular embodiments, an external unit, such as a unit previously described and illustrated in FIGS. 9A, 9B, and/or 11, may be present as a connecting module between the distal end of the connection tubing and the proximal end of the aspirating catheter. In particular embodiments, the external unit may additionally comprise one or more pressure sensors.

In particular embodiments, the system may be provided with one or more pressure sensors, and one or more controllable valves. By way of example and not limitation, as illustrated in the embodiment of FIG. 85, a vacuum valve 3560 may control a level of vacuum in the connection tubing, such as provided by vacuum source 3520. In particular embodiments, a distal pressure sensor 3570 may be associated with distal end 8514 of the connection tubing 3510. Separately or additionally, a vacuum sensor 8522 may be associated with proximal end 8512, according to particular embodiments.

In particular embodiments, a fluid source 8562 of a flushing fluid medium may be provided. As a non-limiting example, fluid source 8562 may comprise a saline solution. In particular embodiments, fluid source 8562 may be elevated, or otherwise pressurized, which may permit the fluid medium to flow into the connection tubing. In particular embodiments, a pressure level of fluid source 8562 may exceed a vacuum pressure level of vacuum source 3520. In particular embodiments, a pressure level of fluid source 8562 may be more than an external pressure level, such as an ambient or atmospheric pressure level. In particular embodiments, a pressure level of fluid source 8562 may be more than an external pressure level, such as a systolic blood pressure level of a patient. In particular embodiments, fluid flow from fluid source 8562 may be controlled by selectively opening a controllable valve, such as fluid medium valve 8564. In particular embodiments, fluid source 8562 may be configured to provide one or more different fluid media other than saline, such as air.

According to particular embodiments, fluid medium tubing 8568 may be used to connect fluid source 8562 with connection tubing 3510, such as at a T-junction or Y-junction (e.g., T-junction 8574). A fluid medium pressure sensor 8566, such as a saline pressure sensor, may be optionally provided. In particular embodiments, a fluid medium valve 8564, such as a saline valve, may be used to control introduction of a fluid medium from fluid source 8562 into the connection tubing 3510.

In particular embodiments, a controller 3550 may be configured to detect system quantities of interest, such as one or more pressure levels associated with connection tubing 3510 via one or more of distal pressure sensor 3570, vacuum sensor 8522, and/or fluid medium pressure sensor 8566. As will be further discussed, in particular embodiments, based on detecting pressure levels, controller 3550 may be configured to determine whether connection tubing 3510 is occluded. If connection tubing 3510 is determined to be occluded, in particular embodiments, controller 3550 may determine a location of the occlusion. In particular embodiments, based on determining that connection tubing 3510 is occluded and/or determining a location of the occlusion, controller 3550 may selectively operate one or more valves, such as vacuum valve 3560 and/or fluid medium valve 8564, to selectively introduce a fluid medium from fluid source 8562 into connection tubing 3510. In particular embodiments, controller 3550 may selectively operate one or more valves during one or more time intervals to flush occlusive material located in the connection tubing 3510. In particular embodiments, controller 3550 may selectively introduce a fluid medium during one or more time intervals.

It will be appreciated that while particular arrangements, numbers, locations, types, and/or connectivity of sensors and valves are disclosed for illustrating detection and control methods for tube and system flushing, any suitable arrangements, numbers, locations, types, and/or connectivity of sensors, actuators, and/or valves for appropriate detection and control is fully contemplated.

By way of example and not limitation, detection may include, but is not limited to, detection of the presence and/or location of occlusive material in the aspiration catheter, connection tubing, and/or other relevant portions of the aspiration thrombectomy system. By way of example and not limitation, control may include, but is not limited to, controlling levels, degrees, and/or locations, of selectively permitting fluid communication, corresponding isolation, introduction, change, and/or maintenance of vacuum and/or fluid flow of one or more media in particular portions of the tubing and system. Based on the parameters used for operating actuators or valves, such as the number, sequence, frequencies, and/or duty cycles of triggering open/closed states, many operational states of operating one or more actuators or valves are possible.

Figure 86:
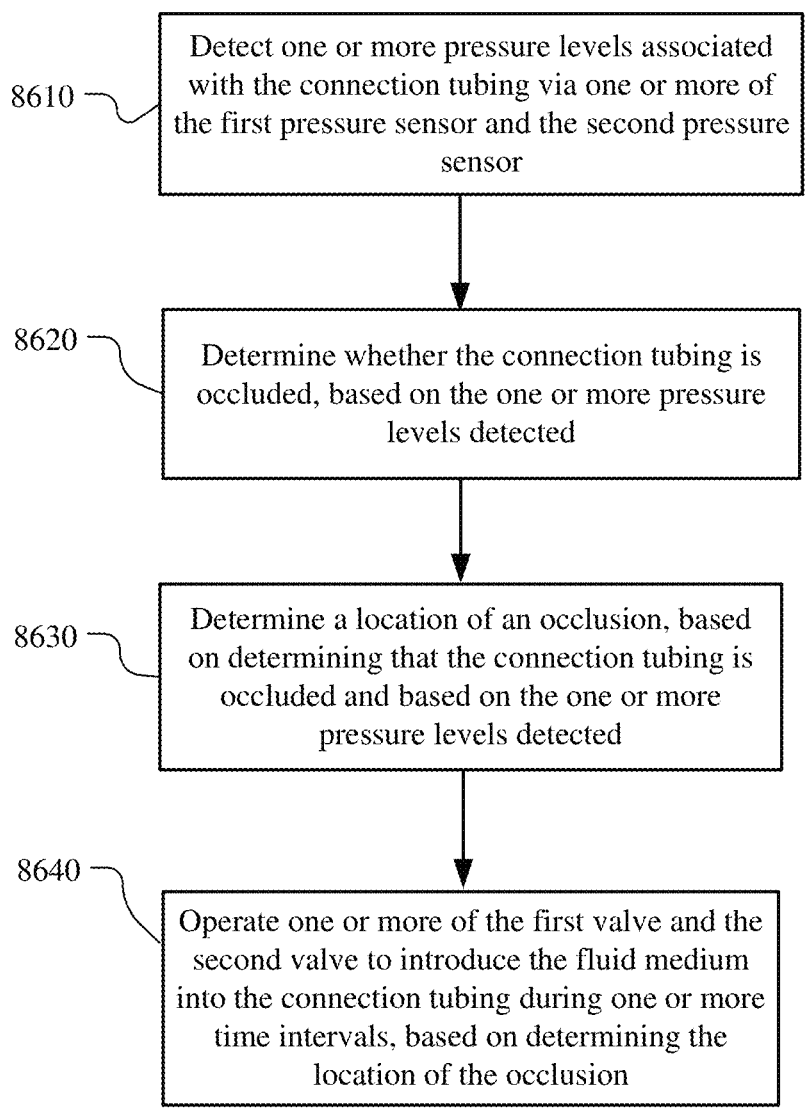
FIG. 86 illustrates a particular embodiment of an algorithm suitable for implementing tube and system flushing.

FIG. 86 illustrates an exemplary process 8600 for implementing tube and system flushing, such as in the aspiration catheter or the connection tubing of an aspiration thrombectomy system.

In a first step 8610 of the illustrated algorithm, the controller may detect one or more system quantities associated with the aspiration catheter or connection tubing via one or more sensors. By way of example and not limitation, one or more of a first pressure sensor and a second pressure sensor associated with the connection may be used for such detection, whereby one or more pressure levels are detected.

In a second step 8620 of the illustrated algorithm, the controller may determine, based on the one or more detected associated system quantities, whether parts of the system, such as the aspiration catheter or the connection tubing, are occluded. By way of example and not limitation, the controller may determine whether the connection tubing is occluded based on the one or more pressure levels detected via one or more of the first pressure sensor and the second pressure sensor.

In a third step 8630 of the illustrated algorithm, based on determining that the aspiration catheter or connection tubing is occluded, the controller may determine a location of the occlusion based on the one or more detected system quantities. By way of example and not limitation, based on the one or more pressure levels detected via one or more of the first pressure sensor and the second pressure sensor, the controller may determine that the connection tubing is occluded, and further, that the occlusion is located between the first and second pressure sensors.

In a fourth step 8640 of the illustrated algorithm, the controller may operate one or more actuators or valves of the system to flush particular parts of the aspiration catheter or connection tubing. By way of example and not limitation, the controller may operate one or more of the first valve and the second valve to introduce the fluid medium into the connection tubing during one or more time intervals, based on the determined location of the occlusion.

Figure 87:
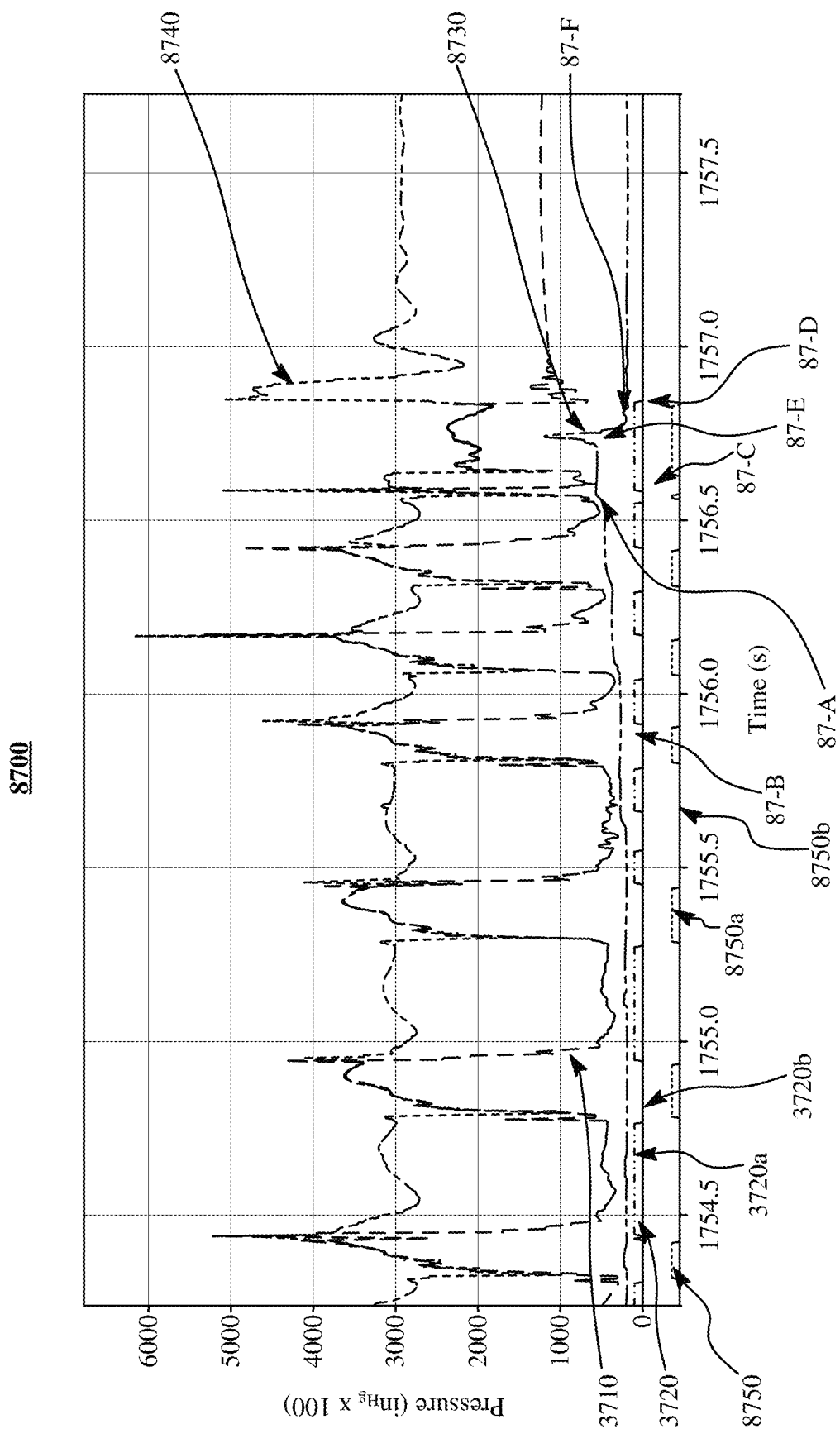
FIG. 87 illustrates detection and flushing of an occlusion located in the connection tubing proximal to the vacuum source, according to particular embodiments.
Figure 88:
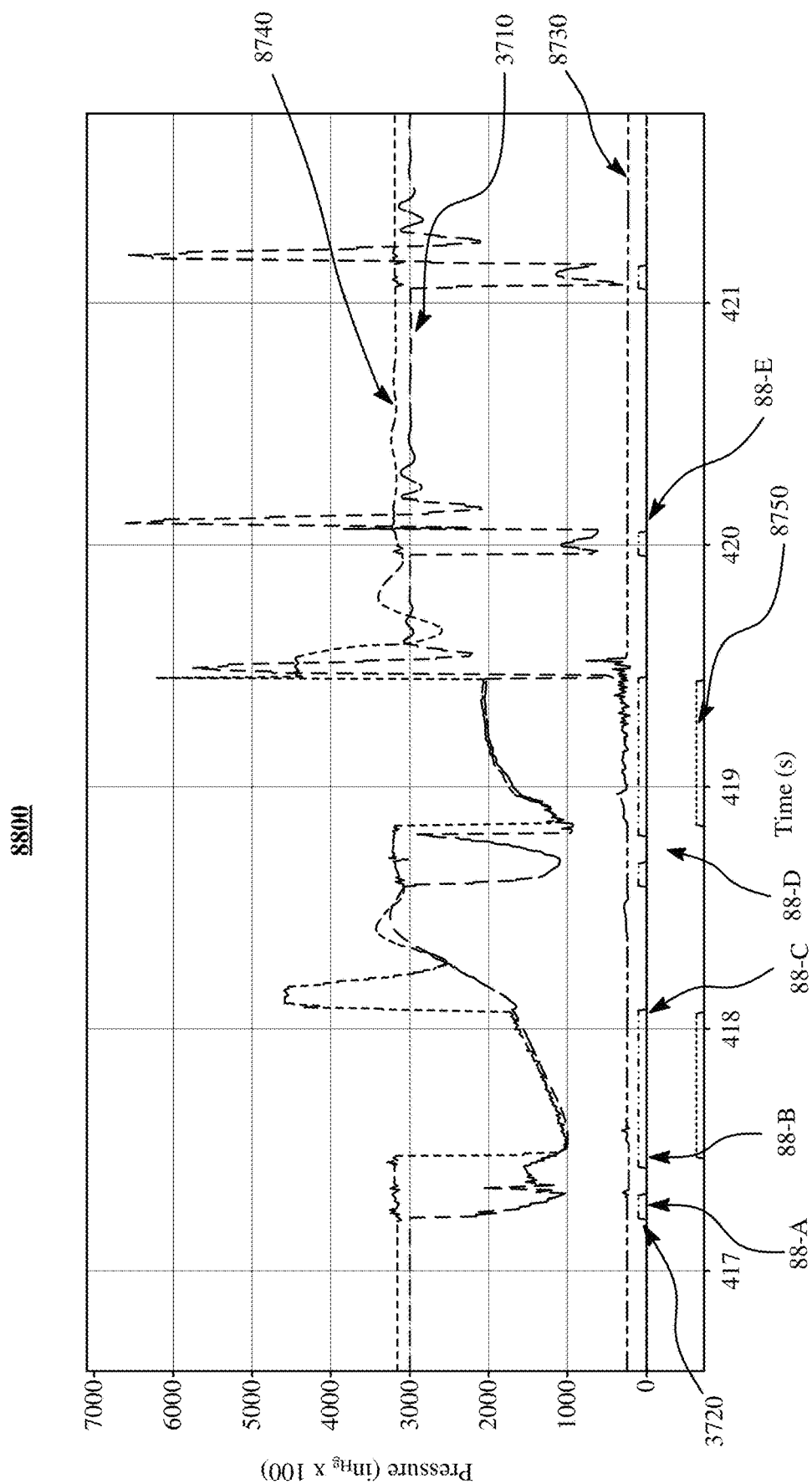
FIG. 88 illustrates detection and flushing of an occlusion located in the connection tubing between a distally located sensor of the connection tubing and the vacuum source, according to particular embodiments.

FIGS. 87 and 88 illustrate examples 8700 and 8800 of time-varying pressure profiles and valve operations as examples of tube and system flushing execution in aspiration thrombectomy systems, according to particular embodiments.

By way of example and not limitation, these figures include a distal pressure profile 3710 based on the time-varying pressure detected by a distal pressure sensor, such as distal pressure sensor 3570. A vacuum valve profile 3720 indicates the time-varying state of a vacuum valve, such as vacuum valve 3560. An open state of the vacuum valve is indicated herein as a relatively elevated level along the y-axis, such as 3720*a*, and a closed state of the vacuum valve is indicated herein as a relatively lowered level, such as in 3720*b*.

The illustrated pressure profile marked 8730 is an exemplary vacuum pressure profile 8730 based on the time-varying pressure detected by a pressure sensor associated with a proximal portion of the connection tubing, such as vacuum sensor 8522. The illustrated pressure profile marked 8740 is an exemplary saline pressure profile 8740 based on the time-varying pressure detected by a pressure sensor associated with a fluid medium or pressure source, such as fluid medium pressure sensor 8566.

The illustrated valve profile marked 8750 is an exemplary saline valve profile 8750 indicating the time-varying state of a saline valve as a control valve for a fluid medium, such as fluid medium valve 8564. As with the vacuum valve states described above, the open or closed states of the saline valve profile 8750 in illustrations herein may also be indicated by the relative elevated (e.g., 8750*a*) or lowered (e.g., 8750*b*) levels of the respective valve profiles along the y-axis.

FIG. 87 illustrates an example 8700 of detection and flushing of an occlusion located in the connection tubing proximal to the vacuum source. Referring to FIG. 85 by way of illustration and without limitation, an occlusion located between vacuum sensor 8522 and vacuum source 3520 may be considered as one representative example, among other possible examples.

In particular embodiments, such as illustrated in FIG. 87, in the absence of an occlusion between vacuum sensor 8522 and vacuum source 3520, vacuum pressure profile 8730 may be representative of an evolving pressure level associated with vacuum source 3520. Accordingly, vacuum pressure profile 8730 may be monitored, for example, for pressure values and/or changes, such as relative to particular known or determined reference and/or threshold levels. In particular embodiments, change of one or more values of vacuum pressure profile 8730 above a threshold value may indicate the presence of an occlusion between vacuum sensor 8522 and vacuum source 3520. In particular embodiments, an occlusion distal to vacuum source 3520, located in proximal end 8512 of connection tubing 3510, and/or located in proximity to vacuum source 3520, such as an occlusion between vacuum sensor 8522 and vacuum source 3520, may create a corresponding intermediate pressure rise in vacuum pressure profile 8730.

As illustrated in approximately the first half of the time window depicted in FIG. 87 as a non-limiting example, vacuum pressure profile 8730 generally maintains a relatively constant and low value over time. During this early part of the illustrated time window, without limitation, the aspiration thrombectomy system is depicted in modulated aspiration, pulsated aspiration, or any sequenced or varied aspiration, with vacuum valve profile 3720 and saline valve profile 8750 being alternately operated (i.e., one valve of the two is open and other is closed at a given time, with periodic reversal of the open/close state of both valves), such as to selectively expose the aspiration catheter to the vacuum source, and/or to the pressure or fluid medium source. In particular embodiments, one or more valves, such as vacuum valve 3560, may be selectively operated to sample the pressure state of the aspiration catheter or connection tubing. In particular embodiments, one or more valves, such as vacuum valve 3560 and/or a pressure source valve such as fluid medium valve 8564, may be selectively operated to generate pressure changes in the aspiration catheter or connection tubing.

As also illustrated, by way of example and not limitation, vacuum valve profile 3720 and saline valve profile 8750 in the early part of the window (such as prior to the approximate point in time indicated by 87-A) indicate that the corresponding vacuum and saline valves are not simultaneously held open. Accordingly, and as previously disclosed in detail herein, saline released or introduced by the fluid medium source during this early portion of the time window (prior to 87-A) may be solely directed toward the aspiration catheter to provide modulated aspiration, rather than toward the vacuum source.

Beyond about the approximate point in time indicated by 87-B illustrated in FIG. 87, vacuum pressure profile 8730 can be seen to be notably increasing with time relative to its hitherto low and approximately steady pressure level. In particular embodiments, based on vacuum pressure profile 8730 exceeding one or more threshold values, such as around 87-A, the controller may be configured to determine the presence of an occlusion. In particular embodiments, the controller may be configured to determine, based on one or more of the pressure levels detected by vacuum sensor 8522 exceeding one or more threshold values, that the connection tubing is occluded between vacuum sensor 8522 and vacuum valve 3560. In particular embodiments, one or more threshold values may be pre-determined, or empirically determined. In particular embodiments, one or more threshold values may be tuned based on particular one-time or ongoing measurements, which may comprise one or more detected pressure levels via one or more pressure sensors. In particular embodiments, one or more detected pressure levels may be filtered and/or processed based on suitable criteria. By way of example and not limitation, detected pressure levels may be processed to filter out transient pressure spikes, such as pressure spikes due to clots passing through connection tubing 3510. By way of example and not limitation, detected pressure levels may be processed to filter out pressure measurement acquisition artifacts and/or other noise factors.

Separately or additionally, based on one or more of the respective locations of corresponding sensors, particular detected pressure profile characteristics, and/or input from other sensors, the controller may be configured to localize a location of a detected occlusion. By way of example and not limitation, in the example of FIG. 87 and following an example configuration of FIG. 85, a detected occlusion may be determined to be present between vacuum sensor 8522 and vacuum source 3520 based on a pressure level from vacuum sensor 8522 exceeding a threshold value.

In particular embodiments, based on determining the presence and/or location of an occlusion in the connection tubing or aspiration catheter, controller 3550 may be configured to take action to reduce, displace, and/or remove the occlusion. In particular embodiments, as further illustrated in FIG. 87 between 87-C and 87-D, controller 3550 may initiate a flushing operation. In particular embodiments, a flushing operation may comprise introduction of a fluid medium, such as air and/or saline, into the connection tubing and/or aspiration catheter. In particular embodiments, a flushing operation may be provided by controller 3550 during one or more time intervals.

In particular embodiments, a fluid medium introduced into the connection tubing and/or aspiration catheter may provide flushing based on flowing due to a pressure gradient produced by one or more pressure sources and/or vacuum sources. In particular embodiments, a pressure source may comprise a fluid medium source, a pump, and/or a pressurized reservoir. In particular embodiments, one or more of the pressure sources and/or vacuum sources may be controllable, such as via a controller operating one or more controllable valves, actuators, and/or pumps.

By way of example and not limitation, as illustrated, both of the vacuum and fluid medium valves may be simultaneously opened, as indicated by the corresponding open vacuum valve profile 3720 and saline valve profile 8750, such that fluid medium, such as saline or air, that is released or introduced from the fluid medium source may now be directed through the connection tubing or aspiration catheter toward the vacuum source. In particular embodiments, the occlusive material present in the connection tubing may be flushed or dislodged based on an introduction of a fluid medium.

In particular embodiments, instead of simultaneously holding both of the vacuum and fluid medium valves open for flushing, other combinations of valve operation may be used. As a non-limiting example, during a flushing operation, one of the valves may be held open while cycling or fluttering another valve. By way of example and not limitation, vacuum valve 3560 may be held open while flushing is underway, along with fluttering fluid medium valve 8564, i.e., repeatedly opening and closing fluid medium valve 8564.

In particular embodiments, the controller may be configured to determine, based on detecting a pressure level spike, that an occlusion has been cleared. By way of example and not limitation, a pressure level spike may comprise a rapid increase in detected pressure, followed by a rapid decrease in detected pressure, such as illustrated by 87-E in FIG. 87. In particular embodiments, the controller may be configured to discontinue a flushing operation based on detection of a pressure spike, such as by closing fluid medium valve 8564 and/or vacuum valve 3560.

While this disclosure discusses particular ways of operating or interoperating valves during the steps of tube and system flushing, it will be appreciated that any suitable ways of operating or interoperating one or more valves and/or actuators are fully contemplated in this disclosure. Particular examples disclosed herein are included merely to provide a better understanding of configurational and operational principles. This disclosure is not limited to any specific types, configurations, or number of valves or actuators disclosed herein.

In particular embodiments, a fluid medium may be introduced or flushed into the connection tubing during one or more time intervals. In particular embodiments, a time interval for introducing a fluid medium into the connection tubing may be a predetermined time interval, such as 200 ms.

In particular embodiments, a time interval for introducing a fluid medium into the connection tubing may be based on determining that an occlusion has been reduced or eliminated. By way of example and not limitation, the controller 3550 may be configured to determine that the occlusion has cleared, such as based on a decrease (e.g., at 87-F) of vacuum pressure profile 8730 below a threshold value, and accordingly cease flushing of the connection tubing with the fluid medium by operating one or more of the corresponding valves.

In particular embodiments, the one or more time intervals may be separately or additionally based on determining a location of the occlusion. For instance, a localization of occlusion position may permit valve or actuator operation for introduction of the fluid medium based on a priori knowledge and/or empirical determination of additional relevant parameters, such as effective tubing length, diameter, type and number of bends, and/or other geometric and configurational aspects. Such an optimized flushing operation may enable more efficient and/or effective operation of the aspiration thrombectomy system, such as by limiting fluid medium waste, reducing fluid medium replenishment cycles, decreasing procedure time, and/or system power and size requirements.

By way of example and not limitation, for an occlusion determined to be present between vacuum sensor 8522 and vacuum source 3520, an interval for introducing the fluid medium into the connection tube may be between 70 and 300 ms. In some embodiments, an interval for introducing the fluid medium into the connection tube may be between 150 and 200 ms. In some embodiments, an interval for introducing the fluid medium into the connection tube may be in the range of 15-800 ms. In particular embodiments, an interval for introducing a fluid medium into the connection tube may be empirically determined.

It should be appreciated that such aspects of determination of time interval may be predetermined, and/or be determined or modified based on processing empirical input from other sensor(s), such as pressure sensors. In particular embodiments, pressure detected by, or in combination with, other sensors may be used to estimate fluid, occlusion, geometric and/or other relevant parameters. In particular embodiments, pressure detection may be combined with other known or detected system quantities to establish operation of one or more valves or actuators to flush the connection tubing, aspiration catheter, or other parts of the system.

FIG. 88 illustrates an example 8800 of detection and flushing of an occlusion located in the connection tubing between a distally located sensor of the connection tubing and the vacuum source. Referring to FIG. 85 by way of illustration and without limitation, an occlusion located between distal pressure sensor 3570 and vacuum sensor 8522 may be considered herein as a representative example of localization being depicted in FIG. 88, among other possible examples.

The controller may be configured to determine the presence of an occlusion in the connection tubing. In particular embodiments, the controller may sample the pressure levels in the connection tubing based on one or more available pressure sensors. Separately or additionally, in particular embodiments, the controller may generate changes of pressure in the connection tubing for determining the presence of an occlusion, such as by operating one or more valves.

In particular embodiments, one or more controllable valves may be operated (e.g., opened and/or closed) for controller 3550 to sample the conditions in the connection tubing 3510 and/or aspiration catheter 3540 based on detecting pressure levels from one or more pressure sensors. By way of example and not limitation, as depicted at time marker 88-A, vacuum valve 3560 may be cycled for sampling the pressure levels and conditions in connection tubing 3510. Separately or additionally, exposing the aspiration catheter and/or connection tubing to the vacuum sensor 8522 based on cycling vacuum valve 3560 may generate pressure changes in the aspiration catheter and/or connection tubing, and the detection of correlated pressure levels may permit determination of the presence of an occlusion.

By way of example and not limitation, pressure values at the start and end of valve cycling, peak, minimum, and/or average pressure values within a temporal window of valve cycling, as well as dynamic aspects of pressure change and recovery based on valve cycling may be detected and used by the controller to determine the presence of an occlusion. By way of example and not limitation, such as previously discussed herein with reference to determining flow or system state, one or more parameters used in determining a state of flow based on detected pressure profiles may be predetermined, and/or empirically determined based on operational data, and/or determined based on training and using machine learning algorithms, data analytics, or any combination thereof. Additional non-limiting details and examples of determining a flow or system state have been disclosed herein, for e.g., for determining the presence of an occlusion in the connection tubing or aspiration catheter.

In particular embodiments, controller 3550 may determine that an occlusion is present based on one or more pressure levels, and/or changes in pressure levels, detected by a pressure sensor. In the non-limiting example illustrated at the approximate point in time indicated by 88-A of FIG. 88, controller 3550 may determine that an occlusion is present based on a heavily damped or absent recovery of distal pressure profile 3710 to its hitherto higher-pressure level following closure of vacuum valve 3560 at the end of 88-A. Vacuum valve profile 3720 is illustrated to be opening and closing at 88-A corresponding to the operation of vacuum valve 3560, as discussed above.

In particular embodiments, the controller may simultaneously or sequentially detect pressure profiles from more than one pressure sensor to determine a location of an occlusion.

By way of example and not limitation, controller 3550 may compute a difference, such as instantaneous or weighted difference, between the respective pressure levels corresponding to distal pressure profile 3710 and vacuum pressure profile 8730, to localize the occlusion.

By way of example and not limitation, the controller may localize the occlusion by sequentially checking if an occlusion is proximal to particular sensors, or sets of sensors. In the depicted non-limiting example, vacuum pressure profile 8730 remains steady at a relatively low value, such as may be established to be within particular limits or threshold values, throughout the illustrated time window. Accordingly, the controller may determine, following the example of FIG. 23 discussed above, that no occlusion is present at the proximal portion of the connection tubing, i.e., between vacuum sensor 8522 and vacuum source 3520. Subsequently, having determined at 24-A that an occlusion is present between distal pressure sensor 3570 and vacuum source 3520, but further having determined that no occlusion exists at the proximal portion of connection tubing 3510, the controller 3550 may more specifically determine that the occlusion is located between distal pressure sensor 3570 and vacuum sensor 8522.

In particular embodiments, based on determining that the occlusion is located between distal pressure sensor 3570 and vacuum sensor 8522, controller 3550 may be configured to operate one or more valves, such as vacuum valve 3560 and/or fluid medium valve 8564, to introduce a fluid medium into connection tubing 3510 during one or more time intervals.

Accordingly, continuing to follow the non-limiting example of FIG. 88, with specific reference to the time window between 88-B and 88-C, controller 3550 may initiate a flushing operation, such as by introducing a flushing medium into the connection tubing. By way of example and not limitation, based on aspects and factors related to the determined location of the occlusion that have been previously discussed herein (e.g., a length of tubing between the occlusion and a reference location such as vacuum source 3520), controller 3550 may initiate a flushing operation. In particular embodiments, a flushing operation may be provided by controller 3550 during one or more time intervals.

In particular embodiments, such as illustrated by way of non-limiting example in FIG. 88, controller 3550 may simultaneously open both vacuum valve 3560 and fluid medium valve 8564 during a predetermined time interval, such as 600 ms. In particular embodiments, a predetermined time interval may be between 200 ms and 800 ms. In some embodiments, the predetermined time interval may be between 15 ms and 900 ms. In particular embodiments, a time interval for a flushing operation may be longer for locations of occlusion determined to be respectively farther from vacuum source 3520. In particular embodiments, an interval for introducing a fluid medium into the connection tube may be empirically determined.

As previously disclosed as non-limiting examples, a flushing operation may cease based on completion of predetermined time interval, and/or based on detection and determination of change in a status of occlusion, such as a reduction or elimination of occlusion detected via one or more pressure sensors and determined based on their corresponding pressure profiles and/or fluid flow characteristics.

In particular embodiments, as depicted at 88-D, controller 3550 may be configured to re-sample and/or otherwise determine if the occlusion is still present. In particular embodiments, controller 3550 may trigger one or more additional flushing operations and/or sequences, each flushing operation having identical or modified parameters. By way of example and not limitation, controller 3550 may trigger additional or separate actions based on continued detection of occlusion over time, such as longer flushing sequences, different valve operation patterns (e.g., duration, frequency, interleaving, and/or duty cycle of opening and closing) involving one or more valves, and/or providing an alerts and information to the user regarding the occluded status and/or known occlusion parameters of the system.

In particular embodiments, as depicted by way of non-limiting example at the approximate point in time indicated by 88-E, controller 3550 may determine, such as by sampling one or more pressure sensors, that the occlusion has cleared. As previously discussed, and as further detailed by incorporation by reference, a state of flow comprising non-occluded flow may be determined by controller 3550, such as based on the detected pressure profiles. Accordingly, in particular embodiments, normal operation of the aspiration thrombectomy system may be subsequently restored. In the non-limiting example of FIG. 88, the timeline past 88-E indicates that controller 3550 may continue to intermittently cycle vacuum valve 3560 and/or sample the correlated pressure changes from one or more of the detected pressure profiles.

Figure 89:
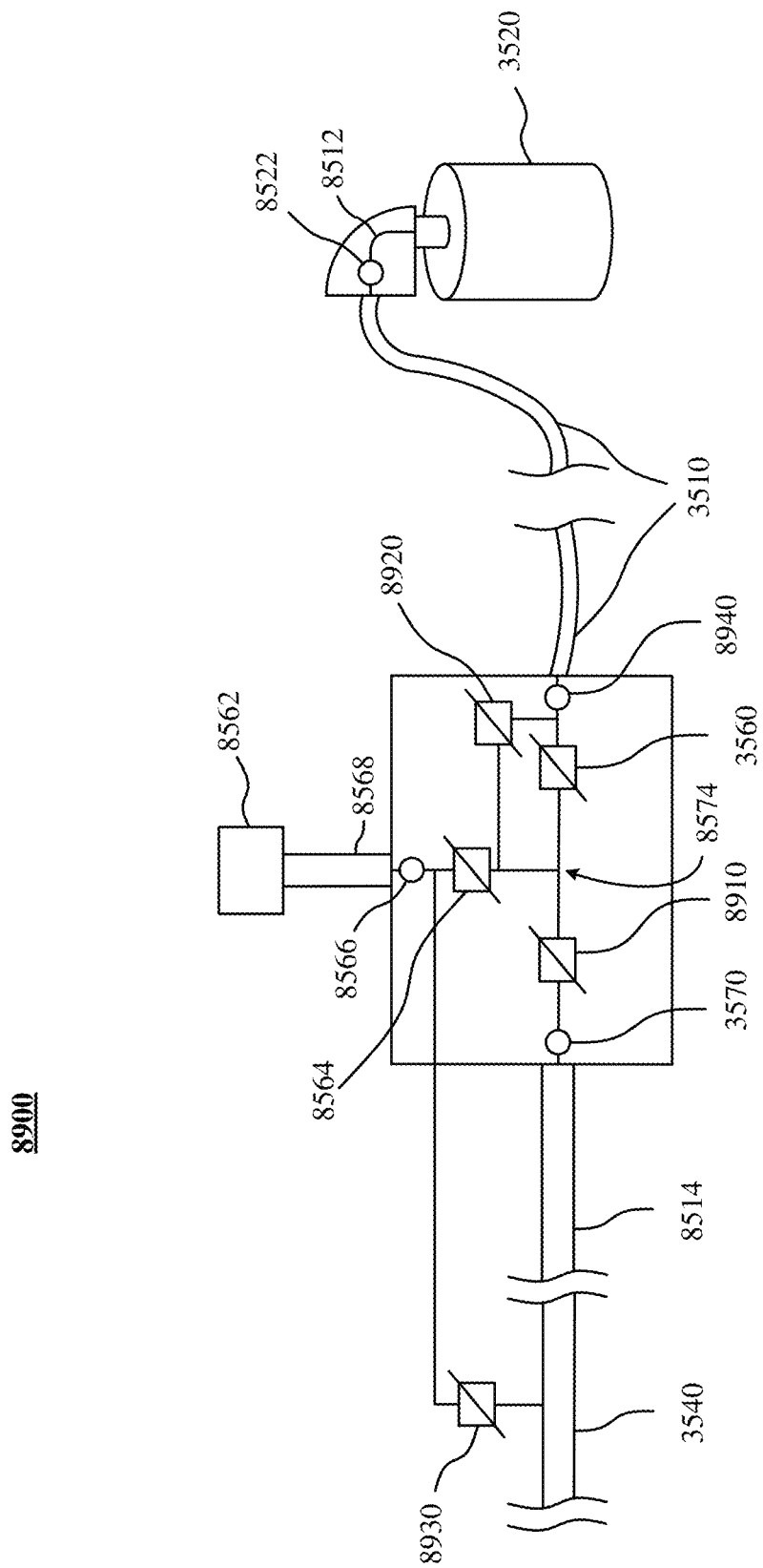
FIG. 89 illustrates a schematic representation of particular embodiments configured for tube and system flushing.

FIG. 89 is a schematic representation 8900 of another embodiment configured for tube and system flushing. Relative to the embodiment depicted in FIG. 85, the embodiment of FIG. 89 incorporates additional non-limiting valves and/or additional non-limiting sensors by way of illustration, as will be discussed. Controller 3550 is omitted in FIG. 89 for illustrative clarity, but may be assumed to be present and communicatively coupled to the additional valves, in addition to the original connections illustrated in FIG. 85.

It will be appreciated that particular aspects and features illustrated in FIG. 85 or 89, among others, are included to provide a better understanding of the scope and operation of disclosed aspects; features depicted herein need not be cumulatively or simultaneously present in every embodiment, nor should their respective specific configurations, locations, or other characteristics, as illustrated, be considered to be limiting in any way.

In particular embodiments, a control valve 8910 may be separately or additionally provided to permit selective isolation of the distal portion of the connection tubing and/or aspiration catheter 3540, such as from vacuum source 3520. By way of example and not limitation, closing control valve 8910 while flushing connection tubing 3510, such as while having vacuum valve 3560 and fluid medium valve 8564 simultaneously open as an illustrative example without limitation, may reduce the risk of unintentionally exposing a tip of aspiration catheter 3540 to a vacuum. By way of example and not limitation, such a control valve 8910 may be beneficial when the catheter tip encounters non-occluded or free flow of blood.

In particular embodiments, a bypass valve 8920 may be separately or additionally provided to permit selective isolation of the distal portion of the connection tubing and/or aspiration catheter 3540, such as from vacuum source 3520. By way of example and not limitation, bypass valve 8920 may permit concurrent introduction of the fluid medium into the connection tubing and fluid disconnection of the aspiration catheter from the vacuum source. For example, closing vacuum valve 3560 while opening fluid medium valve 8564 and bypass valve 8920 may reduce the risk of unintentionally exposing a tip of aspiration catheter 3540 to a vacuum.

In particular embodiments, aspects of the disclosure described relative to connection tubing 3510 may be extended to include aspiration catheter 3540. By way of example and not limitation, one or more control valves and/or pressure sensors associated with the aspiration catheter 3540 may be provided. In particular embodiments, a catheter valve 8930 may be separately or additionally provided to permit selective introduction of a fluid medium into the aspiration catheter. By way of example and not limitation, such upstream introduction (relative to flow directed toward vacuum source 3520) may provide benefits of flushing longer extents of aspiration catheter 3540 and/or connection tubing 3510.

In particular embodiments, based on methods previously discussed in detail herein, controller 3550 may be configured to determine the presence of an occlusion within or proximal to aspiration catheter 3540, and/or determine a location of the occlusion, and/or provide flushing operation. By way of example and not limitation, an occlusion may be detected between the distal tip of aspiration catheter 3540 and a pressure sensor associated with aspiration catheter 3540. As another non-limiting example, an occlusion may be detected between a pressure sensor associated with aspiration catheter 3540 and a pressure sensor associated with connection tubing 3510.

By way of example and not limitation, a flushing operation may include introduction or release of a fluid medium into aspiration catheter 3540, such as by operating catheter valve 8930, wherein the introduced fluid medium is flushed in a direction away from the distal tip of aspiration catheter 3540.

In particular embodiments, one or more pressure sensors disclosed herein may be configured to provide differential pressure sensing relative to a reference atmospheric and/or ambient pressure. In particular embodiments, one or more additional or alternative pressure sensors may be provided to compare pressure sensors to a reference atmospheric and/or ambient pressure.

In particular embodiments, one or more additional pressure sensors may be provided in the fluid path of vacuum sensor 8522. In particular embodiments, pressure sensor 8940 may be provided proximate to vacuum valve 3560, i.e., near vacuum valve 3560. In particular embodiments, pressure sensor 8940 may be disposed proximal to vacuum valve 3560. In particular embodiments, pressure sensor 8940 may be provided in the same static and/or contiguous fluid path as a vacuum sensor 8522, which may be provided in proximity to vacuum source 3520. By way of example and not limitation, pressure sensor 8940 may sense the same, or a substantially similar, value of static fluid pressure as sensed by vacuum sensor 8522 when there is no flow through the portion of connection tubing 3510 connecting them, such as by closing one or more valves distal to pressure sensor 8940. In particular embodiments, pressure sensor 8940 may be additional or alternative to vacuum sensor 8522.

In particular embodiments, the presence of an occlusion located between vacuum valve 3560 and vacuum sensor 8522 may be detected based on using pressure sensor 8940. Separately or additionally, in particular embodiments, the presence of an occlusion located between vacuum valve 3560 and vacuum source 3520 may be detected using pressure sensor 8940. By way of example and not limitation, pressure sensor 8940 may be used to detect one or more occlusions, such as described above, without requiring vacuum valve 3560 to be opened.

Separator-Based Occlusion Detection

In particular embodiments, as discussed herein, thrombectomy systems disclosed and contemplated herein may use devices and systems based on aspiration and/or other instruments, such as cutting instruments. By way of example and not limitation, a separator or other suitable instrument may be, separately or in combination with other devices and/or systems (e.g., aspiration systems), may be used for occlusion detection, as will be discussed further.

Figure 90:
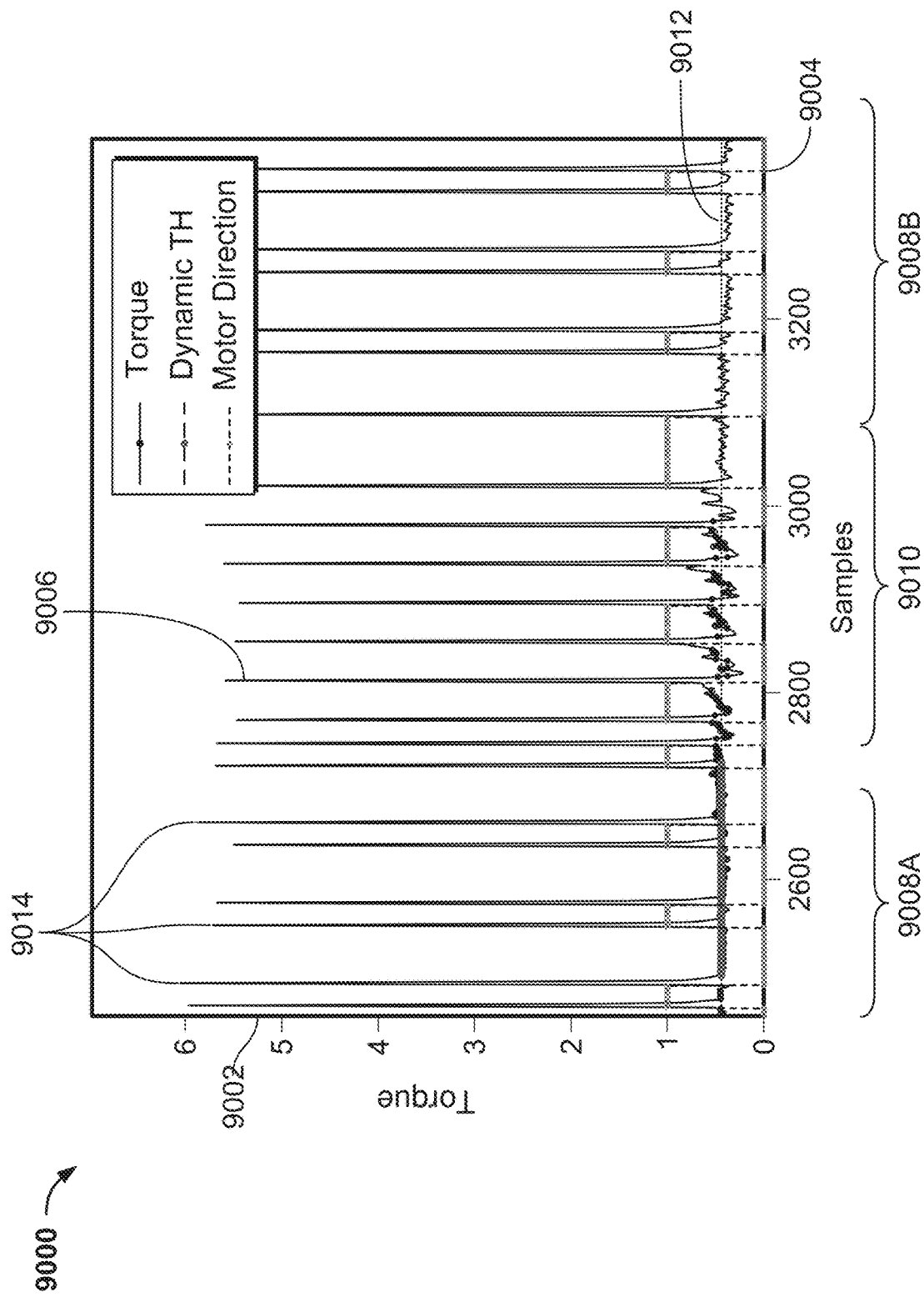
FIG. 90 illustrates a schematic representation of an exemplary operational parameter relative to a baseline of the operational parameter, according to particular embodiments.

FIG. 90 illustrates a schematic representation of an exemplary operational parameter relative to a baseline of the operational parameter, according to particular embodiments. By way of example and not limitation, separator torque data 9006 are depicted in graph 9000 as an exemplary operational parameter in FIG. 90. By way of example and not limitation, graph 9000 depicts exemplary data of separator torque measurements based on a separator instrument engaging with occlusive material and/or other elements within a vascular system. By way of example and not limitation, the data of graph 9000 may be used in whole or in part to illustrate execution of any or all of processes 9200 of FIG. 92, process 9300 of FIG. 93, process 9400 of FIG. 94, process 9500 of FIG. 95, process 9600 of FIG. 96, and/or process 9700 of FIG. 97. By way of example and not limitation, graph 9000 may be used to schematically illustrate exemplary characteristic operation of one or more elements and/or components in or described in reference to FIGS. 22A-34.

With reference to FIG. 90, graph 9000 includes vertical axis 9002, horizontal axis 9004, and separator torque data 9006. In particular embodiments, separator torque data 9006 may include normal operation samples 9008A and 9008B as well as wrap condition operation samples 9010. In particular embodiments, dynamic threshold 9012 may provide a baseline for expected operational deviations. In particular embodiments, such as illustrated in FIG. 90 by way of example and not limitation corresponding to wrap condition operation samples 9010, deviations from dynamic threshold 9012 may correspond to the separator instruction being intertwined with tissue of the vascular system being treated.

In particular embodiments, such as illustrated by separator torque data 9006, the motor torque of one or more motors driving a separator may generate peaks 9014. By way of example and not limitation, a torque peak may be generated each time a change of direction of the motor occurs. Although it may not be depicted via graph 9000, in particular embodiments, separator torque data 9006 may include unwanted noise in the recorded data, such as based on processing rate and/or abrupt changes in engagement status of the separator. In particular embodiments, dynamic threshold 9012 may separately or additionally differ based on a different patient having a procedure done using a particular separator embodiment, and/or a different piece of hardware (e.g., motor and separator combination). By way of example and not limitation, there may be physiological differences between patients, and/or there may be manufacturing tolerances with devices. In particular embodiments, dynamic threshold 9012 may be unaffected by a wrap situation. By way of example and not limitation, a change in values depicted in wrap condition operation samples 9010 may be based on a rotation rate of the device removing occlusive material.

In particular embodiments, a wrap condition may be detected based on variation in cyclical responses of the device. By way of example and not limitation, a wrap condition may be detected based on periodic direction changes with varying device responses. In particular embodiments, a wrap condition may not affect the baseline in a manner that a different patient or different device may modify dynamic threshold 9012. In particular embodiments, calculations related to establishing dynamic threshold 9012 may be intentionally set such that a baseline may not be modified in response to detection of a wrap condition. In particular embodiments, conversely, dynamic threshold 9012 may be calculated and established to verify wrap conditions may be occurring. In particular embodiments, dynamic threshold 9012 may be presented based on intelligent consideration of varying device level variations, such as before a particular device experiences a wrap condition.

In particular embodiments, the system may store in memory communicatively coupled to the processing circuitry a maximum value corresponding to the one or more operational values. In particular embodiments, the system may store a minimum value corresponding to the one or more operational parameters, such as for each respective manufactured iteration of the system. In particular embodiments, processing circuitry may utilize these values for additional processing. By way of example and not limitation, in particular embodiments, the baseline of the one or more operational parameters may be compared to the maximum value and/or the minimum value. In particular embodiments, based on the comparing, a value corresponding to the baseline of the one or more operational parameters may be determined to exceed the maximum value. In particular embodiments, the value may be determined to be less than the minimum value. In particular embodiments, in response to the determining, the processing circuitry may cause one or more of modifying the one or more operational parameters and/or terminating operation of the system, such as without updating the baseline.

In particular embodiments, to obtain a baseline for using to identify an engagement status, tracking baselines for different patients may not be affected by the unwanted peaks, noise, and/or wrapping.

By way of example and not limitation, an algorithm is described herein that may rapidly learn a patient and/or device baseline biased toward the beginning of an operation cycle. In particular embodiments, an early cycle learning bias may be used to ensure particular adjustment and/or modification of operation of the device for a particular patient, such as to prevent or avoid a wrapping condition (e.g., as characterized by the data of wrap condition operation samples 9010).

In particular embodiments, separator torque data 9006 may be represented from a computation perspective as x(i), where i=1, 2, ..., N, where N may represent a total number of data samples under consideration for use. By way of example and not limitation, N may be determined based on a sampling rate of a sensor associated with one or more of the motor or the separator instrument. In particular embodiments, the dynamic threshold (for e.g., as represented by dynamic threshold 9012) may be computationally represented as the function DT(i), where i=1, 2, ..., N may correspond to the computation of the threshold based on a first data sample, a second data sample, and up to N data samples. In particular embodiments, an initial value of dynamic threshold 9012 (for e.g., based on a scale of vertical axis 9002) may be computed via the function DT(i), such as to provide more complete sampling and/or input to subsequent iterations of the computations performed via function DT(i). In particular embodiments, such an approach can improve accuracy of the magnitude of dynamic threshold 9012 with less repeated computations.

In particular embodiments, by way of continuing non-limiting example of computing learning rate of dynamic threshold 9012, the value of dynamic threshold 9012 may be represented by the formula below, wherein N is the number of samples utilized in the computation:

$$\lambda(i) = 1 - (\tau/i), i = 2, 3, \ldots, N$$

In particular embodiments, the learning rate may then be fed back into the dynamic threshold function as exemplified below:

$$DT(i) = \lambda(i) * DT(i-1) + (1 - \lambda(i)) * x(i)$$

In particular embodiments, a time constant (e.g., a period of time which captures a particular number of data samples) may be applied to one or more of the above referenced formulas, such as to modify the weight of a currently computed value of the dynamic threshold as it may be used in a computation for a predictive or subsequent dynamic threshold. In particular embodiments, a time constant may be represented by the character t.

In particular embodiments, a time constant may also be applied to newer data samples. By way of example and not limitation, a time constant may be applied to newer data sample in cases where an initially computed dynamic threshold may be based on a one data sample, and/or there may be significantly more subsequent data samples available which may impact the dynamic threshold value with more significance than the first data sample. In particular embodiments, the value of t may be a scalar value, such as 1, such as to avoid significant impact of weighting different samples of data. In particular embodiments, the value of t may be adjusted to any suitable value, such as depending on the calibration settings of a device based on one or more of manufacturing tolerances and/or based on specific patient characteristics.

In particular embodiments, computer readable instructions may incorporate logic to modify the dynamic threshold function. By way of example and not limitation, the dynamic threshold function may be modified to avoid or filter peaks from motor direction change, and/or noise affecting the dynamic threshold. By way of example and not limitation, the following algorithm illustrates an updating function to modify the dynamic threshold function.

$$DT(i) = \lambda(i) * DT(i-1) + (1 - \lambda(i)) * x(i), \text{ when } x(i) < \eta * DT(i-1),$$

$$\text{where } i = 2, 3, \ldots, N.$$

By way of example and not limitation, by modifying the value, or range of values, corresponding to $\eta$ (e.g., a noise limiting parameter), this updated formula provides a built-in processing loop for computing means to minimize the effect of noise in the data and/or wrap situation data on the dynamic threshold. By way of example and not limitation, to determine if the wrap occurs or not, the number of data samples that are larger than the dynamic threshold may be computed based on the following relationship:

$$\text{If } x(i) > \eta * DT(i-1), \text{ then } DT(i) = DT(i-1), \text{ where } i = 2, 3, \ldots, N.$$

In particular embodiments, for each data point, if $x(i) > 2*DT(i)$, where $i=2, 3, \ldots, N$ and the factor of two is a non-limiting example, then a value that exceeds the dynamic threshold may be denoted as $\delta(k)=i$, wherein i may be updated based on the scalar number of data points above the threshold within a group of data samples.

In particular embodiments, the data points may have significant differences in values when exceeding the dynamic threshold (e.g., as represented by the variation in values of peaks 9008). By way of example and not limitation, when two values are far from each other (e.g., if $\delta(k)-\delta(k-1)>5$, such as for a sampling rate of 100 Hz), then a reset of the value of $\delta$ may occur to ensure the data points exceeding the threshold may be correctly fed into a corrective algorithm for operating the separator.

In particular embodiments, torque values that are below the dynamic threshold may be separately or additionally considered to improve detection of wrap conditions. By way of example and not limitation, the following relationship may be used for insight and/or to determine when deviations below the threshold may be considered:

$$\text{when } x(i) < 0.5 * DT(i-1), \text{ where } i = 2, 3, \ldots, N.$$

By way of example and not limitation, although wrap detection may be detected based on a determination that a certain number of data points within a sampling period or sampling cycle exceed the dynamic threshold, torque values that are below the dynamic threshold may separately or additionally be indicative of a wrap condition, such as illustrated via wrap condition operation samples 9010. In particular embodiments, as a result, by using data from both sides of the dynamic threshold, a wrap condition may be identified earlier than if only one set of data is utilized. In particular embodiments, accordingly, modification of operation of the separator may be achieved prior to causing any patient level issues.

Figure 91:
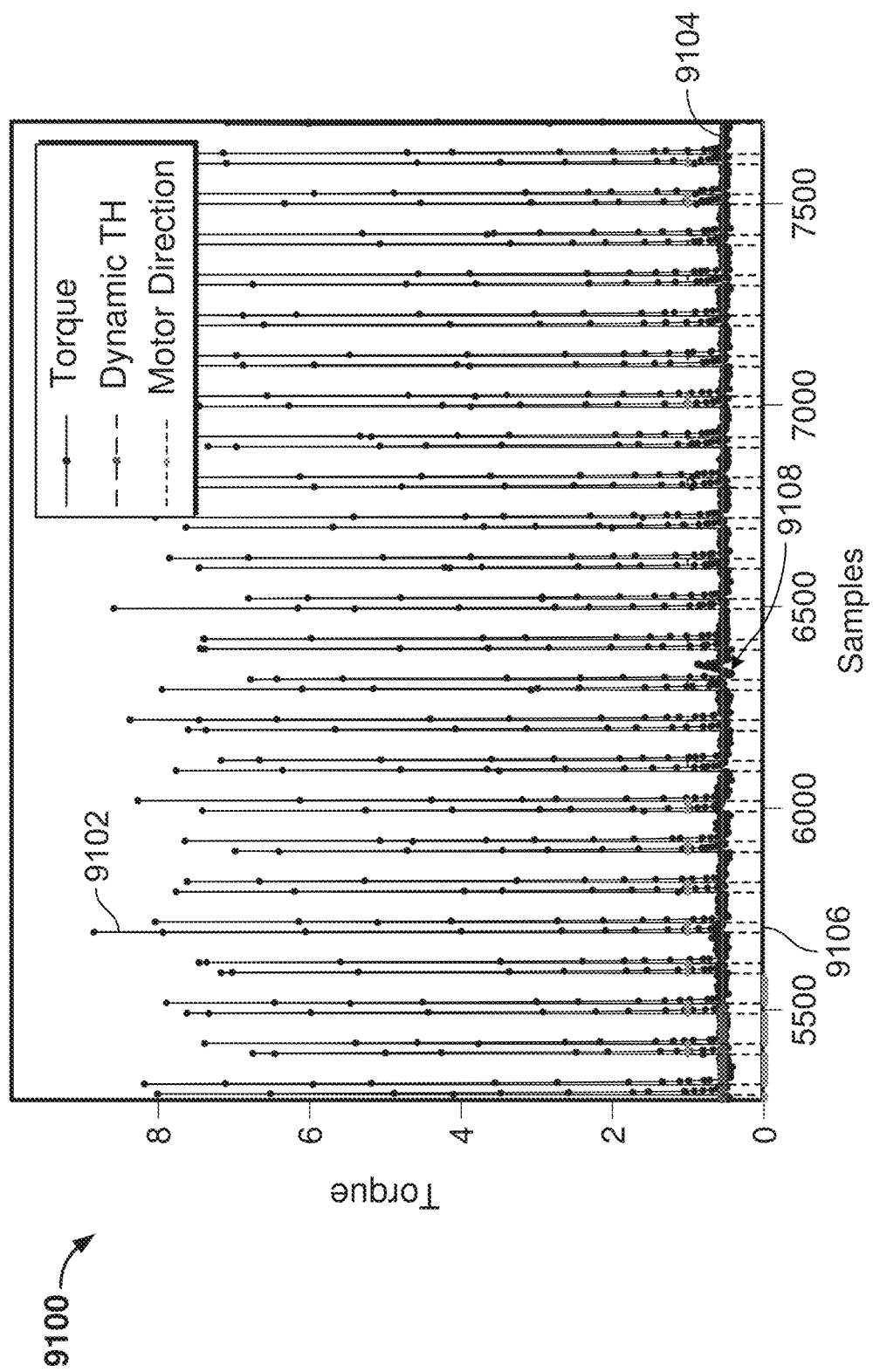
FIG. 91 illustrates a schematic representation of an exemplary operational parameter when an instrument interfaces with an occlusion, according to particular embodiments.

FIG. 91 illustrates a schematic representation of an exemplary operational parameter when an instrument interfaces with an occlusion, according to particular embodiments. By way of example and not limitation, with reference to FIG. 91, graph 9100 represents data collected with respect to a torque measurement as a separator instrument engages one or more of occlusive material or other elements within a vascular system. By way of example and not limitation, the data of graph 9100 may be used in whole or in part to illustrate execution of any or all of processes 9200 of FIG. 92, process 9300 of FIG. 93, process 9400 of FIG. 94, process 9500 of FIG. 95, process 9600 of FIG. 96, and/or process 9700 of FIG. 97. By way of example and not limitation, graph 9100 may be used to schematically illustrate exemplary characteristic operation of one or more elements and/or components in or described in reference to FIGS. 22A-34.

With reference to FIG. 91, graph 9100 schematically illustrates data wherein a wrap condition may not be realized (e.g., based on adjustments or modifications to operational parameters of the separator instrument or motor). As illustrated in FIG. 91 by way of example and not limitation, data profile 9102 represents data samples of a motor torque, and data profile 9106 represents a step function that characterizes a rotational direction of a motor (e.g., to interface with and/or to remove an occlusion). In particular embodiments, dynamic threshold 9104 may be computed based on the algorithms described herein. In particular embodiments, dynamic threshold 9104 may be updated based on changes in data profile 9102 (for e.g., in the event data profile 9102 changes from a profile similar to normal operation samples 9008A and 9008B to a profile similar to wrap condition operation samples 9010). In particular embodiments, presence of occlusive material may be detected based on data profile 9102. By way of example and not limitation, a clot may be identified based on the presence of data deviation 9108, which may indicate an increase in torque over a number of data samples.

Figure 92:
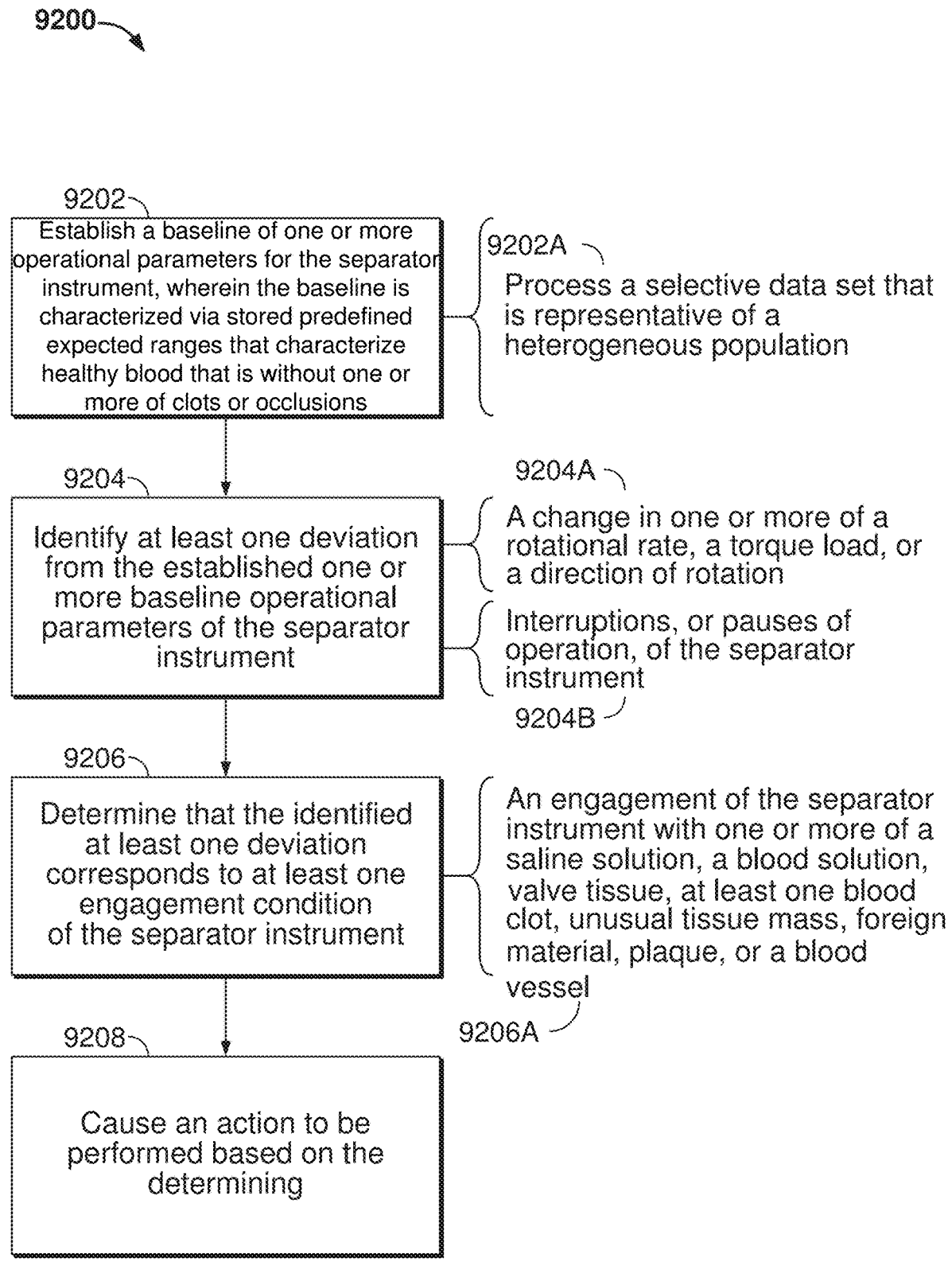
FIG. 92 illustrates an exemplary process for detecting different engagement conditions, according to particular embodiments.

FIG. 92 illustrates an exemplary process for detecting different engagement conditions, according to particular embodiments. By way of example and not limitation, process 9200 illustrated in FIG. 92 may be executed by processing and control circuitry 108 of FIG. 1. Additionally or alternatively, in particular embodiments, process 9200 may be executed, in whole or in part, as part of and/or contemporaneous with any or all of process 9300 of FIG. 93, process 9400 of FIG. 94, process 9500 of FIG. 95, process 9600 of FIG. 96, and/or process 9700 of FIG. 97. In particular embodiments, data as characterized by graph 9000 of FIG. 90 and/or graph 9100 of FIG. 91 may separately or additionally be utilized as part of the execution of process 9200.

With reference to FIG. 92, at process block 9202, a baseline of one or more operation parameters for the separator instrument may be determined in particular embodiments. In particular embodiments, the baseline may be characterized via stored predefined expected ranges that characterize healthy blood that may be without one or more of clots or occlusions. In particular embodiments, such as characterized by callout 9202A, a selective data set that may be representative of a heterogeneous population is processed. In particular embodiments, such as illustrated by process block 9204, at least one deviation from the established one or more baseline operation parameters of the separator instrument may be identified. In particular embodiments, such as illustrated by callout 9204A, deviation from the baseline of the one or more operation parameters may include one or more of a change in one or more of a rotational rate, a torque load, or a direction or rotation. In particular embodiments, additionally or alternatively, as illustrated by callout 9204B, a deviation from the baseline of the one or more operation parameters may include interruptions, and/or pauses of operation, of the separator instrument. In particular embodiments, such as illustrated at process block 9206, the identified at least one deviation may be determined to correspond to at least one engagement condition of the separator instrument. In particular embodiments, such as illustrated by callout 9206A, the engagement condition may include one or more of an engagement of the separator instrument with one or more of a saline solution, a blood solution, valve tissue, at least one blood clot, unusual tissue mass, foreign material, plaque, and/or a blood vessel. In particular embodiments, such as illustrated by process block 9208, an action may be caused to be performed based on the determining (e.g., modifying torque or speed of a rotating component engaged with occlusive material, and/or modifying a distance which the separator may be extended).

Figure 93:
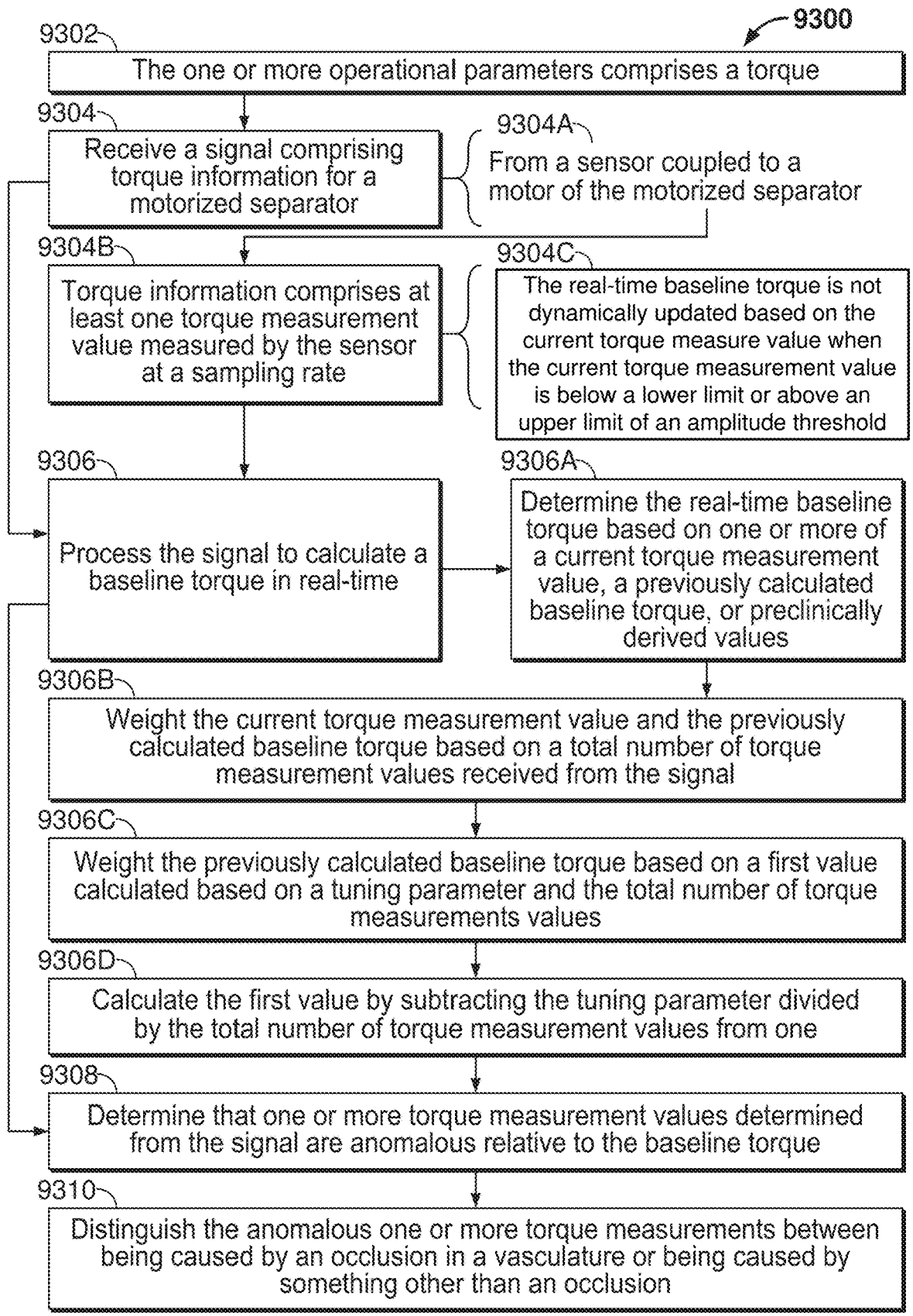
FIG. 93 illustrates an exemplary process for reviewing operational parameters of an instrument, according to particular embodiments.

FIG. 93 illustrates an exemplary process for reviewing operational parameters of an instrument, according to particular embodiments. By way of example and not limitation, process 9300 illustrated in FIG. 93 may be executed by processing and control circuitry 108 of FIG. 1. Additionally or alternatively, in particular embodiments, process 9300 may be executed, in whole or in part, as part of and/or contemporaneous with any or all of process 9200 of FIG. 92, process 9400 of FIG. 94, process 9500 of FIG. 95, process 9600 of FIG. 96, and/or process 9700 of FIG. 97. In particular embodiments, data as characterized by graph 9000 of FIG. 90 and/or graph 9100 of FIG. 91 may be separately or additionally utilized as part of the execution of process 9300.

With reference to FIG. 93, at process block 9302, an operational parameter may comprise a torque, such as a motor torque, in particular embodiments. In particular embodiments, such as illustrated by process block 9304, a signal comprising torque information for a motorized separator may be received. In particular embodiments, such as illustrated by callout 9304A, the signal may be from a sensor coupled to a motor of the motorized separator. In particular embodiments, if the torque information is from the sensor, the process block 9304B may be used to determine the torque information comprising at least one torque measurement value measured by the sensor at a particular sampling rate. In particular embodiments, such as illustrated by callout 9304C, real-time baseline torque may not be dynamically updated based on the current torque measurement value when the current torque measurement value is above an amplitude threshold. In particular embodiments, such as illustrated by process block 9306, the signal may be processed to calculate a baseline torque in real time. In particular embodiments, process block 9308 may be employed immediately after process block 9306. In particular embodiments, process block 9306A-9306D may be employed after process block 9306 and before process block 9308. In particular embodiments, such as illustrated by process block 9306A, the real-time baseline torque may be determined based on one or more of a current torque measurement value, a previously calculated baseline torque, and/or pre-clinically derived values (e.g., stored in memory or communicatively accessible via a server). In particular embodiments, such as illustrated by process block 9306B, the current torque measurement value and the previously calculated baseline torque may be weighted based on a total number of torque measurement values received from the signal. In particular embodiments, such as illustrated by process block 9306C, the previously calculated baseline torque may be weighted based on a first value calculated based on a tuning parameter and the total number of torque measurement values. In particular embodiments, such as illustrated by process block 9306D, the first value may be calculated by subtracting the tuning parameter divided by the total number of torque measurement values from an integer with a value of one. In particular embodiments, such as illustrated by process block 9308, the one or more torque measurement values determined from the signal may be determined to be anomalous relative to the baseline torque. In particular embodiments, such as illustrated by process block 9310, the anomalous one or more torque measurements may be distinguished between being caused by an occlusion in a vasculature or being caused by something other than an occlusion (e.g., a mechanical failure of part of the system).

Figure 94:
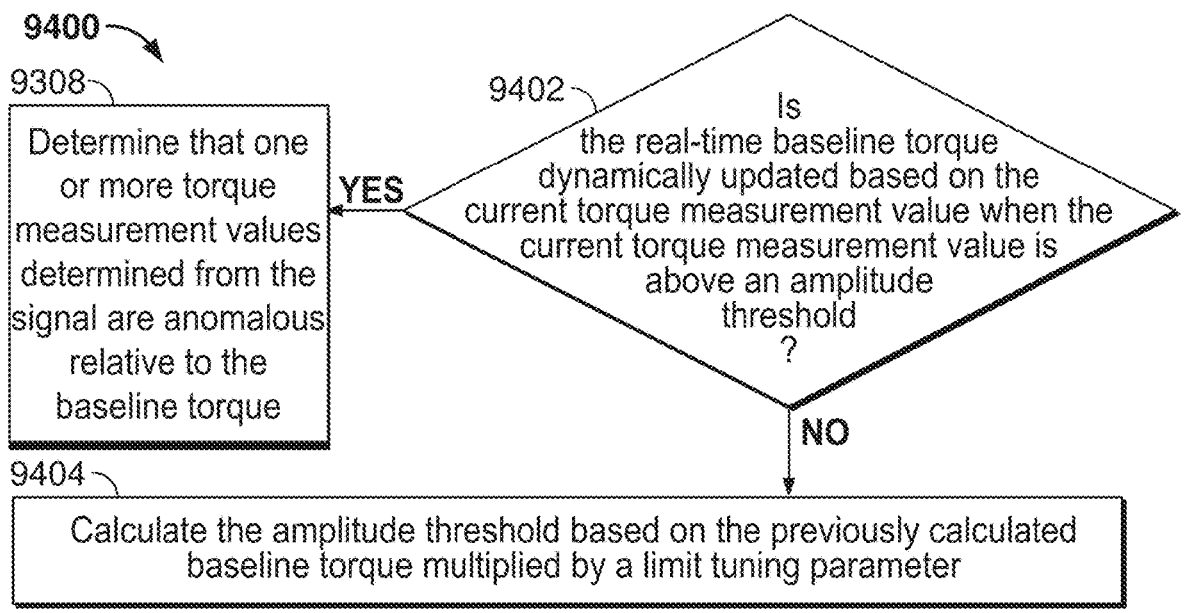
FIG. 94 illustrates an exemplary process for calculating an amplitude threshold, according to particular embodiments.

FIG. 94 illustrates an exemplary process for calculating an amplitude threshold, according to particular embodiments. By way of example and not limitation, process 9400 illustrated in FIG. 94 may be executed by processing and control circuitry 108 of FIG. 1. Additionally or alternatively, in particular embodiments, process 9400 may be executed, in whole or in part, as part of and/or contemporaneous with any or all of process 9200 of FIG. 92, process 9300 of FIG. 93, process 9500 of FIG. 95, process 9600 of FIG. 96, and/or process 9700 of FIG. 97. In particular embodiments, data as characterized by graph 9000 of FIG. 90 and/or graph 9100 of FIG. 91 may be utilized as part of the execution of process 9400.

In particular embodiments, decision block 9402 may be utilized to determine whether the real-time baseline torque is dynamically updated based on the current torque measurement value when the current torque measurement value is above an amplitude threshold. By way of example and not limitation, if the real-time baseline torque may be dynamically updated based on the current torque measurement value when the current torque measurement value may be above an amplitude threshold (YES at 9402), the process block 9308 of process 9300 may be utilized for further processing. By way of example and not limitation, if the real-time baseline torque may not be dynamically updated based on the current torque measurement value when the current torque measurement value is above an amplitude threshold (NO at 9402), the process block 9404 may be utilized for further processing. In particular embodiments, such as illustrated by process block 9404, the amplitude threshold may be calculated based on the previously calculated baseline torque multiplied by a limit tuning parameter (e.g., as provided, identified, or determined based on one or more of system capabilities, system calibrations, or encoded operational limits).

Figure 95:
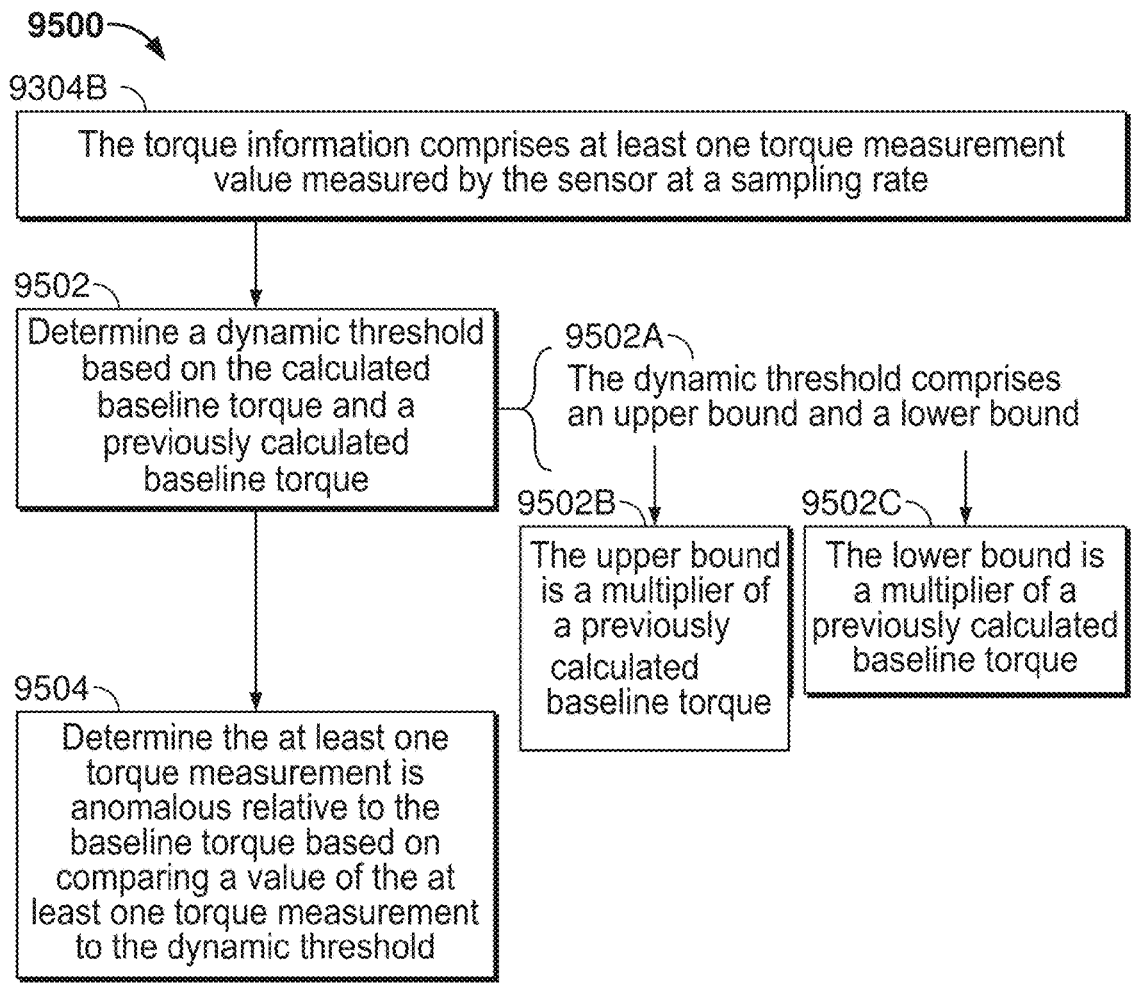
FIG. 95 illustrates an exemplary process for determining that an operational parameter measurement may be anomalous, according to particular embodiments.

FIG. 95 illustrates an exemplary process for determining that an operational parameter measurement may be anomalous, according to particular embodiments. By way of example and not limitation, an operational parameter may be anomalous relative to a baseline measurement. By way of example and not limitation, process 9500 illustrated in FIG. 95 may be executed by processing and control circuitry 108 of FIG. 1. Additionally, or alternatively, in particular embodiments, process 9500 may be executed, in whole or in part, as part of and/or contemporaneous with any or all of process 9200 of FIG. 92, process 9300 of FIG. 93, process 9400 of FIG. 94, process 9600 of FIG. 96, and/or process 9700 of FIG. 97. In particular embodiments, data as characterized by one or more of graph 9000 of FIG. 90 and/or graph 9100 of FIG. 91 may be utilized as part of the execution of process 9500.

With reference to FIG. 95, in particular embodiments, process 9500 may be utilized in the event process 9300 progresses to process block 9304B, such as based on one or more conditions described in reference to FIG. 93. In particular embodiments, such as illustrated by process block 9502, a dynamic threshold may be determined based on a calculated baseline torque and a previously calculated baseline torque. In particular embodiments, such as illustrated by callout 9502A, the dynamic threshold may comprise an upper bound and a lower bound. By way of example and not limitation, callout 9502B clarifies the upper bound may be a multiplier of the previously calculated baseline torque, in particular embodiments. By way of example and not limitation, callout 9502C clarifies the lower bound may be a multiplier of a previously calculated baseline torque, in particular embodiments. In particular embodiments, such as illustrated by process block 9504, at least one torque measure may be determined to be anomalous relative to the baseline torque based on comparing a value of the at least one torque measure to the dynamic threshold.

Figure 96:
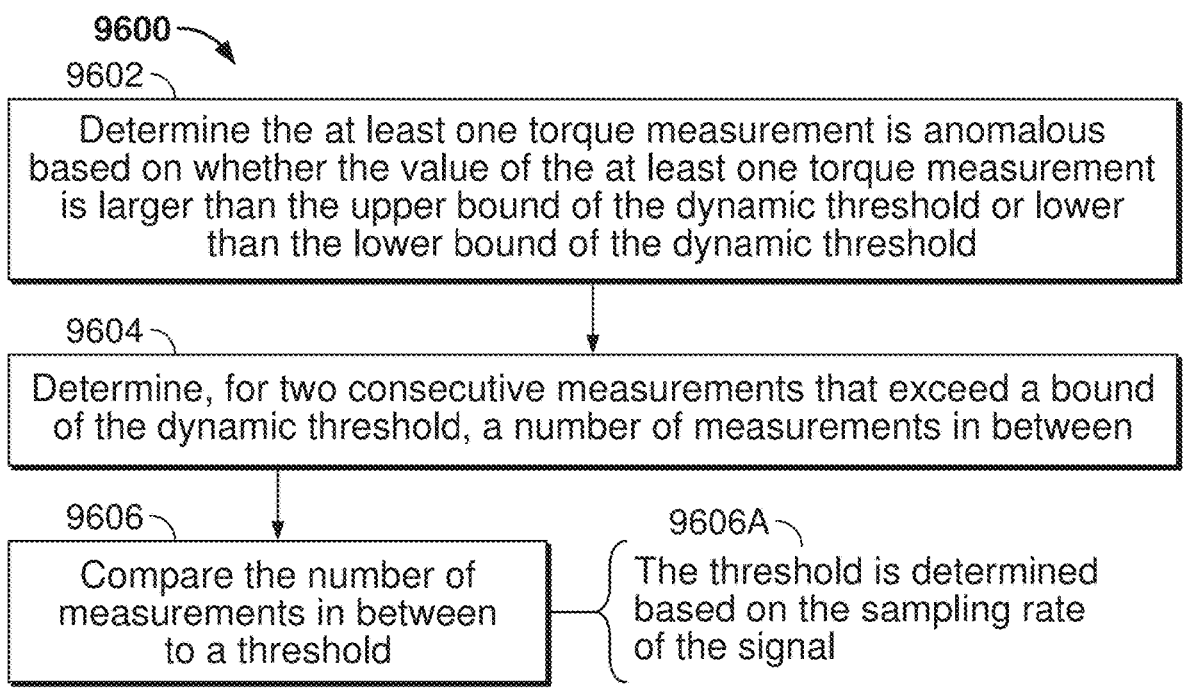
FIG. 96 illustrates an exemplary process for using a bound of a dynamic threshold to identify a number of measurements to process, according to particular embodiments.

FIG. 96 illustrates an exemplary process for using a bound of a dynamic threshold to identify a number of measurements to process, according to particular embodiments. By way of example and not limitation, process 9600 may be executed by processing and control circuitry 108 of FIG. 1. Additionally or alternatively, in particular embodiments, process 9600 may be executed, in whole or in part, as part of and/or contemporaneous with any or all of process 9200 of FIG. 92, process 9300 of FIG. 93, process 9400 of FIG. 94, process 9500 of FIG. 95, and/or process 9700 of FIG. 97. In particular embodiments, data as characterized by graph 9000 of FIG. 90 and/or graph 9100 of FIG. 91 may be utilized as part of the execution of process 9600.

In particular embodiments, such as illustrated by process block 9602, at least one torque measure may be determined to be anomalous based on whether the value of the at least one torque measurement is larger than the upper bound of the dynamic threshold or lower than the lower bound of the dynamic threshold. By way of example and not limitation, a torque measure may be determined to be anomalous based on the upper and/or lower bounds characterized by callouts 9502B and 9502C of FIG. 95. In particular embodiments, such as illustrated by process block 9604, a number of measurements may be determined for subsequent measurements (e.g., two subsequent measurements) that exceed a bound of the dynamic threshold. By way of example and not limitation, the number of measurements may correspond to values in between the two subsequent measurements. In particular embodiments, such as illustrated by process block 9606, the number of measures in between may be compared to a threshold. In particular embodiments, such as illustrated by callout 9606A, the threshold may be determined based on the sampling rate of the signal (e.g., a signal communicating torque data as measured by a torque sensor in the system).

Figure 97:
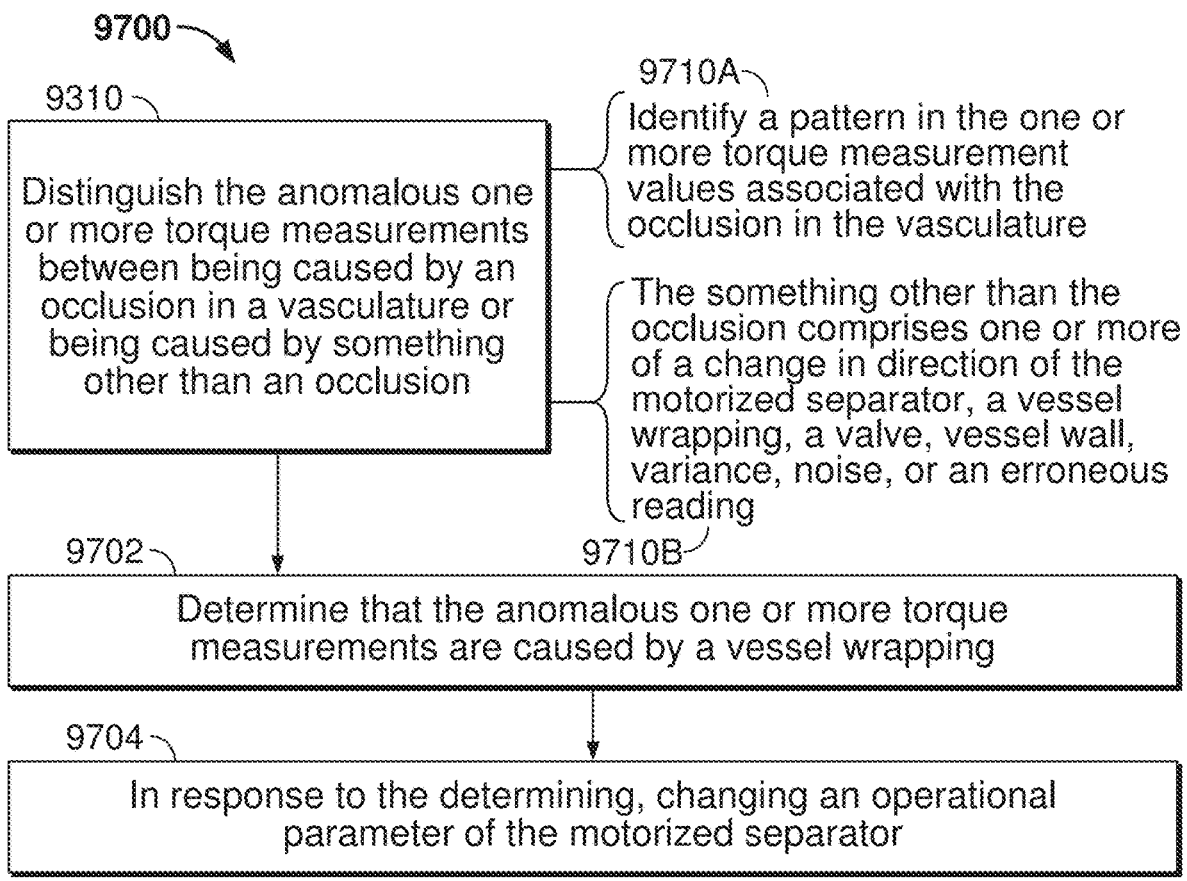
FIG. 97 illustrates an exemplary process for determining a cause of an anomalous measurement, according to particular embodiments.

FIG. 97 illustrates an exemplary process for determining a cause of an anomalous measurement, according to particular embodiments. By way of example and not limitation, process 9700 illustrated in FIG. 97 may be executed by processing and control circuitry 108 of FIG. 1. Additionally or alternatively, in particular embodiments, process 9700 may be executed, in whole or in part, as part of and/or contemporaneous with any or all of process 9200 of FIG. 92, process 9300 of FIG. 93, process 9400 of FIG. 94, process 9500 of FIG. 95, and/or process 9600 of FIG. 96. In particular embodiments, data as characterized by graph 9000 of FIG. 90 and/or graph 9100 of FIG. 91 may be utilized as part of the execution of process 9700.

With reference to FIG. 97, in particular embodiments, process 9700 may be utilized in the event process 9300 progresses to process block 9310, such as based on one or more conditions described in reference to FIG. 93. In particular embodiments, such as illustrated by callout 9710A, a pattern in the one or more torque measurement values associated with the occlusion in the vasculature may be identified and/or may be used to distinguish, such as via process block 9310, an anomalous one or more torque measurements as being causing by an occlusion instead of something other than an occlusion. Additionally or alternative, in particular embodiments, such as illustrated by 9710B, a something other than the occlusion may be distinguished from the occlusion, such as via process block 9310, as comprising, by way of example and not limitation, one or more of a change in direction of the motorized separator, a vessel wrapping, a valve, vessel wall, variance, noise, or an erroneous reading. In particular embodiments, each of the conditions affiliated with a something other than the occlusion may be based on one or more stored or communicatively accessible data ranges and/or patterns characterized for the system to decide a corrective action in response to certain data ranges or patterns.

In particular embodiments, as illustrated by process block 9702, the anomalous one or more torque measurements may be determined to be caused by a vessel wrapping. In particular embodiments, as illustrated by process block 9704, an operational parameter of the motorized separator may be changed in response to the determining (e.g., modifying torque or speed of a rotating component engaged with occlusive material, or modifying a distance which the separator may be extended).

The systems and processes discussed above are intended to be illustrative and not limiting. One skilled in the art would appreciate that the actions of the processes discussed herein may be omitted, modified, combined, and/or rearranged, and any additional actions may be performed without departing from the scope of the invention. More generally, the above disclosure is meant to be exemplary and not limiting. Only the claims that follow are meant to set bounds as to what the present disclosure includes. Furthermore, it should be noted that the features and limitations described in any one embodiment may be applied to any other embodiment herein, and flowcharts or examples relating to one embodiment may be combined with any other embodiment in a suitable manner, done in different orders, or done in parallel. In addition, the systems and methods described herein may be performed in real time. It should also be noted that the systems and/or methods described above may be applied to, or used in accordance with, other systems and/or methods.

While some portions of this disclosure may refer to "convention" or examples, any such reference may be merely to provide context to the instant disclosure and does not form any admission as to what constitutes the state of the art.

Benefits, advantages, and solutions to problems have been described above with regard to particular examples. However, any particular benefit, advantage, or solution may not be construed as critical, required, or essential. Nor is any particular element that may cause or amplify a benefit, advantage, or solution to be construed as critical, required, or essential.

The examples illustrated have been described to promote clarity of understanding, and it will be obvious that any equivalent modifications will fall within the scope of the appended claims. Equivalent modifications are understood to include, but not be limited by, the following examples: (1) performing the steps recited in a method in any order or skipping steps altogether, (2) varying dimensions and materials within reasonable limits, (3) varying the configuration of elements in way that achieves substantially the same result, and (4) combining different examples in a way that achieves substantially the same result.

The present disclosure, and the examples illustrated herein, makes substantial, non-obvious improvements over the conventional systems and methods for aspirating a clot. In particular, the examples in accordance with the subject matter disclosure herein fragment target substances in a discrete, bite-like manner. The complimentary geometries of the substantially spherical element and the helical body enables the helical cutting instrument to efficiently cut a clot into smaller portions and aspirate the resulting fragments into a lumen of a catheter without expelling them into the vasculature. The fragmentation occurs safely within a defined space. The discrete fragments are immediately aspirated further within the device's lumen. The cycle of cutting the substance and aspirating a fragment may then be repeated. This improves on prior art where the devices fragment target substances within the vasculature, whereby the fragments are simultaneously dispersed throughout the vasculature. Such dispersal may cause further complications that the present invention avoids. The present examples do not release fragments within the vasculature. The creation of the fragments may be simultaneous with their removal. The fragments are thereby immediately removed, rather than dispersed into the patient's vasculature.

Examples Using Combined Subsystems and Methods

While several subsystems and methods relating to thrombectomy systems may have been separately discussed herein to provide a clear understanding, it will be appreciated that multiple such subsystems and/or methods may be connected and/or combined in particular embodiments of thrombectomy systems, and may operate and/or interact in such combinations in particular embodiments. Such combinations of structures and/or functions are fully contemplated by this disclosure, including any sections of the disclosure herein. In particular embodiments, synergistic benefits may be obtained by combinations of structures, technical aspects, and/or operational interaction of subsystems disclosed herein. Particular embodiments will be described further in this section for further illustration, by way of example and not limitation.

In particular embodiments, determination of system states based on torque sensing of a separator instrument, e.g., presence of an occlusion or potential vessel damage, may be implemented based on the systems and methods disclosed herein. In particular embodiments, one or more dynamic thresholds may be established and used to establish operational deviations, such as for detecting occlusions and/or potential vessel damage. In particular embodiments, predetermined or adaptively determined bounds may be used to detect occlusions and/or potential vessel damage.

In particular embodiments, one or more system scores may be directly or indirectly derived from sensor data, such as torque data. In particular embodiments, system score determination may be based on automatically identifying specific features from the detected torque profiles, extracting torque parameters based on values and trends derived from those specific features, and calculating one or more system scores based on the torque parameters of those features. In particular embodiments, determining system scores based on torque parameters may further comprise appropriate weighting of the parameters, and/or use of correction factors.

In particular embodiments, the torque parameters may comprise one or more of a starting torque; motor direction change torque; torque amplitude maxima, minima, and/or variation; instantaneous dynamic threshold(s), and/or changes in dynamic threshold(s).

It will be appreciated that while particular examples associated with a separator instrument and/or cutting instrument described in this document may disclose particular operational parameters, such as torque parameters, for making particular detections and/or determinations, this disclosure fully contemplates other parameters for making these detections and/or determinations. By way of example and not limitation, particular detections and/or determinations can include system state detection, such as occlusion detection, contact or other engagement with vessel, wrap conditions, detection of occlusion clearing, and/or detection of clogging within connection tubing. By way of example and not limitation, detection and/or determination of a system state may be based on one or more operational parameters associated with an aspiration subsystem and/or separator subsystem.

By way of example and not limitation, one or more operational parameters associated with a separator subsystem, such as based on operating a cutting instrument, may comprise one or more of: (i) one or more torque levels, (ii) one or more rotational rates, (iii) one or more motor current levels, and/or (iv) a rotational direction or change thereof. By way of example and not limitation, one or more operational parameters associated with a separator subsystem, such as based on operating a cutting instrument, may comprise one or more of: (i) one or more axial positions, (ii) one or more axial motion rates, (iii) one or more axial motion acceleration levels, (iv) one or more axial motion force levels, and/or (v) one or more motor torque levels associated with the axial motion.

In particular embodiments, measures of torque variance may be further extracted as torque parameters. By way of example and not limitation, a Mean Absolute Deviation of torque about a Median torque may be identified as a measure of torque variation. By way of example and not limitation, torque values at the start and end of valve cycling, peak, minimum, and/or average torque values within a temporal window of valve cycling, as well as dynamic aspects of pressure change and recovery based on valve cycling may be detected and used by the controller to determine the presence of an occlusion.

In particular embodiments, one or more parameters used in computing a system score and/or determining a system state may be based on detected pressure, torque, and/or electric current profiles. By way of example and not limitation, one or more such parameters may be used for determining a state of flow and/or potential damage to a vessel. In particular embodiments, one or more parameters may be empirically determined based on operational data, such as measured time series data. In particular embodiments, one or more parameters may be determined based on training and using machine learning algorithms, data analytics, or any combination thereof. Additional non-limiting details and examples of determining systems scores (e.g., an open score) and/or system states (e.g., an occluded flow state) have been disclosed herein.

In particular embodiments, sensor data derived from an aspiration subsystem of thrombectomy systems (e.g., pressure data) may be used to determine actions for separator operation or other instruments. In particular embodiments, aspiration subsystem-based sensor data (e.g., pressure data) may be combined with torque sensor data and/or electric current sensor data.

In particular embodiments, as discussed herein, aspiration subsystem data (e.g., pressure data) may be used to determine a state of occlusion of the catheter, such as incipient or persistent clogging. In particular embodiments, aspiration subsystem-based sensor data (e.g., pressure data) may be combined with torque sensor data and/or electric current senor data. By way of example and not limitation, such a determination of occluded or partially occluded state may be used to operate a separator instrument to engage with and/or act on the occlusion. In particular embodiments, one or more motors may be instructed by the controller to rotate a separator instrument with increased torque, at varying speeds, in one or the other direction, in alternating directions, at different frequencies of rotation and/or direction change. In particular embodiments, one or more motors may be instructed by the separator to produce specific axial motions of the separator instrument.

It will be appreciated that a separator instrument or cutting instrument, as used throughout this disclosure, may refer to any instrument used to cut, fragment, and/or ingest, by mechanical or other means, occlusive material in a vessel or passage of the body. Additionally or alternatively, a separator instrument or cutting instrument, as used throughout this disclosure, may refer to any instrument used to engage with and/or otherwise act upon occlusive material in a vessel or passage of the body.

In particular embodiments, as discussed herein, pressure data may be used to determine a state of open flow, such as a state wherein no occlusion is detected. In particular embodiments, aspiration subsystem data (e.g., pressure sensor data) may be combined with separator subsystem data (e.g., torque sensor data, electric current sensor data). In particular embodiments, based on a determination of open flow, one or more valves may be operated to reduce or pause exposure of a vessel to vacuum. Separately or additionally, in particular embodiments, a separator instrument may be operated based on a determination of open flow, for e.g., by advancing the instrument distally, to establish proximity to any residual clot that may be present. Separately or additionally, in particular embodiments, the separator subsystem may also use a pressure sensor at its tip. By way of example and not limitation, a pressure sensor may be incorporated at a distal tip of the cutting instrument. In particular embodiments, an absence of further residual occlusion may be used to determine that the stage of the thrombectomy procedure is complete. By way of example and not limitation, such a process may be used to ensure complete clot removal with reduced loss of healthy blood.

In particular embodiments, as discussed herein, separator subsystem data (e.g., torque data, electric current data) may be used to determine a state of occlusion of the catheter, such as incipient or persistent clogging, and/or potential damage to vessels. In particular embodiments, aspiration subsystem data (e.g., pressure sensor data) may be combined with separator subsystem data (e.g., torque sensor data, electric current sensor data). By way of example and not limitation, such a determination of occluded or partially occluded state may be used to operate one or more actuators (e.g., valves, motors) of an aspiration subsystem for clearing the occlusion. In particular embodiments, a determination of occluded flow may be used by the controller to implement a more aggressive algorithm for operating one or more valves or motors for occlusion removal. By way of example and not limitation, based on a determination of occluded flow, the controller may be used to change a vacuum level and/or change a level of RPM of the motor of the motorized separator by operating one or more valves, by operating the motor, and/or to change pulsing parameters for more effective and/or faster clot removal. In particular embodiments, a sampling time used by the aspiration subsystem may be modified, for e.g., to reduce overall procedure time.

In particular embodiments, detection of complete ingestion of clot based on separator subsystem data (e.g., torque sensor data, electric current sensor data) may be used by the controller to operate one or more valves of the aspiration subsystem to reduce or cease vacuum exposure of the vessel, e.g., to minimize blood loss, and/or to determine that clot removal is complete.

In particular embodiments, as will be illustrated further herein, sensing based on a separator instrument may provide the benefit of shorter lag times for sensing particular events and/or system states, e.g., relative to pressure-based sensing of an aspiration subsystem. By way of example and not limitation, shortened lag times may be based on a closer spatial proximity of a separator instrument and/or one or more related sensors to the events and structural status in the vessel, e.g., distal tip proximity relative to pressure sensors, which may be located farther downstream in particular embodiments. By way of example and not limitation, transmission speed of sensed stimuli in different background media (e.g., fluid contents of a vessel or catheter, solid instrument materials) may contribute to shorter lag time for sensing based on a separator instrument, in particular embodiments. In particular embodiments, an ability to check for residual clot and removal while minimizing additional blood loss using separator system sensing, either separately or in combination with other methods disclosed herein, can reduce overall procedure time while improving patient safety and outcomes.

In particular embodiments, one or more system scores may be determined based on sensor data from multiple subsystems of a thrombectomy system. By way of example and not limitation, a flow state (e.g., occlusion) detection based on torque sensing for a separator instrument may be combined with pressure-based detection of flow state to determine one or more system scores related to flow state (e.g., a multi-level Open Score, and a multi-level Occlusion Score). By way of example and not limitation, a system score corresponding to an occluded state deriving from torque sensing may be based on an increase in torque value relative to a dynamic threshold and/or a bound, such as a primary bound. In particular embodiments, a primary bound may be a multiple of a dynamic threshold value. By way of example and not limitation, a primary bound may be 1.25 to 2 times the dynamic threshold.

By way of example and not limitation, a system score corresponding to an occluded state deriving from torque sensing may be based on an increasing variance of torque amplitude, e.g., exceeding a bound, such as a primary bound. By way of example and not limitation, a system score corresponding to an open flow state deriving from torque sensing may be based on consistent torque values relative to a dynamic threshold, and/or decreasing variance of torque amplitude. By way of example and not limitation, a system score corresponding to potential vessel damage deriving from torque sensing may be based on significant changes (e.g., very large increase or decrease) in torque values relative to a dynamic threshold, and/or relative to a bound, such as a secondary bound.

In particular embodiments, one or more such system scores obtained based on sensor data from individual or multiple subsystems of a thrombectomy system may be used separately or in combination to determine one or more system states. Accordingly, in particular embodiments, system score determination based on combined sensing based on multiple subsystems can be used for rapid clot removal while minimizing healthy blood loss.

Figure 98:
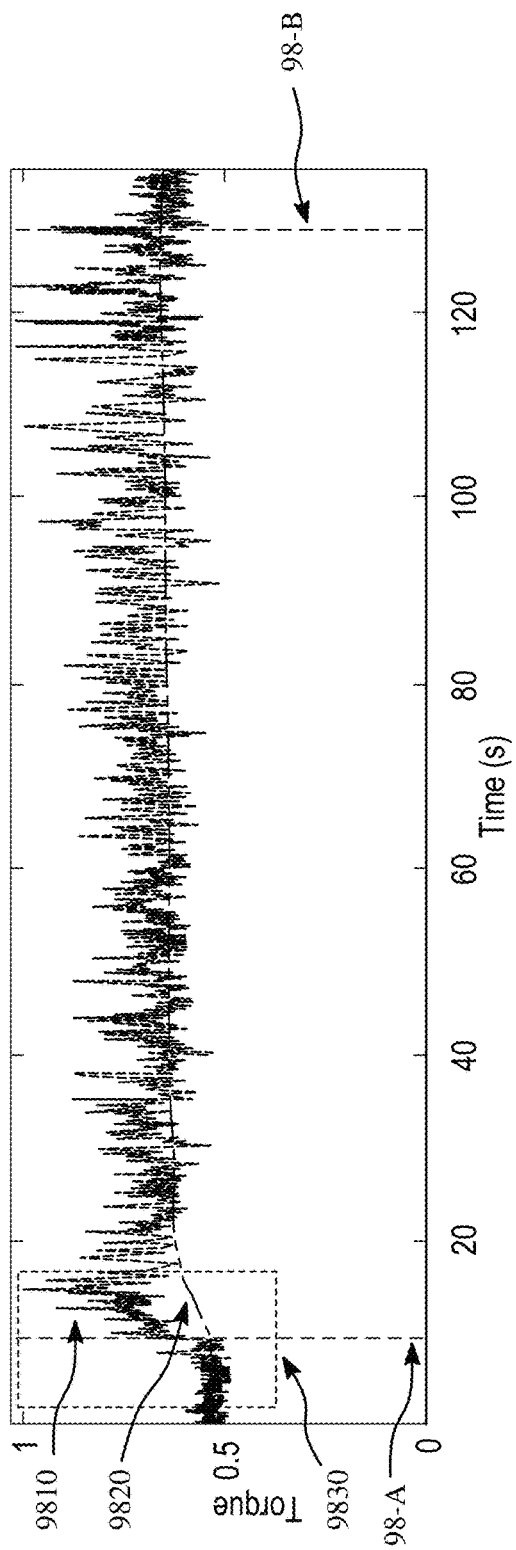
FIG. 98 illustrates an exemplary torque profile captured within a time interval, according to particular embodiments.
Figure 99:
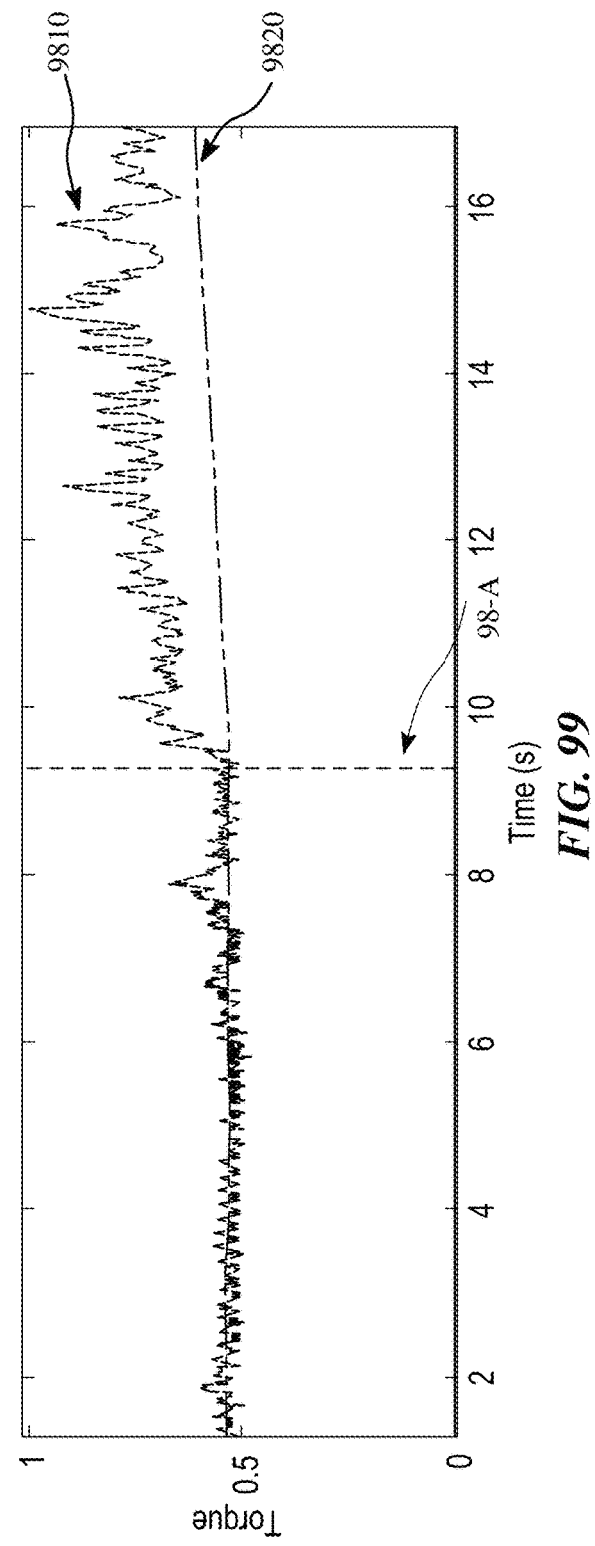
FIG. 99 illustrates an enlarged view of a portion of the time interval of FIG. 98, according to particular embodiments.

FIG. 98 illustrates an exemplary torque profile captured within a time interval, according to particular embodiments. Profiles of torque 9810 and dynamic threshold 9820 collected from a test are depicted over the illustrated time window. The torque values depicted are normalized to a range between 0 and 1 for discussion and illustration of relative values. By way of example and not limitation, torque values may be normalized based on a maximum sampled torque value during an interval. FIG. 99 illustrates an enlarged view of a portion of the time interval of FIG. 98, according to particular embodiments. By way of example and not limitation, the time interval depicted in FIG. 99 approximately corresponds to a portion 9830 of FIG. 99.

Figure 100:
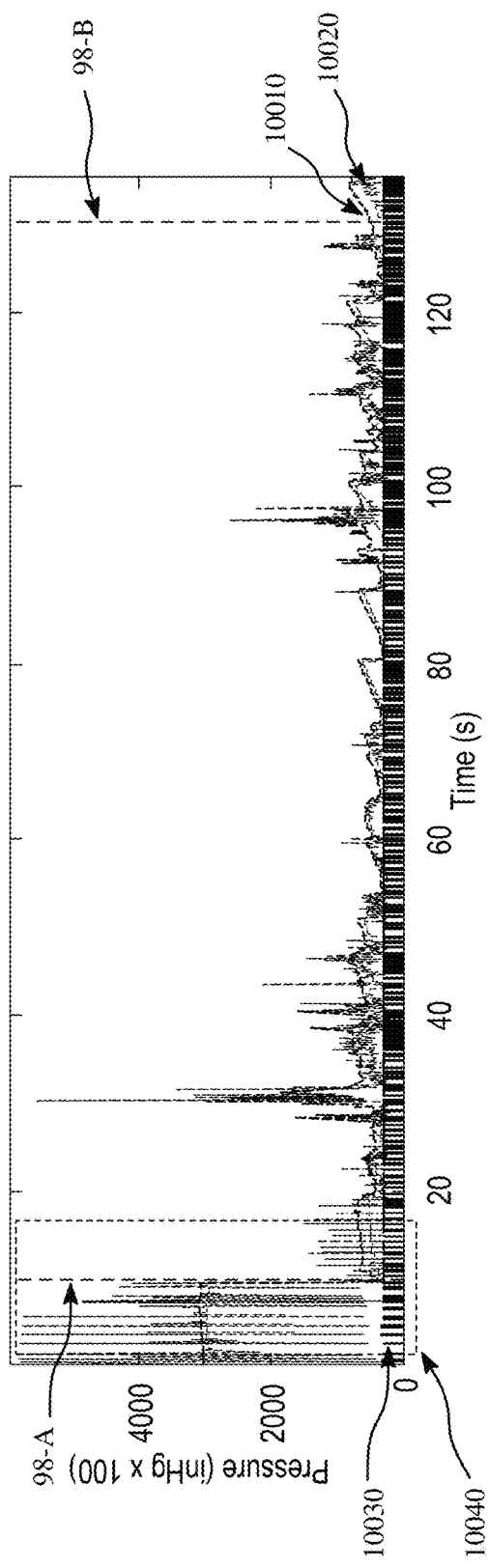
FIG. 100 illustrates exemplary pressure profiles simultaneously captured during the time interval of FIG. 98, according to particular embodiments.
Figure 101:
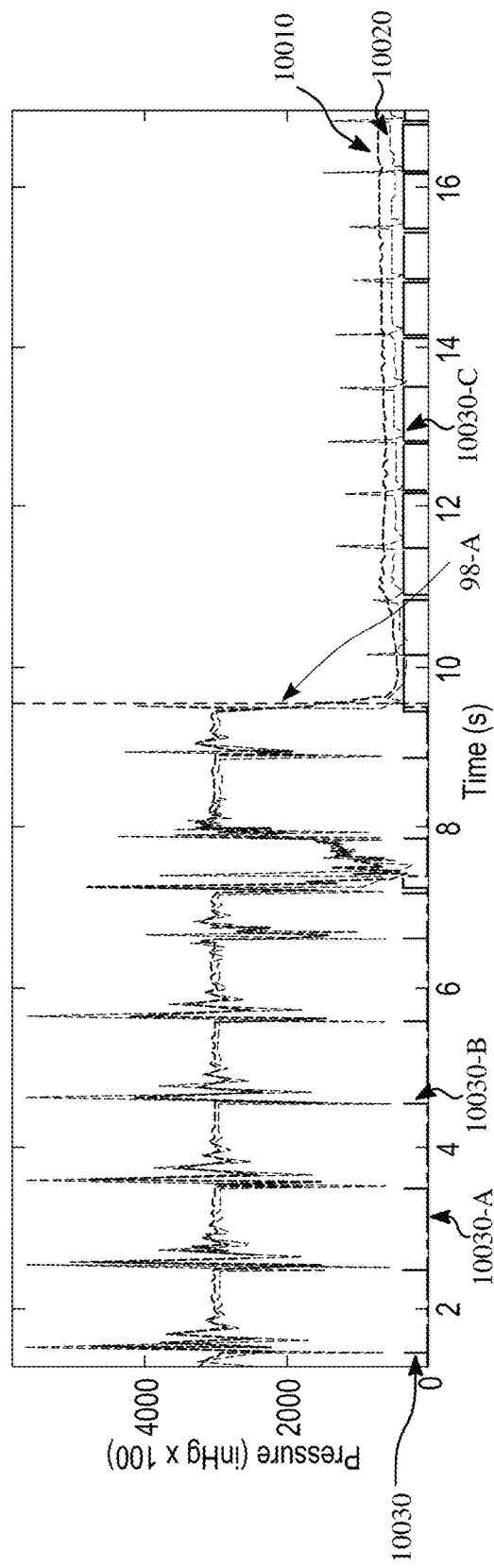
FIG. 101 illustrates an enlarged view of a portion of the time interval of FIG. 100, according to particular embodiments.

FIG. 100 illustrates exemplary pressure profiles simultaneously captured with torque 9810 during the time interval of FIG. 98, according to particular embodiments. A first pressure profile 10010 indicates the time-varying pressure measured by a pressure sensor proximal to the catheter. By way of example and not limitation, first pressure profile 10010 may be considered to correspond to distal pressure sensor 3570 for illustration. A second pressure profile 10020 indicates the time-varying pressure measured by a pressure sensor proximal to a canister vacuum source. By way of example and not limitation, second pressure profile 10020 may be considered to correspond to vacuum sensor 8522 for illustration. A valve profile 10030 indicates the time-varying state of a valve of the aspiration subsystem. By way of example and not limitation, valve profile 10030 may be considered to correspond to the state of vacuum valve 3560 for illustration. A '0' state of valve profile 10030 indicates a closed valve, such as depicted by 10030-A. An elevated state of valve profile 10030 indicates an open valve, such as depicted by 10030-B. In particular cases, a valve may be cycled, and/or held open over extended time intervals, such as depicted by 10030-C. FIG. 101 illustrates an enlarged view of a portion of the time interval of FIG. 100 approximately indicated by 10040, according to particular embodiments.

In particular embodiments, sensing based on a particular subsystem may receive different and/or better information (e.g., earlier, and/or with higher confidence) than sensing based on one or more other subsystems. In particular embodiments, combined sensing using particular subsystems may outperform particular or all individual subsystems. Such advantages may be used by the controller to make determinations and implement operational actions using one or more subsystems. In particular embodiments, actuator action (e.g., for occlusion removal) based on a particular subsystem and/or combination of subsystems may provide different and/or better efficiency, effectiveness, and/or safety than other subsystems or combinations. Separately or additional, such advantages for optimized actuation may be used by the controller in thrombectomy systems having multiple subsystems.

By way of example and not limitation, a separator subsystem (e.g., based on torque sensing) and an aspiration subsystem (e.g., based on measured pressure) may sense a system state change with comparable time lags and/or within similar time intervals. By way of example and not limitation, as depicted in FIGS. 98-101, an occlusion may be nearly simultaneously sensed by a separator subsystem and an aspiration subsystem, in particular embodiments and/or situations, such as at the approximate point in time indicated by 98-A in FIGS. 98-101. As depicted in FIGS. 98 and 99 by way of example and not limitation, the presence of an occlusion sensed based on torque sensing may manifest as an increase in torque value of torque 9810 exceeding a primary bound, e.g., 1.25 to 2 times the dynamic threshold 9820. By way of example and not limitation, the presence of an occlusion sensed based on torque sensing may separately or additionally manifest as increased variation of torque value. As depicted in FIGS. 100 and 101 by way of example and not limitation, the presence of an occlusion sensed by pressure sensing may manifest as a significant rise in pressure value recorded by first pressure profile 10010 and/or second pressure profile 10020.

By way of example and not limitation, a separator subsystem (e.g., based on torque sensing) and an aspiration subsystem (e.g., based on measured pressure) may sense a system state change differently in particular embodiments and/or conditions. By way of example and not limitation, as depicted in the simultaneously captured data profiles of FIGS. 98 and 100, a noticeable decrease in amplitude variation of torque 9810 is sensed at the approximate point in time indicated by 98-B. By way of example and not limitation, the decreased value of amplitude variation of torque 9810 at time periods past about 98-B may lie below an occlusion detection or presence threshold, indicating that the occlusion has cleared, and no clot remains at the distal tip of the separator. By way of example and not limitation, by contrast and as illustrated in FIG. 100, the first pressure profile 10010 and/or the second pressure profile 10020 may not provide noticeable indications that the occlusion has cleared; both profiles remain low as before, which may falsely indicate continued presence of a clot. By way of example and not limitation, the system may accordingly continue to expose the vessel to vacuum by opening and/or cycling a vacuum valve, as depicted by valve profile 10030 past about 98-B in FIG. 100, which can cause unnecessary loss of blood.

Figure 102:
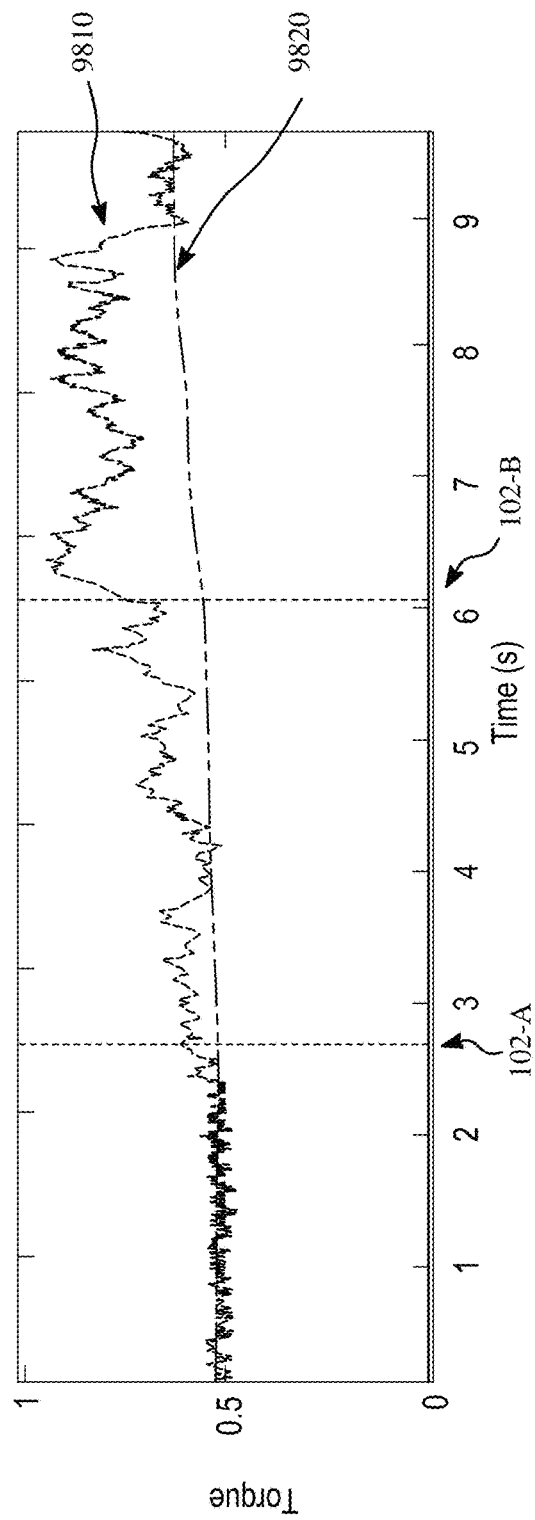
FIG. 102 illustrates an exemplary torque profile captured within a time interval, according to particular embodiments.
Figure 103:
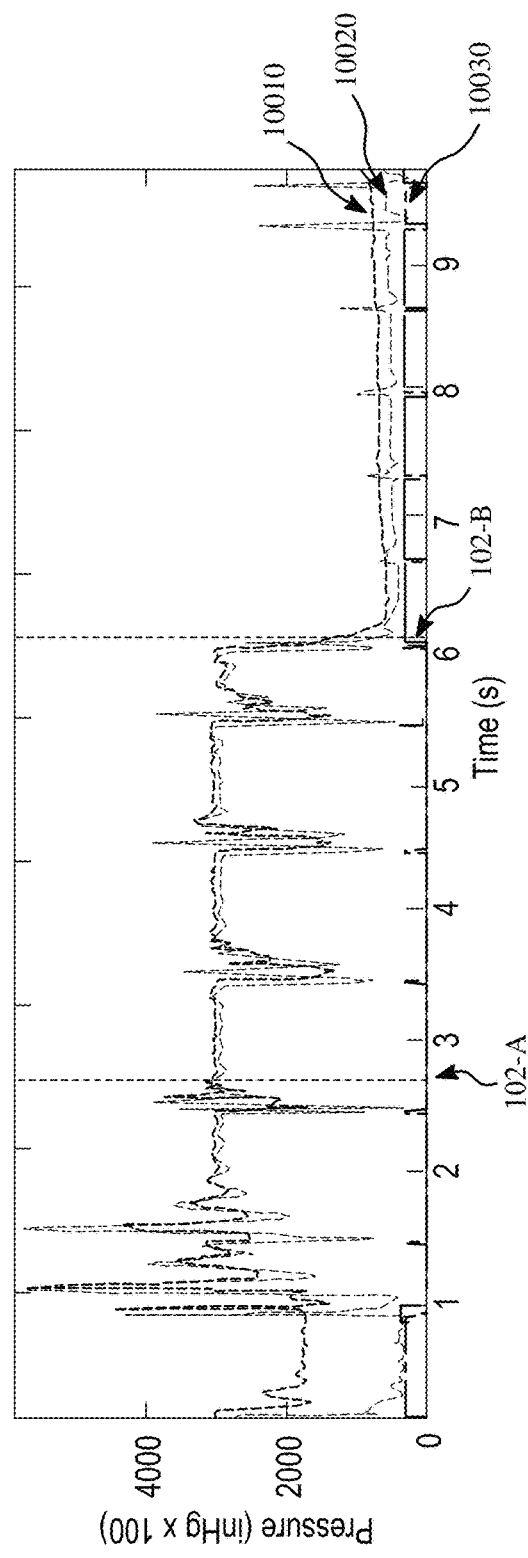
FIG. 103 illustrates exemplary pressure profiles captured within the same time interval as the torque profile of FIG. 102, according to particular embodiments.

As discussed herein, in particular embodiments and/or conditions, sensing based on a separator instrument may benefit from shorter lag times for sensing particular events and/or system states. FIG. 102 illustrates an exemplary torque profile captured within a time interval, according to particular embodiments. As with FIGS. 98 and 99, torque values are normalized in FIG. 102 on a scale of 0 to 1. FIG. 103 illustrates exemplary pressure profiles captured within the same time interval as the torque profile of FIG. 102, according to particular embodiments.

As depicted with reference to the simultaneously captured profiles illustrated in FIGS. 102 and 103 by way of example and not limitation, the profile of torque 9810 already provides indications of sensing the presence of an occlusion at the approximate point in time indicated by 102-A, for example, based on an increase in value of torque 9810. By way of example and not limitation, by contrast, the first pressure profile 10010 and/or the second pressure profile 10020 may not provide noticeable indications of sensing an occlusion until the approximate point in time indicated by 102-B. In particular embodiments, a primary bound for determining the presence of such an occlusion may be determined based on torque value of torque 9810, for e.g., relative to dynamic threshold 9820. In particular embodiments, a threshold for determining the presence of such an occlusion may be determined based on measured frequency spectra and/or variation of torque value of torque 9810. As discussed herein, in particular embodiments and/or conditions, sensing based on a particular subsystem, e.g., a separator torque, can provide earlier and/or additional information, which may be acted upon by one or more subsystems for efficient, effective, and safe removal of occlusions and completion of the procedure.

Figure 104:
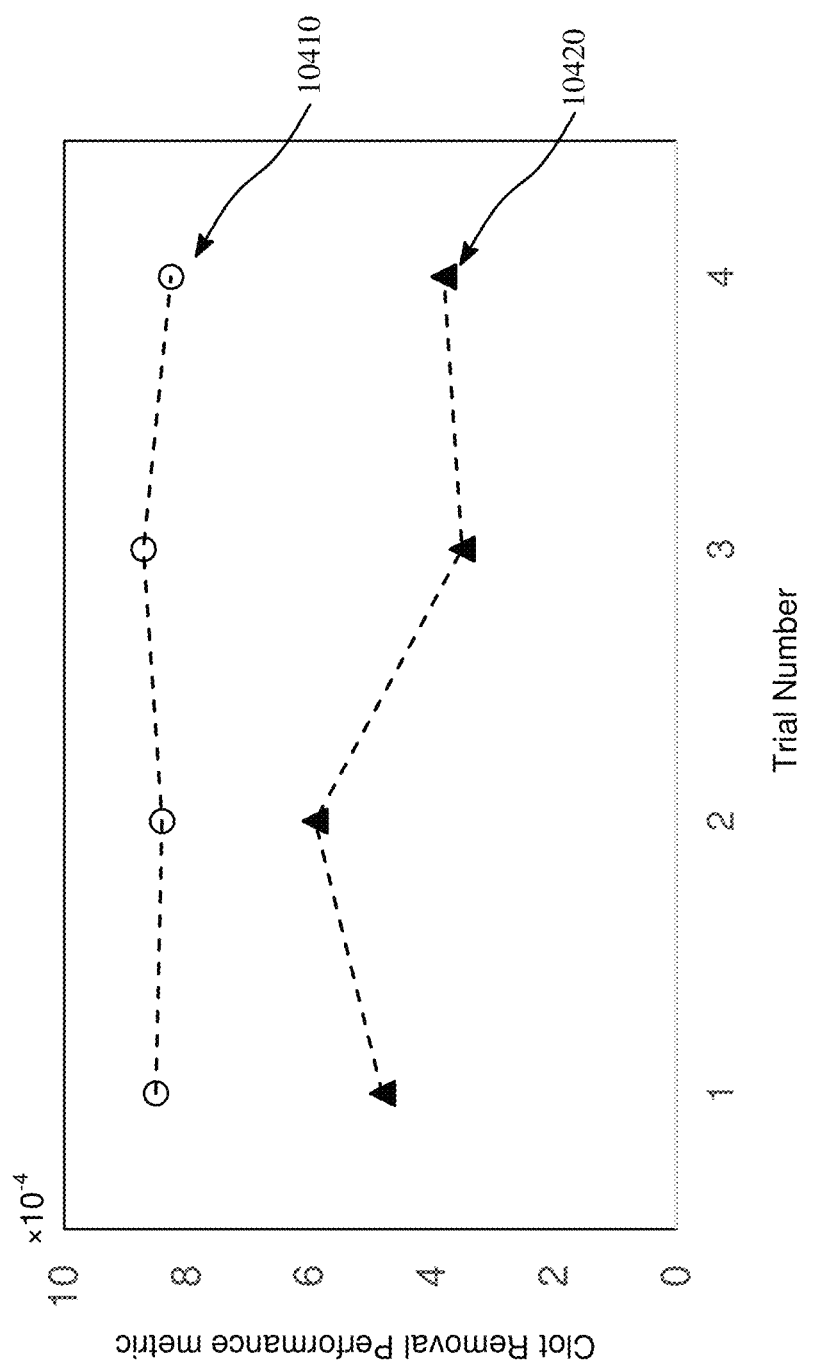
FIG. 104 illustrates a schematic of relative clot removal performance for exemplary systems, according to particular embodiments.

As discussed herein, in particular embodiments, sensor data from both aspiration system (e.g., pressure data) and separator system (e.g., torque data) may be used as complementary information, for e.g., to enhance the performance of each system for effective and safe clot removal. FIG. 104 illustrates a schematic of relative clot removal performance for exemplary systems, according to particular embodiments.

In particular embodiments, as schematically depicted in FIG. 104 by way of example and not limitation, a combined performance metric for clot removal (e.g., per cc or mL of clot) per second of blood loss (e.g., in cc or mL of blood loss) can provide a useful relative indication of rapid clot removal rate while minimizing blood loss. By way of example and not limitation, maximizing amount of clot removed, minimizing procedure time, and/or minimizing loss of healthy blood can be positively correlated with improved patient safety and outcomes. As illustrated in FIG. 104 over four trials for demonstration, complementary combination of aspiration-based and separator-based systems (10410) for sensing and operation can significantly outperform aspiration system-based sensing and operation alone (10420), in particular embodiments.

MISCELLANEOUS

Herein, "or" may be inclusive and not exclusive, unless expressly indicated otherwise or indicated otherwise by context. Therefore, herein, "A or B" means "A, B, or both," unless expressly indicated otherwise or indicated otherwise by context. Moreover, "and" may be both joint and several, unless expressly indicated otherwise or indicated otherwise by context. Therefore, herein, "A and B" means "A and B, jointly or severally," unless expressly indicated otherwise or indicated otherwise by context.

The scope of this disclosure encompasses all changes, substitutions, variations, alterations, and modifications to the example embodiments described or illustrated herein that a person having ordinary skill in the art would comprehend. The scope of this disclosure is not limited to the example embodiments described or illustrated herein. Moreover, although this disclosure describes and illustrates respective embodiments herein as including particular components, elements, feature, functions, operations, or steps, any of these embodiments may include any combination or permutation of any of the components, elements, features, functions, operations, or steps described or illustrated anywhere herein that a person having ordinary skill in the art would comprehend. Furthermore, reference in the appended claims to an apparatus or system or a component of an apparatus or system being adapted to, arranged to, capable of, configured to, enabled to, operable to, or operative to perform a particular function encompasses that apparatus, system, component, whether or not it or that particular function may be or is activated, turned on, or unlocked, as long as that apparatus, system, or component may be so adapted, arranged, capable, configured, enabled, operable, or operative. Additionally, although this disclosure describes or illustrates particular embodiments as providing particular advantages, particular embodiments may provide none, some, or all of these advantages.

Figures provided herein may be illustrated schematically rather than literally or precisely; components and aspects of the figures may not necessarily be to scale. Moreover, while like reference numerals may designate corresponding parts throughout the different views in many cases, like parts may not always be provided with like reference numerals in each view.

What is claimed is:

1. A thrombectomy system, comprising:
   a catheter having a proximal end and a distal end, wherein the catheter comprises a lumen configured to accommodate fluid;
   a first valve, wherein the first valve is in fluid communication with the catheter, and wherein the first valve is configured to operate in a plurality of operating modes, wherein one or more of the operating modes is configured to alter a level of pressure in the catheter;
   a cutting instrument at the distal end of the catheter, wherein the cutting instrument is configured for one or more motions comprising one or more of axial motion and rotational motion;
   a first sensor associated with the cutting instrument; and
   a controller configured to:
   detect, via the first sensor, one or more operational parameters associated with the cutting instrument;
   determine, based on one or more of the detected operational parameters associated with the cutting instrument at the distal end of the catheter, a current flow state indicating whether the distal end of the catheter is engaging with occlusive material, wherein the current flow state is determined via a machine learning algorithm trained on training data to predict one or more flow states associated with the catheter based on one or more of the operational parameters associated with the cutting instrument at the distal end of the catheter;
   operate, based on a determination that the current flow state indicates that the distal end of the catheter is engaging with the occlusive material, the first valve in a first operating mode of the plurality of operating modes to alter the level of pressure in the catheter, and
   operate, based on a determination that the current flow state indicates that the distal end of the catheter is not engaging with the occlusive material, the first valve in a second operating mode of the plurality of operating modes.

2. The thrombectomy system of claim 1, wherein the first operating mode is configured to alter the level of pressure by moving at least a portion of the occlusive material through the lumen towards a proximal region of the catheter.

3. The thrombectomy system of claim 1, wherein the first valve is configured to allow fluid communication between the distal end of the catheter and an aspiration source.

4. The thrombectomy system of claim 3, wherein the first operating mode is configured to remove fluid from the catheter.

5. The thrombectomy system of claim 4, wherein the second operating mode is configured to stop the removal of fluid from the catheter associated with the first operating mode.

6. The thrombectomy system of claim 1, wherein a first set of the operational parameters associated with the cutting instrument comprise one or more of (i) one or more torque levels, (ii) one or more rotational rates, (iii) one or more motor current levels, (iv) a rotational direction, or (v) a change of a rotational direction.

7. The thrombectomy system of claim 1, wherein a second set of the operational parameters associated with the cutting instrument comprise one or more of (i) one or more axial positions, (ii) one or more axial motion rates, (iii) one or more axial motion acceleration levels, (iv) one or more axial motion force levels, or (v) one or more motor torque levels associated with the axial motion.

8. The thrombectomy system of claim 1, wherein the cutting instrument is configured to distally advance outside of the lumen of the catheter.

9. The thrombectomy system of claim 1, wherein the cutting instrument is configured to proximally retract inside of the lumen of the catheter.

10. The thrombectomy system of claim 1, wherein the axial motion comprises a reciprocal axial motion.

11. The thrombectomy system of claim 1, wherein the rotational motion comprises a rotationally oscillating motion.

12. The thrombectomy system of claim 1, further comprising at least one motor operatively coupled with the cutting instrument, wherein the at least one motor is configured to operate the cutting instrument based on one or more of the rotational motion and the axial motion.

13. The thrombectomy system of claim 1, wherein the cutting instrument comprises a spiral body having one or more helical structures.

14. The thrombectomy system of claim 13, wherein the cutting instrument is configured to fragment the occlusive material, and wherein the fragmenting of the occlusive material is confined within the lumen of the catheter based at least in part on one or more of the helical structures of the cutting instrument and the first operating mode configured to alter the level of pressure.

15. The thrombectomy system of claim 1, wherein the cutting instrument comprises one or more of a rounded element and a macerating portion.

16. The thrombectomy system of claim 1, further comprising a second valve in fluid communication with the catheter, wherein the second valve is configured to control an introduction of a fluid medium into the catheter via one or more portions of a set of connection tubing.

17. The thrombectomy system of claim 16, further comprising one or more pressure sensors associated with one or more of the connection tubing and the catheter.

18. A thrombectomy method for removal of occlusive material from a body passageway, comprising:
  positioning a cutting instrument within the body passageway, wherein the cutting instrument is at a distal end of a catheter of a thrombectomy system, and wherein the cutting instrument is configured for one or more motions comprising one or more of axial motion and rotational motion;
  detecting, via a first sensor associated with the cutting instrument, one or more operational parameters associated with the cutting instrument;
  determining, by a controller, based on one or more of the detected operational parameters associated with the at the distal end of the catheter, a current flow state indicating whether the distal end of the catheter is engaging with the occlusive material, wherein the current flow state is determined via a machine learning algorithm trained on training data to predict one or more flow states associated with the catheter based on one or more of the operational parameters associated with the cutting instrument at the distal end of the catheter;
  operating, by the controller, based on a determination that the current flow state indicates that the distal end of the catheter is engaging with the occlusive material, a first valve of the thrombectomy system in a first operating mode of a plurality of operating modes to alter a level of pressure in the catheter, and
  operating, by the controller, based on a determination that the current flow state indicates that the distal end of the catheter is not engaging with the occlusive material, the first valve in a second operating mode of the plurality of operating modes.

19. The method of claim 18, wherein the first operating mode is configured to alter the level of pressure to remove fluid from the catheter.

20. The method of claim 18, wherein the second operating mode is configured to stop the removal of fluid from the catheter associated with the first operating mode.

* * * * *